(12) United States Patent
Tawada et al.

(10) Patent No.: US 6,359,134 B1
(45) Date of Patent: Mar. 19, 2002

(54) SULFONAMIDE DERIVATIVES, THEIR PRODUCTION AND USE

(75) Inventors: Hiroyuki Tawada, Takatsuki; Fumio Ito, Toyonaka; Norihiko Moriya, Hyogo; Zen-ichi Terashita, Toyonaka, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/424,892
(22) PCT Filed: May 28, 1998
(86) PCT No.: PCT/JP98/02346
  § 371 Date: Nov. 30, 1999
  § 102(e) Date: Nov. 30, 1999
(87) PCT Pub. No.: WO98/54164
  PCT Pub. Date: Dec. 3, 1998

(30) Foreign Application Priority Data

May 30, 1997 (JP) .............................. 9-142250
Dec. 19, 1997 (JP) .............................. 9-351806

(51) Int. Cl.[7] ................... C07D 295/18; C07D 295/20; A61K 31/495; A61P 7/02
(52) U.S. Cl. ................... 544/333; 544/238; 544/242; 514/252.1; 514/252.13; 514/256; 514/269
(58) Field of Search ................ 544/238, 242, 544/333; 514/252.1, 252.13, 256, 269

(56) References Cited

U.S. PATENT DOCUMENTS 5,559,232 A  9/1996 Ackermann et al. ........ 544/121

FOREIGN PATENT DOCUMENTS

| | | |
|---|---|---|
| EP | 0203743 A1 | 12/1986 |
| EP | 0299493 A2 | 1/1989 |
| EP | 0529858 A | 3/1993 |
| EP | 0805149 | 11/1995 |
| EP | 0739886 A2 | 10/1996 |
| EP | 0838460 A1 | 4/1998 |
| JP | 49-110680 | 10/1974 |
| JP | 62-502339 | 9/1987 |
| WO | WO 90/05523 | 5/1990 |
| WO | WO 94/18185 | 8/1994 |
| WO | WO 96/05189 | 2/1996 |
| WO | WO 96/10022 | 4/1996 |
| WO | WO96/33982 | 10/1996 |
| WO | WO 96/40679 | 12/1996 |
| WO | WO 96/40737 | 12/1996 |
| WO | WO 97/03060 | 1/1997 |
| WO | WO 97/19919 | 6/1997 |
| WO | WO 97/40023 | 10/1997 |
| WO | WO98/21188 | 5/1998 |
| WO | WO99/06395 | 2/1999 |

Primary Examiner—Richard L. Raymond
Assistant Examiner—Venkataraman Balasubramanian
(74) Attorney, Agent, or Firm—Mark Chao; Elaine M. Ramesh

(57) ABSTRACT

The present invention provides compounds which specifically inhibit FXa, which are effective when orally administered and which are useful as a safe medicine for the prevention or treatment of diseases caused by thrombus or infarction.

Compounds of this invention are piperazinones of the formula:

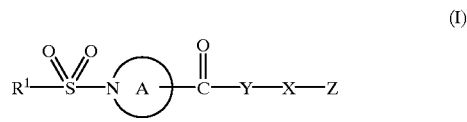

(I)

wherein $R^1$ is an optionally substituted hydrocarbon group or an optionally substituted heterocyclic group; the ring A is an optionally substituted divalent nitrogen-containing heterocyclic group, in addition to being substituted by the group of the formula:

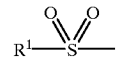

and the group of the formula:

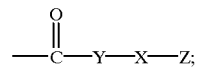

Y is an optionally substituted divalent hydrocarbon group or an optionally substituted divalent heterocyclic group; X is a direct bond or an optionally substituted alkylene chain; Z is (1) an amino group substituted with an optionally substituted hydrocarbon group, (2) an optionally substituted imino group or (3) an optionally substituted nitrogen-containing heterocyclic group; provided that when X is a direct bond and Z is an optionally substituted 6-membered nitrogen-containing aromatic heterocyclic group, Y is an optionally substituted divalent hydrocarbon group or an optionally substituted divalent unsaturated heterocyclic group; or a salt thereof.

17 Claims, No Drawings

SULFONAMIDE DERIVATIVES, THEIR PRODUCTION AND USE

TECHNICAL FIELD

The present invention relates to novel sulfonamide derivatives which are useful as medicine and which inhibit activated coagulation factor X (FXa) to show anti-coagulant activity, their production and use.

BACKGROUND ART

For the purpose of the prevention and treatment of cardiac infarction, cerebral thrombosis, etc., it is important to inhibit formation of thrombus and various researches and developments of thrombus inhibitors such as anti-thrombin agents, platelet aggregation inhibitors, etc. have been carried out. However, anti-thrombin agents as well as platelet aggregation inhibitors have side effects such as bleeding and problems in their safety, since thrombin is a final mediator causing blood coagulation and platelet aggregation. On the other hand, FXa inhibitors specifically inhibit coagulation factor and are useful as an anti-coagulant.

So far, compounds having FXa inhibitory activity are disclosed in e.g. Japanese Unexamined Patent Publication No. 1993(H5)-208946, WO 96/16940, WO 96/40679 and WO 96/10022, etc.

However, the above compounds having FXa inhibitory activity do not have sufficient FXa inhibitory activity and, in particular, do not show sufficient action when orally administered, therefore, they are not practically useful as a medicine.

DISCLOSURE OF INVENTION

The present invention is to provide novel sulfonamide derivatives which specifically inhibit FXa, which are effective when orally administered and which are useful as a safe medicine for the prevention (prophylaxis) or treatment (therapy) of diseases caused by thrombus, ischemia or infarction.

The present inventors diligently made extensive studies and, as a result, they succeeded in synthesizing a compound or a salt thereof [hereinafter, referred to as Compound (I)], whose characteristic feature in the chemical structure lies in having (1) a divalent nitrogen-containing heterocyclic group between a sulfonyl group and a carbonyl group and (2) an amino group substituted with a hydrocarbon group, an imidoyl group or a nitrogen-containing heterocyclic group at terminals of a substituent of the carbonyl group, represented by the formula (I):

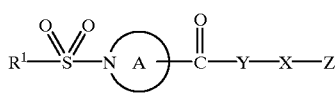

(I)

wherein $R^1$ is an optionally substituted hydrocarbon group or an optionally substituted heterocyclic group; the ring A is an optionally substituted divalent nitrogen-containing heterocyclic group, in addition to being substituted by the group of the formula:

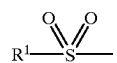

and the group of the formula:

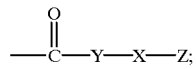

Y is an optionally substituted divalent hydrocarbon group or an optionally substituted divalent heterocyclic group;

X is a direct bond or an optionally substituted alkylene chain; Z is (1) an amino group substituted with an optionally substituted hydrocarbon group, (2) an optionally substituted imidoyl group or (3) an optionally substituted nitrogen-containing heterocyclic group; provided that when X is a direct bond and Z is an optionally substituted 6-membered nitrogen-containing aromatic heterocyclic group, Y is an optionally substituted divalent hydrocarbon group or an optionally substituted divalent unsaturated heterocyclic group; or a salt thereof, and further found that the compound (I) unexpectedly possesses potent FXa inhibitory activity based on its specific chemical structure and that the compound (I) can be safely and orally administered as a medicine for the prevention or treatment of diseases such as thrombus and infarction. Based on the finding, the present invention was accomplished.

More specifically, the present invention relates to (1) the compound (I); (2) a compound of the above (1), wherein $R^1$ is (1) a $C_{1-10}$ alkyl group, (2) a $C_{2-6}$ alkenyl group, (3) a $C_{2-6}$ alkynyl group, (4) a $C_{3-9}$ cycloalkyl group, (5) a $C_{3-6}$ cycloalkenyl group, (6) a $C_{4-6}$ cycloalkanedienyl group, (7) a $C_{6-14}$ aryl group or (8) a heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said groups (1)–(8) being unsubstituted or substituted by 1 to 5 substituents selected from the class consisting of (a) a $C_{1-6}$ alkyl group optionally substituted with $C_{1-6}$ alkoxy, halogen, $C_{1-6}$ alkyl, amino, hydroxy, cyano group or amidino, (b) a $C_{2-6}$ alkenyl group optionally substituted with $C_{1-6}$ alkoxy, halogen, $C_{1-6}$ alkyl, amino, hydroxy, cyano group or amidino, (c) a $C_{2-6}$ alkynyl group optionally substituted with $C_{1-6}$ alkoxy, halogen, $C_{1-6}$ alkyl, amino, hydroxy, cyano group or amidino, (d) a $C_{6-14}$ aryl group optionally substituted with $C_{1-6}$ alkoxy, halogen, $C_{1-6}$ alkyl, amino, hydroxy, cyano group or amidino, (e) a $C_{3-7}$ cycloalkyl or $C_{3-6}$ cycloalkenyl group optionally substituted with $C_{1-6}$ alkoxy, halogen, $C_{1-6}$ alkyl, amino, hydroxy, cyano group or amidino, (f) a heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms, which may be substituted by $C_{1-6}$ alkyl, $C_{1-6}$ alkanoyl or benzoyl, (g) an amino group optionally substituted with $C_{1-6}$ alkyl group, $C_{1-6}$ alkanoyl, benzoyl, optionally halogenated $C_{1-6}$ alkoxy-carbonyl, $C_{1-6}$ alkylimidoyl, formimidoyl or amidino, (g') a 3- to 8-membered cyclic amino group optionally having $C_{1-6}$ alkyl, $C_{7-10}$ aralkyl or $C_{6-10}$ aryl, (h) an imidoyl group optionally substituted with $C_{1-6}$ alkyl group, $C_{1-6}$ alkanoyl, benzoyl or optionally halogenated $C_{1-6}$ alkoxy-carbonyl, (i) an amidino group optionally substituted with $C_{1-6}$ alkyl group, $C_{1-6}$ alkanoyl, benzoyl or optionally halogenated $C_{1-6}$ alkoxy-carbonyl, (j) a hydroxy group optionally substituted with $C_{1-6}$ alkyl group, $C_{1-6}$ alkanoyl, benzoyl or optionally halogenated $C_{1-6}$ alkoxy-carbonyl, (k) a thiol group optionally substituted with $C_{1-6}$ alkyl group, $C_{1-6}$ alkanoyl, benzoyl or optionally halogenated $C_{1-6}$ alkoxy-carbonyl, (l) a carboxyl group, (l') a $C_{1-6}$ alkoxy-carbonyl group, (l'') a $C_{7-2}$ aryloxycarbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (l''') a $C_{6-10}$ aryl-$C_{1-4}$ alkoxy-carbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (m) a carbamoyl group, (m') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (m'') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{7-10}$ aralkyl, (m''') a 3- to 8-membered cyclic amino-carbonyl group optionally having $C_{1-6}$ alkyl, $C_{7-10}$ aralkyl or $C_{6-10}$ aryl, (n) a thiocarbamoyl group, (n') a thiocarbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (n'') a thiocarbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{7-10}$ aralkyl, (n''') a 3- to 8-membered cyclic amino-thiocarbonyl group optionally having $C_{1-6}$ alkyl, $C_{7-10}$ aralkyl or $C_{6-10}$ aryl, (o) a halogen atom, (p) a cyano group, (q) a nitro group, (r) a sulfonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms,
(s) a formyl group and
(s') a carbonyl group having one substituent selected from $C_{1-6}$ alkyl, $C_{3-6}$ cycloalkyl, $C_{6-10}$ aryl, $C_{1-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms;

the ring A is a divalent 6- to 8-membered nitrogen-containing heterocyclic group which may contain, besides carbon atoms, 1 to 2 nitrogen atoms and 1 to 3 hetero-atoms selected from oxygen atom and sulfur atom, and which may be substituted, in addition to the group of the formula:

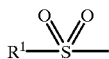

and the group of the formula:

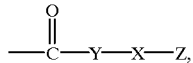

by
(a) a hydroxy group,
(b) a halogen atom,
(c) a nitro group,
(d) a cyano group,
(e) an amino group optionally substituted with 1–2 substituents selected from
  (e-1) a $C_{1-6}$ alkyl group optionally substituted with $C_{1-6}$ alkoxy, halogen, $C_{1-6}$ alkyl, amino, hydroxy, cyano group or amidino,
  (e-2) a carbamoyl group,
  (e-2') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms,
  (e-2") a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{7-10}$ aralkyl,
  (e-2''') a 3- to 8-membered cyclic amino-carbonyl group optionally having $C_{1-6}$ alkyl, $C_{7-10}$ aralkyl or $C_{6-10}$ aryl,
  (e-3) a sulfonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms,
  (e-4) a formyl group and
  (e-4') a carbonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms,
(f) a $C_{1-6}$ alkyl group optionally substituted with halogen, amino, carboxyl or hydroxy,
(g) a $C_{1-6}$ alkoxy group optionally substituted with 1 to 5 halogen atoms,
(h) a carboxyl group,
(h') a $C_{1-6}$ alkoxy-carbonyl group,
(h") a $C_{7-12}$ aryloxycarbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (h''') a $C_{6-10}$ aryl-$C_{1-4}$ alkoxy-carbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (i) a carbamoyl group, (i') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (i'') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{3-6}$ alkoxy optionally substituted with 1 to 5 halogen atoms; and having another substituent selected from $C_{1-6}$ alkyl, $C_{3-6}$ cycloalkyl and $C_{1-10}$ aralkyl or (i''') a 3- to 8-membered cyclic amino-carbonyl group optionally having $C_{1-6}$ alkyl, $C_{1-10}$ aralkyl or $C_{6-10}$ aryl;

Y is (1) a straight-chain $C_{1-10}$ alkylene group, (2) a straight-chain $C_{2-6}$ alkenylene group, (3) a straight-chain $C_{2-6}$ alkynylene group, (4) a $C_{3-9}$ cycloalkylene group, (5) a $C_{3-6}$ cycloalkenylene group, (6) a $C_{4-6}$ cycloalkanedienylene group, (7) a $C_{6-10}$ arylene group, (8) a $C_{7-10}$ aralkylene group, (9) a 5- to 6-membered divalent aromatic heterocyclic group containing, besides carbon atoms, 1 to 3 hetero-atoms selected from oxygen atom, sulfur atom and nitrogen atom or

(10) a 5- to 6-membered divalent saturated or unsaturated non-aromatic heterocyclic group containing, besides carbon atoms, 1 to 3 hetero-atoms selected from oxygen atom, sulfur atom and nitrogen atom, each of said groups (1)–(10) being unsubstituted or substituted by (a) a hydroxy group, (b) a halogen atom, (c) a nitro group, (d) a cyano group, (e) an amino group optionally substituted with 1–2 substituents selected from (e-1) a $C_{1-6}$ alkyl group optionally substituted with $C_{1-6}$ alkoxy, halogen, $C_{1-6}$ alkyl, amino, hydroxy, cyano group or amidino, (e-2) a carbamoyl group, (e-2') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (e-2'') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{7-10}$ aralkyl, (e-2''') a 3- to 8-membered cyclic amino-carbonyl group optionally having $C_{1-6}$ alkyl, $C_{7-10}$ aralkyl or $C_{6-10}$ aryl, (e-3) a sulfonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (e-4) a formyl group and (e-4') a carbonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (f) a $C_{1-6}$ alkyl group optionally substituted with halogen, amino, carboxyl or hydroxy, (g) a $C_{1-6}$ alkoxy group optionally substituted with 1 to 5 halogen atoms, (h) a carboxyl group, (h') a $C_{1-6}$ alkoxy-carbonyl group, (h") a $C_{7-12}$ aryloxycarbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (h''') a $C_{6-10}$ aryl-$C_{1-4}$ alkoxy-carbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (i) a carbamoyl group, (i') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (i") a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{7-10}$ aralkyl or (i''') a 3- to 8-membered cyclic amino-carbonyl group optionally having $C_{1-6}$ alkyl, $C_{7-10}$ aralkyl or $C_{6-10}$ aryl;

X is
(1) a direct bond or
(2) a straight-chain lower ($C_{1-6}$) alkylene optionally substituted with
(a) a $C_{1-6}$ alkyl group,
(b) a halogen atom,
(c) a hydroxy group,
(d) a carboxyl group,
(d') a $C_{1-6}$ alkoxy-carbonyl group,
(d") a $C_{7-12}$ aryloxycarbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms or
(d''') a $C_{6-10}$ aryl-$C_{1-4}$ alkoxy-carbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and Z is
(1) an amino group substituted with 1–2 substituents selected from the class consisting of (1-1) a $C_{1-10}$ alkyl group, (1-2) a $C_{2-6}$ alkenyl group, (1-3) a $C_{2-6}$ alkynyl group, (1-4) a $C_{3-9}$ cycloalkyl group, (1-5) a $C_{3-6}$ cycloalkenyl group, (1-6) a $C_{4-6}$ cycloalkanedienyl group and (1-7) a $C_{6-14}$ aryl group; each of said groups (1-1)–(1-7) being unsubstituted or substituted by 1 to 5 substituents selected from the class consisting of
(a) a $C_{1-6}$ alkyl group optionally substituted with $C_{1-6}$ alkoxy, halogen, $C_{1-6}$ alkyl, amino, hydroxy, cyano group or amidino,
(b) a $C_{2-6}$ alkenyl group optionally substituted with $C_{1-6}$ alkoxy, halogen, $C_{1-6}$ alkyl, amino, hydroxy, cyano group or amidino,
(c) a $C_{2-6}$ alkynyl group optionally substituted with $C_{1-6}$ alkoxy, halogen, $C_{1-6}$ alkyl, amino, hydroxy, cyano group or amidino,
(d) a $C_{6-14}$ aryl group optionally substituted with $C_{1-6}$ alkoxy, halogen, $C_{1-6}$ alkyl, amino, hydroxy, cyano group or amidino,
(e) a $C_{3-7}$ cycloalkyl or $C_{3-6}$ cycloalkenyl group optionally substituted with $C_{1-6}$ alkoxy, halogen, $C_{1-6}$ alkyl, amino, hydroxy, cyano group or amidino,
(f) a heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms, which may be substituted by $C_{1-6}$ alkyl, $C_{1-6}$ alkanoyl or benzoyl, (g) an amino group optionally substituted with $C_{1-6}$ alkyl group, $C_{1-6}$ alkanoyl, benzoyl, optionally halogenated $C_{1-6}$ alkoxy-carbonyl, $C_{1-6}$ alkylimidoyl, formimidoyl or amidino, (g') a 3- to 8-membered cyclic amino group optionally having $C_{1-6}$ alkyl, $C_{7-10}$ aralkyl or $C_{6-10}$ aryl, (h) an imidoyl group optionally substituted with $C_{1-6}$ alkyl group, $C_{1-6}$ alkanoyl, benzoyl or optionally halogenated $C_{1-6}$ alkoxy-carbonyl, (i) an amidino group optionally substituted with $C_{1-6}$ alkyl group, $C_{1-6}$ alkanoyl, benzoyl or optionally halogenated $C_{1-6}$ alkoxy-carbonyl, (j) a hydroxy group optionally substituted with $C_{1-6}$ alkyl group, $C_{1-6}$ alkanoyl, benzoyl or optionally halogenated $C_{1-6}$ alkoxy-carbonyl, (k) a thiol group optionally substituted with $C_{1-6}$ alkyl group, $C_{1-6}$ alkanoyl, benzoyl or optionally halogenated $C_{1-6}$ alkoxy-carbonyl, (l) a carboxyl group, (l') a $C_{1-6}$ alkoxy-carbonyl group, (l'') a $C_{7-12}$ aryloxycarbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (l''') a $C_{6-10}$ aryl-$C_{1-4}$ alkoxy-carbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (m) a carbamoyl group, (m') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (m'') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{7-10}$ aralkyl, (m''') a 3- to 8-membered cyclic amino-carbonyl group optionally having $C_{1-6}$ alkyl, $C_{7-10}$ aralkyl or $C_{6-10}$ aryl, (n) a thiocarbamoyl group, (n') a thiocarbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (n'') a thiocarbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{7-10}$ aralkyl, (n''') a 3- to 8-membered cyclic amino-thiocarbonyl group optionally having $C_{1-6}$ alkyl, $C_{1-10}$ aralkyl or $C_{6-10}$ aryl, (o) a halogen atom, (p) a cyano group, (q) a nitro group, (r) a sulfonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (s) a formyl group and (s') a carbonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms;

(1A) a 3- to 8-membered cyclic amino group optionally having $C_{1-6}$ alkyl, $C_{7-10}$ aralkyl or $C_{6-10}$ aryl, and said cyclic amino group being unsubstituted or substituted by 1 to 5 substituents selected from the class consisting of (a) a $C_{1-6}$ alkyl group optionally substituted with $C_{1-6}$ alkoxy, halogen, $C_{1-6}$ alkyl, amino, hydroxy, cyano group or amidino, (b) a $C_{2-6}$ alkenyl group optionally substituted with $C_{1-6}$ alkoxy, halogen, $C_{1-6}$ alkyl, amino, hydroxy, cyano group or amidino, (c) a $C_{2-6}$ alkynyl group optionally substituted with $C_{1-6}$ alkoxy, halogen, $C_{1-6}$ alkyl, amino, hydroxy, cyano group or amidino, (d) a $C_{6-14}$ aryl group optionally substituted with $C_{1-6}$ alkoxy, halogen, $C_{1-6}$ alkyl, amino, hydroxy, cyano group or amidino, (e) a $C_{3-7}$ cycloalkyl or $C_{3-6}$ cycloalkenyl group optionally substituted with $C_{1-6}$ alkoxy, halogen, $C_{1-6}$ alkyl, amino, hydroxy, cyano group or amidino, (f) a heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms, which may be substituted by $C_{1-6}$ alkyl, $C_{1-6}$ alkanoyl or benzoyl, (g) an amino group optionally substituted with $C_{1-6}$ alkyl group, $C_{1-6}$ alkanoyl, benzoyl, optionally halogenated $C_{1-6}$ alkoxy-carbonyl, $C_{1-6}$ alkylimidoyl, formimidoyl or amidino, (g') a 3- to 8-membered cyclic amino group optionally having $C_{1-6}$ alkyl, $C_{7-10}$ aralkyl or $C_{6-10}$ aryl, (h) an imidoyl group optionally substituted with $C_{1-6}$ alkyl group, $C_{1-6}$ alkanoyl, benzoyl or optionally halogenated $C_{1-6}$ alkoxy-carbonyl, (i) an amidino group optionally substituted with $C_{1-6}$ alkyl group, $C_{1-6}$ alkanoyl, benzoyl or optionally halogenated $C_{1-6}$ alkoxy-carbonyl, (j) a hydroxy group optionally substituted with $C_{1-6}$ alkyl group, $C_{1-6}$ alkanoyl, benzoyl or optionally halogenated $C_{1-6}$ alkoxy-carbonyl, (k) a thiol group optionally substituted with $C_{1-6}$ alkyl group, $C_{1-6}$ alkanoyl, benzoyl or optionally halogenated $C_{1-6}$ alkoxy-carbonyl, (l) a carboxyl group, (l') a $C_{1-6}$ alkoxy-carbonyl group, (l'') a $C_{7-12}$ aryloxycarbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (l''') a $C_{6-10}$ aryl-$C_{1-4}$ alkoxy-carbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (m) a carbamoyl group, (m') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (m'') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{7-10}$ aralkyl, (m''') a 3- to 8-membered cyclic amino-carbonyl group optionally having $C_{1-6}$ alkyl, $C_{7-10}$ aralkyl or $C_{6-10}$ aryl, (n) a thiocarbamoyl group, (n') a thiocarbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (n") a thiocarbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{7-10}$ aralkyl, (n''') a 3- to 8-membered cyclic amino-thiocarbonyl group optionally having $C_{1-6}$ alkyl, $C_{7-1}$ aralkyl or $C_{6-10}$ aryl, (o) a halogen atom, (p) a cyano group, (q) a nitro group, (r) a sulfonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (s) a formyl group and (s') a carbonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic-group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms;

(1B) a group of the formula: —N(R")—C(R')=N—R wherein R" is (i) a hydrogen atom or (ii) a hydrocarbon group selected from the class consisting of a $C_{1-10}$ alkyl group, a $C_{2-6}$ alkenyl group, a $C_{2-6}$ alkynyl group, a $C_{3-9}$ cycloalkyl group, a $C_{3-6}$ cycloalkenyl group, a $C_{4-6}$ cycloalkanedienyl group and a $C_{6-14}$ aryl group; each of said hydrocarbon groups being unsubstituted or substituted by 1 to 5 substituents selected from the class consisting of (a) a $C_{1-6}$ alkyl group optionally substituted with $C_{1-6}$ alkoxy, halogen, $C_{1-6}$ alkyl, amino, hydroxy, cyano group or amidino, (b) a $C_{2-6}$ alkenyl group optionally substituted with $C_{1-6}$ alkoxy, halogen, $C_{1-6}$ alkyl, amino, hydroxy, cyano group or amidino, (c) a $C_{2-6}$ alkynyl group optionally substituted with $C_{1-6}$ alkoxy, halogen, $C_{1-6}$ alkyl, amino, hydroxy, cyano group or amidino, (d) a $C_{6-4}$ aryl group optionally substituted with $C_{1-6}$ alkoxy, halogen, $C_{1-6}$ alkyl, amino, hydroxy, cyano group or amidino, (e) a $C_{3-7}$ cycloalkyl or $C_{3-6}$ cycloalkenyl group optionally substituted with $C_{1-6}$ alkoxy, halogen, $C_{1-6}$ alkyl, amino, hydroxy, cyano group or amidino, (f) a heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms, which may be substituted by $C_{1-6}$ alkyl, $C_{1-6}$ alkanoyl or benzoyl, (g) an amino group optionally substituted with $C_{1-6}$ alkyl group, $C_{1-6}$ alkanoyl, benzoyl, optionally halogenated $C_{1-6}$ alkoxy-carbonyl, $C_{1-6}$ alkylimidoyl, formimidoyl or amidino, (g') a 3- to 8-membered cyclic amino group optionally having $C_{1-6}$ alkyl, $C_{7-10}$ aralkyl or $C_{6-10}$ aryl, (h) an imidoyl group optionally substituted with $C_{1-6}$ alkyl group, $C_{1-6}$ alkanoyl, benzoyl or optionally halogenated $C_{1-6}$ alkoxy-carbonyl, (i) an amidino group optionally substituted with $C_{1-6}$ alkyl group, $C_{1-6}$ alkanoyl, benzoyl or optionally halogenated $C_{1-6}$ alkoxy-carbonyl, (j) a hydroxy group optionally substituted with $C_{1-6}$ alkyl group, $C_{1-6}$ alkanoyl, benzoyl or optionally halogenated $C_{1-6}$ alkoxy-carbonyl, (k) a thiol group optionally substituted with $C_{1-6}$ alkyl group, $C_{1-6}$ alkanoyl, benzoyl or optionally halogenated $C_{1-6}$ alkoxy-carbonyl, (l) a carboxyl group, (l') a $C_{1-6}$ alkoxy-carbonyl group, (l") a $C_{7-12}$ aryloxycarbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (l''') a $C_{6-10}$ aryl-$C_{1-4}$ alkoxy-carbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (m) a carbamoyl group, (m') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (m") a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{7-10}$ aralkyl, (m'") a 3- to 8-membered cyclic amino-carbonyl group optionally having $C_{1-6}$ alkyl, $C_{7-10}$ aralkyl or $C_{6-10}$ aryl, (n) a thiocarbamoyl group, (n') a thiocarbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (n") a thiocarbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{7-10}$ aralkyl, (n'") a 3- to 8-membered cyclic amino-thiocarbonyl group optionally having $C_{1-6}$ alkyl, $C_{7-10}$ aralkyl or $C_{6-10}$ aryl, (o) a halogen atom, (p) a cyano group, (q) a nitro group, (r) a sulfonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (s) a formyl group and (s') a carbonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, R is (i) a hydrogen atom, (ii) a hydrocarbon group selected from the class consisting of a $C_{1-10}$ alkyl group, a $C_{2-6}$ alkenyl group, a $C_{2-6}$ alkynyl group, a $C_{3-9}$ cycloalkyl group, a $C_{3-6}$ cycloalkenyl group, a $C_{4-6}$ cycloalkanedienyl group and a $C_{6-14}$ aryl group; each of said hydrocarbon groups being unsubstituted or substituted by 1 to 5 substituents selected from the class consisting of (a) a $C_{1-6}$ alkyl group optionally substituted with $C_{1-6}$ alkoxy, halogen, $C_{1-6}$ alkyl, amino, hydroxy, cyano group or amidino, (b) a $C_{2-6}$ alkenyl group optionally substituted with $C_{1-6}$ alkoxy, halogen, $C_{1-6}$ alkyl, amino, hydroxy, cyano group or amidino, (c) a $C_{2-6}$ alkynyl group optionally substituted with $C_{1-6}$ alkoxy, halogen, $C_{1-6}$ alkyl, amino, hydroxy, cyano group or amidino, (d) a $C_{6-14}$ aryl group optionally substituted with $C_{1-6}$ alkoxy, halogen, $C_{1-6}$ alkyl, amino, hydroxy, cyano group or amidino, (e) a $C_{3-7}$ cycloalkyl or $C_{3-6}$ cycloalkenyl group optionally substituted with $C_{1-6}$ alkoxy, halogen, $C_{1-6}$ alkyl, amino, hydroxy, cyano group or amidino, (f) a heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 heteroatoms selected from oxygen atom, sulfur atom and nitrogen atom besides carbon atoms, which may be substituted by $C_{1-6}$ alkyl, $C_{1-6}$ alkanoyl or benzoyl, (g) an amino group optionally substituted with $C_{1-6}$ alkyl group, $C_{1-6}$ alkanoyl, benzoyl, optionally halogenated $C_{1-6}$ alkoxy-carbonyl, $C_{1-6}$ alkylimidoyl, formimidoyl or amidino, (g') a 3- to 8-membered cyclic amino group optionally having $C_{1-6}$ alkyl, $C_{7-10}$ aralkyl or $C_{6-10}$ aryl, (h) an imidoyl group optionally substituted with $C_{1-6}$ alkyl group, $C_{1-6}$ alkanoyl, benzoyl or optionally halogenated $C_{1-6}$ alkoxy-carbonyl, (i) an amidino group optionally substituted with $C_{1-6}$ alkyl group, $C_{1-6}$ alkanoyl, benzoyl or optionally halogenated $C_{1-6}$ alkoxy-carbonyl, (j) a hydroxy group optionally substituted with $C_{1-6}$ alkyl group, $C_{1-6}$ alkanoyl, benzoyl or optionally halogenated $C_{1-6}$ alkoxy-carbonyl, (k) a thiol group optionally substituted with $C_{1-6}$ alkyl group, $C_{1-6}$ alkanoyl, benzoyl or optionally halogenated $C_{1-6}$ alkoxy-carbonyl, (l) a carboxyl group, (l') a $C_{1-6}$ alkoxy-carbonyl group, (l") a $C_{7-12}$ aryloxycarbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (l''') a $C_{6-1}$ aryl-$C_{1-4}$ alkoxy-carbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (m) a carbamoyl group, (m') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (m") a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{7-10}$ aralkyl, (m''') a 3- to 8-membered cyclic amino-carbonyl group optionally having $C_{1-6}$ alkyl, $C_{7-10}$ aralkyl or $C_{6-10}$ aryl, (n) a thiocarbamoyl group, (n') a thiocarbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (n") a thiocarbamoyl group having one substituent selected from $C_{1-6}$ alkyl, $C_{3-6}$ cycloalkyl, $C_{6-10}$ aryl, $C_{1-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_16$ alkyl, $C_{3-6}$ cycloalkyl and $C_{7-10}$ aralkyl, (n''') a 3- to 8-membered cyclic amino-thiocarbonyl group optionally having $C_{1-6}$ alkyl, $C_{7-10}$ aralkyl or $C_{6-10}$ aryl, (o) a halogen atom, (p) a cyano group, (q) a nitro group, (r) a sulfonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (s) a formyl group and (s') a carbonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, or (iii) a carbonyl group having a hydrogen atom or one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, and R' is (i) a hydrogen atom, (ii) a hydrocarbon group selected from the class consisting of a $C_{1-10}$ alkyl group, a $C_{2-6}$ alkenyl group, a $C_{2-6}$ alkynyl group, a $C_{3-9}$ cycloalkyl group, a $C_{3-6}$ cycloalkenyl group, a $C_{4-6}$ cycloalkanedienyl group and a $C_{6-14}$ aryl group; each of said hydrocarbon groups being unsubstituted or substituted by 1 to 5 substituents selected from the class consisting of (a) a $C_{1-6}$ alkyl group optionally substituted with $C_{1-6}$ alkoxy, halogen, $C_{1-6}$ alkyl, amino, hydroxy, cyano group or amidino, (b) a $C_{2-6}$ alkenyl group optionally substituted with $C_{1-6}$ alkoxy, halogen, $C_{1-6}$ alkyl, amino, hydroxy, cyano group or amidino, (c) a $C_{2-6}$ alkynyl group optionally substituted with $C_{1-6}$ alkoxy, halogen, $C_{1-6}$ alkyl, amino, hydroxy, cyano group or amidino, (d) a $C_{6-14}$ aryl group optionally substituted with $C_{1-6}$ alkoxy, halogen, $C_{1-6}$ alkyl, amino, hydroxy, cyano group or amidino, (e) a $C_{3-7}$ cycloalkyl or $C_{3-6}$ cycloalkenyl group optionally substituted with $C_{1-6}$ alkoxy, halogen, $C_{1-6}$ alkyl, amino, hydroxy, cyano group or amidino, (f) a heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms, which may be substituted by $C_{1-6}$ alkyl, $C_{1-6}$ alkanoyl or benzoyl, (g) an amino group optionally substituted with $C_{1-6}$ alkyl group, $C_{1-6}$ alkanoyl, benzoyl, optionally halogenated $C_{1-6}$ alkoxy-carbonyl, $C_{1-6}$ alkylimidoyl, formimidoyl or amidino, (g') a 3- to 8-membered cyclic amino group optionally having $C_{1-6}$ alkyl, $C_{1-10}$ aralkyl or $C_{6-10}$ aryl, (h) an imidoyl group optionally substituted with $C_{1-6}$ alkyl group, $C_{1-6}$ alkanoyl, benzoyl or optionally halogenated $C_{1-6}$ alkoxy-carbonyl, (i) an amidino group optionally substituted with $C_{1-6}$ alkyl group, $C_{1-6}$ alkanoyl, benzoyl or optionally halogenated $C_{1-6}$ alkoxy-carbonyl, (j) a hydroxy group optionally substituted with $C_{1-6}$ alkyl group, $C_{1-6}$ alkanoyl, benzoyl or optionally halogenated $C_{1-6}$ alkoxy-carbonyl, (k) a thiol group optionally substituted with $C_{1-6}$ alkyl group, $C_{1-6}$ alkanoyl, benzoyl or optionally halogenated $C_{1-6}$ alkoxy-carbonyl, (l) a carboxyl group, (l') a $C_{1-6}$ alkoxy-carbonyl group, (l") a $C_{7-12}$ aryloxycarbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (l''') a $C_{6-10}$ aryl-$C_{1-4}$ alkoxy-carbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (m) a carbamoyl group, (m') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (m") a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{7-10}$ aralkyl, (m''') a 3- to 8-membered cyclic amino-carbonyl group optionally having $C_{1-6}$ alkyl, $C_{7-10}$ aralkyl or $C_{6-10}$ aryl, (n) a thiocarbamoyl group, (n') a thiocarbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (n'') a thiocarbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{1-710}$ aralkyl, (n''') a 3- to 8-membered cyclic amino-thiocarbonyl group optionally having $C_16$ alkyl, $C_{7-10}$ aralkyl or $C_{6-10}$ aryl, (o) a halogen atom, (p) a cyano group, (q) a nitro group, (r) a sulfonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (s) a formyl group and (s') a carbonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (iii) a carbonyl group having a hydrogen atom or one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5-to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (iv) an amino group optionally substituted with $C_{1-6}$ alkyl group, $C_{1-6}$ alkanoyl, benzoyl, optionally halogenated $C_{1-6}$ alkoxy-carbonyl, $C_{1-6}$ alkylimidoyl, formimidoyl or amidino, (iv') a 3- to 8-membered cyclic amino group optionally having $C_{1-6}$ alkyl, $C_{7-10}$ aralkyl or $C_{6-10}$ aryl, (iv'') an amino group substituted with 1–2 substituents selected from the class consisting of (1-1) a $C_{1-10}$ alkyl group, (1-2) a $C_{2-6}$ alkenyl group, (1-3) a $C_{2-6}$ alkynyl group, (1-4) a $C_{3-9}$ cycloalkyl group, (1-5) a $C_{3-6}$ cycloalkenyl group, (1-6) a $C_{4-6}$ cycloalkanedienyl group and (1-7) a $C_{6-14}$ aryl group; each of said groups (1-1)–(1-7) being unsubstituted or substituted by 1 to 5 substituents selected from the class consisting of (a) a $C_{1-6}$ alkyl group optionally substituted with $C_{1-6}$ alkoxy, halogen, $C_{1-6}$ alkyl, amino, hydroxy, cyano group or amidino, (b) a $C_{2-6}$ alkenyl group optionally substituted with $C_{1-6}$ alkoxy, halogen, $C_{1-6}$ alkyl, amino, hydroxy, cyano group or amidino, (c) a $C_{2-6}$ alkynyl group optionally substituted with $C_{1-6}$ alkoxy, halogen, $C_{1-6}$ alkyl, amino, hydroxy, cyano group or amidino, (d) a $C_{6-14}$ aryl group optionally substituted with $C_{1-6}$ alkoxy, halogen, $C_{1-6}$ alkyl, amino, hydroxy, cyano group or amidino, (e) a $C_{3-7}$ cycloalkyl or $C_{3-6}$ cycloalkenyl group optionally substituted with $C_{1-6}$ alkoxy, halogen, $C_{1-6}$ alkyl, amino, hydroxy, cyano group or amidino, (f) a heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms, which may be substituted by $C_{1-6}$ alkyl, $C_{1-6}$ alkanoyl or benzoyl, (g) an amino group optionally substituted with $C_{1-6}$ alkyl group, $C_{1-6}$ alkanoyl, benzoyl, optionally halogenated $C_{1-6}$ alkoxy-carbonyl, $C_{1-6}$ alkylimidoyl, formimidoyl or amidino, (g') a 3- to 8-membered cyclic amino group optionally having $C_{1-6}$ alkyl, $C_{7-10}$ aralkyl or $C_{6-10}$ aryl, (h) an imidoyl group optionally substituted with $C_{1-6}$ alkyl group, $C_{1-6}$ alkanoyl, benzoyl or optionally halogenated $C_{1-6}$ alkoxy-carbonyl, (i) an amidino group optionally substituted with $C_{1-6}$ alkyl group, $C_{1-6}$ alkanoyl, benzoyl or optionally halogenated $C_{1-6}$ alkoxy-carbonyl, (j) a hydroxy group optionally substituted with $C_{1-6}$ alkyl group, $C_{1-6}$ alkanoyl, benzoyl or optionally halogenated $C_{1-6}$ alkoxy-carbonyl, (k) a thiol group optionally substituted with $C_{1-6}$ alkyl group, $C_{1-6}$ alkanoyl, benzoyl or optionally halogenated $C_{1-6}$ alkoxy-carbonyl, (l) a carboxyl group, (l') a $C_{1-6}$ alkoxy-carbonyl group, (l") a $C_{7-12}$ aryloxycarbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (l''') a $C_{6-10}$ aryl-$C_{1-4}$ alkoxy-carbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (m) a carbamoyl group, (m') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (m") a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{7-10}$ aralkyl, (m''') a 3- to 8-membered cyclic amino-carbonyl group optionally having $C_{1-6}$ alkyl, $C_{7-10}$ aralkyl or $C_{6-10}$ aryl, (n) a thiocarbamoyl group, (n') a thiocarbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (n") a thiocarbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{7-10}$ aralkyl, (n''') a 3- to 8-membered cyclic amino-thiocarbonyl group optionally having $C_{1-6}$ alkyl, $C_{7-10}$ aralkyl or $C_{6-10}$ aryl, (o) a halogen atom, (p) a cyano group, (q) a nitro group, (r) a sulfonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (s) a formyl group and (s') a carbonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being. unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, or (v) a hydroxy group optionally substituted with $C_{1-6}$ alkyl group, $C_{1-6}$ alkanoyl, benzoyl or optionally halogenated $C_{1-6}$ alkoxy-carbonyl;

(2) a group of the formula: —C(R')=N—R wherein each symbol is as defined above; or (3) a 5- to 6-membered aromatic or non-aromatic monocyclic nitrogen-containing heterocyclic group which contains, besides carbon atoms, 1 to 3 nitrogen atoms and optionally contains 1 to 3 hetero-atoms selected from an oxygen atom and a sulfur atom and which may be substituted by (a) a hydroxy group, (b) a halogen atom, (c) a nitro group, (d) a cyano group, (e) an amino group optionally substituted with 1–2 substituents selected from (e-1) a $C_{1-6}$ alkyl group optionally substituted with $C_{1-6}$ alkoxy, halogen, $C_{1-6}$ alkyl, amino, hydroxy, cyano group or amidino, (e-2) a carbamoyl group, (e-2') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (e-2") a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{7-10}$ aralkyl, (e-2''') a 3- to 8-membered cyclic amino-carbonyl group optionally having $C_{1-6}$ alkyl, $C_{7-10}$ aralkyl or $C_{6-10}$ aryl, (e-3) a sulfonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (e-4) a formyl group and (e-4') a carbonyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (f) a $C_{1-6}$ alkyl group optionally substituted with halogen, amino, carboxyl or hydroxy, (g) a $C_{1-6}$ alkoxy group optionally substituted with 1 to 5 halogen atoms, (h) a carboxyl group, (h') a $C_{1-6}$ alkoxy-carbonyl group, (h") a $C_{7-12}$ aryloxycarbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (h''') a $C_{6-10}$ aryl-$C_{1-4}$ alkoxy-carbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (i) a carbamoyl group, (i') a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (i") a carbamoyl group having one substituent selected from $C_{1-6}$ alkyl, $C_{3-6}$ cycloalkyl, $C_{6-10}$ aryl, $C_{7-10}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said alkyl, cycloalkyl, aryl, aralkyl and heterocyclic groups being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms; and having another substituent selected from $C_{1-6}$ alkyl, $C_{3-6}$ cycloalkyl and $C_{1-2}$ aralkyl or (i''') a 3- to 8-membered cyclic amino-carbonyl group optionally having $C_{1-6}$ alkyl, $C_{7-10}$ aralkyl or $C_{6-10}$ aryl;

(3) a compound of the above (1), wherein $R^1$ is an optionally substituted hydrocarbon group;

(4) a compound of the above (1), wherein $R^1$ is an aryl group optionally substituted with a halogen atom;

(5) a compound of the above (1), wherein the ring A is a group of the formula:

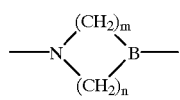

wherein B is CH or a nitrogen atom, and m and n are respectively 2 or 3;

(6) a compound of the above (5), wherein B is a nitrogen atom;

(7) a compound of the above (5), wherein m and n are 2;

(8) a compound of the above (1), wherein Y is an optionally substituted divalent aromatic heterocyclic group;

(9) a compound of the above (1), wherein Y is an optionally substituted phenylene group;

(10) a compound of the above (1), wherein Y is an optionally substituted cyclohexylene group;

(11) a compound of the above (1), wherein Z is an optionally substituted nitrogen-containing heterocyclic group;

(12) a compound of the above (1), wherein Z is an optionally substituted amidino group;

(13) a compound of the above (1), wherein Z is an optionally substituted guanidino group;

(14) a compound of the above (1), wherein

Z is (1) a mono- or di-$C_{1-6}$ alkylamino group which may be further substituted with phenyl at the alkyl moiety, (2) guanidino, (3) formimidoyl-amino, (4) acetimidoylamino or (5) piperidino;

(15) a compound of the above (1), wherein

Z is a group of the formula: —N(R")—C(R')=N—R or a group of the formula: —C(R')=N—R wherein
R" is a hydrogen atom or a $C_{1-6}$ alkyl group,
R is a hydrogen atom, a $C_{1-6}$ alkyl group, a $C_{1-6}$ alkanoyl group or a benzoyl group,
R' is a hydrogen atom, a $C_{1-6}$ alkyl group, a $C_{1-6}$ alkanoyl group, a benzoyl group, an amino group optionally substituted with 1–2 substituents selected from $C_{1-6}$ alkyl, $C_{1-6}$ alkanoyl and benzoyl, or a $C_{1-6}$ alkoxy group;

(16) a compound of the above (1), wherein

Z is a group of the formula: —NH—C(R')=NH or a group of the formula: —C(R')=NH wherein
R' is a $C_{1-6}$ alkyl group or an amino group optionally substituted with 1–2 substituents selected from $C_{1-6}$ alkyl, $C_{1-6}$ alkanoyl and benzoyl;

(17) a compound of the above (1), wherein $R^1$ is (1) a $C_{1-10}$ alkyl group, (2) a $C_{2-6}$ alkenyl group, (3) a $C_{2-6}$ alkynyl group, (4) a $C_{6-14}$ aryl group or (5) a heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; each of said groups (1)–(5) being unsubstituted or substituted by
(a) a $C_{1-6}$ alkyl group optionally substituted with $C_{1-6}$ alkoxy, halogen, $C_{1-6}$ alkyl, amino, hydroxy, cyano or amidino,
(b) a $C_{6-14}$ aryl group optionally substituted with $C_{1-6}$ alkoxy, halogen, $C_{1-6}$ alkyl, amino, hydroxy, cyano or amidino,
(c) a heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 heteroatoms selected from oxygen atom, sulfur atom and nitrogen atom besides carbon atoms, which may be substituted by $C_{1-6}$ alkyl, $C_{1-6}$ alkanoyl or benzoyl,
(d) an amino group optionally substituted with $C_{1-6}$ alkyl, $C_{1-6}$ alkanoyl, benzoyl, optionally halogenated $C_{1-6}$ alkoxy-carbonyl, $C_{1-6}$ alkylimidoyl, formimidoyl or amidino, (e) an imidoyl group optionally substituted with $C_{1-6}$ alkyl, $C_{1-6}$ alkanoyl, benzoyl or optionally halogenated $C_{1-6}$ alkoxy-carbonyl, (f) an amidino group optionally substituted with $C_{1-6}$ alkyl, $C_{1-6}$ alkanoyl, benzoyl or optionally halogenated $C_{1-6}$ alkoxy-carbonyl, (g) a hydroxy group optionally substituted with $C_{1-6}$ alkyl, $C_{1-6}$ alkanoyl, benzoyl or optionally halogenated $C_{1-6}$ alkoxy-carbonyl, (h) a carboxyl group, (i) a $C_{1-6}$ alkoxy-carbonyl group, (j) a $C_{1-12}$ aryloxycarbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (k) a $C_{6-10}$ aryl-$C_{1-4}$ alkoxy-carbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (l) a halogen atom, (m) a cyano group, (n) a nitro group or (o) a carbonyl group having one substituent selected from $C_{1-6}$ alkyl, $C_{3-6}$ cycloalkyl, $C_{6-10}$ aryl, $C_{7-11}$ aralkyl and heterocyclic group selected from the class consisting of (i) a 5- to 6-membered aromatic monocyclic heterocyclic group, (ii) a 8- to 12-membered aromatic fused heterocyclic group and (iii) a 3- to 8-membered saturated or unsaturated non-aromatic heterocyclic group and containing 1 to 4 hetero-atoms selected from oxygen atom, sulfur atom and nitrogen atom besides carbon atoms; the ring A is a group of the formula:

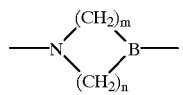

wherein B is CH or a nitrogen atom, and m and n are respectively 2 or 3, said group being unsubstituted or substituted, in addition to the group of the formula:

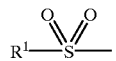

and the group of the formula:

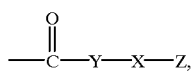

by
(a) a carboxyl group,
(b) a $C_{1-6}$ alkoxy-carbonyl group,
(c) a $C_{7-12}$ aryloxycarbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms or (d) a $C_{6-10}$ aryl-$C_{1-4}$ alkoxy-carbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms;

Y is (1) a straight-chain $C_{1-10}$ alkylene group,
(2) a $C_{3-9}$ cycloalkylene group,
(3) a $C_{6-10}$ arylene group,
(4) a $C_{7-10}$ aralkylene group,
(5) a 5- to 6-membered divalent aromatic heterocyclic group containing, besides carbon atoms, 1 to 3 hetero-atoms selected from oxygen atom, sulfur atom and nitrogen atom or
(6) a 5- to 6-membered divalent saturated or unsaturated non-aromatic heterocyclic group containing, besides carbon atoms, 1 to 3 hetero-atoms selected from oxygen atom, sulfur atom and nitrogen atom, each of said groups (1)–(6) being unsubstituted or substituted by
(a) a halogen atom,
(b) a cyano group,
(c) a $C_{1-6}$ alkyl group optionally substituted with halogen, amino, carboxyl or hydroxy or
(d) a $C_{1-6}$ alkoxy group optionally substituted with 1 to 5 halogen atoms;

X is a direct bond or a straight-chain $C_{1-6}$ alkylene; and

Z is (1) an amino group substituted with 1–2 substituents selected from the class consisting of (1-1) a $C_{1-10}$ alkyl group and (1-2) a $C_{6-14}$ aryl group;
(2) a group of the formula: —N(R")—C(R')=N—R or a group of the formula: —C(R')=N—R wherein
R" is a hydrogen atom or a $C_{1-6}$ alkyl group,
R is a hydrogen atom, a $C_{1-6}$ alkyl group, a $C_{1-6}$ alkanoyl group or a benzoyl group, and
R' is a hydrogen atom, a $C_{1-6}$ alkyl group, a $C_{1-6}$ alkanoyl group, a benzoyl group or an amino group optionally substituted with 1–2 substituents selected from $C_{1-6}$ alkyl, $C_{1-6}$ alkanoyl or benzoyl, or a $C_{1-6}$ alkoxy group; or
(3) a 5- to 6-membered aromatic or non-aromatic monocyclic nitrogen-containing heterocyclic group which contains, besides carbon atoms, 1 to 3 nitrogen atoms and optionally contains 1 to 3 hetero-atoms selected from an oxygen atom and a sulfur atom and which may be substituted by
(a) a halogen atom,
(b) an amino group,
(c) a $C_{1-6}$ alkyl group optionally substituted with halogen, amino, carboxyl or hydroxy,
(d) a carboxyl group,
(e) a $C_{1-6}$ alkoxy-carbonyl group,
(f) a $C_{7-12}$ aryloxycarbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms or
(g) a $C_{6-10}$ aryl-$C_{1-4}$ alkoxy-carbonyl group being unsubstituted or substituted by hydroxy, amino optionally having 1 to 2 substituents selected from $C_{1-6}$ alkyl, $C_{1-6}$ alkanoyl and benzoyl, halogen, nitro, cyano, $C_{1-6}$ alkyl optionally substituted with

33

1 to 5 halogen atoms or $C_{1-6}$ alkoxy optionally substituted with 1 to 5 halogen atoms;

(18) a compound of the above (1), which is 1-(6-chloronaphthalene-2-sulfonyl)-4-[4-(4-pyridyl)benzoyl]piperazine, 1-(6-chloronaphthalene-2-sulfonyl)-4-[4-(1H-imidazol-1-yl)benzoyl]piperazine, 1-(6-chloronaphthalene-2-sulfonyl)-4-[2-(4-pyridyl)-4-methyl-5-thiazolylcarbonyl]piperazine, 1-(trans-4-acetimidoylaminocyclohexan-1-ylcarbonyl)-4-(6-chloronaphthalene-2-sulfonyl)piperazine, 1-(6-chloronaphthalene-2-sulfonyl)-4-(trans-4-guanidinocyclohexan-1-ylcarbonyl)piperazine, or a salt thereof;

(19) a pharmaceutical composition comprising a compound of the above (1) or a salt thereof;

(20) a composition of the above (19) which is an anti-coagulant;

(21) a composition of the above (19) which is an inhibitor of activated coagulation factor X;

(22) a composition of the above (19) which is for the prevention or treatment of deep vein thrombosis, cardiac infarction or cerebral thrombosis;

(23) use of a compound or a salt thereof of the above (1) for manufacturing a pharmaceutical composition;

(24) use of a compound or a salt thereof of the above (1) for manufacturing an anti-coagulant;

(25) use of a compound or a salt thereof of the above (1) for manufacturing a pharmaceutical composition for inhibiting activated coagulation factor X;

(26) use of a compound or a salt thereof of the above (1) for manufacturing a pharmaceutical composition for treating or preventing deep vein thrombosis, cardiac infarction or cerebral thrombosis;

(27) a method for inhibiting activated coagulation factor X in a mammal which comprises administering an effective amount of a compound or a salt thereof of the above (1);

(28) a method for preventing or treating deep vein thrombosis, cardiac infarction or cerebral thrombosis in a mammal which comprises administering an effective amount of a compound or a salt thereof of the above (1) to said mammal;

(29) a method for producing a compound of the above (1) or a salt thereof, which comprises reacting a compound of the formula: $R^1SO_2Q$ wherein Q is a halogen atom and the other symbol is as defined in the above (1), or a salt thereof with a compound of the formula:

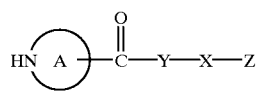

wherein the ring A is an optionally substituted divalent nitrogen-containing heterocyclic group, in addition to being substituted by the group represented by the formula:

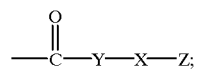

and the other symbols are as defined in the above (1), or a salt thereof; or reacting a compound of the formula:

34

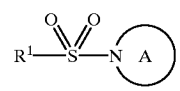

wherein the ring A is an optionally substituted divalent nitrogen-containing heterocyclic group, in addition to being substituted by the group represented by the formula:

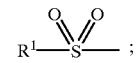

and the other symbols are as defined in the above (1), or a salt thereof with a compound of the formula:

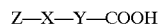

wherein each symbol is as defined in the above (1), or a salt thereof, or its reactive derivatives;

(30) a method for producing a compound of the formula:

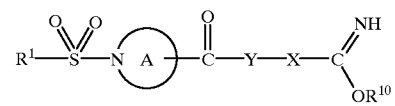

wherein $R^{10}$ is a lower alkyl group and the other symbols are as defined in the above (1), or a salt thereof, which comprises reacting a compound of the formula:

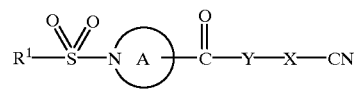

wherein each symbol is as defined above, or a salt thereof with a compound of the formula: $R^{10}OH$ wherein $R^{10}$ is as defined above, or a salt thereof;

(31) a method for producing a compound of the formula:

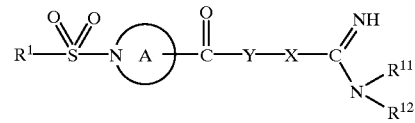

wherein $R^{11}$ and $R^{12}$ are independently a hydrogen atom or an optionally substituted hydrocarbon group and the other symbols are as defined in the above (1), or a salt thereof, which comprises reacting a compound of the formula:

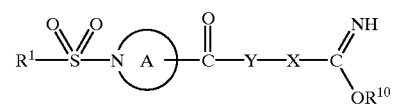

wherein each symbol is as defined in the above (29), or a salt thereof with a compound of the formula:

wherein each symbol is as defined above, or a salt thereof;

(32) a method for producing a compound of the formula:

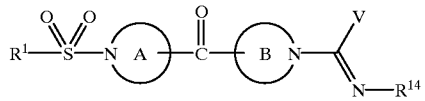

wherein the ring B is an optionally substituted divalent non-aromatic heterocyclic group, $R^{14}$ is a hydrogen atom or an optionally substituted hydrocarbon group, V is a hydrogen atom, an optionally substituted hydrocarbon group or an amino group which may be substituted with an optionally substituted hydrocarbon group and the other symbols are as defined in the above (1), or a salt thereof, which comprises reacting a compound of the formula:

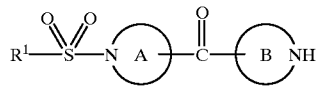

wherein each symbol is as defined above, or a salt thereof with a compound of the formula:

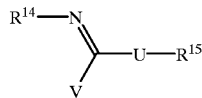

wherein $R^{15}$ is a lower alkyl group, U is an oxygen atom or an sulfur atom and the other symbols are as defined above, or a salt thereof;

(33) a method for producing a compound of the formula:

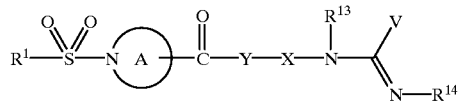

wherein $R^{13}$ is a hydrogen atom or an optionally substituted hydrocarbon group, $R^{14}$ is a hydrogen atom or an optionally substituted hydrocarbon group, V is a hydrogen atom, an optionally substituted hydrocarbon group or an amino group which may be substituted with an optionally substituted hydrocarbon group and the other symbols are as defined in the above (1), or a salt thereof, which comprises reacting a compound of the formula:

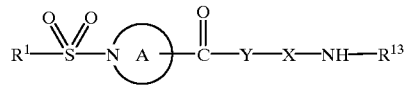

wherein each symbol is as defined above, or a salt thereof with a compound of the formula:

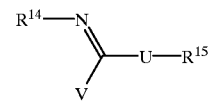

wherein $R^{15}$ is a lower alkyl group, U is an oxygen atom or an sulfur atom, the other symbols are as defined above, or a salt thereof; etc.

In the above formula, $R^1$ is an optionally substituted hydrocarbon group or an optionally substituted heterocyclic group (preferably, an optionally substituted hydrocarbon group).

Examples of hydrocarbon groups in the "optionally substituted hydrocarbon group" represented by $R^1$ include e.g. an aliphatic hydrocarbon group, an alicyclic hydrocarbon group and an aryl group, etc. Among others, an aryl group, etc. is preferable.

Examples of the "aliphatic hydrocarbon group" exemplified by the hydrocarbon group include e.g. a straight-chain or branched aliphatic hydrocarbon group such as an alkyl group, an alkenyl group, an alkynyl group, etc.

Examples of the alkyl group include e.g. $C_{1-10}$ alkyl group (preferably $C_{1-6}$ alkyl, etc.), etc. such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, 1-methylheptyl, 1-ethylhexyl, n-octyl, 1-methyl-heptyl, nonyl, etc.

Examples of the alkenyl group include e.g. $C_{2-6}$ alkenyl group, etc. such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc.

Examples of the alkynyl group include e.g. $C_{2-6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc.

Examples of the "alicyclic hydrocarbon group" exemplified by the hydrocarbon group include e.g. a saturated or unsaturated alicyclic hydrocarbon group such as a cycloalkyl group, a cycloalkenyl group, a cycloalkanedienyl group, etc.

Examples of the "cycloalkyl group" include e.g. $C_{3-9}$ cycloalkyl, etc. such as cyclopropyl, cyclobutyl, cyclopentyl, cyclohexyl, cycloheptyl, cyclooctyl, cyclononyl, etc.

Examples of the "cycloalkenyl group" include e.g. $C_{3-6}$ cycloalkenyl group, etc. such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, etc.

Examples of the "cycloalkanedienyl group" include e.g. $C_{4-6}$ cycloalkanedienyl group, etc. such as 2,4-cyclopentadien-1-yl, 2,4-cyclohexadien-1-yl, 2,5-cyclohexadien-1-yl, etc.

Examples of the "aryl group" exemplified by the hydrocarbon group include e.g. a monocyclic or fused aromatic hydrocarbon group. Among others, $C_{6-14}$ aryl group, etc. such as phenyl, naphthyl, anthryl, phenanthryl, acenaphthyl, etc. is preferable. In particular, phenyl, 1-naphthyl, 2-naphthyl, etc. are preferable.

Examples of the heterocyclic group in the "optionally substituted heterocyclic group" represented by $R^1$ include e.g. an aromatic heterocyclic group, saturated or unsaturated non-aromatic heterocyclic group (alicyclic heterocyclic group) etc., which contains, besides carbon atoms, at least one hetero-atom (preferably 1 to 4 hetero-atoms, more preferably 1 to 2 hetero-atoms) consisting of 1 to 3 kinds of hetero-atoms (preferably 1 to 2 kinds of hetero-atoms) selected from oxygen atom, sulfur atom, nitrogen atom, etc.

Examples of the "aromatic heterocyclic group" include an aromatic monocyclic heterocyclic group such as 5- to 6-membered aromatic monocyclic heterocyclic group, etc. (e.g. furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.); an aromatic fused heterocyclic group such as 8- to 12-membered aromatic fused heterocyclic group (preferably, heterocyclic group consisting of the above-mentioned 5- or 6-membered aromatic monocyclic heterocyclic group fused with a benzene ring or heterocyclic group consisting of the above-mentioned 5- or 6-membered aromatic monocyclic heterocyclic group fused with the same or different above-mentioned 5- or 6-membered aromatic monocyclic heterocyclic group), etc. (e.g. benzofuranyl, isobenzofuranyl, benzothienyl, indolyl, isoindolyl, 1H-indazolyl, benzindazolyl, benzoxazolyl, 1,2-benzoisooxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.); etc.

Examples of the "non-aromatic heterocyclic group" include a 3- to 8-membered (preferably 5- or 6-membered) saturated or unsaturated (preferably saturated) non-aromatic heterocyclic group (alicyclic heterocyclic group), etc. such as oxiranyl, azetidinyl, oxetanyl, thiethanyl, pyrrolidinyl, tetrahydrofuryl, thiolanyl, piperidyl, tetrahydropyranyl, morpholinyl, thiomorpholinyl, piperazinyl, etc.

Examples of the substituent of the "optionally substituted hydrocarbon group" and "optionally substituted heterocyclic group" represented by $R^1$ include an optionally substituted alkyl group, an optionally substituted alkenyl group, an optionally substituted alkynyl group, an optionally substituted aryl group, an optionally substituted cycloalkyl or cycloalkenyl group, an optionally substituted heterocyclic group, an optionally substituted amino group, an optionally substituted imidoyl group, an optionally substituted amidino group, an optionally substituted hydroxyl group, an optionally substituted thiol group, an optionally esterified carboxyl group, an optionally substituted carbamoyl group, an optionally substituted thiocarbamoyl group, a halogen atom (e.g. fluorine, chlorine, bromine, iodine, etc., preferably chlorine, bromine, etc.), a cyano group, a nitro group, an acyl group derived from a sulfonic acid, an acyl group derived from an carboxylic acid, etc.

The "optionally substituted hydrocarbon group" and "optionally substituted heterocyclic group" may have 1 to 5 substituents as described above (preferably 1 to 3 substituents) at any possible position.

Examples of the aryl group in the "optionally substituted aryl group" as the substituent include $C_{6-14}$ aryl group, etc. such as phenyl, naphthyl, anthryl, phenathryl, acenaphthyl, etc. Said aryl groups may have 1 or 2 substituents at any possible positions. Examples of the substituent include a lower alkoxy group (e.g. $C_{1-6}$ alkoxy group, etc. such as methoxy, ethoxy, propoxy, etc.), a halogen atom (e.g. fluorine, chlorine, bromine, iodine, etc.), a lower alkyl group (e.g. $C_{1-6}$ alkyl group, etc. such as methyl, ethyl, propyl, etc.), an amino group, a hydroxy group, a cyano group, an amidino group, etc.

Examples of the cycloalkyl group in the "optionally substituted cycloalkyl group" as the substituent include $C_{3-7}$ cycloalkyl group, etc. such as cyclopropyl, cyclobutyl, cyclopentyl, cyclohexyl, cycloheptyl, etc. Said cycloalkyl groups may have the same kind and number of substituents as those of the above described "optionally substituted aryl.

Examples of the cycloalkenyl group in the "optionally substituted cycloalkenyl group" as the substituent include e.g. $C_{3-6}$ cycloalkenyl group, etc. such as cyclopropenyl, cyclobutenyl, cyclopentenyl, cyclohexenyl, etc. Said cycloalkenyl groups may have the same kind and number of substituents as those of the above described "optionally substituted aryl.

Examples of the alkyl group in the "optionally substituted alkyl group" as the substituent include e.g. $C_{1-6}$ alkyl etc. such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, etc. Said alkyl groups may have the same kind and number of substituents as those of the above described "optionally substituted aryl.

Examples of the alkenyl group in the "optionally substituted alkenyl group" as the substituent include e.g. $C_{2-6}$ alkenyl group, etc. such as vinyl, allyl, isopropenyl, 2-methylallyl, 1-propenyl, 2-methyl-i-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc. Said alkenyl groups may have the same kind and number of substituents as those of the above described "optionally substituted aryl.

Examples of the alkynyl group in the "optionally substituted alkynyl group" as the substituent include e.g. $C_{2-6}$ alkynyl group, etc. such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc. Said alkynyl groups may have the same kind and number of substituents as those of the above described "optionally substituted aryl.

Examples of the heterocyclic group in the "optionally substituted heterocyclic group" as the substituent include e.g. an aromatic heterocyclic group, saturated or unsaturated non-aromatic heterocyclic group (alicyclic heterocyclic group) etc., which contains, besides carbon atoms, at least one hetero-atom (preferably 1 to 4 hetero-atoms, more preferably 1 to 2 hetero-atoms) consisting of 1 to 3 kinds of hetero-atoms (preferably 1 to 2 kinds of hetero-atoms) selected from oxygen atom, sulfur atom, nitrogen atom, etc.

Examples of the "aromatic heterocyclic group" include an aromatic monocyclic heterocyclic group such as a 5- to 6-membered aromatic monocyclic heterocyclic group, etc. (e.g. furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.); an aromatic fused heterocyclic group such as 8- to 12-membered aromatic fused heterocyclic group (preferably, heterocyclic group consisting of the above-mentioned 5- or 6-membered aromatic monocyclic heterocyclic group fused with a benzene ring or heterocyclic group consisting of the above-mentioned 5- or 6-membered aromatic monocyclic heterocyclic group fused with the same or different above-mentioned 5- or 6-membered aromatic monocyclic heterocyclic group), etc. (e.g. benzofuranyl, isobenzofuranyl, benzothienyl, indolyl, isoindolyl, 1H-indazolyl, benzindazolyl, benzoxazolyl, 1,2-benzoisooxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.); etc.

Examples of the "non-aromatic heterocyclic group" include a 3- to 8-membered (preferably 5- or 6-membered) saturated or unsaturated (preferably saturated) non-aromatic heterocyclic group (alicyclic heterocyclic group), etc. such as oxiranyl, azetidinyl, oxetanyl, thiethanyl, pyrrolidinyl, tetrahydrofuryl, thiolanyl, piperidyl, tetrahydropyranyl, morpholinyl, thiomorpholinyl, piperazinyl, etc.

Examples of the substituent of the "optionally substituted heterocyclic group" as the substituent include a lower alkyl group (e.g. $C_{1-6}$ alkyl group, etc. such as methyl, ethyl, propyl, etc.), an acyl group (e.g. $C_{1-6}$ alkanoyl such as formyl, acetyl, propionyl, pivaloyl, etc., benzoyl, etc.), etc.

Examples of the substituent in the "optionally substituted amino group", "optionally substituted imidoyl group", "optionally substituted amidino group", "optionally substituted hydroxy group" and "optionally substituted thiol group" as the substituent include e.g. a lower alkyl group (e.g. $C_{1-6}$ alkyl group, etc. such as methyl, ethyl, propyl, isopropyl, butyl, isobutyl, t-butyl, pentyl, hexyl, etc.), an acyl group such as $C_{1-6}$ alkanoyl (e.g. formyl, acetyl, propionyl, pivaloyl, etc.), benzoyl, etc., an optionally halogenated $C_{1-6}$ alkoxy-carbonyl (e.g. trifluoromethoxycarbonyl, 2,2,2-trifluoroethoxycarbonyl, trichloromethoxycarbonyl, 2,2,2-trichloroethoxycarbonyl, etc.), etc. In addition, the "amino group" in the "optionally substituted amino group" as the substituent may be substituted with an optionally substituted imidoyl group (e.g., $C_{1-6}$ alkylimidoyl, formimidoyl, amidino, etc.), etc. and two substituents of the "amino group" may form a cyclic amino group together with a nitrogen atom. Examples of said cyclic amino group include e.g. 3- to 8-membered (preferably 5- to 6-membered) cyclic amino group, etc. such as 1-azetidinyl, 1-pyrrolidinyl, piperidino, morpholino, 1-piperazinyl and 1-piperazinyl which may have at the 4-position a lower alkyl group (e.g. $C_{1-6}$ alkyl group, etc. such as methyl, ethyl, propyl, isopropyl, butyl, t-butyl, pentyl, hexyl, etc.), an aralkyl group (e.g. $C_{7-10}$ aralkyl group, etc. such as benzyl, phenethyl, etc.), an aryl group (e.g. $C_{6-10}$ aryl group, etc. such as phenyl, 1-naphthyl, 2-naphthyl, etc.), etc.

Examples of the "optionally substituted carbamoyl group" include unsubstituted carbamoyl, N-mono-substituted carbamoyl group and N,N-di-substituted carbamoyl group.

The "N-mono-substituted carbamoyl group" is a carbamoyl group having one substituent on the nitrogen atom and said substituent include e.g. a lower alkyl group (e.g. $C_{1-6}$ alkyl group, etc. such as methyl, ethyl, propyl, isopropyl, butyl, isobutyl, t-butyl, pentyl, hexyl, etc,), a cycloalkyl group (e.g. $C_{3-6}$ cycloalkyl group, etc. such as cyclopropyl, cyclobutyl, cyclopentyl, cyclohexyl, etc.), an aryl group (e.g. $C_{610}$ aryl group, etc. such as phenyl, 1-naphthyl, 2-naphthyl, etc.), an aralkyl group (e.g. $C_{7-10}$ aralkyl group, preferably phenyl-$C_{1-4}$ alkyl group, etc. such as benzyl, phenethyl, etc.), a heterocyclic group (e.g. the above described "heterocyclic group" as the substituent of the "optionally substituted hydrocarbon group" represented by $R^1$, etc.), etc. Said lower alkyl group, cycloalkyl group, aryl group, aralkyl group and heterocyclic group may have a substituent and examples of the substituent include e.g. a hydroxy group, an optionally substituted amino group [said amino group may have 1 to 2 substituents (e.g. a lower alkyl group (e.g. $C_{1-6}$ alkyl group, etc. such as methyl, ethyl, propyl, isopropyl, butyl, isobutyl, t-butyl, pentyl, hexyl, etc.), an acyl group (e.g. $C_{1-6}$ alkanoyl such as formyl, acetyl, propionyl, pivaloyl, etc., benzoyl, etc.), etc.)], a halogen atom (e.g. fluorine, chlorine, bromine, iodine, etc.), a nitro group, a cyano group, a lower alkyl group optionally substituted with 1 to 5 halogen atoms (e.g. fluorine, chlorine, bromine, iodine, etc.), a lower alkoxy group optionally substituted with 1 to 5 halogen atoms (e.g. fluorine, chlorine, bromine, iodine, etc.), etc. Said lower alkyl group include e.g. $C_{1-6}$ alkyl group, etc. such as methyl, ethyl, n-propyl, isopropyl, n-butyl, isobutyl, sec-butyl, tert-butyl, pentyl, hexyl, etc. and in particular methyl, ethyl, etc. are preferable. Said lower alkoxy group include e.g. $C_{,6}$ alkoxy group, etc. such as methoxy, ethoxy, n-propoxy, isopropoxy, n-butoxy, isobutoxy, sec-butoxy, tert-butoxy, etc. and in particular methoxy, ethoxy, etc. are preferable. These substituents may be same or different and the above described lower alkyl group, cycloalkyl group, aryl group, aralkyl group and heterocyclic group may have 1 or 2 to 3 (preferably 1 or 2) substituents.

The "N,N-di-substituted carbamoyl group" is a carbamoyl group having two substituents on the nitrogen atom. Examples of one of the substituents include the same as those of the above described "N-mono-substituted carbamoyl group" and examples of the other substituent include e.g. a lower alkyl group (e.g. $C_{1-6}$ alkyl group, etc. such as methyl, ethyl, propyl, isopropyl, butyl, t-butyl, pentyl, hexyl, etc.), $C_{3-6}$ cycloalkyl group (e.g. cyclopropyl, cyclobutyl, cyclopentyl, cyclohexyl, etc.), $C_{7-10}$ aralkyl group (e.g. benzyl, phenethyl, etc., preferably phenyl-$C_{1-4}$ alkyl group, etc.), etc. In addition, two substituents of the "N,N-di-substituted carbamoyl group" may form a cyclic amino-carbamoyl group together with a nitrogen atom. Examples of said cyclic amino-carbamoyl group include e.g. 3- to 8-membered (preferably 5- to 6-membered) cyclic amino-carbamoyl group, etc. such as 1-azetidinylcarbonyl, 1-pyrrolidinylcarbonyl, piperidinocarbonyl, morpholinocarbonyl, 1-piperazinylcarbonyl and 1-piperazinylcarbonyl which may have at the 4-position a lower alkyl group (e.g. $C_{1-6}$ alkyl group, etc. such as methyl, ethyl, propyl, isopropyl, butyl, t-butyl, pentyl, hexyl, etc.), an aralkyl group (e.g. $C_{7-10}$ aralkyl group, etc. such as benzyl, phenethyl, etc.), an aryl group (e.g. $C_{6-10}$ aryl group, etc. such as phenyl, 1-naphthyl, 2-naphthyl, etc.), etc.

Examples of the substituent in the "optionally substituted thiocarbamoyl group" include the same substituent as those in the above described "optionally substituted carbamoyl group".

Examples of the "optionally esterified carboxyl group" in the present specification include a carboxyl group as well as a lower alkoxycarbonyl group, an aryloxycarbonyl group, aralkyloxycarbonyl group, etc.

Examples of the "lower alkoxycarbonyl group" include e.g. $C_{1-6}$ alkoxy-carbonyl group, etc. methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, etc. Among others, $C_{1-3}$ alkoxy-carbonyl group, etc. such as methoxycarbonyl, ethoxycarbonyl, propoxycarbonyl, etc. are preferable.

Examples of the "aryloxycarbonyl group" include e.g. $C_{7-10}$ aryloxy-carbonyl group, etc. such as phenoxycarbonyl, 1-naphthoxycarbonyl, 2-naphthoxycarbonyl, etc.

Examples of the "aralkyloxycarbonyl group" include e.g. $C_{7-10}$ aralkyloxy-carbonyl group, etc. (preferably, $C_{6-10}$ aryl-$C_{1-4}$ alkoxy-carbonyl, etc.) such as benzyloxycarbonyl, phenethyloxycarbonyl, etc.

Said "aryloxycarbonyl group" and "aralkyloxycarbonyl group" may have a substituent. Examples of the substituent include the same kind and number of the substituents of the aryl group and aralkyl group as the substituent for the above described N-mono-substituted carbamoyl group.

Examples of the "acyl group derived from a sulfonic acid" as the substituent include a sulfonyl group having one substituent which the above described "N-mono-substituted carbamoyl group" have on the nitrogen atom, etc., preferably, $C_{1-6}$ alkyl sulfonyl, etc. such as methanesulfonyl, ethane-sulfonyl, etc.

Examples of the "acyl group derived from a carboxylic acid" as the substituent include a carbonyl group having a hydrogen atom or one substituent which the above described "N-mono-substituted carbamoyl group" have on the nitrogen atom, etc., preferably, $C_{1-6}$ alkanoyl such as formyl, acetyl, propionyl, pivaloyl, etc. benzoyl, etc.

In the above formula, the ring A represents an optionally substituted divalent nitrogen-containing heterocyclic group, in addition to the group of the formula:

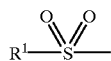

and the group of the formula:

Examples of the "divalent nitrogen-containing heterocyclic group" in the "optionally substituted divalent nitrogen-containing heterocyclic group" represented by the ring A include a divalent 6- to 8-membered nitrogen-containing heterocyclic group which may contain, besides carbon atoms, at least one nitrogen atom (preferably 1 to 2 nitrogen atoms) and 1 to 3 hetero-atoms selected from oxygen atom, sulfur atom, etc.

Examples of the "divalent 6- to 8-membered nitrogen-containing heterocyclic group" include e.g. a divalent 6-membered nitrogen-containing heterocyclic group which contains 1 to 2 nitrogen atoms such as piperidinediyl (piperidine-1,2-, 1,3- or 1,4-diyl), piperazinediyl (piperazine-1,2-, 1,3- or 1,4-diyl), molpholinediyl (molpholine-2,4- or 3,4-diyl), thiomolpholinediyl (thiomolpholine-2,4- or 3,4-diyl), etc.; a divalent 7-membered nitrogen-containing heterocyclic group which contains 1 to 2 nitrogen atoms such as homopiperidinediyl (homopiperidine-1,2-, 1,3- or 1,4-diyl), homopiperazinediyl (piperazine-1,2-, 1,3-, 1,4-, 1,5-, 1,6- or 1,7-diyl), etc.; a divalent 8-membered nitrogen-containing heterocyclic group which contains 1 to 2 nitrogen atoms such as 1,4-diazacyclooctanediyl (1,4-diazacyclooctane-1,2-, 1,3-, 1,4-, 1,5-, 1,6-, 1,7- or 1,8-diyl), 1,5-diazacyclooctanediyl (1,5-diazacyclooctane-1,2-, 1,3-, 1,4- or 1,5-diyl) etc.; etc.

Examples of the substituents of the "divalent nitrogen-containing heterocyclic group" include e.g. a hydroxy group, a halogen atom (e.g. fluorine, chlorine, bromine, iodine, etc.), a nitro group, a cyano group, an optionally substituted amino group, an optionally substituted lower alkyl group, a lower alkoxy group optionally substituted with 1 to 5 halogen atoms (e.g. fluorine, chlorine, bromine, iodine, etc.), an optionally esterified carboxyl group, an optionally substituted carbamoyl group, etc. Said "divalent nitrogen-containing heterocyclic group" may have 1 to 3 (preferably 1 to 2) of these substituents at any possible position.

Examples of the substituents of the "optionally substituted amino group" include 1–2 substituents selected from an optionally substituted alkyl group, an optionally substituted carbamoyl group, an acyl group derived from a sulfonic acid, an acyl group derived from a carboxylic acid, etc. Examples of said "optionally substituted alkyl group", "optionally substituted carbamoyl group", "an acyl group derived from a sulfonic acid" and "an acyl group derived from a carboxylic acid" include the "optionally substituted alkyl group", "optionally substituted carbamoyl group", "an acyl group derived from a sulfonic acid" and "an acyl group derived from a carboxylic acid" as exemplified by the substituents for the above described "optionally substituted hydrocarbon group" represented by $R^1$.

Preferable examples of the "optionally substituted amino group" include an amino group optionally substituted by 1–2 substituents selected from (1) a lower ($C_{1-6}$) alkyl group such as methyl, ethyl, n-propyl, isopropyl, n-butyl, isobutyl, sec-butyl, tert-butyl, etc., (2) mono- or di-lower ($C_{1-6}$) alkyl carbamoyl group, (3) $C_{1-6}$ alkyl sulfonyl such as methanesulfonyl, ethanesulfonyl, etc., (4) $C_{1-6}$ alkanoyl such as formyl, acetyl, propionyl, pivaloyl, etc. and (5) benzoyl.

Examples of the "lower alkyl group" in the "the optionally substituted a lower alkyl group" include e.g. $C_{1-6}$alkyl group, etc. such as methyl, ethyl, n-propyl, isopropyl, n-butyl, isobutyl, sec-butyl, tert-butyl, etc., and in particular methyl, ethyl, etc. are preferable.

Examples of the substituents for the "lower alkyl group" include e.g. a halogen atom (e.g. fluorine, chlorine, bromine, iodine, etc.), an amino group, a carboxyl group, hydroxy group, etc. Said "lower alkyl group" may have 1 to 5 (preferably 1 or 2) substituents at any possible position.

Examples of the "lower alkoxy group" in the "lower alkoxy group optionally substituted with 1 to 5 halogen atoms" include e.g. $C_{1-6}$ alkoxy group, etc. such as methoxy, ethoxy, n-propoxy, isopropoxy, n-butoxy, isobutoxy, sec-butoxy, tert-butoxy, etc. and in particular methoxy, ethoxy, etc. are preferable.

Examples of the "optionally esterified carboxyl group" include the optionally esterified carboxyl group as exemplified by the substituents for the above described "optionally substituted hydrocarbon group" represented by $R^1$.

Examples of the "optionally substituted carbamoyl group" include the optionally substituted carbamoyl group as exemplified by the substituents for the above described "optionally substituted hydrocarbon group" represented by $R^1$.

As the ring A, a group of the formula:

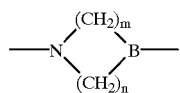

wherein B is CH or a nitrogen atom, and m and n are 2 or 3 is preferable.

In the above formula, B is CH or a nitrogen atom and a nitrogen atom is preferable, as B.

In the above formula, m and n are 2 or 3, and preferably m and n are 2.

In particular, the ring A is preferably piperazinediyl (more preferably piperazine-1,4-diyl).

In the above formula, Y is an optionally substituted divalent hydrocarbon group or an optionally substituted divalent heterocyclic group (preferably divalent hydrocarbon group or divalent unsaturated heterocyclic group, and more preferably, divalent hydrocarbon group or divalent aromatic heterocyclic group).

Among others, Y is preferably an optionally substituted divalent hydrocarbon group or an optionally divalent unsaturated heterocyclic group, and more preferably an optionally substituted divalent hydrocarbon group or an optionally divalent aromatic heterocyclic group. In particular, Y is preferably an optionally substituted phenylene group, an optionally substituted cyclohexylene group or an optionally substituted divalent aromatic heterocyclic group.

Examples of the "divalent hydrocarbon group" in the "optionally substituted divalent hydrocarbon group" represented by Y include a saturated or unsaturated, straight-chain or cyclic divalent hydrocarbon group (preferably, a saturated straight-chain divalent hydrocarbon group, a saturated cyclic divalent hydrocarbon group or a unsaturated cyclic divalent hydrocarbon group, more preferably, a saturated straight-chain divalent hydrocarbon group, a saturated cyclic divalent hydrocarbon group or an divalent aromatic hydrocarbon group, etc.).

Examples of the saturated straight-chain divalent hydrocarbon group include a straight-chain $C_{1-6}$ alkylene (preferably, a straight-chain $C_{1-4}$ alkylene, etc. such as methylene, ethylene, etc.), etc. such as methylene, ethylene, propylene, butylene, pentylene, etc. which is a divalent group formed by removing a terminal hydrogen atom from a straight-chain alkyl group (e.g. $C_{1-10}$ alkyl group (preferably $C_{1-6}$ alkyl, more preferably $C_{1-4}$ alkyl, etc.), etc. such as methyl, ethyl, n-propyl, n-butyl, n-pentyl, n-hexyl, n-heptyl, n-octyl, n-nonyl, etc.

Examples of the unsaturated straight-chain divalent hydrocarbon group include a straight-chain $C_{2-6}$ alkenylene, $C_{2-6}$ alkynylene, etc. which is a divalent group formed by removing a terminal hydrogen atom from a straight-chain alkenyl group (e.g. $C_{2-6}$ alkenyl group, etc. such as vinyl, allyl, 1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, etc.), a straight-chain alkynyl group (e.g. $C_{2-6}$ alkynyl group, etc. such as ethynyl, 1-propynyl, 2-propynyl, 1-butynyl, 2-butynyl, 3-butynyl, 1-pentynyl, 2-pentynyl, 3-pentynyl, 4-pentynyl, 1-hexyntl, 2-hexyntl, 3-hexyntl, 4-hexyntl, 5-hexyntl, etc.), etc.

Examples of the saturated cyclic divalent hydrocarbon group include a divalent group formed by removing a hydrogen atom at an optional position (preferably a hydrogen atom on a carbon atom which is different from the carbon atom at the 1-position, more preferably a hydrogen atom on a carbon atom which is farthest from the carbon atom at the 1-position) from a cycloalkyl group (e.g. $C_{3-9}$ cycloalkyl (preferably $C_{5-7}$ cycloalkyl, more preferably cyclohexyl, etc.), etc. such as cyclopropyl, cyclobutyl, cyclopentyl, cyclohexyl, cycloheptyl, cyclooctyl, cyclononyl, etc.). Preferable examples of the saturated cyclic divalent hydrocarbon group include $C_{5-7}$ cycloalkylene (more preferably 1,4-cyclohexylene, etc.). etc.

Examples of the unsaturated cyclic divalent hydrocarbon group include a divalent group formed by removing a hydrogen atom at an optional position (preferably a hydrogen atom on a carbon atom which is different from the carbon atom at the 1-position, more preferably a hydrogen atom on a carbon atom which is farthest from the carbon atom at the 1-position) from a cycloalkenyl group (e.g. $C_{3-6}$ cycloalkenyl group, etc. such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, etc.), a cycloalkanedienyl group (e.g. $C_{4-6}$ cycloalkanedienyl group, etc. such as 2,4-cycloalkanedien-1-yl, 2,4-cyclohexadien-1-yl, 2,5-cyclohexadien-1-yl, etc.), an aryl group (e.g. $C_{6-10}$ aryl group, etc. such as phenyl, naphthyl, etc., preferably phenyl), an aralkylyl group (e.g. $C_{7-10}$ aralkyl group, etc. such as benzyl, phenethyl, etc., preferably benzyl), etc. Among others, phenylene is preferable and in particular 1,4-phenylene is preferable.

Examples of the substituents for the "optionally substituted divalent hydrocarbon group" represented by Y include the same substituents as those of the above described "divalent nitrogen-containing heterocyclic group" represented by the ring A.

Examples of the "divalent heterocyclic group" in the "optionally substituted divalent heterocyclic group" represented by Y include a 5- to 6-membered divalent aromatic heterocyclic group, a 5- to 6-membered divalent saturated or unsaturated non-aromatic heterocyclic group (alicyclic heterocyclic group), etc., which contains, besides carbon atoms, at least one hetero-atom (preferably 1 to 3 hetero-atoms, more preferably 1 to 2 hetero-atoms) consisting of 1 to 3 kinds of hetero-atoms (preferably 1 to 2 kinds of hetero-atoms) selected from oxygen atom, sulfur atom, nitrogen atom, etc.

Examples of the "divalent aromatic heterocyclic group" include a divalent group formed by removing two hydrogen atoms at different positions from a 5-membered heterocyclic ring such as furan, thiophene, pyrrole, oxazole, isooxazole, thiazole, isothiazole, imidazole, pyrazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, etc., a 6-membered heterocyclic ring such as pyridine, pyridazine, pyrimidine, 1,2,4-triazine, 1,3,5-triazine, etc.

Examples of the "divalent non-aromatic heterocyclic group" include a 5- to 6-membered saturated or unsaturated (preferably saturated) non-aromatic heterocyclic group (alicyclic heterocyclic group), etc. such as pyrrolidine, tetrahydrofuran, piperidine, tetrahydropyran, molpholine, thiomolpholine, piperazine, etc.

Examples of the substituents for the "optionally substituted divalent heterocyclic group" represented by Y include the same substituents as those of the above described "divalent nitrogen-containing heterocyclic group" represented by the ring A.

Among others, Y is preferably an optionally substituted divalent aromatic group.

In the above formula, Z is an amino group substituted with an optionally substituted hydrocarbon group, an optionally substituted imidoyl group or an optionally substituted nitrogen-containing heterocyclic group, and said amino group, imidoyl group or nitrogen-containing heterocyclic group binds to the group Y through "a direct bond or an optionally substituted alkylene chain" represented by X.

Examples of the "alkylene chain" in the "optionally substituted alkylene chain" represented by X include a straight-chain lower ($C_{1-6}$) alkylene, etc. such as methylene, ethylene, propylene, butylene, pentylene, etc. Among others, $C_{1-4}$ alkylene, etc. such as methylene, ethylene, etc. is preferable.

Examples of the substituents for the "alkylene chain" include a lower alkyl group (e.g. $C_{1-6}$ alkyl, etc. such as methyl, ethyl, n-propyl, isopropyl, n-butyl, isobutyl, sec-butyl, tert-butyl, etc.), a halogen atom (e.g. fluorine, chlorine, bromine, iodine, etc.), hydroxy group, an optionally esterified carboxyl group (the same "optionally esterified carboxyl group" as exemplified by the substituents for the above described "optionally substituted hydrocarbon group" represented by $R^1$), etc. Said "alkylene chain" may have 1 to 3 of these substituents at any possible position.

Examples of the "optionally substituted hydrocarbon group" in the "amino group substituted with (one or two) optionally substituted hydrocarbon group" are similar to the above described "optionally substituted hydrocarbon group" represented by $R^1$. In addition, two of the "optionally substituted hydrocarbon group" may be combined to form a cyclic amino together with a nitrogen atom. Examples of said cyclic amino group include a 3- to 8-membered (preferably 5- to 6-membered) cyclic amino such as 1-azetidinyl, 1-pyrrolidinyl, piperidino, morpholino, 1-piperazinyl optionally having a lower alkyl group (e.g. $C_{1-6}$ alkyl group, etc. such as methyl, ethyl, propyl, isopropyl, butyl, t-butyl, pentyl, hexyl, etc.), an aralkyl group (e.g. $C_{7-10}$ aralkyl group, etc. such as benzyl, phenethyl, etc.), an aryl group (e.g. $C_{6-10}$ aryl group, etc. such as phenyl, 1-naphthyl, 2-naphthyl, etc.), etc. at the 4-position., etc. Said cyclic amino group may have the same kind and number of the substituents as exemplified by those for the above described "optionally substituted hydrocarbon group" represented by $R^1$.

In addition, when the "optionally substituted hydrocarbon group" as the substituent in the "amino group substituted with an optionally substituted hydrocarbon group" is substituted by an optionally substituted imidoyl group, the "amino group substituted with an optionally substituted hydrocarbon group" represented by Z represents an amino group substituted with an optionally substituted imidoyl group shown below represented by Z. Examples of said amino group substituted with an optionally substituted imidoyl group include a group of the formula:

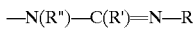

—N(R")—C(R')=N—R wherein R" is a hydrogen atom or an optionally substituted hydrocarbon group, R is a hydrogen atom, an optionally substituted hydrocarbon group or an acyl group derived from a carboxylic acid and, R' is a hydrogen atom, an optionally substituted hydrocarbon group, an acyl group derived from a carboxylic acid, an optionally substituted amino group or an optionally substituted hydroxy group.

In the above formula, examples of "an optionally substituted hydrocarbon group" represented by R, R' and R" include the same "optionally substituted hydrocarbon group" as the above described "optionally substituted hydrocarbon group" represented by $R^1$. Examples of the "acyl group derived from a carboxylic acid" represented by R and R' include the same "acyl group derived from a carboxylic acid" as the substituent for the above described "optionally substituted hydrocarbon group" represented by $R^1$. Examples of the "optionally substituted hydroxy group" represented by R' include the same "optionally substituted hydroxy group" as the substituent for the above described "optionally substituted hydrocarbon group" represented by $R^1$. Examples of the "optionally substituted amino group" represented by R' include the same "optionally substituted amino group" as the substituent for the above described "optionally substituted hydrocarbon group" represented by $R^1$ or an amino group optionally having 1–2 of the "optionally substituted hydrocarbon group" represented by $R^1$.

The compound (I) wherein R is an acyl group derived from a carboxylic acid is useful for a pro-drug of the compound (I) wherein R is an hydrogen atom.

Examples of the "acyl group derived from a carboxylic acid" represented by R include the same "acyl group derived from a carboxylic acid" as the substituent for the above described "optionally substituted hydrocarbon group" represented by $R^1$. In addition, the "acyl group derived from a carboxylic acid" represented by R may be an optionally esterified carboxyl group such as a group of the formula: —COOR'" wherein R'" is an optionally substituted hydrocarbon group. Examples of the "optionally substituted hydrocarbon group" represented by R'" include the same "optionally substituted hydrocarbon group" represented by $R^1$. Preferred examples of the "hydrocarbon group" in the "optionally substituted hydrocarbon group" represented by R'" include $C_{1-6}$alkyl, $C_{2-6}$ alkenyl, $C_{3-6}$ cycloalkyl, $C_{6-10}$ aryl, $C_{6-10}$ aryl-$C_{1-4}$ alkyl, etc. Each of them may have the same kind and number of the substituents as exemplified by those for the "optionally substituted hydrocarbon group" represented by $R^1$. Among others, as the group of the formula: —COOR'", $C_{1-6}$ alkoxy-carbonyl (e.g. methoxycarbonyl, ethoxycarbonyl, isopropoxycarbonyl, etc.), $C_{1-6}$ alkanoyloxy-$C_{1-6}$ alkoxy-carbonyl (e.g. pivaloyloxymethoxycarbonyl, 1-(acetoxy)-ethoxycarbonyl, acetoxy-tert-butoxycarbonyl, etc.), $C_{1-6}$ alkoxy-carbonyloxy-$C_{1-6}$ alkoxy-carbonyl (e.g. ethoxycarbonyloxymethoxycarbonyl, etc.), 5-$C_{1-4}$ alkyl-2-oxo-dioxolen-4-yl-$C_{1-6}$ alkoxy-carbonyl (e.g. 5-methyl-2-oxo-dioxolen-4-ylmethoxycarbonyl, etc.), etc. are preferable.

Specific examples of the "amino group substituted with an optionally substituted hydrocarbon group" include a mono- or di-lower ($C_{1-6}$) alkyl amino group which may be further substituted with an aryl group (preferably, phenyl), etc. (e.g. methylamino, ethylamino, benzylmethylamino, dimethylamino, diethylamino, diisobutylamino, diisopropylamino, N-ethyl-t-butylamino, benzylmethylamino, etc.), a guanidino group, a formimidoylamino group, an acetimidoylamino group, piperidino group, etc.

Specific examples of the "optionally substituted imidoyl group" include a group of the formula: —C(R')=N—R wherein each symbol is as defined above.

In the above formula, R" is preferably a hydrogen atom or a lower alkyl group (e.g. $C_{1-6}$ alkyl group such as methyl, ethyl, propyl, isopropyl, butyl, isobutyl, etc.), R is preferably a hydrogen atom, a lower alkyl group (e.g. $C_{1-6}$ alkyl group such as methyl, ethyl, propyl, isopropyl, butyl, isobutyl, etc.), or an acyl group (e.g. $C_{1-6}$ alkanoyl such as formyl, acetyl, propionyl, pivaloyl, etc., benzoyl, etc.), and R' is preferably a hydrogen atom, a lower alkyl group (e.g. $C_{1-6}$ alkyl group such as methyl, ethyl, propyl, isopropyl, butyl, isobutyl, etc.), an acyl group (e.g. $C_{1-6}$ alkanoyl such as formyl, acetyl, propionyl, pivaloyl, etc., benzoyl, etc.), an optionally substituted amino group (e.g. an amino group optionally substituted with same or different substituents selected from a lower alkyl group (e.g. $C_{1-6}$ alkyl group such as methyl, ethyl, propyl, isopropyl, butyl, isobutyl, etc.) and an acyl group (e.g. $C_{1-6}$ alkanoyl such as formyl, acetyl, propionyl, pivaloyl, etc., benzoyl, etc.)), or a lower alkoxy group (e.g. $C_{1-6}$ alkoxy group such as methoxy, ethoxy, propoxy, isopropoxy, butoxy, isobutoxy, etc.).

In the above formula, as R" and R, a hydrogen atom or a lower alkyl group is preferable. Among others, a hydrogen atom is preferable.

In the above formula, as R', a hydrogen atom, a lower alkyl group or an optionally substituted amino group is preferable. Among others, a lower alkyl group or an optionally substituted amino group is preferable and, in particular, an optionally substituted amino group (preferably, amino optionally substituted with $C_{1-4}$alkyl, etc.) is preferable.

Examples of the "nitrogen-containing heterocyclic group" in the "optionally substituted nitrogen-containing heterocyclic group" include an aromatic nitrogen-containing heterocyclic group and a saturated or unsaturated non-aromatic nitrogen-containing heterocyclic group (alicyclic heterocyclic group), which contains, besides carbon atoms, at least one nitrogen atom (preferably 1 to 3 nitrogen atoms) and optionally contains 1 to 3 hetero-atoms selected from a oxygen atom, a sulfur atom, etc.

Examples of the "aromatic nitrogen-containing heterocyclic group" include aromatic monocyclic nitrogen-containing heterocyclic group, its N-oxide, etc. such as pyrrolyl, oxazolyl, isooxazolyl, thiazolyl, isothiazolyl, imidazolyl (1H-imidazol-1-yl, 1H-imidazol-4-yl, etc.), pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl (1,2,4-triazolyl-1-yl, 1,2,4-triazolyl-4-yl, etc.), tetrazolyl, pyridyl (2-, 3- or 4-pyridyl), pyridazinyl, pyrimidinyl, pyrazinyl, triazinyl, etc. Among others, 5- to 6-membered aromatic monocyclic nitrogen-containing heterocyclic groups are preferable.

Examples of the "non-aromatic nitrogen-containing heterocyclic group" include azetidinyl, pyrrolidinyl, piperidyl (2-, 3- or 4-piperidyl), morpholinyl, thiomorpholinyl, piperazinyl (1-piperazinyl, etc.), homopiperazinyl, etc. Among others, 5- to 6-membered non-aromatic monocyclic nitrogen-containing heterocyclic groups are preferable.

Examples of the substituents of the "nitrogen-containing heterocyclic group" represented by Z include the same substituents as those of the above described "divalent nitrogen-containing heterocyclic group" represented by the ring A.

Z is preferably an optionally substituted nitrogen-containing heterocyclic group, etc. and an optionally substituted aromatic nitrogen-containing heterocyclic group, etc. is more preferable, provided that when X is a direct bond and Z is an optionally substituted 6-membered nitrogen-containing heterocyclic group, Y is preferably an optionally substituted divalent hydrocarbon group or an optionally substituted divalent unsaturated heterocyclic group.

Preferable combinations of Y and Z include
(1) Y is an optionally substituted divalent hydrocarbon group or an optionally substituted divalent heterocyclic group, and Z is an amino group substituted with an optionally substituted hydrocarbon group, an optionally substituted imidoyl group, an optionally substituted 5-membered aromatic nitrogen-containing heterocyclic group or an optionally substituted non-aromatic nitrogen-containing heterocyclic group (preferably an amino group substituted with hydrocarbon group, an optionally substituted imidoyl group or an optionally substituted non-aromatic nitrogen-containing heterocyclic group, more preferably an amino group substituted with a hydrocarbon group or an optionally substituted imidoyl group);

(2) Z is an amino group substituted with an optionally substituted hydrocarbon group, an optionally substituted imidoyl group or an optionally substituted nitrogen-containing heterocyclic group, and Y is an optionally substituted divalent hydrocarbon group or an optionally substituted divalent unsaturated heterocyclic group (preferably an optionally substituted divalent hydrocarbon group or an optionally substituted divalent aromatic heterocyclic group, more preferably an optionally substituted, an optionally substituted phenylene group or an optionally substituted divalent aromatic heterocyclic group);

(3) Z is an optionally substituted 6-membered nitrogen-containing heterocyclic group, and Y is an optionally substituted, divalent hydrocarbon group or an optionally substituted divalent unsaturated heterocyclic group (preferably an optionally substituted divalent hydrocarbon group or an optionally substituted divalent aromatic heterocyclic group, more preferably an optionally substituted, phenylene group or an optionally substituted divalent aromatic heterocyclic group);

(4) Y is a divalent saturated heterocyclic group, Z is an amino group substituted with an optionally substituted hydrocarbon group, an optionally substituted imidoyl group, an optionally substituted 5-membered aromatic nitrogen-containing heterocyclic group or an optionally substituted non-aromatic nitrogen-containing heterocyclic group (preferably an amino group substituted with a hydrocarbon group, an optionally substituted imidoyl group or an optionally substituted non-aromatic nitrogen-containing heterocyclic group, more preferably an amino group substituted with a hydrocarbon group or an optionally substituted imidoyl group);

(5) Z is an amino group substituted with an optionally substituted hydrocarbon group, an optionally substituted imidoyl group, an optionally substituted 5-membered aromatic nitrogen-containing heterocyclic group or an optionally substituted non-aromatic nitrogen-containing heterocyclic group (preferably an amino group substituted with a hydrocarbon group, an optionally substituted imidoyl group or an optionally substituted non-aromatic nitrogen-containing heterocyclic group, more preferably an amino group substituted with a hydrocarbon group or an optionally substituted imidoyl group), and Y is an optionally substituted divalent hydrocarbon group or an optionally substituted divalent unsaturated heterocyclic group (preferably an optionally substituted divalent hydrocarbon group or an optionally substituted divalent aromatic heterocyclic group, more preferably an optionally substituted phenylene group or an optionally substituted divalent aromatic heterocyclic group); etc.

Examples of the salts of the compound (I) include a pharmaceutically acceptable salt, etc. such as an acid addition salt (e.g. a salt with acetic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, phosphoric acid, hydrochloric acid, nitric acid, hydrobromic acid, hydriodic atom acid, sulfamic acid, sulfuric acid, etc.), a metal salt (e.g. a salt with sodium, potassium, magnesium, calcium, etc.), an organic base (e.g. trimethylamine, triethylamine, pyridine, picoline, N-methylpyrrolidine, N-methylpiperidine, N-methylmolpholine, etc.), etc.

The compounds (I) of this invention can be produced by, for example, methods as described below or those similar to the methods described below.

Each compound described in the following reaction schemes may be in the form of a salt, unless it inhibits the reaction and examples of the salts are the same as those of the compound (I).

Method A

A compound (II) or a salt thereof represented by the formula:

  (II)

wherein Q is a halogen atom, and the other symbols are as defined above is reacted with a compound (III) or a salt thereof represented by the formula:

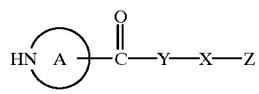  (III)

wherein each symbol is as defined above to produce the compound (I).

In the formula (II), Q is a halogen atom. Examples of the halogen atom represented by Q include fluorine, chlorine, bromine, iodine, etc.

This production method is carried out by reacting a compound (II) or a salt thereof with a compound (III) or a salt thereof. Examples of the salt of the compound (II) or (III) include an acid addition salt with an acid which can form an acid addition salt with the above described compound (I).

This production method is usually carried out in a solvent. Any solvent can be used unless it inhibits this production method.

Examples of the solvent include alcohols such as methanol, ethanol, propanol, isopropanol, butanol, tert-butanol, etc., ethers such as dioxane, tetrahydrofuran, diethylether, tert-butylmethylether, diisopropylether, ethyleneglycol-dimethylether, etc., esters such as ethyl formate, ethyl acetate, n-butyl acetate, etc., halogenated hydrocarbons such as dichloromethane, chloroform, carbon tetrachloride, trichloroethylene, 1,2-dichloroethane etc., hydrocarbons such as n-hexane, benzene, toluene, etc., amides such as formamide, N,N-dimethylformamide,-N,N-dimethylacetamide, etc., ketones such as acetone, methylethylketone, methylisobutylketone, etc., nitrites such as acetonitrile, propionitrile, etc., etc., and additionally dimethylsulfoxide, sulfolane (tetramethylenesulfone), hexamethylphosphorylamide, water, etc., and these can be used singly or as a mixture.

If necessary, this production method can be carried out in the presence of a base. Examples of the base include an inorganic base such as lithium hydroxide, potassium hydroxide, sodium hydroxide, sodium carbonate, potassium carbonate, sodium hydrogen carbonate, etc., a tertiary amine such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmolpholine, etc.

In the reaction, about 1 to about 5 moles (preferably about 1 to about 3 moles) of the compound (II) is used per 1 mole of compound (III).

The reaction temperature ranges from about −80° C. to about 100° C., preferably about −50° C. to about 80° C.

The reaction time varies depending on kind of the compound (II) or (III), kind of the solvent, the reaction temperature, etc. and usually ranges from about 1 minute to about 72 hours, preferably about 15 minutes to about 24 hours.

Method B

A compound (IV) or a salt thereof represented by the formula:

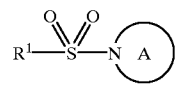  (IV)

wherein each symbol is as defined above is reacted with a compound (V) or a salt thereof or its reactive derivatives represented by the formula:

  (V)

wherein each symbol is as defined above to produce a compound (I) or a salt thereof.

This production method is carried out by reacting a compound (IV) or a salt thereof with a free acid(V) or a salt thereof (iorganic salt, organic salt, etc.) or its reactive derivatives (e.g. acid halide, acid azide, acid anhydride, mixed acid anhydride, active amide, active ester, active thioester, etc.). Examples of the salt of the compound (IV) include an acid addition salt with an acid which can form an acid addition salt with the above described compound (I).

Examples of the in organic salt of the compound (V) include a salt with alkali metal (e.g. a salt with sodium, potassium, etc.), a salt with alkaline earth metal (e.g. a salt with calcium, etc.), etc. Examples of the organic salt of the compound (V) include a salt with trimethylamine, triethylamine, tert-butyldimethylamine, dibenzylmethylamine, benzyl-dimethylamine, N,N-dimethylaniline, pyridine, quinoline, etc.

Examples of the acid halide include acid chloride, acid bromide, etc. Examples of the mixed acid anhydride include mono-$C_{1-4}$alkyl carbonate mixed acid anhydride (e.g. a mixed acid anhydride of a free acid (V) with monomethylcarbonate, monoethylcarbonate, monoisopropylcarbonate, monoisobutylcarbonate, mono-(tert-butyl)carbonate, mono-benzylcarbonate, mono(p-nitrobenzyl)carbonate, monoallylcarbonate, etc.), $C_{1-6}$ alicyclic carboxylic acid mixed acid anhydride (e.g. a mixed acid anhydride of a free acid (V) with acetic acid, cyanoacetic acid, propionic acid, butyric acid, isobutyric acid, valeric acid, isovaleric acid, pivalic acid, trifluoroacetic acid, trichloroacetic acid, acetoacetic acid, etc.), $C_{7-11}$ aromatic carboxylic acid mixed acid anhydride (e.g. a mixed acid anhydride of a free acid (V) with benzoic acid, p-toluic acid, p-chlorobenzoic acid, etc.), organic sulfonic acid mixed acid anhydride (e.g. a mixed acid anhydride with methanesulfonic acid, ethanesulfonic acid, benzenesulfonic acid, p-toluenesulfonic acid, etc.), etc. Examples of the active amide include an amide with nitrogen-containing heterocyclic compound (e.g. an acid amide of a free acid (V) with pyrazole, imidazole, benzotriazole, etc.; Said nitrogen-containing heterocyclic compound is optionally substituted with $C_{1-6}$ alkyl (e.g. methyl, ethyl, propyl, isopropyl, butyl, isobutyl, sec-butyl, tert-butyl, etc.), $C_{1-6}$ alkoxy (e.g. methoxy, ethoxy, propoxy, isopropoxy, butoxy, tert-butoxy, etc.), a halogen atom (e.g. fluorine, chlorine, bromine, etc.), oxo, thioxo, $C_{1-6}$ alkylthio (e.g. methylthio, ethylthio, propylthio, butylthio, etc.), etc.), etc.

Examples of the active ester include organic phosphoric acid ester (e.g. diethoxyphosphoric acid ester, diphenoxyphosphoric acid ester, etc.), p-nitrophenylester, 2,4-dinitrophenylester, cyanomethylester, pentachlorophenylester, N-hydroxysuccinimide ester, N-hydroxy-phthalimide ester, 1-hydroxybenzotriazole ester, 6-chloro-1-hydroxy-benzotriazole ester, 1-hydroxy-1H-2-pyridone ester, etc.

Examples of the active thioester include ester with aromatic heterocyclic thiol compound (e.g. 2-pyridylthiol ester, 2-benzo-thiazolylthiol ester), etc., said heterocyclic group being optionally substituted with $C_{1-6}$alkyl (e.g. methyl, ethyl, propyl, isopropyl, butyl, isobutyl, sec-butyl, tert-butyl, etc.), $C_{1-6}$ alkoxy (e.g. methoxy, ethoxy, propoxy, isopropoxy, butoxy, tert-butoxy, etc.), a halogen atom (e.g. fluorine, chlorine, bromine, etc.), $C_{1-6}$ alkyl thio (e.g. methylthio, ethylthio, propylthio, butylthio, etc.), etc.

This production method is usually carried out in a solvent and, if necessary, in the presence of a base or a condensing agent (e.g. carbodiimides (e.g. DCC, WSC, DIC, etc.), phosphoric acid derivatives (e.g. cyanophosphorate diethyl, DPPA, BOP-Cl, etc.), etc.).

Examples of the solvent and the base are the same as those described in the above Method A.

In the reaction, about 1 to about 5 moles (preferably about 1 to about 2 moles) of the compound (V) is used per 1 mole of the compound (IV).

The reaction temperature ranges about −50° C. to about 150° C., preferably about −20° C. to about 100° C.

The reaction time varies from depending on kind of the compound (IV) or (V), kind of the solvent and. the base, the reaction temperature, etc. and usually ranges from about 1 minute to about 100 hours, preferably about 15 minutes to about 48 hours.

Method C

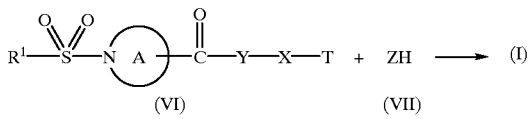

(VI)　　　　　(VII)

wherein T is a halogen atom or —O—SO$_2$R$^4$ (R$^4$ is a lower alkyl group optionally substituted with a halogen atom or a phenyl group which may be substituted, and the other symbols are as defined above.

In the above formula (VI), examples of the halogen atom represented by T include fluorine, chlorine, bromine, iodine, etc.

In the above formula, examples of the lower alkyl group represented by R$^4$ include a $C_{1-6}$ alkyl group such as methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethyl-butyl, 2,2-dimethylbutyl, 3,3-dimethylbutyl, 2-ethylbutyl, etc. Among others, a $C_{1-4}$ alkyl group such as methyl, ethyl, propyl, isopropyl, butyl, isobutyl, etc. is preferable.

Examples of the lower alkyl group substituted with a halogen atom (e.g. fluorine, chlorine, bromine, iodine, etc.) represented by R$^4$ include trichloromethyl, trifluoromethyl, etc.

Examples of the substituents for the phenyl group represented by R$^4$ include a lower alkyl group (the same as the above described lower alkyl group represented by R$^4$), a lower alkoxy group (e.g. $C_{1-6}$ alkoxy group such as methoxy, ethoxy, propoxy, isopropoxy, butoxy, etc.), a halogen atom (e.g. fluorine, chlorine, bromine, iodine, etc.), a nitro group, a cyano group, a carboxyl group, etc.

This production method is carried out by reacting the compound (VI) with the compound (VII). The reaction is usually carried out in a solvent. Any solvent can be used unless it inhibits this production method.

Examples of the solvent include alcohols such as methanol, ethanol, propanol, isopropanol, butanol, tert-butanol, etc., ethers such as dioxane, tetrahydrofuran, diethylether, tert-butylmethylether, diisopropylether, ethyleneglycol-dimethylether, etc., esters such as ethyl formate, ethyl acetate, n-butyl acetate, etc., halogenated hydrocarbons such as dichloromethane, chloroform, carbon tetrachloride, trichloroethylene, 1,2-dichloroethane, etc., hydrocarbons such as n-hexane, benzene, toluene, etc., amides such as formamide, N,N-dimethylformamide, N,N-dimethylacetamide, etc., ketones such as acetone, methylethylketone, methylisobutylketone, etc., nitrites such as acetonitrile, propionitrile, etc., etc., and additionally dimethylsulfoxide, sulforane, hexamethylphosphorylamide, water, etc., and these can be used singly or as a mixture.

If necessary, this production method can be carried out, in the presence of a base. Examples of the base include an alkali metal hydride such as potassium hydride, sodium hydride, etc., a metal $C_{1-6}$ alkoxide such as lithium ethoxide, lithium tert-butoxide, sodium methoxide, sodium ethoxide, sodium tert-butoxide, etc., an inorganic base such as lithium hydroxide, potassium hydroxide, sodium hydroxide, sodium carbonate, potassium carbonate, sodium hydrogen carbonate, etc., a tertiary amine such as triethylamine, tri(n-propyl)amine, tri(n-butyl) amine, diisopropylethylamine, cyclohexyldimethylamine, pyridine, lutidine, γ-collidine, N,N-dimethylaniline, N-methylpiperidine, N-methylpyrrolidine, N-methylmolpholine, etc.

In the reaction, about 1 to about 100 moles (preferably about 1 to about 50 moles) of the compound (VII) is used per 1 mole of compound (VI).

The reaction temperature ranges from about −30° C. to about 250° C., preferably about −10 to about 200° C.

The reaction time varies depending on kind of the compound (VI) or (VII), kind of the solvent, the reaction temperature, etc. and usually ranges from about 1 minute to about 72 hours, preferably about 15 minutes to about 24 hours.

Method D

A compound (D-I) or a salt thereof represented by the formula:

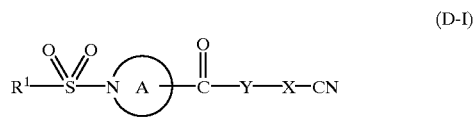

(D-I)

wherein each symbol is as defined above is reacted with a compound (D-II) represented by the formula: R$^{10}$OH wherein R$^{10}$ is a lower alkyl group to produce a compound (D-III) or a salt thereof represented by the formula:

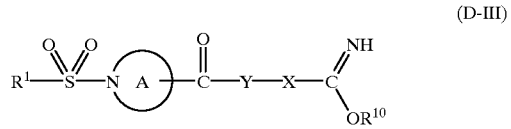
(D-III)

wherein each symbol is as defined above.

In the above formula, examples of the lower alkyl represented by $R^{10}$ include a $C_{1-6}$ alkyl group such as methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, etc. Among others, a $C_{1-4}$ alkyl group such as methyl, ethyl, propyl, isopropyl, butyl, isobutyl, etc. is preferable.

This production method is carried out by reacting the compound (D-I) with the compound (D-II) to produce the compound (D-III). The reaction is usually carried out in a solvent. The compound (D-II) can be used as the solvent and any solvent can be used unless it inhibits this production method.

Examples of the solvent include ethers such as dioxane, tetrahydrofuran, diethylether, tert-butylmethylether, diisopropylether, dimethoxyethane, ethyleneglycol-dimethylether, etc., esters such as ethyl formate, ethyl acetate, n-butyl acetate, etc., halogenated hydrocarbons such as dichloromethane, chloroform, carbon tetrachloride, trichloroethylene, 1,2-dichloroethane, etc., hydrocarbons such as n-hexane, benzene, toluene, etc., amides such as formamide, N,N-dimethylformamide, N,N-dimethylacetamide, etc., ketones such as acetone, methylethylketone, methylisobutylketone, etc., nitriles such as acetonitrile, propionitrile, etc., etc., and additionally dimethylsulfoxide, sulforane, hexamethylphosphorylamide, water, etc., and these can be used singly or as a mixture.

This production method is usually carried out in the presence of acid or base catalyst. Examples of the acid catalyst include an inorganic acid such as hydrochloric acid, hydrobromic acid, phosphoric acid, sulfuric acid, etc., an organic acid such as methanesulfonic acid, ethanesulfonic acid, camphorsulfonic acid, benzenesulfonic acid, toluenesulfonic acid, etc. Among others, halogenated hydride such as hydrochloric acid, hydrobromic acid, etc. is preferable. Examples of base catalyst include metal alkoxide of a compound (D-II). Preferable examples of the metal include alkali metal such as sodium, potassium, lithium, etc.

The reaction is carried out by using about 1 to about 10000 moles (preferably about 1 to about 1000 moles) of the compound (D-II) per 1 mole of the compound (D-I). Amount of the catalyst to be employed ranges from about 0.001 mole to an over excess amount.

The reaction temperature ranges from about −50° C. to about 150° C., preferably −30° C. to about 100° C.

The reaction time varies depending on kind of the compound (D-I) or (D-II), kind of the solvent, the reaction temperature, etc. and usually ranges from about 1 minute to about 96 hours, preferably about 30 minutes to about 48 hours.

The compound (D-III) is reacted with a compound (D-IV) or a salt thereof represented by the formula:

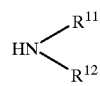
(D-IV)

wherein $R^{11}$ and $R^{12}$ are independently a hydrogen atom or an optionally substituted hydrocarbon group to produce a compound (D-V) or a salt thereof represented by the formula:

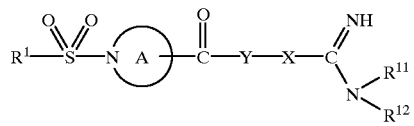
(D-V)

wherein each symbol is as defined above.

This production method is carried out by reacting the compound (D-III) and the compound (D-IV). The reaction is usually carried out in a solvent. Any solvent can be used unless it inhibits this production method.

Examples of the solvent include alcohols such as methanol, ethanol, propanol, isopropanol, butanol, tert-butanol, etc., ethers such as dioxane, tetrahydrofuran, diethylether, tert-butylmethylether, diisopropylether, .ethylenpeglycol-dimethylether, etc., esters such as ethyl formate, ethyl acetate, n-butyl acetate, etc., halogenated hydrocarbons such as dichloromethane, chloroform, carbon tetrachloride, trichloroethylene, 1,2-dichloroethane etc., hydrocarbons such as n-hexane, benzene, toluene, etc., amides such as formamide, N,N-dimethylformamide, N,N-dimethylacetamide, etc., ketones such as acetone, methylethylketone, methylisobutylketone, etc., nitrites such as acetonitrile, propionitrile, etc., etc., and additionally dimethylsulfoxide, sulfolane (tetramethylenesulfone), hexamethylphosphorylamide, water, etc., and these can be used singly or as a mixture.

In the reaction, about 1 mole or more (usually over excess amount) of the compound (D-IV) is used per 1 mole of the compound (D-III).

The reaction temperature ranges from about −50° C. to about 150° C., preferably about −30° C. to about 100° C.

The reaction time varies depending on kind of the compound (D-III) or (D-IV), kind of the solvent, the reaction temperature, etc. and usually ranges from about 15 minutes to about 120 hours, preferably about 30 minutes to about 96 hours.

Method E

A compound (E-I) or a salt thereof represented by the formula:

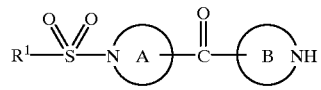
(E-I)

wherein the ring B is an optionally substituted divalent non-aromatic heterocyclic group, and the other symbols are as defined above is reacted with a compound (E-III) or a salt thereof represented by the formula:

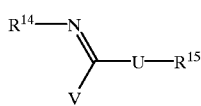

(E-III)

wherein $R^{14}$ is a hydrogen atom or an optionally substituted hydrocarbon group, $R^{15}$ is a lower alkyl group, U is an oxygen atom or an sulfur atom, V is a hydrogen atom, an optionally substituted hydrocarbon group or an amino group optionally having an optionally substituted hydrocarbon group to produce a compound (E-IV) or a salt thereof represented by the formula:

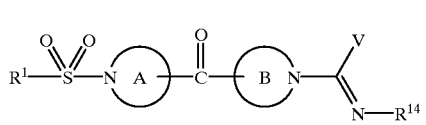

(E-IV)

wherein each symbol is as defined above.

In addition, a compound (E-II) or a salt thereof represented by the formula:

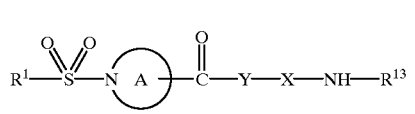

(E-II)

wherein $R^{13}$ is a hydrogen atom or an optionally substituted hydrocarbon group, and the other symbols are as defined above is reacted with a compound (E-II) or a salt thereof to produce a compound (E-V) or a salt thereof represented by the formula:

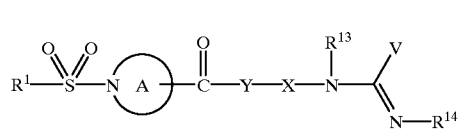

(E-V)

wherein each symbol is as defined above.

In the above formulas (E-I) to (E-V), examples of the "optionally substituted divalent non-aromatic heterocyclic group" represented by the ring B include the same optionally substituted divalent non-aromatic heterocyclic group as exemplified by the above described "optionally substituted divalent heterocyclic group" represented by Y. As the non-aromatic heterocyclic, a 5- to 8-membered (preferably 5- to 6-membered) ring is preferable and a saturated heterocyclic ring is more preferable. Examples of the "optionally substituted hydrocarbon group" represented by $R^{13}$, $R^{14}$ and V include the above described "optionally substituted hydrocarbon group" represented by $R^1$. Examples of the "lower alkyl group" represented by $R^{15}$ include the above described "lower alkyl group" represented by $R^{10}$. Examples of the "amino group optionally having an optionally substituted hydrocarbon group" represented by V include an amino group optionally having one to two of the above described "optionally substituted hydrocarbon group" represented by $R^1$.

The reaction is carried out by reacting the compound (E-I) or (E-II) with the compound (E-III). The reaction is usually carried out in a solvent. Any solvent can be used unless it inhibits this production method.

Examples of the solvent include alcohols such as methanol, ethanol, propanol, isopropanol, butanol, tert-butanol, etc., ethers such as dioxane, tetrahydrofuran, diethylether, tert-butylmethylether, diisopropylether, ethyleneglycol-dimethylether, etc., esters such as ethyl formate, ethyl acetate, n-butyl acetate, etc., halogenated hydrocarbons such as dichloromethane, chloroform, carbon tetrachloride, trichloroethylene, 1,2-dichloroethane etc., hydrocarbons such as n-hexane, benzene, toluene, etc., amides such as formamide, N,N-dimethylformamide, N,N-dimethylacetamide, etc., ketones such as acetone, methylethylketone, methylisobutylketone, etc., nitriles such as acetonitrile, propionitrile, etc., etc., and additionally dimethylsulfoxide, sulfolane (tetramethylenesulfone), hexamethylphosphorylamide, water, etc., and these can be used singly or as a mixture.

The reaction is usually carried out in the presence of a base. Examples of the base to be employed include a tertiary amine such as trimethylamine, triethylamine, tri(n-propyl) amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmolpholine, etc.; an alkali metal salt such as sodium hydrogen carbonate, potassium carbonate, etc.; an alkali hydroxide such as potassium hydroxide, sodium hydroxide, etc.; an alkoxide such as lithium ethoxide, lithium tert-butoxide, sodium methoxide, sodiumethoxide, carboxyl tert-butoxide, etc.; etc.

In the reaction, about 1 to about 100 moles(preferably about 1 to about 50 moles) of the compound (E-III) is used per 1 mole of the compound (E-I) or (E-II).

The reaction temperature ranges from about −30° C. to about 250° C., preferably about −10° C. to about 200° C.

The reaction time varies depending on kind of the compound (E-I), (E-II) or (E-III), kind of the solvent, the reaction temperature, etc. and usually ranges from about 1 minute to about 72 hours, preferably about 15 minutes to about 24 hours.

The starting materials, the compounds (II), (III), (IV), (V) and (VI), used in the above described Methods A to E can be produced by per se known method or a method similar thereto.

In addition, the compounds (D-I), (E-I) and (E-II) can be produced according to the production method of the compound (I) or a method similar thereto.

a) Production method of the compound (II)

i)

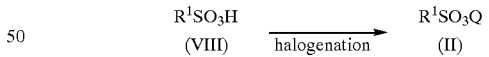

wherein each symbol is as defined above

This production method is carried out by halogenation of the compound (VIII) or a salt thereof (iorganic salt, organic salt, etc.). Examples of the iorganic salt of the compound (VIII) include a salt with alkali metal (e.g. a salt with sodium, a salt with potassium, etc.), a salt with alkaline earth metal (e.g. a salt with calcium, etc.). Examples of the organic salt of the compound (VIII) include a salt with trialkylamine (e.g. a salt with trimethylamine, triethylamine, tert-butyldimethylamine, diisopropylethylamine, etc.), a salt with an aromatic tertiary amine (e.g. N,N-dimethylaniline, pyridine, quinoline, etc.). Examples o a halogenating agent include e.g. phosphorous trichloride, phosphorous tribromide, phosphorous pentachloride, phosphorylchloride, phosphorylbromide, thionylchloride, thionyl-bromide, etc.

The reaction can be carried out by reacting the compound (VIII) with the halogenating agent as a solvent in the presence of no other solvent. The reaction can be carried out in the presence of a solvent other than the halogenating agent. Examples of the solvent include ethers such as dioxane, tetrahydrofuran, diethylether, diisopropyl-ether, dimethoxyethane, etc., halogenated hydrocarbons such as dichloromethane, chloroform, carbon tetrachloride, etc., aromatic hydrocarbons such as benzene, toluene, chlorobenzene, etc., amides such as N,N-dimethylformamide, N,N-dimethylacetamide, etc., and these can be used singly or as a mixture.

In the reaction, about 1 to about 100 moles (preferably about 1 to about 50 moles) of the halogenating agent is used per 1 mole of the compound (VIII). The reaction temperature ranges from about –30° C. to about 250° C., preferably about –20° C. to about 200° C. The reaction time varies depending on kind of the compound (VIII) or the halogenating agent, kind of the solvent, the reaction temperature, etc. and usually ranges from about 1 minute to about 72 hours, preferably about 10 minutes to about 24 hours.

ii)

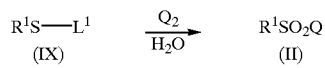

wherein $L^1$ is a hydrogen atom or a leaving group, and the other symbols are as defined above.

This production method is carried out by reacting the compound (IX) with chlorine or bromine in the presence of water to produce the compound (II). Examples of the leaving group represented by $L^1$ include —CN, —C(=NH)NH$_2$, etc. The reaction is usually carried out in a solvent and preferable examples of the solvent include that exemplified in the above described Method C. In the reaction, about 1 to about 100 moles, preferably about 1 to about 30 moles of the chlorine or bromine is used per 1 mole of the compound (IX). The reaction temperature ranges from about –50° C. to about 180 ° C., preferably about –30° C. to about 120° C.

There are many known methods for producing a sulfonyl chloride or a sulfonyl bromide of the compound (II) and the compound (II) can be produced by the above method i) or ii) as well as known methods or a method similar thereto.

b) Production method of the compound (III)

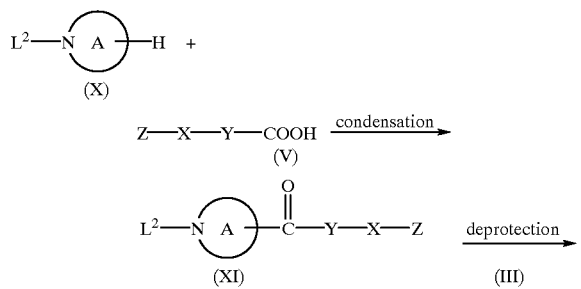

wherein $L^2$ is a protective group for an amino group, and other symbols are as defined above.

In the above formulas (X) and (XI), examples of the protective group represented by $L^2$ include formyl group, $C_{1-6}$ alkyl-carbonyl group (e.g. acetyl, ethylcarbonyl, etc.), benzyl group, tert-butyloxycarbonyl group, benzyloxycarbonyl group, allyloxycarbonyl group, phenylcarbonyl group, $C_{1-6}$ alkoxy-carbonyl group (e.g. methoxycarbonyl, ethoxycarbonyl, etc.), $C_{7-10}$ aralkyl-carbonyl group (e.g. benzylcarbonyl, etc.), trityl group, N,N-dimethylaminomethylene group, etc. These protective groups may be substituted with 1 to 3 halogen atoms (e.g. fluorine, chlorine, bromine, etc.), nitro group, etc.

This production method is carried out by reacting the compound (X) with a compound (V) or its reactive derivatives to produce the compound (XI).

The reaction conditions of this production method is the same as described in the above Method B. The compound (III) can be produced by removing the protective group of the compound (XI).

Examples of the method for removing the protective group include per se known methods or a similar method thereto such as a method using acid, base, reduction, ultraviolet light, acetic acid palladium, etc.

C) Production method of the compound (IV)

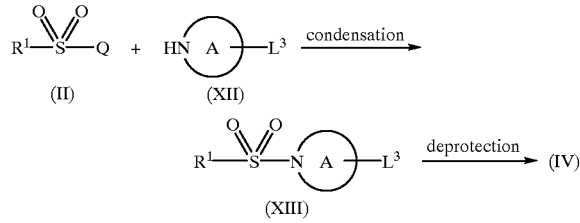

wherein $L^3$ is a protective group of an amino group, and the other symbols are as defined above.

In the formulas (XII) and (XIII), the protective group represented by $L^3$ is the same as that represented by $L^2$ in the above method b).

This production method is carried out by reacting the compound (II) with the compound (XII) to produce the compound (XIII). The reaction conditions of this production method are the same as described in the above Method A. The method for removing the protective group of the compound (XIII) is the same as that for the protective group represented by $L^3$ in the above method b).

d) Production method of the compound (V)

i)

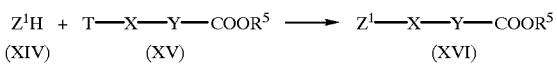

wherein $Z^1$ is an amino group substituted with an optionally substituted hydrocarbon group or an optionally substituted nitrogen-containing heterocyclic group, $R^5$ is a lower alkyl group or an optionally substituted benzyl group, and the other symbols are as defined above.

Examples of the optionally substituted hydrocarbon group, and the substituents f or the optionally substituted hydrocarbon group, the amino group and the optionally substituted nitrogen-containing heterocyclic group represented by $Z^1$ are the same as those of the above Z.

Examples of the lower alkyl group represented by $R^5$ include a $C_{1-6}$ alkyl group (e.g. methyl, ethyl, propyl, isopropyl, butyl, isobutyl, etc.), etc., and examples of the substituents for the optionally substituted benzyl group include a lower alkyl group (e.g. $C_{1-6}$ alkyl group such as methyl, ethyl, propyl, etc.), a lower alkoxy group (e.g. $C_{1-6}$ alkoxy group such as methoxy, ethoxy, propoxy, etc.), a halogen atom (e.g. fluorine, chlorine, bromine, etc.), etc. One to three of these optional substituent may be substituted at any possible position.

This production method is carried out by reacting the compound (XIV) with the compound (XV) to produce the compound (XVI). The reaction conditions of this production method are the same as described in the above Method C.

ii)

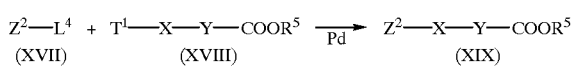

wherein $Z^2$ is an optionally substituted nitrogen-containing heterocyclic group, $L^4$ is —B($R^6$)$_2$ ($R^6$ is a hydroxyl group or a lower alkyl group), —Zn$T^2$, —Cu$T^2$ ($T^2$ is a halogen atom) or —Sn($R^7$)$_3$ ($R^7$ is a lower alkyl group), $T^1$ is a halogen atom or —O—SO$_2$$R^4$, and the other symbols are as defined above.

Examples of the substituents for the optionally substituted nitrogen-containing heterocyclic group represented by $Z^2$ are the same as the above described substituents represented by Z.

Examples of the lower alkyl group represented by $R^6$ and $R^7$ include a $C_{1-6}$ alkyl group such as methyl, ethyl, propyl, isopropyl, butyl, isobutyl, etc. Among others, methyl, ethyl, etc. are preferable. Examples of the halogen atom represented by $T^1$ and $T^2$ include fluorine, chlorine, bromine, iodine, etc.

This production method is usually carried out in a solvent in the presence of an appropriate catalyst and, if necessary, a base. Any solvent can be used unless it inhibits this production method.

Examples of the solvent include alcohols such as methanol, ethanol, propanol, isopropanol, butanol, tert-butanol, etc., ethers such as dioxane, tetrahydrofuran, diethylether, tert-butylmethylether, diisopropylether, ethyleneglycol-dimethylether, etc., esters such as ethyl formate, ethyl acetate, n-butyl acetate, etc., halogenated hydrocarbons such as dichloromethane, chloroform, carbon tetrachloride, trichloroethylene, 1,2-dichloroethane etc., hydrocarbons such as n-hexane, benzene, toluene, etc., amides such as formamide, N,N-dimethylformamide, N,N-dimethylacetamide, etc., ketones such as acetone, methylethylketone, methylisobutylketone, etc., nitriles such as acetonitrile, propionitrile, etc., etc., and additionally dimethylsulfoxide, sulfolane (tetramethylenesulfone), hexamethylphosphorylamide, water, etc., and these can be used singly or as a mixture.

Preferable examples of the catalyst used in the reaction include a palladium catalyst such as palladium chloride, palladium acetate, chlorobis(triphenylphosphine) palladium, tetrakis(triphenylphosphine) palladium, etc. Examples of the base include potassium hydrogen carbonate, sodium hydrogen carbonate, potassium carbonate, sodium carbonate, potassium hydroxide, sodium hydroxide, etc.

In the reaction, about 0.5 to about 4 moles (preferably about 0.7 to about 2 moles) of the compound (XVIII) are used per 1 mole of the compound (XVII) and about 0.0001 to about 0.1 mole of the catalyst is used per 1 mole of the compound (XVIII). The reaction temperature ranges from about −90° C. to about 150° C., preferably about −70° C. to about 100° C. The reaction time varies depending on the kind of compounds (XVII) and (XVIII), the kind of solvent, the reaction temperature, etc. and usually ranges from about 15 minutes to about 48 hours, preferably about 30 minutes to about 24 hours.

iii)

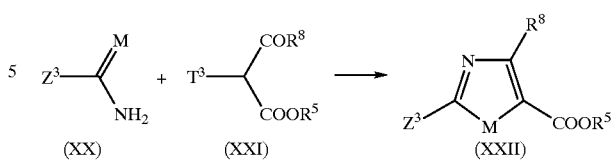

wherein $Z^3$ is an optionally substituted nitrogen-containing heterocyclic group, M is an oxygen atom or a sulfur atom, $T^3$ is a halogen atom, $R^8$ is a hydrogen atom or a lower alkyl group, and the other symbols are as defined above.

Examples of the substituents for the optionally substituted nitrogen-containing heterocyclic group represented by $Z^3$ are the same as those for the above Z. Examples of the lower alkyl group represented by $R^8$ include a $C_{1-6}$ alkyl group such as methyl, ethyl, n-propyl, isopropyl, n-butyl, isobutyl, sec-butyl, tert-butyl, etc.

This production method is carried out by reacting the compound (XX) with the compound (XXI) to produce the compound (XXII). The reaction is usually carried out in a solvent and examples of the solvent are the same as those used in the above method ii).

In the reaction, 1 to 5 moles (preferably 1 to 3 moles) of the compound (XXI) are used per 1 mole of the compound (XX). The reaction temperature ranges from −30° C. to 150° C., preferably −10° C. to 120° C. The reaction time varies depending on the kind of compound (XX) or (XXI), the kind of solvent, the reaction temperature, etc. and usually ranges from 5 minutes to 48 hours, preferably 15 minutes to 24 hours.

iv)

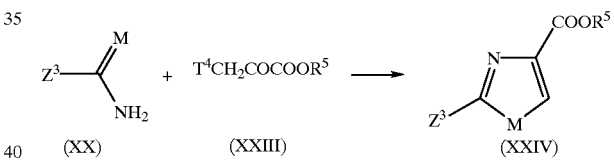

wherein $T^4$ is a halogen atom, and the other symbols are as defined above.

In the above formula, examples of the halogen atom represented by $T^4$ include chlorine, bromine, etc.

This reaction is carried out by reacting the compound (XX) with the compound (XXIII) to produce the compound (XXIV).

The reaction is carried out according to the same method as the above method iii) or a similar method thereto.

v)

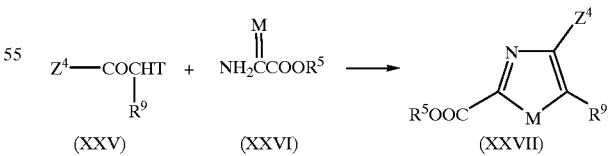

wherein $Z^4$ is an optionally substituted nitrogen-containing heterocyclic group, $R^9$ is a hydrogen atom or a lower alkyl group, and the other symbols are as defined above.

Examples of the substituents for the optionally substituted nitrogen-containing heterocyclic group represented by $Z^4$ are the same as those for the above Z. Examples of the lower alkyl group represented by $R^9$ include a $C_{1-6}$ alkyl group such as methyl, ethyl, n-propyl, isopropyl, n-butyl, isobutyl, sec-butyl, tert-butyl, etc.

The reaction is usually carried out in a solvent and examples of the solvent are the same as those used in the above method ii).

In the reaction, 0.8 to 5 moles (preferably 0.9 to 3 moles) of the compound (XXVI) are used per 1 mole of the compound (XXV). The reaction temperature and the reaction are the same conditions as described in the above described method iv).

The compounds (XVI), (XIX), (XXII), (XXIV) and (XXVII) produced according to the above-described methods can be transformed into a free acid form, if desired. For example, when $R^5$ is a lower alkyl group, hydrolysis with acid or alkali is employed. Preferable examples of the acid include hydrochloric acid, sulfuric acid, hydrobromic acid, etc. Preferable examples of the alkali include lithium hydroxide, potassium hydroxide, sodium hydroxide, calcium hydride, etc. When $R^5$ is an optionally substituted benzyl group, in addition to the above hydrolysis with acid or alkali, catalytic reduction (catalytic hydrogenation) can be employed to produce a free acid. In the catalytic reduction, catalysts are employed. Examples of the catalyst include platinum catalyst such as platinum oxide, platinum black, platinum carbon, etc., palladium catalyst such as palladium chloride, palladium black, palladium carbon, etc., rhodium catalyst such as rhodium carbon, rhodium almina, etc., Raney nickel, etc. The reduction reaction can be carried out under high pressure, if necessary, and said pressure ranges from about 1 to about 50 times atmospheric pressure, preferably about 1 to about 20 times atmospheric pressure. The reaction is usually carried out in a solvent and examples of the solvent are the same as that described in the above method ii). The reaction temperature ranges from about −10° C. to about 150° C., preferably about −5° C. to about 120° C. The reaction time varies depending on kind of the compound, the solvent and the catalyst, and usually ranges from about 15 minutes to about 72 hours, preferably about 30 minutes to about 24 hours.

When a free form of the compound is obtained according to the above described reaction of the present invention, it can be transformed into a salt thereof according to per se methods. When a salt of the compound is obtained according to the above described reaction of the present invention, it can be transformed into a free form thereof according to per se methods.

The compound (I) of this invention can be isolated from the reaction mixture by a conventional methods separation and purification means such as extraction, concentration, neutralization, filtration, recrystallization, column chromatography and thin-layer chromatography, etc.

Salts of the compound (I) can be obtained by per se known methods, e.g. by adding an inorganic acid or an organic acid to the compound (I).

When stereoisomers are present in the compounds (I), individual isomers or a mixture thereof are included in the scope of the present invention. And, it is also possible to produce these isomers individually.

The compounds (I), (I-1) and (I-2) may be hydrated or solvated.

The compounds (I) of the present invention or a salt thereof are low in toxicity, inhibit FXa and have anticoagulant activity, therefore, they are useful for the prevention or treatment of the following diseases of animals, especially mammals (e.g. human, monkey, cat, pig, horse, cow, mouse, rat, guinea pig, dog, rabbit, etc.). Among others, they are preferably used for the prevention or treatment of cerebral infarction (especially due to atrial fibrillation or auricular fibrillation), deep vein thrombosis, etc.

brain:
    cerebral infarction due to atrial fibrillation or auricular fibrillation, acute ischemic cerebral apoplexy, acute phase cerebral thrombosis, cerebral vasospasm after subarachnoid hemorrhage, Alzheimer's disease, transient ischemic attack (TIA), mixed dementia, cerebrovascular dementia, multiple sclerosis dementia, heart:
    acute cardiac infarction, sequela of cardiac infarction, unstable angina, angina pectoris, reobturation or restenosis after, stent-indwelling, PTCA (percutaneous transluminol coronary angioplasty), atherectomy, coronary intervention, periphery:
    deep vein thrombosis, pulmonary embolism, peripheral arterial obstruction, adult respiratory distress syndrome (ARDS), chronic renal disease (e.g. diabetic nephropathy, chronicglomerulonephrits, IgA nephropathy, etc.), diabetic cardiovascular disorder, diabetic pain, diabetic nerve disturbance, thrombosis due to hip and knee replacement surgeries, others:
    thrombocytopenia due to dialysis, thrombocytopenia due to operation, arteriosclerosis, cancer metastasis, systemic inflammation reaction syndrome (SIRS) or disseminated intravascular coagulation (DIC) in cases of pancreatitis, sepsis or cancer, rejection after transplantation, protecting organs or ameliorating function of organs after transplantation, various organ failure (e.g. pulmonary failure, hepatic insufficiency, renal insufficiency, heart failure, etc.) due to shock or DIC.

The compound (I) of the present invention or a salt thereof, alone or in combination with a pharmaceutically acceptable carrier, can be administered orally or non-orally.

Examples of pharmaceutical composition for oral administration of the compound (I) or a salt thereof of the present invention include tablets (including sugar-coated tablet, film coating tablet), pills, granules, powders, capsules (including soft capsules), syrups, emulsions, suspensions, etc. Examples of pharmaceutical composition for oral administration of the compound (I) or a salt thereof of the present invention include injections, inhalations, drops, suppositories, etc.

The content of the compound (I) or a salt thereof in the pharmaceutical composition of this invention varies depending on a kind of formulations and is usually about 2 to about 85 weight %, preferably about 5 to about 70 weight % based on the total weight of the composition.

Examples of the method for preparing the pharmaceutical compositions containing the compound (I) or a salt thereof include conventional methods generally used in this field. In addition, when the above pharmaceutical compositions are prepared, if desired, an appropriate amount of an additive which is generally used in this field such as an excipient, a binder, an disintegrating agent, a lubricant, a sweetener, a surfactant, a suspending agent, an emulsifier, etc. can be added to the compositions.

For example, a tablet of the compound (I) or a salt thereof may contain an excipient, a binder, an disintegrating agent, a lubricant, etc.; a pill and a granulate may contain an excipient, a binder, an disintegrating agent, etc.; a powder and a capsule may contain an excipient, etc.; a syrup may contain a sweetener, etc.; and an emulsion or a suspension may contain a surfactant, a suspending agent, an emulsifier, etc.

Examples of the excipient include lactose, sucrose, glucose, starch, fine crystalline cellulose, powdered glycyrrhiza, mannitol, sodium hydrogen carbonate, calcium phosphorate, calcium sulfate, etc.

Examples of the binder include 5 to 10 weight % of starch solution, 10 to 20 weight % of gum arabic or gelatin solution, 1 to 5 weight % of traganth solution, carboxymethylcellulose solution, sodium alginate solution, glycerin, etc.

Examples of the disintegrating agent include starch, calcium carbonate, etc.

Examples of the lubricant include magnesium stearate, stearic acid, calcium stearate, purified talc, etc.

Examples of the sweetener include glucose, fructose, invert sugar, sorbitol, xylitol, glycerin, simple syrup, etc.

Examples of the surfactant include sodium lauryl sulfate, polysorbate 80, sorbitan mono fatty acid ester, stearic acid, polyoxyl 40, etc.

Examples of the suspending agent include gum arabic, sodium alginate, sodium carboxymethylsellulose, methylcellulose, bentonite, etc.

Examples of the emulsifier include gum arabic, traganth, gelatin, polysorbate 80, etc.

In additition, when the above described compositions are prepared, if desired, an appropriate amount of a colorant, a preservative, an aromatic, a flavoring, a stabilizer, a viscous liquid, etc. which is generally used in this field can be added to the compositions.

The compound (I) or a salt thereof is low in toxicity and stable, therefore, it can be used safely. While the dosage of the compound (I) can vary with condition or body weight of patients, kind of the compound and administration routes, etc., when administered orally to a patient of e.g. thrombosis, a dose of about 1 to 1000 mg, preferably about 3 to 300 mg, more preferably about 1 to 20 mg of the active ingredient [compound (I)], per day for an adult (body weight: about 60 kg), divided into one to three times, is appropriate.

The pharmaceutical composition of the present invention can be used in combination with thrombolytic drug (e.g. tPA, heparin, urokinase, etc.), drug for treating Alzheimer's disease (e.g. Avan, Calan, etc.), drug for treating cholesterol (e.g. HMG-CoA reductase inhibitor such as Simvastatin, Pravastatin, etc., etc.), TG (triglyceride) decreasing drug (antihyperlipoproteinemic agent) (e.g. Clofibrate, etc.), AII antagonist (e.g. Blopress, etc.), anti-thrombocyte drug (e.g. aspirin, etc.), Ca antagonist (e.g. Calslot, Amlodipine, etc.) etc., or the active ingredient of these drugs can be added to the pharmaceutical composition of the present invention.

BEST MODE FOR CARRYING OUT THE INVENTION

The following working examples, experimental examples and reference examples will describe the present invention in further detail, but they are not intended to limit the present invention in any way.

Elution in column chromatography in Reference Examples and Working Examples was observed under TLC (Thin Layer Chromatography). In the TLC observation, silica gel 60F$_{254}$ (Merck) was used as a TLC plate, a solvent used for eluting the column chromatography was used as a mobile phase, and UV detector was employed for detection. Kiesel gel 60 (70 to 230 mesh; Merck) was used for a silica gel column chromatography.

Infrared (IR) spectra were recorded on a Shimazu FT-IR-8100 spectrometer in KBr.

The proton nuclear magnetic resonance ($^1$H-NMR) spectra were recorded on a Varian Gemini-200 (200 MHz) spectrometer using tetramethylsilane as the internal or external standard and chemical shifts are given in δ values (ppm). In the mixture of solvents, the value indicated in the parentheses means the ratio of each solvent. The symbol % for the solution stands for grams per 100 ml solution. The following abbreviations were used in Reference Examples and Working

EXAMPLES

| | |
|---|---|
| s: | singlet |
| d: | doublet |
| t: | triplet |
| q: | quartet |
| quint: | quintet |
| AB q: | AB type quartet |
| dd: | double doublet |
| m: | multiplet |
| br: | broad |
| brs: | broad singlet |
| J: | coupling constant |
| WSC: | water-soluble carbodiimide |

Reference Example 1

1-tert-Butoxycarbonyl-4-(4-chloromethylbenzoyl) piperazine

A THF (8 ml) solution of 4-chloromethylbenzoylchloride (5.3 g) was added dropwise at 0° C. to a THF (16 ml) solution of 1-tert-butoxycarbonylpiperazine (5.19 g) and triethylamine (2.82 g) and the solution was stirred at room temperature for 10 minutes. The reaction solution was concentrated and the obtained solid residue was washed with water and ethyl acetate, and dried to give a colorless solid of the title compound (9.44 g).

$^1$H-NMR (CDCl$_3$) δ: 1.47 (9H, s), 3.30–3.80 (8H, m), 4.61 (2H, s), 7.40 (2H, d, J=8.4 Hz), 7.46 (2H, d, J=8.4 Hz).

Reference Example 2

1-(2-Naphthalenesulfonyl)piperazine hydrochloride

A THF (10 ml) solution of 2-naphthalenesulfonylchloride (23 g, 101 mmol) was added dropwise to a THF (100 ml) solution of 1-formylpiperazine (11.4 g, 100 mmol) and triethylamine (15 g, 150 mmol) under ice-cooling. The solution was stirred at room temperature for 30 minutes, and concentrated. The residue was washed with water and diisopropylether and dried under reduced pressure to give 1-formyl-4-(2-naphthalenesulfonyl)piperazine.

$^1$H-NMR (CDCl$_3$) δ: 3.00–3.20 (4H, m), 3.48 (2H, t, J=5.0 Hz), 3.66 (2H, t, J=5.0 Hz), 7.58–7.77 (3H, m), 7.90–8.02 (4H, m), 8.33 (1H, s). IR (KBr): 1675, 1347, 1166 cm$^{-1}$.

To 1-formyl-4-(2-naphthalenesulfonyl)piperazine was added ethanol (30 ml) and 1 N hydrochloric acid (100 ml), and the solution was stirred for 5 hours under reflux. The reaction solution was concentrated, and the residue was washed with ethyl acetate and dried under reduced pressure to give 1-(2-naphthalenesulfonyl)piperazine hydrochloride (43.3 g).

Reference Example 3

1-(6-Chloronaphthalene-2-sulfonyl)piperazine hydrochloride

To a mixture of aqueous sodium hydrogen carbonate (10 ml) solution, 1-tert-butoxycarbonylpiperazine (1.0 g) and ethyl acetate (10 ml), was added 6-chloronaphthalene-2-sulfonylchloride (1.4 g) and the mixture was stirred at room temperature for 1 hour and extracted with dichloromethane. The extract was washed with water, dried and concentrated. The residue was crystallized from diisopropylether to give colorless crystals of 1-(tert-butoxycarbonyl)-4-(6-chloronaphthalene-2-sulfonyl)piperazine (2.02 g).

$^1$H-NMR (CDCl$_3$) δ: 1.38 (9H, s), 3.04 (4H, m), 3.52 (4H, m), 7.58 (1H, dd, J=2.2, 8.8 Hz), 7.76 (1H, dd, J=1.8, 8.8 Hz), 7.85–7.98 (3H, m), 8.31 (1H, s). IR (KBr): 1697, 1420, 1347, 1249, 1166 cm$^{-1}$.

To 1-(tert-butoxycarbonyl)-4-(6-chloronaphthalene-2-sulfonyl)piperazine (2.0 g) were added methanol (10 ml)and 4 N hydrochloric acid in ethyl acetate solution (20 ml), and the solution was stirred at room temperature 30 minutes. The reaction solution was concentrated, and the residue was treated with acetone to give amorphous powder which was dried under reduced pressure to give the title compound (1.66 g).

Reference Example 4

1-(4-Chloromethylbenzoyl)-4-(2-naphthalenesulfonyl)piperazine

To a mixture of 1-(2-naphthalenesulfonyl)piperazine hydrochloride (5.0 g) in ethyl acetate (60 ml) and an aqueous solution of 10% sodium hydrogen carbonate (40 ml) was added 4-chloromethylbenzoylchloride (3.02 g), and the solution was stirred at room temperature for 30 minutes. The organic layer was separated, washed with water and saturated sodium chloride, dried and concentrated. The residue was washed with diisopropylether and dried under reduced pressure to give the title compound (4.945 g, 78%).

$^1$H-NMR (CDCl$_3$) δ: 3.10 (4H, brs), 3.40–3.95 (4H, br), 4.56 (2H, s), 7.29 (2H, d, J=8.2 Hz), 7.39 (2H, d, J=8.2 Hz), 7.60–7.78 (3H, m), 7.90–8.05 (3H, m), 8.34 (1H, d, J=1.8 Hz).

Reference Example 5

1-(3-Chloromethylbenzoyl)-4-(2-naphthalenesulfonyl)piperazine

The title compound was synthesized according to a similar method described in Reference Example 4, using 3-chloromethylbenzoylchloride instead of 4-chloromethylbenzoylchloride.

$^1$H-NMR (CDCl$_3$) δ: 3.11 (4H, brs), 3.40–4.00 (4H, br), 4.54 (2H, s), 7.19–7.48 (4H, m), 7.58–7.78 (3H, m), 7.90–8.05 (3H, m), 8.33 (1H, d, J=1.8 Hz).

Reference Example 6

1-(4-Chloromethylbenzoyl)-4-(6-chloronaphthalene-2-sulfonyl)piperazine

The title compound was synthesized according to a similar method described in Reference Example 4, using 1-(6-chloronaphthalene-2-sulfonyl)piperazine hydrochloride instead of 1-(2-naphthalenesulfonyl)piperazine hydrochloride.

$^1$H-NMR (CDCl$_3$) δ: 3.10 (4H, brs), 3.40–4.00 (4H, br), 4.57 (2H, s), 7.30 (2H, d, J=8.4 Hz), 7.40 (2H, d, J=8.4 Hz), 7.60 (1H, dd, J=1.8, 8.6 Hz), 7.76 (1H, dd, J=1.8, 8.6 Hz), 7.93 (2H, d, J=8.6 Hz), 7.95 (1H, d, J=1.8 Hz), 8.31 (1H, d, J=1.8 Hz). IR (KBr): 1635, 1432, 1347, 1166 cm$^{-1}$.

Reference Example 7

1-(tert-Bbutoxycarbonyl)-4-(4-diisopropylaminomethylbenzoyl)piperazine

A DMF (50 ml) solution of 1-(tert-butoxycarbonyl)-4-(4-chloromethylbenzoyl)piperazine (5.185 g), potassium carbonate (2.114 g) and diisopropylamine (15.45 g) was stirred at 100° C. for 10 hours. The reaction solution was concentrated and the residue was dissolved in ethyl acetate, washed with water and sodium chloride solution, dried and concentrated to give a colorless solid of the title compound (4.707 g).

$^1$H-NMR (CDCl$_3$) δ: 1.02 (12H, d, J=6.6 Hz), 1.47 (9H, s), 3.00 (2H, quint, J=6.6 Hz), 3.46 (4H, brs), 3.65 (2H, s), 3.30–3.80 (4H, brs), 7.31 (2H, d, J=8.4 Hz), 7.43 (2H, d, J=8.4 Hz). IR (KBr): 1699, 1629, 1421, 1245, 1168 cm$^{-1}$.

Reference Example 8

1-(4-Diisopropylaminomethylbenzoyl)piperazine)

To a solution of 1-(tert-butoxycarbonyl)-4-(4-diisopropylaminomethylbenzoyl)piperazine (4.6 g) in ethyl acetate (10 ml) was added trifluoroacetic acid (20 ml), and the solution was stirred at room temperature for 1 hour and concentrated. The residue was dissolved in water. The solution was made alkaline with sodium hydroxide solution, extracted with dichloromethane. The extract was dried and concentrated to give amorphous powders which were filtered, washed with hexane and dried to afford the title compound (3.12 g).

$^1$H-NMR (CDCl$_3$) δ: 1.01 (12H, d, J=6.6 Hz), 2.88 (4H, brs), 3.00 (2H, quint, J=6.6 Hz), 3.30–3.85 (4H, brs), 3.65 (2H, s), 7.31 (2H, d, J=8.0 Hz), 7.42 (2H, d, J=8.0 Hz). IR (KBr): 3309, 1615, 1606, 1463, 1434, 1288 cm$^{-1}$.

Reference Example 9

1-(tert-Butoxycarbonyl)-4-[4-(N-ethyl-tert-butylaminomethyl)benzoyl]piperazine

The title compound (colorless solid) was synthesized according to a similar method described in Reference Example 7, using N-ethyl-tert-butylamine instead of diisopropylamine.

$^1$H-NMR (CDCl$_3$) δ: 0.88 (3H, t, J=7.0 Hz), 1.10 (9H, s), 1.47 (9H, s), 2.62 (2H, q, J=7.0 Hz), 3.45 (4H, brs), 3.30–3.90 (4H, brs), 3.69 (2H, s), 7.32 (2H, d, J=8.0 Hz), 7.45 (2H, d, J=8.0 Hz). IR (KBr): 1700, 1641, 1419, 1247, 1170, 1008 cm$^{-1}$.

Reference Example 10

1-(tert-Butoxycarbonyl)-4-[4-(2,6-dimethylpiperidinomethyl)benzoyl]piperazine

The title compound (pale yellow syrups) was synthesized according to a similar method described in Reference Example 7, using 2,6-dimethylpiperidine instead of diisopropylamine.

$^1$H-NMR (CDCl$_3$) δ: 1.02 (6H, d, J=6.2 Hz), 1.20–1.40 (4H, m), 1.47 (9H, s), 1.50–1.70 (2H, m), 2.48 (2H, m), 3.46 (4H, brs), 3.60 (4H, brs), 3.78 (2H, s), 7.32 (2H, d, J=8.0 Hz), 7.44 (2H, d, J=8.0 Hz). IR (Neat): 1699, 1639, 1419, 1247, 1172, 1008 cm$^{-1}$.

Reference Example 11

1-(tert-Butoxycarbonyl)-4-[4-(2-diisopropylaminoethyl)benzoyl]piperazine

To a DMF (10 ml) solution of 4-(2-diisopropylaminoethyl)benzoic acid (300 mg) was added 1,1-carbonyldiimidazole (215 mg), and the solution was stirred at room temperature for 15 minutes. To the solution was added 1-tert-butoxycarbonylpiperazine (247 mg), and the solution was stirred at room temperature for 4 hours. The reaction solution was concentrated, and the residue was dissolved in ethyl acetate, washed with water and sodium chloride solution, dried and concentrated to give colorless oil of the title compound (483 mg).

$^1$H-NMR (CDCl$_3$) δ: 1.01 (12H, d, J=6.6 Hz), 1.47 (9H, s), 2.55–2.80 (4H, m), 3.05 (2H, quint, J=6.6 Hz), 3.30–3.90 (8H, m), 7.23 (2H, d, J=8.2 Hz), 7.32 (2H, d, J=8.2 Hz). IR (Neat): 1700, 1644, 1419, 1245, 1170 cm$^{-1}$.

Reference Example 12

1-(6-Bromonaphthalene-2-sulfonyl)piperazine hydrochloride

To a mixture of 1-tert-butoxycarbonylpiperazine (1.25 g), sodium hydrogen carbonate solution (10 ml) and ethyl acetate (10 ml), was added 6-bromonaphthalene-2-sulfonylchloride (2.05 g), and the mixture was stirred at room temperature for 1 hour and extracted with dichloromethane. The extract was washed with water, dried and concentrated. The residue was crystallized with diisopropylether to give 1-(tert-butoxycarbonyl)-4-(6-bromonaphthalene-2-sulfonyl)piperazine as colorless crystals (2.83 g).

$^1$H-NMR (CDCl$_3$) δ: 1.38 (9H, s), 3.04 (4H, t, J=5.0 Hz), 3.52 (4H, t, J=5.0 Hz), 7.65–7.95 (4H, m), 8.11 (1H, s), 8.29 (1H, s). IR (KBr): 1695, 1423, 1347, 1249, 1166 cm$^{-1}$.

To the obtained 1-(tert-butoxycarbonyl)-4-(6-bromonaphthalene-2-sulfonyl)piperazine (2.80 g) were added methanol (10 ml) and 4 N hydrochloric acid in ethyl acetate solution (25 ml), and the solution was stirred at room temperature for 30 minutes. The reaction solution was concentrated and the residue was treated with acetone to give amorphous powders. The powders were dried under reduced pressure to give the title compound (2.358 g).

Reference Example 13

4-(3-Pyridyl)benzoic acid

To a solution of ethyl 4-bromobenzoate (1.15 g), 3-pyridyldiethyl barate (888 mg), tetrakistriphenylphosphine palladium(0) (500 mg) in dimethoxyethane (20 ml) was added 2 M sodium carbonate solution (5 ml) and the solution was heated for 15 hours under reflux. The reaction solution was diluted with ethyl acetate, and the organic layer was separated, washed with water and extracted with 1 N hydrochloric acid. The extract was made alkaline with sodium hydroxide solution, extracted with ethyl acetate. The extract was dried and concentrated to give oil of ethyl 4-(3-pyridyl)benzoate (2.14 g).

$^1$H-NMR (CDCl$_3$) δ: 1.43 (3H, t, J=7.0 Hz), 4.42 (2H, q, J=7.0 Hz), 7.41 (1H, dd, J=4.8, 8.2 Hz), 7.66 (2H, d, J=8.8 Hz), 7.92 (1H, dt, J=2.0, 8.2 Hz), 8.16 (2H, d, J=8.8 Hz), 8.65 (1H, dd, J=2.0, 4.8 Hz), 8.89 (1H, d, J=2.0 Hz). IR (Neat): 1716, 1274 cm$^{-1}$.

To a solution of the obtained ethyl 4-(3-pyridyl)benzoate (2.14 g) in ethanol (20 ml) was added 1 N sodium hydroxide solution (15 ml), and the solution was stirred at room temperature for 2 hours. The reaction solution was concentrated and the residue was dissolved in water, to which was added 1 N hydrochloric acid (15 ml). The precipitate was filtered, washed with water and dried to give the title compound (1.488 g).

Reference Example 14

5-(4-Pyridyl)-2-thiophenecarboxylic acid

To a solution of methyl 5-bromo-2-thiophenecarboxylate (884 mg), 4-pyridyl boric acid (500 mg), tetrakistriphenylphosphine palladium(0) (250 mg) in dimethoxyethane (15 ml) was added 2 M sodium carbonate solution (4 ml) and the solution was heated for 15 hours under reflux. The reaction solution was diluted with ethyl acetate and the organic layer was separated, washed with water and extracted with 1 N hydrochloric acid. The extract was made alkaline with sodium hydroxide solution and extracted with ethyl acetate. The extract was dried and concentrated to give pale yellow solid of methyl 5-(4-pyridyl)-2-thiophenecarboxylate (428 mg).

$^1$H-NMR (CDCl$_3$) δ: 3.93 (3H, s), 7.47 (1H, d, J=4.0 Hz), 7.50 (2H, d, J=6.2 Hz), 7.80 (1H, d, J=4.0 Hz), 8.65 (2H, d, J=6.2 Hz). IR (KBr): 1712, 1453, 1417, 1282, 1247 cm$^{-1}$.

To a solution of the obtained methyl 5-(4-pyridyl)-2-thiophenecarboxylate (410 mg) in ethanol (20 ml) was added 1 N sodium hydroxide solution (4 ml) and the mixture was stirred at room temperature for 2 hours. The reaction solution was concentrated, and the residue was dissolved in water, to which was added 1 N hydrochloric acid (4 ml). The precipitate was filtered, washed with water and dried to give the title compound (363 mg).

Reference Example 15

5-(4-Pyridyl)-2-furancarboxylic Acid

To a solution of methyl 5-bromo-2-furancarboxylate (820 mg), 4-pyridyl boric acid (500 mg), tetrakistriphenylphosphine palladium(0) (250 mg) in dimethoxyethane (15 ml) was added 2 M sodium carbonate solution (4 ml) and the solution was heated for 15 hours under reflux. The reaction solution was diluted with ethyl acetate, and the organic layer was separated, washed with water, extracted with 1 N hydrochloric acid. The extract was made alkaline with sodium hydroxide solution, extracted with ethyl acetate, dried and concentrated to give a colorless solid of methyl 5-(4-pyridyl)-2-furancarboxylate (126 mg). $^1$H-NMR (CDCl$_3$) δ: 3.94 (3H, s), 6.96 (1H, d, J=3.8 Hz), 7.27 (1H, d, J=3.8 Hz), 7.64 (2H, d, J=6.2 Hz), 8.68 (2H, d, J=6.2 Hz). IR (KBr): 1727, 1608, 13,7, 1145 cm$^{-1}$.

To a solution of the obtained methyl 5-(4-pyridyl)-2-furancarboxylate (100 mg) in ethanol (10 ml) was added 1 N sodium hydroxide solution (4 ml) and the solution was stirred at room temperature for 2 hours. The reaction solution was concentrated and the residue was dissolved in water, to which was added 1 N hydrochloric acid (4 ml). The precipitate was filtered, washed with water and dried to give the title compound (59 mg).

Reference Example 16

4-(1H-Imidazol-1-yl)benzoic acid

A mixture of ethyl 4-fluorobenzoate (8.4 g), imidazole (4.08 g) and potassium carbonate (20.7 g) in DMF (30 ml) was stirred at 100° C. for 10 hours and concentrated. To the residue was added ethyl acetate, and the mixture was washed with water, dried and concentrated. To the residue was added hexane and insoluble materials were filtered, washed with hexane, dried to give a colorless solid ethyl of 4-(1H-imidazol-1-yl)benzoate (1.74 g).

$^1$H-NMR (CDCl$_3$) δ: 1.42 (3H, t, J=7.2 Hz), 4.42 (2H, q, J=7.2 Hz), 7.25 (1H, s), 7.36 (1H, t, J=1.4 Hz), 7.48 (2H, d, J=8.8 Hz), 7.95 (1H, s), 8.18 (2H, d, J=8.8 Hz).

To a solution of the ethyl obtained 4-(1H-imidazol-1-yl) benzoate (1.73 g) in ethanol (18 ml) was added 1 N sodium hydroxide solution (10 ml) and the solution was stirred at room temperature for 2 hours. The reaction solution was concentrated, and the residue was dissolved in water, to which was added 1 N hydrochloric acid (10 ml). The precipitate was filtered, washed with water and dried to give the title compound (1.43 g).

Reference Example 17

4-(1,2,4-Triazol-1-yl)benzoic acid and 4-(1,2,4-triazol-4-yl)benzoic acid

A mixture of ethyl 4-fluorobenzoate (8.4 g), 1,2,4-triazole (4.14 g) and potassium carbonate (20.7 g) in DMF (30 ml) was stirred at 100° C. for 3 hours and concentrated. To the residue was added dichloromethane, and the mixture was washed with water, dried and concentrated. The residue was purified with silica gel column chromatography (dichloromethane:methanol=50:1→20:1) to give a colorless solid of ethyl 4-(1,2,4-triazol-1-yl)benzoate (4.0 g) and ethyl 4-(1,2,4- triazol-4- yl)benzoate (369 mg).

Ethyl 4-(1,2,4-triazol-1-yl)benzoate:
$^1$H-NMR (CDCl$_3$) δ: 1.43 (3H, t, J=7.0 Hz), 4.42 (2H, q, J=7.0 Hz), 7.79 (2H, d, J=8.8 Hz), 8.15 (1H, s), 8.20 (2H, d, J=8.8 Hz), 8.66 (1H, s). IR (KBr): 1722, 1610, 1523, 1440, 1278, 1224, 1106 cm$^{-1}$.

Ethyl 4-(1,2,4-triazol-4-yl)benzoate:
$^1$H-MMR (CDCl$_3$) δ: 1.43 (3H, t, J=7.0 Hz), 4.44 (2H, q, J=7.0 Hz), 7.49 (2H, d, J=8.8 Hz), 8.24 (2H, d, J=8.8 Hz), 8.56 (2H, s). IR (KBr): 1700, 1614, 1529, 1504, 1284, 1259, 1241, 1085 cm$^{-1}$.

To a solution of the obtained ethyl 4-(1,2,4-triazol-1-yl)benzoate (3.8 g) in ethanol (20 ml)-THF (10 ml) was added 1 N sodium hydroxide solution (20 ml), and the solution was stirred at room temperature for 2 hours. The reaction solution was concentrated and the residue was dissolved in water, to which was added 1 N hydrochloric acid (20 ml). The precipitate was filtered, washed with water and dried to give the title compound, 4-(1H-imidazol-1-yl)benzoic acid (3.147 g).

To a solution of the obtained ethyl 4-(1,2,4-triazol-4-yl)benzoate (365 mg) in ethanol (4 ml)-THF (4 ml) was added 1 N sodium hydroxide solution (4 ml), and the solution was stirred at room temperature for 2 hours. The reaction solution was concentrated and the residue was dissolved in water, to which was added 1 N hydrochloric acid (4 ml). The precipitate was filtered, washed with water and dried to give the title compound, 4-(1H-imidazol-4-yl)benzoic acid (275 mg).

Reference Example 18

4-(4-Pyridyl)-2-thiazolecarboxylic acid

A solution of 4-bromoacetylpyridine hydrobromide (5.62 g) and ethyl thiooxamate (2.66 g) in ethanol (80 ml) was heated for 1 hour under reflux and concentrated. To the residue was added sodium bicarbonate solution and ethyl acetate. The organic layer was separated, washed with water and sodium chloride solution, dried and concentrated. The residue was purified with silica gel column chromatography (ethyl acetate) to give pale yellow solid of ethyl 4-(4-pyridyl)-2-thiazolecarboxylate (2.64 g).
$^1$H-NMR (CDCl$_3$) δ: 1.47 (3H, t, J=6.5 Hz), 4.52 (2H, q, J=6.5 Hz), 7.90 (2H, d, J=6.2 Hz), 8.02 (1H, s), 8.71 (2H, d, J=6.2 Hz).

To the obtained ethyl 4-(4-pyridyl)-2-thiazolecarboxylate (1.5 g) in ethanol (10 ml) solution was added 1 N sodium hydroxide solution (10 ml), and the solution was stirred at room temperature for 2 hours. The reaction solution was concentrated and the residue was dissolved in water, to which was added 1 N hydrochloric acid (10 ml). The precipitate was filtered, washed with water and dried to give the title compound (1.105 g).

Reference Example 19

2-(4-Pyridyl)-4-thiazolecarboxylic acid

A solution of thioisonicotinamide (5.0 g) and ethyl bromopyruvate (7.22 g) in ethanol (90 ml) was heated for 5 hours under reflux and concentrated. To the residue were added sodium bicarbonate solution and ethyl acetate, and the organic layer was separated, washed with water and sodium chloride solution, dried and concentrated. The residue was purified with silica gel column chromatography (ethyl acetate) to give pale yellow solid of ethyl 2-(4-pyridyl)-4-thiazolecarboxylate (4.55 g).
$^1$H-NMR (CDCl$_3$) δ: 1.44 (3H, t, J=7.0 Hz), 4.47 (2H, q, J=7.0 Hz), 7.88 (2H, d, J=6.2 Hz), 8.28 (1H, s), 8.75 (2H, d, J=6.2 Hz).

To a solution of the obtained ethyl 2-(4-pyridyl)-4-thiazolecarboxylate (1.5 g) in ethanol (10 ml) was added 1 N sodium hydroxide solution (10 ml), and the solution was stirred at room temperature for 2 hours. The reaction solution was concentrated and the residue was dissolved in water, to which was added 1 N hydrochloric acid (10 ml). The precipitate was filtered, washed with water and dried to give the title compound (1.264 g).

Reference Example 20

Ethyl 4-methyl-2-(4-pyridyl)thiazole-5-carboxylate

A mixture of thioisonicotinamide (2.76 g) and ethyl 2-chloroacetoacetate (3.6 g) in ethanol (30 ml) was heated for 20 hours under reflux and the solvent was evaporated. To the residue was added saturated sodium hydrogen carbonate solution, and the solution was extracted with ethyl acetate. The extract was washed with water, dried and concentrated. The residue was subjected to silica gel chromatography, and eluted with hexane-ethyl acetate (2:1) to give the title compound as crystals (2.0 g, 40.3%).
$^1$H-NMR (CDCl$_3$) δ: 1.40(3H, t, J=7.2 Hz), 2.81(3H, s), 4.38(2H, q, J=7.2 Hz), 7.81(2H, d, J=6.2 Hz), 8.73(2H, d, J=6.2 Hz).

Reference Example 21

4-Methyl-2-(4-pyridyl)thiazol-5-carboxylic acid

A mixture of ethyl 4-methyl-2-(4-pyridyl)thiazole-5-carboxylate (744 mg), 1 N NaOH (4 ml) and tetrahydrofuran-ethanol (1:1, 6 ml) was stirred at room temperature for 1 hour and diluted with water, to which was added 1 N hydrochloric acid (4 ml) to give the title compound as crystals (595 mg, 90.2%).
$^1$H-NMR (DMSO-d$_6$) δ: 2.71(3H, s), 7.90(2H, d, J=5.2 Hz), 8.74(2H, d, J=5.2 Hz).

Reference Example 22

2-(4-Pyridyl)thiazol-5-carboxylic acid ethyl

According to a similar method described in Reference Example 20, the title compound was obtained as crystals, from thioisonicotinamide and ethyl 2-chloro-2-formylacetate.
$^1$H-NMR (CDCl$_3$) δ: (1.42, 3H, t, J=7.2 Hz), 4.42(2H, q, J=7.2 Hz), 7.84(2H, d, J=6.4 Hz), 8.50(1H, s), 8.76(2H, d, J=6.2 Hz).

Reference Example 23

2-(4-Pyridyl)thiazol-5-carboxylic acid

According to a similar method described in Reference Example 21, the title compound was obtained as crystals.

$^1$H-NMR (DMSO-d$_6$) δ: 7.95(2H, d, J=6.2 Hz), 8.52(1H, s), 8.76(2H, d, J=6.2 Hz).

Reference Example 24

Ethyl 4-(4-pyridyl)benzoate

To a mixture of ethyl 4-bromobenzoate (2.29 g), 4-pyridyl borate (1.23 g), 1 M sodium hydrogen carbonate solution (30 ml) and 1,2-dimethoxyethane (40 ml) was added tetrakis (triphenylphosphine)palladium (0.3 g) and the mixture was stirred for 3 hours with reflux under nitrogen atmosphere. To the mixture was added water and the solution was extracted with ethyl acetate. The extract was washed with water, dried (MgSO$_4$) and concentrated. The residue was subjected to silica gel chromatography, and eluted with hexane-ethyl acetate (2:1) to give the title compound as crystals (1.15 g, 50.7%).

$^1$H-NMR (CDCl$_3$) δ: 1.43(3H, t, J=6.8 Hz), 4.41(2H, q, J=6.8 Hz), 7.54(2H, d, J=5.2 Hz), 7.70(2H, d, J=8.8 Hz), 8.16(2H, d, J=8.8 Hz), 8.70(2H, d, J=5.2 Hz).

Reference Example 25

4-(4-Pyridyl)benzoic acid

A mixture of ethyl 4-(4-pyridyl)benzoate (1.0 g), 1 N NaOH (8.8 ml) and ethanol (8.8 ml) was stirred at room temperature for 1 hour and diluted with water, to which was added 1 N hydrochloric acid (8.8 ml) to give the title compound as crystals (0.76 g, 86.4%).

$^1$H-NMR (DMSO-d$_6$) δ: 7.75(2H, d, J=6.2 Hz), 7.92(2H, d, J=8.2 Hz), 8.07(2H, d, J=8.2 Hz), 8.68(2H, d, J=6.2 Hz).

Reference Example 26

Methyl 6-(4-pyridyl)nicotinate

The title compound was obtained from methyl 6-chloronicotinate and 4-pyridyl borate, according to a similar method described in Reference Example 24.

$^1$H-NMR (CDCl$_3$) δ: 4.00(3H, s), 7.89(1H, d, J=8.0 Hz), 7.94(2H, d, J=6.2 Hz), 8.42(1H, dd, J=1.8, 8.0 Hz), 8.77(2H, d, J=6.2 Hz), 9.32(1H d, J=1.8 Hz).

Reference Example 27

6-(4-Pyridyl)nicotinic acid

The title compound was obtained as crystals, according to a similar method described in Reference Example 25.

$^1$H-NMR (DMSO-d$_6$) δ: 8.11(2H, d, J=6.0 Hz), 8.25(1H, d, J=8.2 Hz), 8.41(1H, dd, J=2.2, 8.2 Hz), 8.75(2H, d, J=6.0 Hz), 9.21(1H, d, J=2.2 Hz).

Reference Example 28

4-(Diisopropylaminomethyl)-2-methoxybenzoic acid

A mixture of methyl 2-methoxy-4-methylbenzoate (5.0 g), N-bromosuccinimide (4.94 g), 2,2'-azobis (isobutyronitrile) (0.23 g) and carbon tetrachloride (50 ml) was heated for 40 minutes under reflux. The mixture was cooled and the precipitate was filtered off. The filtrate was concentrated to give methyl 4-bromomethyl-2-methoxybenzoate as an oil.

$^1$H-NMR (CDCl$_3$) δ: 3.89(3H, s), 3.93(3H, s), 7.00(2H, m), 7.77(1H, d, J=8.0 Hz).

A mixture of methyl 4-bromomethyl-2-methoxybenzoate (2.59 g), diisopropylamine (3.92 ml), potassium carbonate (1.38 g) and dimethylformamide (30 ml) was stirred at 80° C. for 2 hours, to which was added water and extracted with ethyl acetate. The extract was washed with water, dried (MgSO$_4$) and concentrated. The residue was dissolved in THF-EtOH (1:1, 30 ml), to which was added 1 N sodium hydroxide solution (15 ml) and the solution was stirred at 80° C. for 20 minutes. To the solution was added water and the solution was washed with ether, made acidic with 1 N hydrochloric acid and extracted with ethyl acetate. The extract was washed with water, dried (MgSO$_4$) and concentrated. The residue was dissolved in THF and insoluble materials were filtered off. The filtrate was concentrated and crystallized with isopropylether to give the title compound (0.3 g).

$^1$H-NMR (DMSO-d$_6$) δ: 1.07(12H, d, J=6.6 Hz), 3.14(1H, m), 3.63(1H, m), 3.82(3H, s), 7.04(1H, d, J=7.6 Hz), 7.21 (1H, s), 7.62(1H, d, J=7.6 Hz).

Reference Example 29

1-(tert-Butoxycarbonyl)-4-[4-methyl-2-(4-pyridyl)-5-thiazolecarbonyl]piperazine To a mixture of 1-(tert-butoxycarbonyl)piperazine (3.72 g), 4-methyl-2-(4-pyridyl)-5-thiazolecarboxylic acid (4.4 g), triethylamine (2.5 g) and HOBt (2.7 g) in DMF (60 ml), was added WSC hydrochloride (4.217 g) under ice-cooling and the mixture was stirred at room temperature for 2 hours. The reaction solution was concentrated, and to the residue were added dichloromethane and sodium bicarbonate aqueous solution. The organic layer was separated, washed with water and brine, dried and concentrated. The residue was purified with silica gel chromatography (dichloromethane:methanol=50:1) to give colorless crystals of the title compound (6.49 g).

$^1$H-NMR (CDCl$_3$) δ: 1.48 (9H, s), 2.52 (3H, s), 3.50 (4H, m), 3.61 (4H, m), 7.77 (2H, d, J=6.2 Hz), 8.72 (2H, d, J=6.2 Hz). IR (KBr): 1688, 1626, 1418, 1244 cm$^{-1}$.

Reference Example 30

1-[4-Methyl-2-(4-pyridyl)-5-thiazolecarbonyl] piperazine dihydrochloride

To 1-(tert-butoxycarbonyl)-4-[4-methyl-2-(4-pyridyl)-5-thiazolecarbonyl]piperazine (6.40 g) were added methanol (30 ml) and 4N hydrochloric acid in ethyl acetate (30 ml), and the mixture was stirred at room temperature for 30 minutes. The reaction solution was concentrated, and the residue was washed with ether and dried under reduced pressure to give powders of the title compound (5.8 g).

$^1$H-NMR (DMSO-d$_6$) δ: 2.09 (3H, s), 3.19 (4H, m), 3.79 (4H, m), 8.20–8.30 (2H, m), 8.90 (2H, d, J=6.6 Hz), 9.45 (2H, brs).

Reference Example 31

N,O-Dimethyl-N-(1-tritylpiperidine-4-carbonyl) hydroxyl-amine.

To a mixture of 1-tritylpiperidine-4-carboxylic acid (7.0 g), O,N-dimethylhydroxylamine hydrochloride (2.0 g) and triethylamine (2.9 ml) in dichloromethane (70 ml) was added WSC (3.97 g), and the mixture was stirred at room temperature for 1 hour and concentrated. To the residue was added ethyl acetate, and the mixture was washed with water, dried (MgSO$_4$) and concentrated. The resulting crystals (6.3 g) were washed with isopropylether.

NMR (CDCl$_3$): 1.34–1.72(4H,m), 2.00–2.20(2H, m), 2.54(2H, m), 3.17(3H, s), 3.21(2H, m), 3.59(3H, s), 7.12–7.48(15H, m).

Reference Example 32

N-(4-Bromobenzyl)-N,N-diisopropylamine

A mixture of 4-bromobenzylbromide (5.0 g), N,N-diisopropylamine (7.85 ml) and potassium carbonate (2.76 g) in dimethylformamide (50 ml) was stirred at 80° C. for 2 hours. To the mixture was added water, and the mixture was extracted with ether. The extract was washed with water, dried (MgSO$_4$) and concentrated to give the title compound (5.0 g).

NMR (CDCl$_3$): 1.00 (12H, d, J=6.6 Hz), 2.99 (2H, m), 3.57 (2H, s), 7.25 (2H, d, J=8.8 Hz), 7.40 (2H, d, J=8.8 Hz).

Reference Example 33

4-(4-Diisopropylaminomethylbenzoyl)-1-tritylpiperidine

To a solution of N-(4-bromobenzyl)-N,N-diisopropylamine (2.3 g) in THF (10 ml) was added dropwise at −78° C. n-BuLi (1.6 mmol/ml hexane solution, 3.8 ml). Ten minutes later, N,O-dimethyl-N-(1-trityl-piperidine-4-carbonyl)hydroxylamine (1.5 g) in THF (20 ml) was added dropwise to the mixture, and the mixture was stirred at the same temperature for 30 minutes. To the mixture was added ammonium chloride aqueous solution, and the mixture was extracted with ethyl acetate. The extract was washed with water, dried (MgSO$_4$) and concentrated to give the title compound (5.0 g).

NMR (CDCl$_3$): 0.98 (6H, d, J=4.8 Hz), 1.02 (6H, d, J=4.8 Hz), 1.50 (2H, m), 1.83 (2H, m), 2.08 (2H, m), 3.01 (2H, m), 3.08 (1H, m), 3.64 (2H, s), 7.12–7.48 (17H, m), 7.81 (2H, d, J=8.0 Hz).

Reference Example 34

2-(6-tert-Butoxycarbonylamino-3-pyridyl)-4-methyl-5-thiazolecarboxylic acid

A mixture of 6-tert-butoxycarbonylaminonicotinamide (1.66 g) and phosphorous pentasulfide (2.33 g) in THF (150 ml) was heated for 15 minutes under reflux and filtered. The filtrate was concentrated, and to the residue was added sodium hydrogen carbonate aqueous solution. The mixture was extracted with ethyl acetate, and the extract was washed with water, dried (MgSO$_4$) and concentrated to give 6-tert-butoxycarbonylaminothionicotinamide as crystals (0.75 g), which was filtered and washed with ether.

A mixture of 6-tert-butoxycarbonylaminothionicotinamide (506 mg), ethyl 2-chloro-acetoacetate (492 mg) and sodium acetate (252 mg) in ethanol (20 ml) was heated for 2 hours under reflux, and to the mixture were added sodium hydrogen carbonate aqueous solution and water. The precipitated crystals were collected by filtration, and the crystals were successively washed with water, ethanol and ether to give ethyl 2-(6-tert-butoxycarbonylamino-3-pyridyl)-4-methyl-5-thiazolecarboxylate (200 mg).

NMR (CDCl$_3$): 1.39 (3H, t, J=6.2 Hz), 1.57 (9H, s), 2.77 (3H, s), 4.35 (2H, q, J=6.2 Hz), 8.09 (1H, d, J=8.8 Hz), 8.20 (1H, dd, J=2.2, 8.8 Hz), 8.55 (1H, bs), 8.89 (1H, d, J=2.2 Hz).

A mixture of ethyl 2-(2-tert-butoxycarbonylamino-5-pyridyl)-4-methyl-5-thiazolecarboxylate (180 mg), 1N NaOH (2 ml) and EtOH-THF (2:1, 6 ml) was stirred at 70° C. for 1 hour, to which was added 1 N HCl (2 ml) to give the title compound (151 mg).

NMR (DMSO-d$_6$): 1.50 (9H, s), 2.67 (3H, s), 7.94( 1H, d, J=8.8 Hz), 8.26 (1H, d, J=8.8 Hz), 8.80 (1H, s).

Reference Example 35

1-tert-Butoxycarbonyl-4-(3,4-methylenedioxybenzenesulfonyl)piperazine

The title compound was obtained, using 1-tert-butoxycarbonylpiperazine and 3,4-methylenedioxybenzenesulfonylchloride according to a similar method as described in Reference Example 12.

NMR (CDCl$_3$): 1.42 (9H, s), 2.97 (4H, m), 3.51 (4H, m), 6.09 (2H, s), 6.91 (1H, d, J=8.2 Hz), 7.15 (1H, d, J=2.1 Hz), 7.29 (1H, dd, J=2.1, 8.2 Hz).

Reference Example 36

4-(6-Chloronaphthalene-2-sulfonyl)-1-[4-(2-cyanoethyl)benzoyl]piperazine 4-(6-Chloronaphthalene-2-sulfonyl)-1-[4-(2-cyano-1-ethenyl)benzoyl]piperazine (699 mg) was dissolved in pyridine (15 ml) and methanol (5 ml), and to the mixture was added sodium borohydride (68 mg). The mixture was stirred at 60° C. for 2 hours and concentrated. To the residue was added diluted hydrochloric acid, and the mixture was extracted with ethyl acetate. The extract was washed with saturated sodium bicarbonate aqueous solution and brine in this order, dried and concentrated. The residue was purified with silica gel column chromatography (hexane: ethyl acetate=2:3) to give colorless crystals of the title compound (450 mg).

$^1$H-NMR (CDCl$_3$) δ: 2.62 (2H, t, J=7.2 Hz), 2.96 (2H, t, J=7.2 Hz), 3.09 (4H, brs), 3.71 (4H, br), 7.20–7.33 (4H, m), 7.59 (1H, dd, J=8.9, 1.9 Hz), 7.75 (1H, dd, J=8.7, 1.7 Hz), 7.89–7.97 (3H, m), 8.30 (1H, s). IR (KBr): 2247, 1636, 1433, 1348, 1161, 939, 735, 579 cm$^{-1}$.

Reference Example 37

1-(tert-Butoxycarbonyl)-4-(4-chlorobenzoylmethanesulfonyl)piperazine

To a solution of 1-(tert-butoxycarbonyl)-4-methanesulfonylpiperazine (1.32 g) in tetrahydrofurane (10 ml) was added dropwise at 0° C. 1.6 M n-butyllithium in hexane (6.25 ml), and the mixture was stirred at room temperature for 30 minutes. The reaction solution was cooled to −78° C., and to the mixture was added a solution of methyl 4-chlorobenzoate (853 mg) in tetrahydrofurane (5 ml). The mixture was stirred for 3 hours at the same temperature and raised to 0° C. To the reaction solution was added water (10 ml), and the mixture was made acidic with citric acid aqueous solution and extracted with ether. The organic layer was washed with brine, dried, concentrated, and purified with silica gel column chromatography (hexane/ethyl acetate=2/1) to give a colorless solid of the title compound (790 mg).

Reference Example 38

1-[2-(4-Chlorophenyl)ethynesulfonyl]piperazine hydrochloride

To a solution of 1-(tert-butoxycarbonyl)-4-(4-chlorobenzoylmethanesulfonyl)piperazine (640 mg) and 2-chloro-1-methylpyridinium iodide (650 mg) in dichloromethane (8 ml) was added dropwise triethylamine (4 ml) at 0° C., and the mixture was stirred at room temperature for 24 hours. The reaction solution was concentrated and purified with silica gel column chromatography (hexane/ethyl acetate=2/1) to give a colorless solid of 1-(tert-butoxycarbonyl)-4-[2-(4-chlorophenyl)ethynesulfonyl] piperazine (521 mg).

$^1$H-NMR (CDCl$_3$) δ: 1.47 (9H, s), 3.22 (4H, m), 3.62 (4H, m), 7.40 (2H, d, J=8.8 Hz), 7.52 (2H, d, J=8.8 Hz). IR (KBr): 2184, 1698, 1368, 1171 cm$^{-1}$.

1-(tert-Butoxycarbonyl)-4-[2-(4-chlorophenyl) ethynesulfonyl]piperazine (500 mg) was treated with 4N hydrochloric acid in ethyl acetate to give a colorless solid of the title compound (380 mg).

$^1$H-NMR (DMSO-d$_6$) δ: 3.34 (4H, m), 3.44 (4H, m), 7.62 (2H, d, J=8.6 Hz), 7.85 (2H, d, J=8.6 Hz), 9.34 (2H, brs).

Reference Example 39

1-(2H-Benzopyrane-3-sulfonyl)piperazine hydrochloride

A solution of 1-(ethenesulfonyl)piperazine (1.38 g), salicylaldehyde (610 mg) and potassium tert-butoxide (168 mg) in tert-butanol (20 ml) was refluxed for 4 days. The reaction solution was concentrated, and to the residue was added ethyl acetate. The organic layer was washed with water and brine, dried, concentrated and purified with silica gel column chromatography (hexane/ethyl acetate=2/1) to give a colorless solid of 1-(2H-benzopyrane-3-sulfonyl)-4-(tert-butoxycarbonyl)piperazine (420 mg).

$^1$H-NMR (CDCl$_3$) δ: 1.45 (9H, s), 3.21 (4H, m), 3.54 (4H, m), 4.88 (2H, s), 6.90 (1H, d, J=7.6 Hz), 6.99 (1H, dt, J=0.8, 7.6 Hz), 7.16–7.36 (3H, m). IR (Kbr): 1698, 1628, 1605, 1161 cm$^{-1}$.

1-(2H-Benzopyrane-3-sulfonyl)-4-(tert-butoxycarbonyl) piperazine was treated with 4N hydrochloric acid in ethyl acetate to give a colorless solid of the title compound.

Reference Example 40

According to a similar method described in Reference Example 39, the following compounds were synthesized using corresponding salicylaldehyde derivatives:

1-(5-chloro-2H-benzopyran-3-sulfonyl)-4-(tert-butoxycarbonyl)piperazine $^1$H-NMR (CDCl$_3$) δ: 1.45 (9H, s), 3.22 (4H, m), 3.54 (4H, m), 4.85 (2H, d, J=1.2 Hz), 6.82 (1H, d, J=8.2 Hz), 7.04 (1H, dd, J=1.2, 8.2 Hz), 7.22 (1H, t, J=8.2 Hz), 7.56 (1H, d, J=1.2 Hz). IR (KBr): 1698, 1697, 1454, 1422, 1248, 1161 cm$^{-1}$.

1-(6-chloro-2H-benzopyran-3-sulfonyl)-4-(tert-butoxycarbonyl)piperazine $^1$H-NMR (CDCl$_3$) δ: 1.45 (9H, s), 3.21 (4H, m), 3.54 (4H, m), 4.87 (2H, d, J=1.0 Hz), 6.84 (1H, d, J=8.4 Hz), 7.15–7.28 (3H, m). IR (KBr): 1696, 1630, 1480, 1406, 1343, 1329, 1155 cm$^{-1}$.

1-(7-chloro-2H-benzopyran-3-sulfonyl)-4-(tert-butoxycarbonyl)piperazine $^1$H-NMR (CDCl$_3$) δ: 1.45 (9H, s), 3.21 (4H, m), 3.54 (4H, m), 4.88 (2H, d, J=1.2 Hz), 6.92 (1H, d, J=2.2 Hz), 6.98 (1H, dd, J=2.2, 8.2 Hz), 7.11 (1H, d, J=8.2 Hz), 7.21 (1H, s). IR (KBr): 1688, 1601, 1418, 1281, 1248, 1150 cm$^{-1}$.

Reference Example 41

1-(5-chlorobenzofuran-2-sulfonyl)piperazine hydrochloride

A mixture of 1-(chloromethanesulfonyl)-4-formylpiperazine (2.26 g), 5-chlorosalicylaldehyde (1.56 g) and potassium carbonate (1.38 g) in DMF (30 ml) was stirred at 100° C. for 48 hours. The reaction solution was concentrated, and to the residue was added ethyl acetate. The organic layer was washed with water and brine, dried, concentrated and purified with silica gel column chromatography (ethyl acetate) to give colorless crystals of 1-(5-chlorobenzofurane-2-sulfonyl)-4-formylpiperazine (406 mg).

$^1$H-NMR (CDCl$_3$) δ: 3.34 (4H, m), 3.51 (2H, m), 3.68 (2H, m), 7.34 (1H, s), 7.45 (1H, dd, J=1.8, 8.8 Hz), 7.50 (1H, d, J=8.8 Hz), 7.68 (1H, d, J=1.8 Hz), 8.02 (1H, s).

To a solution of 1-(5-chlorobenzofuran-2-sulfonyl)-4-formylpiperazine (405 mg) in ethanol (15 ml) was added concentrated hydrochloric acid (1 ml), and the mixture was heated for 30 minutes under reflux. The solid obtained by concentration was washed with ethyl acetate and dried to give a colorless solid of the title compound (312 mg).

$^1$H-NMR (DMSO-d$_6$) δ: 3.22 (4H, m), 3.43 (4H, m), 7.62 (1H, dd, J=2.2, 9.2 Hz), 7.75 (1H, d, J=1.0 Hz), 7.85 (1H, dd, J=1.0, 9.2 Hz), 7.95 (1H, d, J=2.2 Hz), 9.15 (2H, brs).

Reference Example 42

1-(6-Chlorobenzofurane-2-sulfonyl)piperazine hydrochloride

According to a similar method as described in Reference Example 41, the title compound was synthesized using 4-chloro-salicylaldehyde instead of 5-chlorosalicylaldehyde.

$^1$H-NMR (DMSO-d$_6$) δ: 3.20 (4H, m), 3.40 (4H, m), 7.50 (1H, m), 7.82 (1H, s), 7.88 (1H, d, J=8.0 Hz), 8.03 (1H, m), 9.09 (2H, brs).

Working Example 1

1-(4-Diisopropylaminomethylbenzoyl)-4-(2-naphthalenesulfonyl)piperazine

A solution of 1-(4-chloromethylbenzoyl)-4-(2-naphthalenesulfonyl)piperazine (300 mg), potassium carbonate (200 mg) and diisopropylamine (4 ml) in DMF (6 ml) was stirred at 100° C. for 10 hours and concentrated. To the residue was added ethyl acetate, and the mixture was washed with water, and extracted with 1 N hydrochloric acid. The extract was made alkaline with sodium hydroxide solution and extracted with dichloromethane. The extract was dried and concentrated. The residue was purified with silica gel column chromatography (hexane:ethyl acetate=1:2) to give the title compound (70 mg).

$^1$H-NMR (CDCl$_3$) δ: 0.99 (12H, d, J=6.6 Hz), 2.97 (2H, quint, J=6.6 Hz), 3.10 (4H, brs), 3.61 (2H, s), 3.71 (4H, brs), 7.21 (2H, d, J=8.4 Hz), 7.37 (2H, d, J=8.4 Hz), 7.59–7.78 (3H, m), 7.90–8.04 (3H, m), 8.33 (1H, s). IR (KBr): 1637, 1457, 1424, 1283, 1166 cm$^{-1}$.

Working Example 2

1-(2-Naphthalenesulfonyl)-4-(4-piperidinomethylbenzoyl)piperazine

According to a similar method described in Working Example 1, the title compound (353 mg) was obtained as colorless amorphous, by stirring a solution of 1-(4-chloromethylbenzoyl)-4-(2-naphthalenesulfonyl)piperazine (300 mg), potassium carbonate (313 mg) and piperidine (321 mg)in DMF (6 ml) at 70° C. for 10 hours.

$^1$H-NMR (CDCl$_3$) δ: 1.35–1.65 (6H, m), 2.34 (4H, m), 3.10 (4H, brs), 3.44 (2H, s), 3.73 (4H, brs), 7.22 (2H, d, J=8.0 Hz), 7.31 (2H, d, J=8.0 Hz), 7.58–7.80 (3H, m), 7.90–8.07 (3H, m), 8.33 (1H, s). IR (KBr): 1636, 1347, 1166 cm$^{-1}$.

Working Example 3

1-(2-Naphthalenesulfonyl)-4-(4-piperidinomethylbenzoyl)piperazine hydrochloride

To 1-(2-naphthalenesulfonyl)-4-(4-piperidinomethylbenzoyl)piperazine (350 mg) was added 4 N hydrochloric acid in ethyl acetate solution (5 ml) and the precipitated hydrochlorides were filtered to give the title compound (337 mg).

$^1$H-NMR (CDCl$_3$) δ: 1.39 (1H, m), 1.70–2.00 (3H, m), 2.20–2.40 (2H, m), 2.40–2.62 (2H, m), 3.10 (4H, brs), 3.37–3.95 (6H, m), 4.08 (2H, d, J=5.0 Hz), 7.36 (2H, d, J=8.2 Hz), 7.60–7.80 (5H, m), 7.93–8.06 (3H, m), 8.35 (1H, s), 12.47 (1H, brs). IR (KBr): 1636, 1347, 1166 cm$^{-1}$.

Working Example 4

1-[4-(1H-Imidazol-1-ylmethyl)benzoyl]-4-(2-naphthalenesulfonyl)piperazine

According to a similar method described in Working Example 1, the title compound (305 mg) was obtained as colorless amorphous by stirring a solution of 1-(4-chloromethylbenzoyl)-4-(2-naphthalenesulfonyl)piperazine (300 mg), potassium carbonate (313 mg) and imidazole (257 mg)in DMF (6 ml) at 70r for 10 hours.

$^1$H-NMR (CDCl$_3$) δ: 3.09 (4H, brs), 3.40–4.00 (4H, br), 5.12 (2H, s), 6.88 (1H, s), 7.10 (1H, s), 7.13 (2H, d, J=8.0 Hz), 7.28 (2H, d, J=8.0 Hz), 7.53 (1H, s), 7.58–7.76 (3H, m), 7.90–8.04 (3H, m), 8.32 (1H, d, J=1.6 Hz). IR (KBr): 1633, 1432, 1347, 1284, 1166 cm$^{-1}$.

Working Example 5

1-[4-(1H-Imidazol-1-ylmethyl)benzoyl]-4-(2-naphthalenesulfonyl)piperazine hydrochloride To 1-[4-(1H-imidazol-1-ylmethyl)benzoyl]-4-(2-naphthalenesulfonyl)piperazine (300 mg) was added 4 N hydrochloric acid in ethyl acetate solution (5 ml) and the precipitated hydrochlorides were filtered to give the title compound (299 mg).

$^1$H-NMR (CDCl$_3$) δ: 3.11 (4H, brs), 3.40–3.95 (4H, m), 5.54 (2H, s), 7.07 (1H, s), 7.30–7.46 (5H, m), 7.60–7.78 (3H, m), 7.90–8.05 (3H, m), 8.33 (1H, s), 9.84 (1H, s). IR (KBr): 3400, 1631, 1440, 1347, 1284, 1164 cm$^{-1}$.

Working Example 6

1-(4-Diethylaminomethylbenzoyl)-4-(2-naphthalenesulfonyl)piperazine

According to a similar method described in Working Example 1, the title compound (326 mg) was obtained as colorless amorphous by stirring a solution of 1-(4-chloromethylbenzoyl)-4-(2-naphthalenesulfonyl)piperazine (300 mg), potassium carbonate (313 mg) and diethylamine (276 mg) in DMF (6 ml) at 70° C. for 10 hours.

$^1$H-NMR (CDCl$_3$) δ: 1.01 (6H, t, J=7.0 Hz), 2.59 (4H, q, J=7.0 Hz), 3.11 (4H, brs), 3.54 (2H, s), 3.72 (4H, brs), 7.23 (2H, d, J=8.0 Hz), 7.33 (2H, d, J=8.0 Hz), 7.58–7.80 (3H, m), 7.90–8.05 (3H, m), 8.33 (1H, s). IR (KBr): 1635, 1428, 1347, 1282, 1166 cm$^{-1}$.

Working Example 7

1-(4-Diethylaminomethylbenzoyl)-4-(2-naphthalenesulfonyl)piperazine hydrochloride To 1-(4-diethylaminomethylbenzoyl)-4-(2-naphthalenesulfonyl)piperazine (320 mg) was added 4 N hydrochloric acid in ethyl acetate solution (5 ml), and the precipitated hydrochlorides were filtered to give the title compound (268 mg).

$^1$H-NMR (CDCl$_3$) δ: 1.41 (6H, t, J=7.0 Hz), 2.90–3.30 (8H, m), 3.40–4.00 (4H, m), 4.13 (2H, d, J=5.6 Hz), 7.37 (2H, d, J=8.0 Hz), 7.60–7.83 (5H, m), 7.92–8.07 (3H, m), 8.35 (1H, s), 12.47 (1H, brs). IR (KBr): 3340, 1631, 1459, 1434, 1347, 1284, 1166 cm$^{-1}$.

Working Example 8

1-(4-Benzylmethylaminomethylbenzoyl)-4-(2-naphthalenesulfonyl)piperazine

According to a similar method described in Working Example 1, the title compound (359 mg) was obtained as colorless amorphous, by stirring a solution of 1-(4-chloromethylbenzoyl)-4-(2-naphthalenesulfonyl)piperazine (300 mg), potassium carbonate (105 mg) and benzylmethylamine (100 mg) in DMF (6 ml) at 70° C. for 10 hours.

$^1$H-NMR (CDCl$_3$) δ: 2.16 (3H, s), 3.09 (4H, brs), 3.49 (2H, s), 3.50 (2H, s), 3.70 (4H, brs), 7.18–7.42 (9H, m), 7.58–7.80 (3H, m), 7.90–8.03 (3H, m), 8.33 (1H, s). IR (KBr): 1639, 1428, 1347, 1283, 1166 cm$^{-1}$.

Working Example 9

1-(4-Benzylmethylaminomethylbenzoyl)-4-(2-naphthalenesulfonyl)piperazine hydrochloride To 1-(4-benzylmethylaminomethylbenzoyl)-4-(2-naphthalenesulfonyl)piperazine (358 mg) was added 4 N hydrochloric acid in ethyl acetate solution (5 ml), and the precipitated hydrochlorides were filtered to give the title compound (391 mg).

$^1$H-NMR (CDCl$_3$) δ: 2.56 (3H, d, J=4.4 Hz), 3.12 (4H, brs), 3.40–4.16 (6H, m), 4.25–4.38 (2H, m), 7.30–7.50 (5H, m), 7.50–7.80 (7H, m), 7.91–8.06 (3H, m), 8.34 (1H, s), 12.82 (1H, brs). IR (KBr): 3400, 1633, 1459, 1434, 1347, 1284, 1166 cm$^{-1}$.

Working Example 10

1-(4-Dimethylaminomethylbenzoyl)-4-(2-naphthalenesulfonyl)piperazine

According to a similar method described in Working Example 1, the title compound (42 mg) was obtained as colorless amorphous, by stirring a solution of 1-(4-chloromethylbenzoyl)-4-(2-naphthalenesulfonyl)piperazine (300 mg) and 50% dimethylamine solution (2 ml) in DMF (6 ml) at 50° C. for 1 hours.

¹H-NMR (CDCl₃) δ: 2.22 (6H, s), 3.10 (4H, brs), 3.41 (2H, s), 3.40–4.00 (4H, br), 7.25 (2H, d, J=8.2 Hz), 7.31 (2H, d, J=8.2 Hz), 7.60–7.80 (3H, m), 7.90–8.05 (3H, m), 8.33 (1H, d, J=1.6 Hz). IR (KBr): 1635, 1455, 1428, 1347, 1166 cm⁻¹.

Working Example 11

1-(4-Dimethylaminomethylbenzoyl)-4-(2-naphthalenesulfonyl)piperazine hydrochloride To 1-(4-dimethylaminomethylbenzoyl)-4-(2-naphthalenesulfonyl)piperazine (42 mg) was added 4 N hydrochloric acid in ethyl acetate solution (1 ml), and the precipitated hydrochlorides were filtered to give the title compound (40 mg).

¹H-NMR (CDCl₃) δ: 2.22 (6H, d, J=4.4 Hz), 3.12 (4H, brs), 3.40–3.95 (4H, m), 4.14 (2H, d, J=4.6 Hz), 7.38 (2H, d, J=8.2 Hz), 7.60–7.80 (5H, m), 7.90–8.06 (3H, m), 8.34 (1H, s). IR (KBr): 3354, 1633, 1463, 1436, 1347, 1284, 1166 cm⁻¹.

Working Example 12

1-(4-Methylaminomethylbenzoyl)-4-(2-naphthalenesulfonyl)piperazine

According to a similar method described in Working Example 1, the title compound (473 mg) was obtained as colorless amorphous, by stirring a solution of 1-(4-chloromethylbenzoyl)-4-(2-naphthalenesulfonyl)piperazine (600 mg), potassium carbonate (616 mg) and 40% methylamine solution (2 ml) in DMF (6 ml) at 50° C. for 1 hour.

¹H-NMR (CDCl₃) δ: 2.43 (3H, s), 3.10 (4H, brs), 3.74 (2H, s), 3.40–3.95 (4H, br), 7.25 (2H, d, J=8.0 Hz), 7.32 (2H, d, J=8.0 Hz), 7.58–7.78 (3H, m), 7.90–8.03 (3H, m), 8.33 (1H, s). IR (KBr): 3322, 1635, 1430, 1347, 1166 cm⁻¹.

Working Example 13

1-(4-Methylaminomethylbenzoyl)-4-(2-naphthalenesulfonyl)piperazine hydrochloride To 1-(4-methylaminomethylbenzoyl)-4-(2-naphthalenesulfonyl)piperazine (373 mg) was added 4 N hydrochloric acid in ethyl acetate solution (5 ml), and the precipitated hydrochlorides were filtered to give the title compound (387 mg).

¹H-NMR (CDCl₃) δ: 2.49 (3H, s), 3.10 (4H, brs), 3.40–3.90 (4H, m), 4.05 (2H, s), 7.31 (2H, d, J=7.8 Hz), 7.59 (2H, d, J=7.8 Hz), 7.60–7.78 (3H, m), 7.90–8.05 (3H, m), 8.33 (1H, s), 9.88 (2H, brs). IR (KBr): 1635, 1461, 1434, 1347, 1284, 1166 cm⁻¹.

Working Example 14

1-(4-Diisobutylaminomethylbenzoyl)-4-(2-naphthalenesulfonyl)piperazine

According to a similar method described in Working Example 1, the title compound (127 mg) was obtained as colorless crystals, by stirring a solution of 1-(4-chloromethylbenzoyl)-4-(2-naphthalenesulfonyl)piperazine (300 mg), potassium carbonate (208 mg) and diisobutylamine (292 mg) in DMF (10 ml) at 100° C. for 5 hours.

¹H-NMR (CDCl₃) δ: 0.83 (12H, d, J=6.6 Hz), 1.74 (2H, m), 2.05 (4H, d, J=7.2 Hz), 3.10 (4H, brs), 3.45 (2H, s), 3.40–3.90 (4H, br), 7.22 (2H, d, J=8.2 Hz), 7.33 (2H, d, J=8.2 Hz), 7.58–7.80 (3H, m), 7.90–8.03 (3H, m), 8.33 (1H, s). IR (KBr): 1635, 1455, 1428, 1349, 1283, 1168 cm⁻¹.

Working Example 15

1-[4-(N-Ethyl-N-tert-butylamino)benzoyl]-4-(2-naphthalenesulfonyl)piperazine

According to a similar method described in Working Example 1, the title compound (127 mg) was obtained as colorless crystals, by stirring a solution of 1-(4-chloromethylbenzoyl)-4-(2-naphthalenesulfonyl)piperazine (300 mg), potassium carbonate (310 mg) and N-ethyl-tert-butylamine (757 mg) in DMF (10 ml) at 100° C. for 5 hours.

¹H-NMR (CDCl₃) δ: 0.84 (3H, t, J=7.0 Hz), 1.08 (9H, s), 2.59 (2H, q, J=7.0 Hz), 3.10 (4H, brs), 3.65 (2H, s), 3.40–3.90 (4H, br), 7.21 (2H, d, J=8.2 Hz), 7.40 (2H, d, J=8.2 Hz), 7.60–7.77 (3H, m), 7.90–8.04 (3H, m), 8.33 (1H, d, J=1.6 Hz). IR (KBr): 1635, 1455, 1347, 1282, 1168 cm⁻¹.

Working Example 16

1-[4-(2,6-Dimethylpiperidinomethyl)benzoyl]-4-(2-naphthalenesulfonyl)piperazine

According to a similar method described in Working Example 1, the title compound (61 mg) was obtained as colorless crystals, by stirring a solution of 1-(4-chloromethylbenzoyl)-4-(2-naphthalenesulfonyl)piperazine (300 mg), potassium carbonate (209 mg) and 2,6-dimethylpiperidine (256 mg) in DMF (10 ml) at 100° C. for 8 hours.

¹H-NMR (CDCl₃) δ: 0.98 (6H, d, J=6.2 Hz), 1.20–1.40 (4H, m), 1.62 (2H, m), 2.46 (2H, s), 3.11 (4H, brs), 3.73 (2H, s), 3.50–3.90 (4H, br), 7.21 (2H, d, J=8.0 Hz), 7.38 (2H, d, J=8.0 Hz), 7.60–7.80 (3H, m), 7.90–8.04 (3H, m), 8.32 (1H, s). IR (KBr): 1635, 1428, 1349, 1284, 1166 cm⁻¹.

Working Example 17

1-[4-(3,5-Dimethylpiperidinomethyl)benzoyl]-4-(2-naphthalenesulfonyl)piperazine

According to a similar method described in Working Example 1, the title compound (170 mg) was obtained as colorless crystals, by stirring a solution of 1-(4-chloromethylbenzoyl)-4-(2-naphthalenesulfonyl)piperazine (300 mg), potassium carbonate (156 mg) and 3,5-dimethylpiperidine (171 mg) in DMF (10 ml) at 100° C. for 5 hours.

¹H-NMR (CDCl₃) δ: 0.56 (1H, m), 0.80 (6H, d, J=6.2 Hz), 0.88 (1H, m), 1.35–1.80 (4H, m), 2.74 (2H, m), 3.12 (4H, brs), 3.44 (2H, s), 3.75 (4H, brs), 7.23 (2H, d, J=.8.0 Hz), 7.31 (2H, d, J=8.0 Hz), 7.60–7.80 (3H, m), 7.90–8.05 (3H, m), 8.33 (1H, d, J=1.8 Hz). IR (KBr): 1639, 1459, 1430, 1349, 1284, 1168 cm⁻¹.

Working Example 18

1-(3-Diisopropylaminomethylbenzoyl)-4-(2-naphthalenesulfonyl)piperazine

According to a similar method described in Working Example 1, the title compound (216 mg) was obtained as colorless amorphous, by stirring a solution of 1-(3-chloromethylbenzoyl)-4-(2-naphthalenesulfonyl)piperazine (500 mg), potassium carbonate (500 mg) and diisopropylamine (2 ml) in DMF (10 ml) at 100° C. for 10 hours.

¹H-NMR (CDCl₃) δ: 0.95 (12H, d, J=6.6 Hz), 2.93 (2H, quint, J=6.6 Hz), 3.10 (4H, brs), 3.58 (2H, s), 3.40–4.00 (4H, br), 7.08–7.44 (4H, m), 7.58–7.78 (3H, m), 7.90–8.04 (3H, m), 8.33 (1H, d, J=1.8 Hz). IR (KBr): 1635, 1349, 1168 cm⁻¹.

Working Example 19

1-(3-Diisopropylaminomethylbenzoyl)-4-(2-naphthalenesulfonyl)piperazine hydrochloride

To 1-(3-diisopropylaminomethylbenzoyl)-4-(2-naphthalenesulfonyl)piperazine (215 mg) was added 4 N hydrochloric acid in ethyl acetate solution (5 ml), and the precipitated hydrochlorides were filtered to give the title compound (219 mg).

$^1$H-NMR (CDCl$_3$) δ: 1.48 (6H, d, J=6.6 Hz), 1.51 (6H, d, J=6.6 Hz), 3.18 (4H, m), 3.40–3.90 (6H, m), 4.14 (2H, d, J=5.6 Hz), 7.33 (1H, d, J=7.8 Hz), 7.44 (1H, t, J=7.8 Hz), 7.58–7.80 (4H, m), 7.85–8.05 (4H, m), 8.34 (1H, s), 11.74 (1H, brs). IR (KBr): 1633, 1461, 1430, 1347, 1286, 1166 cm$^{-1}$.

Working Example 20

4-(2-Naphthalenesulfonyl)-1-(3-piperidinomethylbenzoyl)piperazine

According to a similar method described in Working Example 1, the title compound (256 mg) was obtained as colorless amorphous, by stirring a solution of 1-(3-chloromethylbenzoyl)-4-(2-naphthalenesulfonyl)piperazine (300 mg), potassium carbonate (313 mg) and piperidine (321 mg) in DMF (10 ml) at 70° C. for 3 hours.

$^1$H-NMR (CDCl$_3$) δ: 1.35–1.65 (6H, m), 2.32 (4H, m), 3.10 (4H, brs), 3.43 (2H, s), 3.40–4.00 (4H, br), 7.16 (1H, dt, J=1.6, 7.2 Hz), 7.24–7.39 (3H, m), 7.60–7.80 (3H, m), 7.90–8.05 (3H, m), 8.33 (1H, d, J=1.6 Hz). IR (KBr): 1635, 1347, 1166 cm$^{-1}$.

Working Example 21

1-(6-Chloronaphthalene-2-sulfonyl)-4-(4-diisopropylaminomethylbenzoyl)piperazine

According to a similar method described in Working Example 1, the title compound (113 mg) was obtained as colorless amorphous, by stirring a solution of 1-(4-chloromethylbenzoyl)-4-(6-chloronaphthalene-2-sulfonyl)piperazine (376 mg), potassium carbonate (250 mg) and diisopropylamine (2 ml) in DMF (20 ml) at 100° C. for 4 hours.

$^1$H-NMR (CDCl$_3$) δ: 0.98 (12H, d, J=6.6 Hz), 2.97 (2H, quint, J=6.6 Hz), 3.10 (4H, brs), 3.61 (2H, s), 3.70 (4H, brs), 7.21 (2H, d, J=8.2 Hz), 7.37 (2H, d, J=8.2 Hz), 7.59 (1H, dd, J=2.0, 8.4 Hz), 7.75 (1H, dd, J=2.0, 8.4 Hz), 7.92 (2H, d, J=8.4 Hz), 7.95 (1H, d, J=2.0 Hz), 8.30 (1H, d, J=2.0 Hz). IR (KBr): 1637, 1347, 1166 cm$^{-1}$.

Working Example 22

1-(6-Chloronaphthalene-2-sulfonyl)-4-(4-diisopropylaminomethylbenzoyl)piperazine hydrochloride

To 1-(6-chloronaphthalene-2-sulfonyl)-4-(4-diisopropylaminomethylbenzoyl)piperazine (110 mg) was added 4 N hydrochloric acid in ethyl acetate solution (5 ml), and the precipitated hydrochlorides were filtered to give the title compound (113 mg).

$^1$H-NMR (CDCl$_3$) δ: 1.50 (6H, d, J=6.6 Hz), 1.52 (6H, d, J=6.6 Hz), 3.12 (4H, brs), 3.40–3.90 (6H, m), 4.17 (2H, d, J=5.4 Hz), 7.36 (2H, d, J=8.0 Hz), 7.59 (1H, dd, J=1.8, 8.8 Hz), 7.77 (1H, dd, J=1.8, 8.8 Hz), 7.88–8.00 (5H, m), 8.31 (1H, s), 11.73 (1H, brs). IR (KBr): 3311, 1635, 1455, 1432, 1345, 1284, 1166 cm$^{-1}$.

Working Example 23

1-(6-Bromonaphthalene-2-sulfonyl)-4-(4-diisopropylaminomethylbenzoyl)piperazine

To a mixture of 1-(4-diisopropylaminomethylbenzoyl)piperazine (200 mg) in 10% sodium hydrogen carbonate solution (10 ml) and ethyl acetate (15 ml), was added 6-bromonaphthalene-2-sulfonylchloride (179 mg), and the solution was stirred at room temperature for 30 minutes. The organic layer was separated, washed with water and extracted with 1 N hydrochloric acid. The extract was made alkaline with sodium hydroxide solution and extracted with dichloromethane. The extract was dried and concentrated. The residue was crystallized with ether to give the title compound (201 mg), as colorless crystals.

$^1$H-NMR (CDCl$_3$) δ: 0.99 (12H, d, J=6.6 Hz), 2.97 (2H, quint, J=6.6 Hz), 3.10 (4H, brs), 3.61 (2H, s), 3.71 (4H, brs), 7.20 (2H, d, J=8.0 Hz), 7.37 (2H, d, J=8.0 Hz), 7.67–7.78 (2H, m), 7.85 (1H, d, J=8.8 Hz), 7.91 (1H, d, J=8.6 Hz), 8.12 (1H, s), 8.29 (1H, s). IR (KBr): 1637, 1459, 1347, 1284, 1164 cm$^{-1}$.

Working Example 24

1-(4-Diisopropylaminomethylbenzoyl)-4-(1-naphthalenesulfonyl)piperazine

According to a similar method described in Working Example 23, the title compound (181 mg) was obtained as colorless amorphous, by reacting 1-(4-diisopropylaminomethylbenzoyl)piperazine (200 mg) and 1-naphthalenesulfonylchloride (144 mg).

$^1$H-NMR (CDCl$_3$) δ: 0.99 (12H, d, J=6.6 Hz), 2.97 (2H, quint, J=6.6 Hz), 3.20 (4H, brs), 3.61 (2H, s), 3.40–3.80 (4H, br), 7.21 (2H, d, J=8.2 Hz), 7.37 (2H, d, J=8.2 Hz), 7.50–7.73 (3H, m), 7.96 (1H,m), 8.11 (1H, d, J=8.4 Hz), 8.21 (1H, d, J=7.2 Hz), 8.73 (1H, d, J=7.4 Hz). IR (KBr): 1635, 1428, 1349, 1162 cm$^{-1}$.

Working Example 25

1-(4-Diisopropylaminomethylbenzoyl)-4-(1-naphthalenesulfonyl)piperazine hydrochloride

To 1-(4-diisopropylaminomethylbenzoyl)-4-(1-naphthalenesulfonyl)piperazine (181 mg) was added 4 N hydrochloric acid in ethyl acetate solution (5 ml), and the precipitated hydrochlorides were filtered to give the title compound (180 mg).

$^1$H-NMR (CDCl$_3$) δ: 1.51 (6H, d, J=6.4 Hz), 1.53 (6H, d, J=6.4 Hz), 3.21 (4H, brs), 3.40–3.90 (6H, m), 4.18 (2H, d, J=5.6 Hz), 7.37 (2H, d, J=7.2 Hz), 7.53–7.75 (3H, m), 7.85–8.00 (3H, m), 8.13 (1H, d, J=8.0 Hz), 8.22 (1H, d, J=7.4 Hz), 8.74 (1H, d, J=8.2 Hz), 11.73 (1H, brs). IR (KBr): 1635, 1436, 1284, 1162, 1137 cm$^{-1}$.

Working Example 26

1-(4-Diisopropylaminomethylbenzoyl)-4-(4-toluenesulfonyl)piperazine

According to a similar method described in Working Example 23, the title compound (141 mg) was obtained as colorless crystals, by reacting 1-(4-diisopropylaminomethylbenzoyl)piperazine (200 mg) and 4-toluenesulfonyl chloride (122 mg).

$^1$H-NMR (CDCl$_3$) δ: 1.00 (12H, d, J=6.6 Hz), 2.46 (3H, s), 2.90–3.10 (6H, m), 3.63 (2H, s), 3.40–3.90 (4H, br), 7.23

(2H, d, J=8.4 Hz), 7.35 (2H, d, J=8.4 Hz), 7.39 (2H, d, J=8.4 Hz), 7.63 (2H, d, J=8.4 Hz). IR (KBr): 1640, 1428, 1351, 1168 cm$^{-1}$.

Working Example 27

1-(4-Bromobenzenesulfonyl)-4-(4-diisopropylaminomethylbenzoyl)piperazine

According to a similar method described in Working Example 23, the title compound (190 mg) was obtained as colorless crystals, by reacting 1-(4-diisopropylaminomethylbenzoyl)piperazine (200 mg) and 4-bromobenzenesulfonyl chloride (149 mg).

$^1$H-NMR (CDCl$_3$) δ: 1.00 (12H, d, J=66 Hz), 2.85–3.10 (6H, m), 3.63 (2H, s), 3.45–3.85 (4H, br), 7.24 (2H, d, J=8.4 Hz), 7.40 (2H, d, J=8.4 Hz), 7.60 (2H, d, J=8.6 Hz), 7.71 (2H, d, J=8.6 Hz). IR (KBr): 1635, 1428, 1361, 1248, 1168 cm$^{-1}$.

Working Example 28

1-(Benzylsulfonyl)-4-(4-diisopropylaminomethylbenzoyl)piperazine

According to a similar method described in Working Example 23, the title compound (124 mg) was obtained as colorless crystals, by reacting 1-(4-diisopropylaminomethylbenzoyl)piperazine (200 mg) and benzylsulfonyl chloride (112 mg).

$^1$H-NMR (CDCl$_3$) δ: 1.01 (12H, d, J=6.6 Hz), 3.00 (2H, quint, J=6.6 Hz), 3, 09 (4H, brs), 3.64 (2H, s), 3.40–3.80 (4H, br), 4.25 (2H, s), 7.20–7.30 (3H, m), 7.33–7.50 (6H, m). IR (KBr): 1635, 1455, 1428, 1345, 1283, 1158 cm$^{-1}$.

Working Example 29

1-(4-Diisopropylaminomethylbenzoyl)-4-(6-methoxynaphthalene-2-sulfonyl)piperazine According to a similar method described in Working Example 23, the title compound (200 mg) was obtained as colorless crystals, by reacting 1-(4-diisopropylaminomethylbenzoyl)piperazine (200 mg) and 6-methoxynaphthalene-2-sulfonylchloride (150 mg).

$^1$H-NMR (CDCl$_3$) δ: 0.98 (12H, d, J=6.6 Hz), 2.97 (2H, quint, J=6.6 Hz), 3.07 (4H, brs), 3.61 (2H, s), 3.40–3.95 (4H, br), 3.97 (3H, s), 7.16–7.40 (6H, m), 7.68 (1H, dd, J=1.8, 8.8 Hz), 7.86 (2H, d, J=8.8 Hz), 8.23 (1H, s). IR (KBr): 1633, 1347, 1264, 1162 cm$^{-1}$.

Working Example 30

1-(4'-Chlorobiphenyl-4-sulfonyl)-4-(4-diisopropylaminomethylbenzoyl)piperazine

According to a similar method described in Working Example 23, the title compound (270 mg) was obtained as colorless crystals, by reacting 1-(4-diisopropylaminomethylbenzoyl)piperazine (200 mg) and 4'-chlorobiphenyl-4-sulfonylchloride (209 mg).

$^1$H-NMR (CDCl$_3$) δ: 0.99 (12H, d, J=6.6 Hz), 2.98 (2H, quint, J=6.6 Hz), 3.08 (4H, brs), 3.63 (2H, s), 3.72 (4H, brs), 7.24 (2H, d, J=8.0 Hz), 7.39 (2H, d, J=8.0 Hz), 7.47 (2H, d, J=8.8 Hz), 7.56 (2H, d, J=8.8 Hz), 7.71 (2H, d, J=8.8 Hz), 7.81 (2H, d, J=8.8 Hz). IR (KBr): 1637, 1427, 1351, 1283, 1168 cm$^{-1}$.

Working Example 31

1-[2(E)-(4-Chlorophenyl)ethenylsulfonyl]-4-(4-diisopropylaminomethylbenzoyl)piperazine According to a similar method described in Working Example 23, the title compound (200 mg) was obtained as colorless amorphous, by reacting 1-(4-diisopropylaminomethylbenzoyl)piperazine (200 mg) and 2(E)-(4-chlorophenyl)ethenylsulfonyl chloride (172 mg).

$^1$H-NMR (CDCl$_3$) δ: 1.01 (12H, d, J=6.6 Hz), 2.99 (2H, quint, J=6.6 Hz), 3.22 (4H, brs), 3.64 (2H, s), 3.75 (4H, brs), 6.63 (1H, d, J=15.8 Hz), 7.25–7.50 (9H, m). IR (KBr): 1635, 1434, 1347, 1154 cm$^{-1}$.

Working Example 32

1-(4-Diisopropylaminomethylbenzoyl)-4-(7-methoxynaphthalene-2-sulfonyl)piperazine According to a similar method described in Working Example 23, the title compound (316 mg) was obtained as colorless crystals, by reacting 1-(4-diisopropylaminomethylbenzoyl)piperazine (200 mg) and 7-methoxynaphthalene-2-sulfonylchloride (203 mg).

$^1$H-NMR (CDCl$_3$) δ: 0.99 (12H, d, J=6.6 Hz), 2.97 (2H, quint, J=6.6 Hz), 3.10 (4H, brs), 3.61 (2H, s), 3.72 (4H, brs), 3.96 (3H, s), 7.17–7.40 (6H, m), 7.58 (1H, dd, J=1.8, 8.8 Hz), 7.83 (2H, d, J=9.2 Hz), 7.91 (1H, d, J=8.8 Hz), 8.20 (1H, s). IR (KBr): 1629, 1347, 1257, 1218, 1166 cm$^{-1}$.

Working Example 33

1-(7-Chloronaphthalene-2-sulfonyl)-4-(4-diisopropylaminomethylbenzoyl)piperazine According to a similar method described in Working Example 23, the title compound (200 mg) was obtained as colorless crystals, by reacting 1-(4-diisopropylaminomethylbenzoyl)piperazine (150 mg) and 7-chloronaphthalene-2-sulfonylchloride (142 mg).

$^1$H-NMR (CDCl$_3$) δ: 0.98 (12H, d, J=6.6 Hz), 2.97 (2H, quint, J=6.6 Hz), 3.10 (4H, brs), 3.62 (2H, s), 3.71 (4H, brs), 7.20 (2H, d, J=8.0 Hz), 7.37 (2H, d, J=8.0 Hz), 7.62 (1H, dd, J=1.8, 8.8 Hz), 7.73 (1H, dd, J=1.8, 8.8 Hz), 7.85–8.03 (3H, m), 8.23 (1H, s); IR (KBr): 1635, 1428, 1363, 1347, 1284, 1166 cm$^{-1}$.

Working Example 34

1-(5-Chloronaphthalene-2-sulfonyl)-4-(4-diisopropylaminomethylbenzoyl)piperazine According to a similar method described in Working Example 23, the title compound (179 mg) was obtained as colorless crystals, by reacting 1-(4-diisopropylaminomethylbenzoyl)piperazine (150 mg) and 5-chloronaphthalene-2-sulfonylchloride (142 mg).

$^1$H-NMR (CDCl$_3$) δ: 0.99 (12H, d, J=6.6 Hz), 2.97 (2H, quint, J=6.6 Hz), 3.11 (4H, brs), 3.61 (2H, s), 3.71 (4H, brs), 7.21 (2H, d, J=8.2 Hz), 7.37 (2H, d, J=8.2 Hz), 7.57 (1H, t, J=8.0 Hz), 7.78 (1H, d, J=8.0 Hz), 7.84 (1H, dd, J=2.0, 8.8 Hz), 7.91 (1H, d, J=8.0 Hz), 8.33 (1H, d, J=2.0 Hz), 8.45 (1H, d, J=8.8 Hz). IR (KBr): 1635, 1426, 1361, 1332, 1284, 1166 cm$^{-1}$.

Working Example 35

1-(4-Diisopropylaminomethylbenzoyl)-4-[6-(2,2,2-trichloroethoxycarbonylamino)naphthalene-2-sulfonyl]piperazine According to a similar method described in Working Example 23, the title compound (303 mg) was obtained as colorless crystals, by reacting 1-(4-diisopropylaminomethylbenzoyl)piperazine (200 mg) and 6-(2,2,2-trichloroethoxycarbonylamino)naphthalene-2-sulfonylchloride (289 mg).

$^1$H-NMR (CDCl$_3$) δ: 0.99 (12H, d, J=6.6 Hz), 2.97 (2H, quint, J=6.6 Hz), 3.09 (4H, brs), 3.61 (2H, s), 3.71 (4H, brs), 4.89 (2H, s), 7.21 (2H, d, J=8.2 Hz), 7.23 (1H, brs), 7.37 (2H, d, J=8.2 Hz), 7.56 (1H, dd, J=2.2, 8.8 Hz), 7.72 (1H, dd, J=2.0, 8.8 Hz), 7.94 (1H, d, J=8.8 Hz), 7.95 (1H, d, J=8.8 Hz), 8.20 (1H, d, J=2.2 Hz), 8.27 (1H, d, J=2.0 Hz). IR (KBr): 3241, 1747, 1616, 1558, 1347, 1210, 1164 cm$^{-1}$.

Working Example 36

1-(4-Diisopropylaminomethylbenzoyl)-4-(6-hydroxynaphthalene-2-sulfonyl)piperazine To a solution of 1-(4-diisopropylaminomethylbenzoyl)-4-(6-methoxynaphthalene-2-sulfonyl)piperazine (100 mg) in CH$_2$Cl$_2$ (6 ml) was added dropwise at 0° C. a solution of 3.5 M BBr$_3$ in CH$_2$Cl$_2$ (0.12 ml), and the solution was stirred at room temperature for 1 hour. To the reaction solution was added sodium bicarbonate solution and the organic layer was separated, dried and concentrated to give a colorless solid of the title compound (91 mg).

$^1$H-NMR (CDCl$_3$) δ: 0.98 (12H, d, J=6.6 Hz), 2.97 (2H, quint, J=6.6 Hz), 3.07 (4H, brs), 3.62 (2H, s), 3.72 (4H, brs), 7.08–7.26 (4H, m), 7.39 (2H, d, J=7.8 Hz), 7.60 (1H, dd, J=1.8, 8.8 Hz), 7.69 (1H, d, J=8.8 Hz), 7.79 (1H, d, J=8.8 Hz), 8.19 (1H, s). IR (KBr): 3163 (br), 1610, 1465, 1438, 1347, 1284, 1162 cm$^{-1}$.

Working Example 37

1-(4-Diisopropylaminomethylbenzoyl)-4-(7-hydroxynaphthalene-2-sulfonyl)piperazine According to a similar method described in Working Example 36, to a solution of 1-(4-diisopropylaminomethylbenzoyl)-4-(7-methoxynaphthalene-2-sulfonyl)piperazine (150 mg) in CH$_2$Cl$_2$ (6 ml) was added dropwise at 0° C. a solution of 3.5 M BBr$_3$ in CH$_2$Cl$_2$ (0.18 ml), and the solution was stirred at room temperature for 1 hour. To the reaction solution was added sodium bicarbonate solution and the organic layer was separated, dried and concentrated to give a colorless solid of the title compound (119 mg).

$^1$H-NMR (DMSO-d$_6$) δ: 0.96 (12H, d, J=6.6 Hz), 2.80–3.10 (6H, m), 3.30–3.75 (6H, m), 7.18–7.40 (6H, m), 7.48 (1H, d, J=8.6 Hz), 7.93 (1H, d, J=9.0 Hz), 8.02 (1H, d, J=8.6 Hz), 8.17 (1H, s), 10.18 (1H, brs). IR (KBr): 3100 (br), 1627, 1587, 1442, 1345, 1282, 1170 cm$^{-1}$.

Working Example 38

1-(6-Aminonaphthalene-2-sulfonyl)-4-(4-diisopropylaminomethylbenzoyl)piperazine

To a solution of 1-(4-diisopropylaminomethylbenzoyl)-4-[6-(2,2, 2-trichloroethoxycarbonylamino)naphthalene-2-sulfonyl]piperazine (125 mg) in acetic acid (3 ml) was added zinc dust (1.0 g), and the solution was stirred at room temperature for 3 hours. Insoluble materials were filtered off, and the filtrate was concentrated. The residue was dissolved in 1 N hydrochloric acid and the solution was made alkaline with 1 N sodium hydroxide solution. The precipitate was filtered, washed with water and dried to give pale purple solid of the title compound (92 mg).

$^1$H-NMR (DMSO-d$_6$) δ: 0.97 (12H, d, J=6.6 Hz), 2.80–3.10 (6H, m), 3.57 (4H, brs), 3.60 (2H, s), 5.95 (2H, s), 6.88 (1H, d, J=2.0 Hz), 7.07 (1H, dd, J=2.0, 8.8 Hz), 7.23 (2H, d, J=8.0 Hz), 7.35 (2H, d, J=8.0 Hz), 7.47 (1H, dd, J=1.6, 8.8 Hz), 7.66 (1H, d, J=8.8 Hz), 7.83 (1H, d, J=8.8 Hz), 8.08 (1H, d, J=1.6 Hz). IR (KBr): 1629, 1508, 1430, 1347, 1162 cm$^{-1}$.

Working Example 39

1-(6-Chloronaphthalene-2-sulfonyl)-4-[4-(N-ethyl-tert-butylaminomethyl)benzoyl]piperazine A solution of 1-(tert-butoxycarbonyl)-4-[4-(N-ethyl-tert-butylaminomethyl)benzoyl]piperazine (200 mg), methanol (0.5 ml) and 4 N hydrochloric acid in ethyl acetate solution (2 ml) were stirred at room temperature for 10 minutes. The reaction solution was concentrated and the residue was dissolved in ethyl acetate (10 ml) and sodium bicarbonate solution (10 ml). To the solution was added 6-chloro-naphthalene-2-sulfonylchloride (135 mg), and the mixture was stirred at room temperature for 30 minutes. The organic layer was separated, washed with water, and extracted with 1 N hydrochloric acid. The extract was made alkaline with sodium hydroxide solution, extracted with dichloromethane. The extract was dried and concentrated. The residue was crystallized with ether/hexane to give colorless crystals of the title compound (163 mg).

$^1$H-NMR (CDCl$_3$) δ: 0.85 (6H, t, J=7.0 Hz), 1.08 (9H, s), 2.59 (2H, q, J=7.0 Hz), 3.09 (4H, brs), 3.65 (2H, s), 3.72 (4H, brs), 7.21 (2H, d, J=7.8 Hz), 7.40 (2H, d, J=7.8 Hz), 7.60 (1H, d, J=9.0 Hz), 7.75 (1H, d, J=9.0 Hz), 7.90–7.97 (3H, m), 8.31 (1H, s). IR (KBr): 1637, 1457, 1430, 1349, 1284, 1166 cm$^{-1}$.

Working Example 40

1-(6-Bromonaphthalene-2-sulfonyl)-4-[4-(N-ethyl-tert-butylaminomethyl)benzoyl]piperazine According to a similar method described in Working Example 39, the title compound (166 mg) was obtained as colorless crystals, by treating 1-(tert-butoxycarbonyl)-4-[4-(N-ethyl-tert-butylaminomethyl)benzoyl]piperazine (200 mg) with hydrochloric acid, followed by reacting with 6-bromonaphthalene-2-sulfonylchloride (160 mg).

$^1$H-NMR (CDCl$_3$) δ: 0.85 (6H, t, J=7.0 Hz), 1.08 (9H, s), 2.59 (2H, q, J=7.0 Hz), 3.10 (4H, brs), 3.65 (2H, s), 3.72 (4H, brs), 7.20 (2H, d, J=8.2 Hz), 7.39 (2H, d, J=8.2 Hz), 7.67–7.79 (2H, m), 7.85 (1H, d, J=8.8 Hz), 7.91 (1H, d, J=8.8 Hz), 8.12 (1H, s), 8.29 (1H, s). IR (KBr): 1637, 1428, 1347, 1330, 1284, 1164 cm$^{-1}$.

Working Example 41

1-(6-Chloronaphthalene-2-sulfonyl)-4-[4-(2,6-dimethylpiperidinomethyl)benzoyl]piperazine According to a similar method described in Working Example 39, the title compound (40 mg) was obtained as colorless crystals, by treating 1-(tert-butoxycarbonyl)-4-[4-(2,6-dimethylpiperidinomethyl)benzoyl]piperazine (200 mg) with hydrochloric acid, followed by reacting with 6-chloronaphthalene-2-sulfonylchloride (132 mg).

$^1$H-NMR (CDCl$_3$) δ: 0.98 (6H, t, J=6.2 Hz), 1.28 (4H, m), 1.61 (2H, m), 2.45 (2H, m), 3.11 (4H, brs), 3.70 (4H, brs), 3.73 (2H, s), 7.21 (2H, d, J=8.0 Hz), 7.39 (2H, d, J=8.0 Hz), 7.59 (1H, dd, J=2.0, 8.8 Hz), 7.75 (1H, dd, J=1.8, 8.8 Hz), 7.90–8.00 (3H, m), 8.30 (1H, s). IR (KBr): 1635, 1455, 1432, 1347, 1284, 1166 cm$^{-1}$.

Working Example 42

1-(6-Bromonaphthalene-2-sulfonyl)-4-[4-(2,6-dimethylpiperidinomethyl)benzoyl]piperazine According to a similar method described in Working Example 39, the title compound (47 mg) was obtained as colorless crystals, by treating 1-(tert-butoxycarbonyl)-4-[4-(2,6-dimethylpiperidinomethyl)benzoyl]piperazine (200 mg) with hydrochloric acid, followed by reacting with 6-bromonaphthalene-2-sulfonylchloride (155 mg).

$^1$H-NMR (CDCl$_3$) δ: 0.97 (6H, t, J=6.2 Hz), 1.28 (4H, m), 1.60 (2H, m), 2.46 (2H, m), 3.10 (4H, brs), 3.71 (4H, brs), 3.73 (2H, s), 7.21 (2H, d, J=8.2 Hz), 7.39 (2H, d, J=8.2 Hz), 7.67–7.80 (2H, m), 7.80 (1H, d, J=9.0 Hz), 7.91 (1H, d, J=8.8 Hz), 8.12 (1H, s), 8.29 (1H, s). IR (KBr): 1639, 1459, 1432, 1345, 1284, 1164 cm$^{-1}$.

Working Example 43

1-[4-(2-Diisopropylaminoethyl)benzoyl]-4-(2-naphthalenesulfonyl)piperazine

According to a similar method described in Working Example 39, the title compound (76 mg) was obtained as colorless amorphous solid by treating 1-(tert-butoxycarbonyl)-4-[4-(2-diisopropylaminoethyl)benzoyl]piperazine (161 mg) with hydrochloric acid, followed by reacting with 2-naphthalenesulfonylchloride (95 mg).

$^1$H-NMR (CDCl$_3$) δ: 0.98 (12H, d, J=6.6 Hz), 2.50–2.74 (4H, m), 3.02 (2H, quint, J=6.6 Hz), 3.09 (4H, brs), 3.70 (4H, brs), 7.16 (2H, d, J=8.4 Hz), 7.21 (2H, d, J=8.4 Hz), 7.58–7.77 (3H, m), 7.90–8.04 (3H, m), 8.33 (1H, s); IR (KBr): 1637, 1457, 1426, 1347, 1284, 1166 cm$^{-1}$.

Working Example 44

1-(6-Chloronaphthalene-2-sulfonyl)-4-[4-(2-diisopropylaminoethyl)benzoyl]piperazine According to a similar method described in Working Example 39, the title compound (69 mg) was obtained as colorless amorphous solid by treating 1-(tert-butoxycarbonyl)-4-[4-(2-diisopropylaminoethyl)benzoyl]piperazine (161 mg) with hydrochloric acid, followed by reacting with 6-chloronaphthalene-2-sulfonylchloride (110 mg).

$^1$H-NMR (CDCl$_3$) δ: 0.99 (12H, d, J=6.6 Hz), 2.50–2.75 (4H, m), 3.03 (2H, quint, J=6.6 Hz), 3.09 (4H, brs), 3.70 (4H, brs), 7.16 (2H, d, J=8.4 Hz), 7.21 (2H, d, J=8.4 Hz), 7.59 (1H, dd, J=2.0, 8.8 Hz), 7.75 (1H, dd, J=1.6, 8.8 Hz), 7.92 (2H, d, J=8.8 Hz), 7.94 (1H, s), 8.29 (1H, s). IR (KBr): 1635, 1455, 1428, 1347, 1283, 1166 cm$^{-1}$.

Working Example 45

1-(6-Bromonaphthalene-2-sulfonyl)-4-[4-(2-diisopropylaminoethyl)benzoyl]piperazine According to a similar method described in Working Example 39, the title compound (68 mg) was obtained as colorless amorphous solid by treating 1-(tert-butoxycarbonyl)-4-[4-(2-diisopropylaminoethyl)benzoyl]piperazine (161 mg) with hydrochloric acid, followed by reacting with 6-bromonaphthalene-2-sulfonylchloride (128 mg).

$^1$H-NMR (CDCl$_3$) δ: 0.99 (12H, d, J=6.6 Hz), 2.50–2.77 (4H, m), 2.92–3.20 (6H, m), 3.73 (4H, brs), 7.16 (2H, d, J=8.4 Hz), 7.21 (2H, d, J=8.4 Hz), 7.69–7.80 (2H, m), 7.85 (1H, d, J=8.8 Hz), 7.91 (1H, d, J=8.8 Hz), 8.13 (1H, s), 8.29 (1H, s). IR (KBr): 1635, 1455, 1428, 1347, 1284, 1166 cm$^{-1}$.

Working Example 46

1-(6-Chloronaphthalene-2-sulfonyl)-4-(4-diisopropylaminomethyl-2-methoxybenzoyl)piperazine To a solution of 1-(6-chloronaphthalene-2-sulfonyl)piperazine hydrochloride(100 mg), 4-diisopropylaminomethyl-2-methoxybenzoic acid (77 mg), triethylamine (35 mg) and HOBt (43 mg) in DMF (10 ml) was added WSC hydrochloride (61 mg) under ice-cooling, and the solution was stirred at room temperature for 4 hours and concentrated. To the residue were added ethyl acetate and sodium bicarbonate solution. The organic layer was separated, washed with water and extracted with 1 N hydrochloric acid. The extract was made alkaline with sodium hydroxide solution and extracted with dichloromethane. The extract was dried and concentrated and the residue was crystallized with ether to give colorless crystals of the title compound (99 mg).

$^1$H-NMR (CDCl$_3$) δ: 0.99 (12H, d, J=6.6 Hz), 2.98 (2H, quint, J=6.6 Hz), 3.00 (2H, m), 3.18 (2H, m), 3.36 (2H, m), 3.61 (5H, s), 3.89 (2H, m), 6.91 (1H, d, J=7.6 Hz), 6.98 (1H, s), 7.02 (1H, d, J=7.6 Hz), 7.60 (1H, dd. J=2.2, 8.8 Hz), 7.76 (1H, dd, J=2.0, 8.8 Hz), 7.88–7.96 (3H, m), 8.30 (1H, s). IR (KBr): 1635, 1463, 1436, 1347, 1166 cm$^{-1}$.

Working Example 47

1-(6-Chloronaphthalene-2-sulfonyl)-4-[4-(4-pyridyl)benzoyl]piperazine

To a solution of 1-(6-chloronaphthalene-2-sulfonyl)piperazine hydrochloride (90 mg), 4-(4-pyridyl)benzoic acid (52 mg), triethylamine (35 mg) and HOBt (39 mg) in DMF (10 ml) was added WSC hydrochloride (55 mg) under ice-cooling and the solution was stirred at room temperature 4 hours and concentrated. To the residue was added ethyl acetate and sodium bicarbonate solution. The organic layer was separated, washed with water, and extracted with 1 N hydrochloric acid. The extract was made alkaline with sodium hydroxide solution and extracted with dichloromethane. The extract was dried and concentrated, and the residue was crystallized with ether to give colorless crystals of the title compound (122 mg).

$^1$H-NMR (CDCl$_3$) δ: 3.14 (4H, brs), 3.76 (4H, brs), 7.38–7.49 (4H, m), 7.56–7.68 (3H, m), 7.75 (1H, d, J=8.4 Hz), 7.89–7.98 (3H, m), 8.31 (1H, s), 8.68 (2H, d, J=5.8 Hz). IR (KBr): 1635, 1596, 1432, 1347, 1330, 1284, 1166 cm$^{-1}$.

Working Example 48

1-(6-Chloronaphthalene-2-sulfonyl)-4-[4-(3-pyridyl)benzoyl]piperazine

According to a similar method described in Working Example 46, the title compound (106 mg) was obtained as colorless crystals, by reacting a solution of 1-(6-chloronaphthalene-2-sulfonyl)piperazine hydrochloride (100 mg), 4-(3-pyridyl)benzoic acid (57 mg), triethylamine (40 mg) and HOBt (43 mg) in DMF (10 ml) with WSC hydrochloride (61 mg).

$^1$H-NMR (CDCl$_3$) δ: 3.13 (4H, brs), 3.76 (4H, brs), 7.34–7.46 (3H, m), 7.54–7.64 (3H, m), 7.77 (1H, dd, J=2.0, 8.8 Hz), 7.85 (1H, dt, J=1.4, 8.0 Hz), 7.89–7.97 (3H, m), 8.32 (1H, s), 8.63 (1H, dd, J=1.4, 4.8 Hz), 8.82 (1H, d, J=1.4 Hz). IR (KBr): 1635, 1428, 1347, 1284, 1166 cm$^{-1}$.

Working Example 49

1-(6-Chloronaphthalene-2-sulfonyl)-4-[4-(1H-imidazol-1-yl)benzoyl]piperazine

According to a similar method described in Working Example 46, the title compound (124 mg) was obtained as colorless crystals, by reacting a solution of 1-(6-chloronaphthalene-2-sulfonyl)piperazine hydrochloride (100 mg), 4-(1H-imidazol-1-yl)benzoic acid (55 mg), triethylamine (40 mg) and HOBt (43 mg) in DMF (10 ml) with WSC hydrochloride (61 mg).

$^1$H-NMR (CDCl$_3$) δ: 3.12 (4H, brs), 3.74 (4H, brs), 7.22 (1H, s), 7.27 (1H, s), 7.40 (2H, d, J=9.2 Hz), 7.45 (2H, d, J=9.2 Hz), 7.60 (1H, dd, J=2.0, 8.8 Hz), 7.76 (1H, dd, J=2.0, 8.8 Hz), 7.86 (1H, s), 7.88–7.97 (3H, m), 8.31 (1H, s). IR (KBr): 1635, 1455, 1436, 1345, 1286, 1166 cm$^{-1}$.

Working Example 50

1-(6-Chloronaphthalene-2-sulfonyl)-4-[4-(1,2,4-triazol-1-yl)benzoyl]piperazine

According to a similar method described in Working Example 46, the title compound (107 mg) was obtained as colorless crystals, by reacting a solution of 1-(6-chloronaphthalene-2-sulfonyl)piperazine hydrochloride (100 mg), 4-(1,2,4-triazol-1-yl)benzoic acid (55 mg), triethylamine (40 mg) and HOBt (43 mg) in DMF (10 ml) with WSC hydrochloride (61 mg).

$^1$H-NMR (CDCl$_3$) δ: 3.14 (4H, brs), 3.72 (4H, brs), 7.47 (2H, d, J=8.8 Hz), 7.60 (1H, dd, J=1.8, 8.8 Hz), 7.67–7.80 (3H, m), 7.89–7.98 (3H, m), 8.12 (1H, s), 8.31 (1H, d, J=1.8 Hz), 8.58 (1H, s). IR (KBr): 1637, 1610, 1459, 1438, 1345, 1330, 1280 cm$^{-1}$.

Working Example 51

1-(6-Chloronaphthalene-2-sulfonyl)-4-[4-(1,2,4-triazol-4-yl)benzoyl]piperazine

According to a similar method described in Working Example 46, the title compound (54 mg) was obtained as colorless crystals, by reacting a solution of 1-(6-chloronaphthalene-2-sulfonyl)piperazine hydrochloride (100 mg), 4-(1,2,4-triazol-4-yl)benzoic acid (55 mg), triethylamine (40 mg) and HOBt (43 mg) in DMF (10 ml) solution with WSC hydrochloride (61 mg).

$^1$H-NMR (CDCl$_3$) δ: 3.14 (4H, brs), 3.74 (4H, brs), 7.42 (2H, d, J=8.8 Hz), 7.52 (2H, d, J=8.8 Hz), 7.61 (1H, dd, J=1.8, 8.8 Hz), 7.76 (1H, dd, J=1.8, 8.8 Hz), 7.90–7.98 (3H, m), 8.12 (1H, s), 8.32 (1H, d, J=1.8 Hz), 8.48 (2H, s). IR (KBr): 1633, 1610, 1527, 1459, 1436, 1345, 1330, 1164 cm$^{-1}$.

Working Example 52

1-[4-(N-tert-Butoxycarbonylpiperidin-4-yl)benzoyl]-4-(6-chloronaphthalene-2-sulfonyl)piperazine According to a similar method described in Working Example 46, the title compound (153 mg) was obtained as colorless crystals, by reacting a solution of 1-(6-chloronaphthalene-2-sulfonyl)piperazine hydrochloride (100 mg), 4-(N-tert-butoxycarbonylpiperidin-4-yl)benzoic acid (88 mg), triethylamine (40 mg) and HOBt (43 mg) in DMF (10 ml) with WSC hydrochloride (61 mg).

$^1$H-NMR (CDCl$_3$) δ: 1.48 (9H, s), 1.50–1.85 (4H, m), 2.58–2.90 (3H, m), 3.11 (4H, brs), 3.71 (4H, brs), 4.23 (2H, brd, J=11.0 Hz), 7.18 (2H, d, J=8.4 Hz), 7.25 (2H, d, J=8.4 Hz), 7.60 (1H, dd, J=2.2, 8.8 Hz), 7.75 (1H, dd, J=1.8, 8.8 Hz), 7.88–7.96 (3H, m), 8.30 (1H, s). IR (KBr): 1683, 1635, 1428, 1347, 1284, 1166 cm$^{-1}$.

Working Example 53

1-[4-(1-tert-Butoxycarbonyl-4-piperazinyl)benzoyl]-4-(6-chloronaphthalene-2-sulfonyl)piperazine According to a similar method described in Working Example 46, the title compound (128 mg) was obtained as colorless crystals, by reacting a solution of 1-(6-chloronaphthalene-2-sulfonyl)piperazine hydrochloride (100 mg), 4-(1-tert-butoxycarbonyl-4-piperazinyl)benzoic acid (88 mg), triethylamine (40 mg) and HOBt (43 mg) in DMF (10 ml) with WSC hydrochloride (61 mg).

$^1$H-NMR (CDCl$_3$) δ: 1.48 (9H, s), 3.09 (4H, m), 3.18 (4H, m), 3.56 (4H, m), 3.74 (4H, m), 6.82 (2H, d, J=8.8 Hz), 7.25 (2H, d, J=8.8 Hz), 7.59 (1H, dd, J=2.2, 8.8 Hz), 7.75 (1H, dd, J=1.4, 8.8 Hz), 7.87–7.96 (3H, m), 8.29 (1H, s). IR (KBr): 1695, 1627, 1608, 1427, 1232, 1166 cm$^{-1}$.

Working Example 54

1-(6-Chloronaphthalene-2-sulfonyl)-4-[2-(4-pyridyl)-4-thiazolcarbonyl]piperazine According to a similar method described in Working Example 46, the title compound (133 mg) was obtained as colorless crystals, by reacting a solution of 1-(6-chloronaphthalene-2-sulfonyl)piperazine hydrochloride (100 mg), 2-(4-pyridyl)-4-thiazolecarboxylic acid (60 mg), triethylamine (40 mg) and HOBt (43 mg) in DMF (10 ml) with WSC hydrochloride (61 mg).

$^1$H-NMR (CDCl$_3$) δ: 3.22 (4H, brs), 3.92 (2H, brs), 4.18 (2H, brs), 7.58 (1H, dd, J=2.0, 8.8 Hz), 7.73 (2H, d, J=6.2 Hz), 7.78 (1H, dd, J=1.8, 8.8 Hz), 7.87–7.96 (3H, m), 8.05 (1H, s), 8.33 (1H, s), 8.74 (2H, d, J=6.2 Hz). IR (KBr): 1629, 1596, 1461, 1345, 1330, 1241, 1164 cm$^{-1}$.

Working Example 55

1-(6-Chloronaphthalene-2-sulfonyl)-4-[4-(4-pyridyl)-2-thiazolcarbonyl]piperazine According to a similar method described in Working Example 46, the title compound (113 mg) was obtained as colorless crystals, by reacting a solution of 1-(6-chloronaphthalene-2-sulfonyl)piperazine hydrochloride (100 mg), 4-(4-pyridyl)-2-thiazolcarboxylic acid (60 mg), triethylamine (40 mg) and HOBt (43 mg) in DMF (10 ml) with WSC hydrochloride (61 mg).

$^1$H-NMR (CDCl$_3$) δ: 3.26 (4H, t, J=5.0 Hz), 3.95 (2H, brs), 4.70 (2H, brs), 7.58 (1H, dd, J=2.0, 8.8 Hz), 7.68 (2H, d, J=6.2 Hz), 7.78 (1H, dd, J=1.8, 8.8 Hz), 7.85–7.96 (4H, m), 8.34 (1H, s), 8.70 (2H, d, J=6.2 Hz). IR (KBr): 1625, 1600, 1492, 1459, 1345, 1330, 1280, 1164 cm$^{-1}$.

Working Example 56

1-(6-Chloronaphthalene-2-sulfonyl)-4-[2-(4-pyridyl)-5-thiazolcarbonyl]piperazine According to a similar method described in Working Example 46, the title compound (118 mg) was obtained as colorless crystals, by reacting a solution of 1-(6-chloronaphthalene-2-sulfonyl)piperazine hydrochloride (100 mg), 2-(4-pyridyl)-5-thiazolcarboxylic acid (60 mg), triethylamine (40 mg) and HOBt (43 mg) in DMF (10 ml) with WSC hydrochloride (61 mg).

$^1$H-NMR (CDCl$_3$) δ: 3.18 (4H, t, J=5.0 Hz), 3.88 (4H, t, J=5.0 Hz), 7.60 (1H, dd, J=1.8, 8.8 Hz), 7.73–7.80 (3H, m), 7.90–7.98 (4H, m), 8.32 (1H, m), 8.74 (2H, d, J=6.2 Hz). IR (KBr): 1623, 1594, 1436, 1345, 1164 cm$^{-1}$.

Working Example 57

1-(6-Bromonaphthalene-2-sulfonyl)-4-[2-(4-pyridyl)-5-thiazolcarbonyl]piperazine

According to a similar method described in Working Example 46, the title compound (47 mg) was obtained as colorless crystals, by reacting a solution of 1-(6-bromonaphthalene-2-sulfonyl)piperazine hydrochloride (112 mg), 2-(4-pyridyl)-5-thiazolcarboxylic acid (60 mg), triethylamine (40 mg) and HOBt (43 mg) in DMF (10 ml) with WSC hydrochloride (61 mg).

$^1$H-NMR (CDCl$_3$) δ: 3.18 (4H, t, J=5.0 Hz), 3.88 (4H, t, J=5.0 Hz), 7.69–7.80 (4H, m), 7.86 (1H, d, J=8.8 Hz), 7.92 (1H, d, J=8.8 Hz), 7.96 (1H, s), 8.12 (1H, s), 8.31 (1H, s), 8.73 (2H, d, J=6.0 Hz). IR (KBr): 1622, 1435, 1346, 1163 cm$^{-1}$.

Working Example 58

1-(6-Chloronaphthalene-2-sulfonyl)-4-[5-(4-pyridyl)-2-thenoyl]piperazine

According to a similar method described in Working Example 46, the title compound (82 mg) was obtained as colorless crystals, by reacting a solution of 1-(6-chloronaphthalene-2-sulfonyl)piperazine hydrochloride (100 mg), 5-(4-pyridyl)-2-thiophenecarboxylic acid (60 mg), triethylamine (40 mg) and HOBt (43 mg) in DMF (10 ml) with WSC hydrochloride (61 mg).

$^1$H-NMR (CDCl$_3$) δ: 3.16 (4H, t, J=5.0 Hz), 3.89 (4H, t, J=5.0 Hz), 7.23 (1H, d, J=4.0 Hz), 7.38 (1H, d, J=4.0 Hz), 7.43 (2H, d, J=6.2 Hz), 7.59 (1H, dd, J=1.8, 8.8 Hz), 7.76 (1H, dd, J=1.8, 8.8 Hz), 7.88–7.96 (3H, m), 8.31 (1H, d, J=1.8 Hz), 8.62 (2H, d, J=6.0 Hz). IR (KBr): 1622, 1597, 1460, 1418, 1346, 1331, 1283, 1264, 1165 cm$^{-1}$.

Working Example 59

1-(6-Bromonaphthalene-2-sulfonyl)-4-[4-(4-pyridyl)benzoyl]piperazine

According to a similar method described in Working Example 46, the title compound (84 mg) was obtained as colorless crystals, by reacting a solution of 1-(6-bromonaphthalene-2-sulfonyl)piperazine hydrochloride (112 mg), 4-(4-pyridyl)benzoic acid (57 mg) triethylamine (40 mg) and HOBt (43 mg) in DMF (10 ml) with WSC hydrochloride (61 mg).

$^1$H-NMR (CDCl$_3$) δ: 3.13 (4H, brs), 3.73 (4H, brs), 7.42 (2H, d, J=8.2 Hz), 7.46 (2H, d, J=6.2 Hz), 7.63 (2H, d, J=8.2 Hz), 7.70–7.80 (2H, m), 7.86 (1H, d, J=8.8 Hz), 7.92 (1H, d, J=8.8 Hz), 8.13 (1H, s), 8.30 (1H, m), 8.68 (2H, d, J=6.2 Hz). IR (KBr): 1636, 1456, 1431, 1346, 1329, 1285, 1165 cm$^{-1}$.

Working Example 60

1-(6-Bromonaphthalene-2-sulfonyl)-4-[4-(3-pyridyl)benzoyl]piperazine

According to a similar method described in Working Example 46, the title compound (101 mg) was obtained as colorless crystals, by reacting a solution of 1-(6-bromonaphthalene-2-sulfonyl)piperazine hydrochloride (112 mg), 4-(3-pyridyl)benzoic acid (57 mg), triethylamine (40 mg) and HOBt (43 mg) in DMF (10 ml) with WSC hydrochloride (61 mg).

$^1$H-NMR (CDCl$_3$) δ: 3.13 (4H, brs), 3.74 (4H, brs), 7.34–7.47 (3H, m), 7.58 (2H, d, J=8.4 Hz), 7.68–7.96 (5H, m), 8.13 (1H, s), 8.30 (1H, s), 8.62 (1H, dd, J=1.4, 4.8 Hz), 8.81 (1H, d, J=2.2 Hz). IR (KBr): 1634, 1456, 1427, 1346, 1329, 1285, 1163 cm$^{-1}$.

Working Example 61

1-(6-Bromonaphthalene-2-sulfonyl)-4-[4-(1H-imidazol-1-yl)benzoyl]piperazine

According to a similar method described in Working Example 46, the title compound (122 mg) was obtained as colorless crystals, by reacting a solution of 1-(6-bromonaphthalene-2-sulfonyl)piperazine hydrochloride (112 mg), 4-(1H-imidazol-1-yl)benzoic acid (55 mg), triethylamine (40 mg) and HOBt (43 mg) in DMF (10 ml) with WSC hydrochloride (61 mg).

$^1$H-NMR (CDCl$_3$) δ: 3.13 (4H, brs), 3.74 (4H, brs), 7.22 (1H, s), 7.28 (1H, s), 7.40 (2H, d, J=8.8 Hz), 7.45 (2H, d, J=8.8 Hz), 7.73 (1H, dd, J=2.0, 8.8 Hz), 7.76 (1H, dd, J=2.0, 8.8 Hz), 7.82–7.88 (2H, m), 7.92 (1H, d, J=8.8 Hz), 8.13 (1H, d, J=2.0 Hz), 8.30 (1H, s). IR (KBr): 1636, 1611, 1456, 1433, 1344, 1329, 1285, 1262, 1163 cm$^{-1}$.

Working Example 62

1-(6-Chloronaphthalene-2-sulfonyl)-4-[5-(4-pyridyl)-2-furoyl]piperazine

According to a similar method described in Working Example 46, the title compound (90 mg) was obtained as pale green crystals, by reacting a solution of 1-(6-chloronaphthalene-2-sulfonyl)piperazine hydrochloride (80 mg), 5-(4-pyridyl)-2-furancarboxylic acid (44 mg), triethylamine (30 mg) and HOBt (33 mg) in DMF (10 ml) with WSC hydrochloride (49 mg).

$^1$H-NMR (CDCl$_3$) δ: 3.21 (4H, t, J=5.0 Hz), 3.98 (4H, brs), 6.90 (1H, d, J=3.6 Hz), 7.07 (1H, d, J=3.6 Hz), 7.47 (2H, d, J=6.2 Hz), 7.58 (1H, dd, J=1.8, 8.8 Hz), 7.57 (1H, dd, J=1.8, 8.8 Hz), 7.88–7.96 (3H, m), 8.33 (1H, s), 8.65 (2H, d, J=6.2 Hz). IR (KBr): 1626, 1607, 1427, 1346, 1165 cm$^{-1}$.

Working Example 63

1-(6-Chloronaphthalene-2-sulfonyl)-4-[6-(4-pyridyl)nicotinoyl]piperazine

According to a similar method described in Working Example 46, the title compound (103 mg) was obtained as colorless crystals, by reacting a solution of 1-(6-chloronaphthalene-2-sulfonyl)piperazine hydrochloride (80 mg), 6-(4-pyridyl)nicotinic acid (47 mg), triethylamine (30 mg) and HOBt (33 mg) in DMF (10 ml) with WSC hydrochloride (49 mg).

$^1$H-NMR (CDCl$_3$) δ: 3.15 (4H, brs), 3.77 (4H, brs), 7.60 (1H, dd, J=2.0, 8.8 Hz), 7.76 (1H, dd, J=1.8, 8.8 Hz), 7.80–7.97 (7H, m), 8.31 (1H, s), 8.66 (1H, d, J=1.6 Hz), 8.74 (2H, d, J=5.8 Hz). IR (KBr): 1634, 1593, 1456, 1435, 1346, 1331, 1285, 1165 cm$^{-1}$.

Working Example 64

1-(6-Chloronaphthalene-2-sulfonyl)-4-[2-(4-pyridyl)-4-methyl-5-thiazolcarbonyl]piperazine According to a similar method described in Working Example 46, the title compound (100 mg) was obtained as colorless crystals, by reacting a solution of 1-(6-chloronaphthalene-2-sulfonyl)piperazine hydrochloride (80 mg), 2-(4-pyridyl)-4-methyl-5-thiazolcarboxylic acid (51 mg), triethylamine (30 mg) and HOBt (33 mg) in DMF (10 ml) with WSC hydrochloride (49 mg).

$^1$H-NMR (CDCl$_3$) δ: 2.43 (3H, s), 3.15 (4H, t, J=5.0 Hz), 3.77 (4H, m), 7.60 (1H, dd, J=1.8, 8.8 Hz), 7.69–7.80 (3H, m), 7.90–7.98 (3H, m), 8.32 (1H, s), 8.71 (2H, d, J=6.2 Hz). IR (KBr): 1634, 1597, 1456, 1435, 1346, 1329, 1281, 1258, 1165 cm$^{-1}$.

Working Example 65

1-(6-Bromonaphthalene-2-sulfonyl)-4-[5-(4-pyridyl)-2-thenoyl]piperazine

According to a similar method described in Working Example 46, the title compound (131 mg) was obtained as colorless crystals, by reacting a solution of 1-(6-bromonaphthalene-2-sulfonyl)piperazine hydrochloride (112 mg), 5-(4-pyridyl)-2-thiophenecarboxylic acid (60 mg), triethylamine (40 mg) and HOBt (43 mg) in DMF (10 ml) with WSC hydrochloride (61 mg).

$^1$H-NMR (CDCl$_3$) δ: 3.16 (4H, t, J=4.9 Hz), 3.88 (4H, t, J=4.9 Hz), 7.22 (1H, d, J=4.2 Hz), 7.37 (1H, d, J=4.2 Hz), 7.42 (2H, d, J=5.8 Hz), 7.68–7.80 (2H, m), 7.85 (1H, d, J=8.8 Hz), 7.92 (1H, d, J=8.8 Hz), 8.12 (1H, s), 8.30 (1H, s), 8.62 (2H, d, J=5.8 Hz). IR (KBr): 1620, 1597, 1456, 1418, 1344, 1331, 1283, 1264, 1163 cm$^{-1}$.

Working Example 66

1-(6-Bromonaphthalene-2-sulfonyl)-4-[4-(1,2,4-triazol-4-yl)benzoyl]piperazine

According to a similar method described in Working Example 46, the title compound (139 mg) was obtained as colorless crystals, by reacting a solution of 1-(6-bromonaphthalene-2-sulfonyl)piperazine hydrochloride (112 mg), 4-(1,2,4-triazol-4-yl)benzoic acid (55 mg), triethylamine (40 mg) and HOBt (43 mg) in DMF (10 ml) with WSC hydrochloride (61 mg).

$^1$H-NMR (CDCl$_3$) δ: 3.13 (4H, brs), 3.72 (4H, brs), 7.42 (2H, d, J=8.2 Hz), 7.50 (2H, d, J=8.2 Hz), 7.73 (1H, dd, J=1.8, 8.8 Hz), 7.75 (1H, dd, J=1.8, 8.8 Hz), 7.86 (1H, d, J=8.8 Hz), 7.92 (1H, d, J=8.8 Hz), 8.12 (1H, s), 8.29 (1H, s), 8.48 (2H, s). IR (KBr): 1634, 1526, 1456, 1435, 1345, 1329, 1285, 1163 cm$^{-1}$.

Working Example 67

1-(6-Bromonaphthalene-2-sulfonyl)-4-[2-(4-pyridyl)-4-methyl-5-thiazolcarbonyl]piperazine According to a similar method described in Working Example 46, the title compound (124 mg) was obtained as colorless crystals, by reacting a solution of 1-(6-bromonaphthalene-2-sulfonyl)piperazine hydrochloride (112 mg), 2-(4-pyridyl)-4-methyl-5-thiazolcarboxylic acid (64 mg), triethylamine (40 mg) and HOBt (43 mg) in DMF (10 ml) with WSC hydrochloride (61 mg).

$^1$H-NMR (CDCl$_3$) (: 2.43 (3H, s), 3.15 (4H, t, J=4.8 Hz), 3.76 (4H, m), 7.68–7.80 (4H, m), 7.86 (1H, d, J=8.8 Hz), 7.93 (1H, d, J=8.8 Hz), 8.13 (1H, s), 8.31 (1H, s), 8.70 (2H, d, J=6.2 Hz). IR (KBr): 1634, 1433, 1346, 1329, 1281, 1256, 1165 cm$^{-1}$.

Working Example 68

1-(6-Chloronaphthalene-2-sulfonyl)-4-[4-(4-piperidyl)benzoyl]piperazine hydrochloride To a solution of 1-[4-(N-tert-butoxycarbonylpiperidin-4-yl)benzoyl]-4-(6-chloronaphthalene-2-sulfonyl)piperazine (125 mg) in ethyl acetate (0.5 ml) was added 4 N hydrochloric acid in ethyl acetate solution (4 ml) and the solution was stirred at room temperature for 1 hour, and diluted with ether. The precipitate was filtered, washed with ether and dried to give a colorless solid of the title compound (105 mg).

$^1$H-NMR (CDCl$_3$) δ: 1.90–2.35 (4H, m), 2.77 (1H, m), 2.90–3.20 (6H, m), 3.40–3.90 (6H, m), 7.26 (4H, s), 7.59 (1H, dd, J=1.8, 8.8 Hz), 7.76 (1H, d, J=8.8 Hz), 7.90–7.96 (3H, m), 8.31 (1H, s), 9.50–9.90 (2H, br). IR (KBr): 1627, 1457, 1436, 1345, 1330, 1284, 1164 cm$^{-1}$.

Working Example 69

1-(6-Chloronaphthalene-2-sulfonyl)-4-(4-piperazinylbenzoyl)piperazine hydrochloride According to a similar method described in Working Example 68, the title compound was obtained, using 1-[4-(N-tert-butoxycarbonylpiperazinyl)benzoyl]-4-(6-chloronaphthalene-2-sulfonyl)piperazine instead of 1-[4-(N-tert-butoxycarbonylpiperidin-4-yl)benzoyl]-4-(6-chloronaphthalene-2-sulfonyl)piperazine.

$^1$H-NMR (DMSO-d$_6$) δ: 3.05 (4H, brs), 3.21 (4H, brs), 3.46 (4H, brs), 3.60 (4H, brs), 6.94 (2H, d, J=8.6 Hz), 7.24 (2H, d, J=8.6 Hz), 7.68 (1H, dd, J=1.8, 8.8 Hz), 7.80 (1H, d, J=8.8 Hz), 8.10–8.25 (3H, m), 8.46 (1H, s), 9.10 (2H, brs). IR (KBr): 1625, 1448, 1347, 1332, 1289, 1156 cm$^{-1}$.

Working Example 70

1-(4-Diethylaminobenzoyl)-4-(2-naphthalenesulfonyl)piperazine

To a solution of 1-(2-naphthalenesulfonyl)piperazine hydrochloride (625 mg) and 4-diethylamino benzoic acid (386 mg) in DMF (12 ml) was added diethyl phosphorocyanidate (489 mg) and then triethylamine (606 mg), and the solution was stirred at room temperature for 2 hours. The reaction solution was concentrated and the residue was purified with silica gel column chromatography (dichloromethane:10% ammonia containing methanol= 20:1) to give colorless amorphous of the title compound (250 mg).

$^1$H-NMR (CDCl$_3$) δ: 1.14 (6H, t, J=7.0 Hz), 3.09 (4H, t, J=5.0 Hz), 3.34 (4H, t, J=7.0 Hz), 3.76 (4H, t, J=5.0 Hz), 6.55 (2H, d, J=8.8 Hz), 7.21 (2H, d, J=8.8 Hz), 7.58–7.76 (3H, m), 7.90–8.03 (3H, m), 8.32 (1H, s). IR (KBr): 1606, 1525, 1409, 1347, 1263, 1195, 1166 cm$^{-1}$.

Working Example 71

1-(4-Diethylaminobenzoyl)-4-(2-naphthalenesulfonyl)piperazine hydrochloride

The compound obtained in Working Example 70 was dissolved in ethyl acetate, to which was added 4 N hydrochloric acid in ethyl acetate solution. The precipitate was filtered and dried to give colorless powder of the title compound (230 mg).

$^1$H-NMR (CDCl$_3$) δ: 1.27 (6H, t, J=7.0 Hz), 3.14 (4H, brs), 3.35–4.00 (8H, m), 7.48 (2H, d, J=8.4 Hz), 7.60–7.85 (5H, m), 7.90–8.05 (3H, m), 8.34 (1H, s). IR (KBr): 1635, 1438, 1347, 1166 cm$^{-1}$.

Working Example 72

1-(4-Amidino benzoyl)-4-(2-naphthalenesulfonyl) piperazine

To a solution of 1-(2-naphthalenesulfonyl)piperazine hydrochloride (313 mg) in sodium bicarbonate solution (20 ml)-dioxane (20 ml) was added 4-amidinobenzoyl chloride hydrochloride (219 mg) and the solution was stirred at room temperature for 30 minutes. The reaction solution was concentrated, to which were added dichloromethane and water. The organic layer was separated and extracted with 1 N hydrochloric acid. The extract was made alkaline with sodium hydroxide solution and the precipitate was filtered, washed with water and dried to give a colorless solid of the title compound (223 mg).

$^1$H-NMR (DMSO-d$_6$) δ: 3.08 (4H, brs), 3.00–3.60 (4H, br), 3.70 (1H, brs), 7.39 (2H, d, J=8.0 Hz), 7.60–7.80 (5H, m), 8.00–8.28 (3H, m), 8.45 (1H, s). IR (KBr): 3229, 1638, 1586, 1387, 1348, 1169 cm$^{-1}$.

Working Example 73

1-(4-tert-Butoxycarbonylamidinobenzoyl)-4-(6-chloronaphthalene-2-sulfonyl)piperazine To a solution of 1-(6-chloronaphthalene-2-sulfonyl) piperazine hydrochloride (134 mg) and triethylamine (134 mg) in dichloromethane was added 4-amidinobenzoylchloride hydrochloride (85 mg), and the solution was stirred at room temperature for 1 hour, to which were added DMF (10 ml) and di-tert-butyl bicarbonate (200 mg). The solution was stirred at 50° C. for 30 minutes and the reaction solution was concentrated. The residue was dissolved in ethyl acetate, washed with water and sodium chloride solution, dried and concentrated. The residue was purified with silica gel column chromatography(dichloromethane/ethyl acetate=1:1) to give colorless crystals of the title compound (171 mg).

$^1$H-NMR (CDCl$_3$) δ: 1.54 (9H, s), 3.08 (4H, brs), 3.49 (2H, brs), 3.85 (2H, brs), 7.32 (2H, d, J=8.4 Hz), 7.60 (1H, dd, J=1.8, 8.8 Hz), 7.75 (1H, dd, J=1.8, 8.8 Hz), 7.83 (2H, d, J=8.4 Hz), 7.90–7.98 (3H, m), 8.30 (1H, d, J=1.8 Hz). IR (KBr): 1615, 1281, 1165, 1138 cm$^{-1}$.

Working Example 74

1-(4-Amidinobenzoyl)-4-(6-chloronaphthalene-2-sulfonyl)piperazine hydrochloride

To 1-(4-tert-butoxycarbonylamidino benzoyl)-4-(6-chloronaphthalene-2-sulfonyl)piperazine (150 mg) was added 4 N hydrochloric acid in ethyl acetate solution (15 ml) and the solution was allowed to stand at room temperature for 5 hours, to which was added ether. The precipitate was filtered, washed with ether and dried to give a colorless solid of the title compound (102 mg).

$^1$H-NMR (DMSO-d$_6$) δ: 3.08 (4H, brs), 3.60 (2H, brs), 3.73 (2H, brs), 7.56 (2H, d, J=8.4 Hz), 7.73 (1H, d, J=8.8 Hz), 7.82 (2H, d, J=8.4 Hz), 8.18 (1H, d, J=8.8 Hz), 8.22–8.32 (2H, m), 8.50 (1H, s), 9.11 (2H, brs), 9.39 (2H, brs). IR (KBr): 3061, 1686, 1626, 1462, 1445, 1346, 1334, 1289, 1157 cm$^{-1}$.

Working Example 75

1-[4-(2,3-Di-tert-butoxycarbonylguanidino) benzoyl]-4-(6-chloronaphthalene-2-sulfonyl) piperazine To a solution of 1-(6-chloronaphthalene-2-sulfonyl) piperazine hydrochloride (200 mg), 4-guanidinobenzoic acid hydrochloride (125 mg), HOBt (86 mg) and triethylamine (250 mg) in DMF (15 mg) was added WSC (122 mg) and the solution was stirred at room temperature for 2 hours, to which was added di-tert-butyl bicarbonate (350 mg). The solution was stirred at 50° C. for 30 minutes and the reaction solution was concentrated. The residue was dissolved in ethyl acetate, washed with sodium bicarbonate solution and sodium chloride solution, dried and concentrated. The residue was purified with silica gel column chromatography (hexane/ethyl acetate=1:1) to give colorless crystals of the title compound (325 mg).

$^1$H-NMR (CDCl$_3$) δ: 1.30 (18H, s), 3.11 (4H, brs), 3.73 (4H, brs), 7.13 (2H, d, J=8.4 Hz), 7.32 (2H, d, J=8.4 Hz), 7.60 (1H, dd, J=1.8, 8.8 Hz), 7.76 (1H, dd, J=1.8, 8.8 Hz), 7.90–7.98 (3H, m), 8.32 (1H, s), 9.38 (2H, brs). IR (KBr): 3380, 1723, 1613, 1346, 1273, 1250, 1146 cm$^{-1}$.

Working Example 76

1-(4-Guanidinobenzoyl)-4-(6-chloronaphthalene-2-sulfonyl)piperazine hydrochloride To 1-[4-(2,3-di-tert-butoxycarbonylguanidino)benzoyl]-4-(6-chloronaphthalene-2-sulfonyl)piperazine (295 mg) was added 4 N hydrochloric acid in ethyl acetate solution (20 ml) and the solution was allowed to stand at room temperature for 3 hours, to which was added ether. The precipitate was filtered, washed with ether and dried to give a colorless solid of the title compound (191 mg).

$^1$H-NMR (DMSO-d$_6$) δ: 3.06 (4H, brs), 3.57 (4H, brs), 7.30–7.60 (5H, m), 7.72 (1H, d, J=8.8 Hz), 7.82 (1H, d, J=8.8 Hz), 8.18 (1H, d, J=8.8 Hz), 8.22–8.32 (2H, m), 8.50 (1H, s). IR (KBr): 3102, 1676, 1626, 1603, 1570, 1458, 1439, 1345, 1283, 1264, 1165 cm$^{-1}$.

Working Example 77

1-(6-Chloronaphthalene-2-sulfonyl)-4-[4-(N-methoxycarbonylamidino)benzoyl]piperazine To a solution of 1-(6-chloronaphthalene-2-sulfonyl) piperazine hydrochloride (143 mg) and triethylamine (208 mg) in dichloromethane (10 ml) was added 4-amidinobenzoylchloride hydrochloride (108 mg), and the solution was stirred at room temperature for 1 hour, to which were added DMF (10 ml) and methyl chloroformate (200 mg). The solution was stirred at 50° C. for 30 minutes and the reaction solution was concentrated. The residue was dissolved in ethyl acetate, washed with water and sodium chloride solution, dried and concentrated. The residue was purified with silica gel column chromatography (ethyl acetate/methanol=40:1) to give colorless crystals of the title compound (41 mg).

$^1$H-NMR (CDCl$_3$) δ: 3.01 (4H, brs), 3.35–4.00 (4H, br), 3.79 (3H, s), 6.50 (1H, br), 7.36 (2H, d, J=8.4 Hz), 7.60 (1H, dd, J=1.8, 8.8 Hz), 7.75 (1H, dd, J=1.8, 8.8 Hz), 7.86 (2H, d, J=8.4 Hz), 7.90–7.98 (3H, m), 8.31 (1H, s), 9.60 (1H, br). IR (KBr): 3303, 1618, 1522, 1437, 1346, 1269, 1165, 1138 cm$^{-1}$.

Working Example 78

1-(6-Chloronaphthalene-2-sulfonyl)-4-[4-(2,3-bis (methoxycarbonyl)guanidino)benzoyl]piperazine The title compound (62 mg) was obtained as colorless crystals, using 1-(6-chloronaphthalene-2-sulfonyl) piperazine hydrochloride (200 mg) and 4-(2,3-bis (methoxycarbonyl)guanidino)benzoic acid (170 mg), according to a similar method described in Working Example 46.

$^1$H-NMR (CDCl$_3$) δ: 3.10 (4H, brs), 3.56 (3H, s), 3.67 (3H, s), 3.74 (4H, brs), 7.15 (2H, d, J=8.4 Hz), 7.34 (2H, d, J=8.4 Hz), 7.60 (1H, dd, J=1.8, 8.8 Hz), 7.76 (1H, dd, J=1.8, 8.8 Hz), 7.88–7.98 (3H, m), 8.31 (1H, s), 9.29 (1H, brs), 9.52 (1H, brs). IR (KBr): 3389, 1732, 1615, 1437, 1252, 1165 cm$^{-1}$.

Working Example 79

1-(6-Chloronaphthalene-2-sulfonyl)-4-[4-(3-methoxycarbonylguanidino)benzoyl]piperazine The title compound (90 mg) was obtained as colorless crystals, using 1-(6-chloronaphthalene-2-sulfonyl) piperazine hydrochloride (200 mg) and 4-(3-methoxycarbonylguanidino)benzoic acid (170 mg), according to a similar method described in Working Example 46.

$^1$H-NMR (CDCl$_3$) δ: 3.11 (4H, brs), 3.71 (3H, s), 3.75 (4H, brs), 7.12 (2H, d, J=8.4 Hz), 7.33 (2H, d, J=8.4 Hz), 7.60 (1H, dd, J=1.8, 8.8 Hz), 7.75 (1H, dd, J=1.8, 8.8 Hz), 7.89–7.97 (3H, m), 8.31 (1H, s). IR (KBr): 3302, 3059, 1613, 1528, 1439, 1346, 1285, 1242, 1165 cm$^{-1}$.

Working Example 80

1-[1-(tert-butoxycarbonylamidino)piperidin-4-ylcarbonyl]-4-(6-chloronaphthalene-2-sulfonyl)piperazine

The title compound (295 mg) was obtained as colorless crystals, using 1-(6-chloronaphthalene-2-sulfonyl)piperazine hydrochloride (200 mg) and 1-(tert-butoxycarbonylamidino)piperidin-4-ylcarboxylic acid (214 mg), according to a similar method described in Working Example 46.

$^1$H-NMR (CDCl$_3$) δ: 1.46 (9H, s), 1.55–1.90 (4H, m), 2.60 (1H, m), 2.88–3.14 (6H, m), 3.50–3.77 (4H, m), 4.10 (2H, m), 7.59 (1H, dd, J=1.8, 8.8 Hz), 7.75 (1H, dd, J=2.0, 8.8 Hz), 7.87–7.98 (3H, m), 8.31 (1H, s). IR (KBr): 1747, 1651, 1611, 1302, 1154 cm$^{-1}$.

Working Example 81

1-(1-Amidinopiperidin-4-ylcarbonyl)-4-(6-chloronaphthalene-2-sulfonyl)piperazine hydrochloride

According to a similar method described in Working Example 76, the title compound (164 mg) was obtained as colorless solid, by treating 1-[1-(N$^1$,N$^2$-bis-tert-butoxycarbonylamidino)piperidin-4-ylcarbonyl]-4-(6-chloronaphthalene-2-sulfonyl)piperazine (270 mg) with hydrochloric acid.

$^1$H-NMR (DMSO-d$_6$) δ: 1.30–1.70 (4H, m), 2.77–3.12 (6H, m), 3.20 (1H, m), 3.58 (4H, m), 3.79 (2H, m), 7.41 (4H, s), 7.73 (1H, dd, J=2.2, 8.8 Hz), 7.82 (1H, dd, J=1.8, 8.8 Hz), 8.18 (1H, d, J=8.8 Hz), 8.23–8.34 (2H, m), 8.51 (1H, s). IR (KBr): 3324, 3144, 1659, 1617, 1456, 1345, 1159 cm$^{-1}$.

Working Example 82

1-[1-(tert-Butoxycarbonyl)piperidin-4-ylacetyl]-4-(6-chloronaphthalene-2-sulfonyl)piperazine

The title compound (420 mg) was obtained as colorless amorphous solid, using 1-(6-chloronaphthalene-2-sulfonyl)piperazine hydrochloride(300 mg) and 1-(tert-butoxycarbonyl)piperidin-4-ylacetic acid (211 mg), according to a similar method described in Working Example 46.

$^1$H-NMR (CDCl$_3$) δ: 1.07 (2H, m), 1.43 (9H, s), 1.60 (2H, m), 1.90 (1H, m), 2.13 (2H, d, J=7.0 Hz), 2.66 (2H, m), 3.07 (4H, m), 3.56 (2H, m), 3.71 (2H, m), 4.02 (2H, m), 7.59 (1H, dd, J=1.8, 8.8 Hz), 7.75 (1H, dd, J=2.0, 8.8 Hz), 7.88–7.96 (3H, m), 8.30 (1H, s). IR (KBr): 1686, 1649, 1426, 1346, 1285, 1165 cm$^{-1}$.

Working Example 83

1-(6-Chloronaphthalene-2-sulfonyl)-4-(piperidin-4-ylacetyl)piperazine hydrochloride

According to a similar method described in Working Example 76, colorless solid of the title compound (344 mg) was obtained by treating 1-[1-(tert-butoxycarbonyl)piperidin-4-ylacetyl]-4-(6-chloronaphthalene-2-sulfonyl)piperazine (390 mg) with hydrochloric acid.

$^1$H-NMR (DMSO-d$_6$) δ: 1.28 (2H, m), 1.72 (2H, m), 1.89 (1H, m), 2.21 (2H, d, J=6.6 Hz), 2.78 (2H, m), 2.96 (4H, m), 3.14 (2H, m), 3.54 (4H, brs), 7.73 (1H, dd, J=1.8, 8.8 Hz), 7.82 (1H, dd, J=1.8, 8.8 Hz0, 8.18 (1H, d, J=8.8 HGz), 8.22–8.32 (2H, m), 8.50 (1H, s), 8.60–9.00 (2H, m). IR (KBr): 3532, 3368, 1615, 1456, 1343, 1331, 1277, 1155 cm$^{-1}$.

Working Example 84

1-(4-tert-Butoxycarbonylaminomethylbenzoyl)-4-(6-chloronaphthalene-2-sulfonyl)piperazine

The title compound (163 mg) was obtained as colorless crystals, using 1-(6-chloronaphthalene-2-sulfonyl)piperazine hydrochloride (100 mg) and 4-tert-butoxycarbonylaminomethylbenzoic acid (73 mg), according to a similar method described in Working Example 46.

$^1$H-NMR (CDCl$_3$) δ: 1.45 (9H, s), 3.09 (4H, brs), 3.73 (4H, brs), 4.31 (2H, d, J=6.2 Hz), 4.88 (1H, brs), 7.28 (4H, s), 7.60 (1H, dd, J=1.8, 8.8 Hz), 7.75 (1H, dd, J=2.0, 8.8 Hz0, 7.88–7.98 (3H, m), 8.30 (1H, s). IR (KBr): 3328, 1705, 1628, 1514, 1456, 1431, 1346, 1283, 1264, 1165 cm$^{-1}$.

Working Example 85

1-(4-Aminomethylbenzoyl)-4-(6-chloronaphthalene-2-sulfonyl)piperazine hydrochloride

The title compound (94 mg) was obtained as colorless solid, according to a similar method described in Working Example 76, by treating 1-(4-tert-butoxycarbonylaminomethylbenzoyl)-4-(6-chloronaphthalene-2-sulfonyl)piperazine (133 mg) with hydrochloric acid.

$^1$H-NMR (DMSO-d$_6$) δ: 3.06 (4H, m), 3.20–3.80 (4H, br), 4.04 (2H, m), 7.37 (2H, d, J=8.2 Hz), 7.49 (2H, d, J=8.2 Hz), 7.73 (1H, dd, J=1.8, 8.8 Hz), 7.82 (1H, dd, J=1.6, 8.8 Hz), 8.14–8.44 (6H, m), 8.50 (1H, s). IR (KBr): 1624, 1466, 1442, 1346, 1335, 1292, 1157 cm$^{-1}$.

Working Example 86

1-(4-tert-Butoxycarbonylamino cyclohexane-1-ylcarbonyl)-4-(6-chloronaphthalene-2-sulfonyl)piperazine

The title compound (440 mg) was obtained as colorless crystals, using 1-(6-chloronaphthalene-2-sulfonyl)piperazine hydrochloride (300 mg) and 4-tert-butoxycarbonylaminocyclohexane-1-ylcarboxylic acid (211 mg), according to a similar method described in Working Example 46.

$^1$H-NMR (CDCl$_3$) δ: 1.41 (9H, s), 1.40–1.80 (8H, m), 2.43 (1H, m), 3.07 (4H, m), 3.59 (1H, m), 3.71 (4H, brs), 4.68 (1H, brs), 7.59 (1H, dd, J=2.0, 8.8 Hz), 7.75 (1H, dd, J=2.0, 8.8 Hz), 7.88–7.97 (3H, m), 8.31 (1H, s). IR (KBr): 3326, 1701, 1638, 1456, 1346, 1165 cm$^{-1}$.

Working Example 87

1-(4-Aminocyclohexane-1-ylcarbonyl)-4-(6-chloronaphthalene-2-sulfonyl)piperazine hydrochloride

The title compound (370 mg) was obtained as colorless solid, according to a similar method described in Working Example 76, by treating 1-(4-tert-butoxycarbonylaminocyclohexane- 1-ylcarbonyl)-4-(6-chloronaphthalene-2-sulfonyl)piperazine (410 mg) with hydrochloric acid.

$^1$H-NMR (DMSO-d$_6$) δ: 1.20–2.00 (8H, m), 2.65 (1H, m), 2.97 (4H, brs), 3.17 (1H, m), 3.55 (4H, brs), 7.73 (1H, dd, J=1.8, 8.8 Hz), 7.81 (1H, dd, J=1.8, 8.8 Hz), 7.88 (3H, brs), 8.17 (1H, d, J=8.8 Hz), 8.23–8.31 (2H, m), 8.50 (1H, s). IR (KBr): 3374, 1624, 1452, 1345, 1331, 1163 cm$^{-1}$.

Working Example 88

1-(6-Chloronaphthalene-2-sulfonyl)-4-[4-(2,3-di-tert-butoxycarbonylguanidino)cyclohexane-1-ylcarbonyl]piperazine

To a solution of 1-(4-aminocyclohexane-1-ylcarbonyl)-4-(6-chloronaphthalene-2-sulfonyl)piperazine hydrochloride (220 mg) and triethylamine (232 mg) in methanol (10 ml)-tetrahydrofuran (10 ml) was added N,N'-di-tert-butoxycarbonyl-S-methylisothiourea (135 mg) and the solution was stirred at 40° C. for 24 hours. The reaction solution was concentrated, and the residue was purified with silica gel column chromatography (hexane:ethyl acetate=1:2) to give a colorless solid of the title compound (170 mg).

$^1$H-NMR (CDCl$_3$) δ: 1.20–1.90 (8H, m), 1.46 (9H, s), 1.48 (9H, s), 2.44 (1H, m), 3.07 (4H, m), 3.58 (2H, m), 3.70 (2H, m), 4.27 (1H, m), 7.59 (1H, dd, J=1.8, 8.8 Hz), 7.75 (1H, dd, J=1.8, 8.8 Hz), 7.88–7.96 (3H, s), 8.30 (1H, s), 8.62 (1H, d, J=7.8 Hz), 11.42 (1H, brs). IR (KBr): 3322, 1717, 1643, 1614, 1344, 1165, 1136, 1119 cm$^{-1}$.

Working Example 89

1-(6-Chloronaphthalene-2-sulfonyl)-4-(4-guanidinocyclohexane-1-ylcarbonyl)piperazine hydrochloride The title compound (84 mg) was obtained as colorless solid, according to a similar method described in Working Example 76, by treating 1-(6-chloronaphthalene-2-sulfonyl)-4-[4-(2,3-di-tert-butoxycarbonylguanidino)cyclohexane-1-ylcarbonyl]piperazine (150 mg) with hydrochloric acid.

$^1$H-NMR (DMSO-d$_6$) δ: 1.30–1.70 (8H, m), 2.60 (1H, m), 2.96 (4H, m), 3.50–3.70 (5H, m), 7.05 (4H, br), 7.48 (1H, m), 7.72 (1H, d, J=8.4 Hz), 7.81 (1H, d, J=8.8 Hz), 8.17 (1H, d, J=8.4 Hz), 8.22–8.33 (2H, m), 8.50 (1H, s). IR (KBr): 3162, 1624, 1454, 1345, 1331, 1163 cm$^{-1}$.

Working Example 90

1-[1-(2,3-Di-tert-butoxycarbonylamidino)piperidin-4-ylacetyl]-4-(6-chloronaphthalene-2-sulfonyl)piperazine The title compound (120 mg) was obtained as colorless solid, according to a similar method described in Working Example 88, by reacting 1-(piperidin-4-ylacetyl)-4-(6-chloronaphthalene-2-sulfonyl)piperazine hydrochloride (190 mg) with N,N'-di-tert-butoxycarbonyl-S-methylisothiourea (117 mg).

$^1$H-NMR (CDCl$_3$) δ: 1.47 (18H, s), 1.20–1.80 (4H, m), 2.04 (1H, m), 2.15 (2H, d, J=6.4 Hz), 2.89 (2H, m), 3.07 (4H, m), 3.55 (2H, m), 3.72 (2H, m), 4.08 (2H, m), 7.59 (1H, dd, J=1.8, 8.8 Hz), 7.75 (1H, dd, J=1.8, 8.8 Hz), 7.88–7.96 (3H, m), 8.30 (1H, s), 10.20 (1H, br). IR (KBr): 1746, 1634, 1607, 1366, 1300, 1165 cm$^{-1}$.

Working Example 91

1-(1-Amidinopiperidin-4-ylacetyl)-4-(6-chloronaphthalene-2-sulfonyl)piperazine hydrochloride The title compound (69 mg) was obtained as colorless solid, according to a similar method described in Working Example 76, by treating 1-[1-(2,3-di-tert-butoxycarbonylamidino)piperidin-4-ylacetyl]-4-(6-chloronaphthalene-2-sulfonyl)piperazine (105 mg) with hydrochloric acid.

$^1$H-NMR (DMSO-d$_6$) δ: 1.05 (2H, m), 1.63 (2H, m), 1.91 (1H, m), 2.20 (2H, d, J=6.6 Hz), 2.80–3.03 (6H, m), 3.54 (4H, brs), 3.75 (2H, brd, J=13.6 Hz), 7.35 (4H, brs), 7.73 (1H, dd, J=2.0, 8.8 Hz), 7.82 (1H, dd, J=1.8, 8.8 Hz), 8.17 (1H, d, J=8.8 Hz), 8.22–8.32 (2H, m), 8.50 (1H, s). IR (KBr): 3304, 3144, 1643, 1613, 1452, 1345, 1163 cm$^{-1}$.

Working Example 92

1-(5-tert-Butoxycarbonylaminopentanoyl)-4-(6-chloronaphthalene-2-sulfonyl)piperazine The title compound (377 mg) was obtained as colorless amorphous solid, using 1-(6-chloronaphthalene-2-sulfonyl)piperazine hydrochloride(300 mg) and 5-tert-butoxycarbonylaminopentamoic acid (188 mg), according to a similar method described in Working Example 46.

$^1$H-NMR (CDCl$_3$) δ: 1.40 (9H, s), 1.40–1.62 (4H, m), 2.25 (2H, t, J=7.0 Hz), 3.00–3.15 (6H, m), 3.56 (2H, m), 3.71 (2H, m), 4.55 (1H, brs), 7.59 (1H, dd, J=2.0, 8.8 Hz), 7.75 (1H, dd, J=2.0, 8.8 Hz), 7.88–8.00 (3H, m), 8.30 (1H, s). IR (KBr): 3339, 1701, 1647, 1456, 1346, 1248, 1165 cm$^{-1}$.

Working Example 93

1-(5-Aminopentanoyl)-4-(6-chloronaphthalene-2-sulfonyl)piperazine hydrochloride

The title compound (295 mg) was obtained as colorless solid, according to a similar method described in Working Example 76, by treating 1-(5-tert-butoxycarbonylaminopentanoyl)-4-(6-chloronaphthalene-2-sulfonyl)piperazine (343 mg) with hydrochloric acid.

$^1$H-NMR (DMSO-d$_6$) δ: 1.46 (4H, m), 2.26 (2H, m), 2.70 (2H, m), 2.96 (4H, m), 3.54 (4H, m), 7.73 (1H, dd, J=2.2, 8.8 Hz), 7.82 (1H, dd, J=1.8, 8.8 Hz), 7.93 (3H, brs), 8.18 (1H, d, J=8.8 Hz), 8.22–8.32 (2H, m), 8.50 (1H, s). IR (KBr): 1655, 1435, 1345, 1330, 1157 cm$^{-1}$.

Working Example 94

1-(6-Chloronaphthalene-2-sulfonyl)-4-[5-(N,N'-di-tert-butoxycarbonylguanidino)pentanoyl]piperazine The title compound (175 mg) was obtained as colorless solid, according to a similar method described in Working Example 88, by reacting 1-(5-aminopentanoyl)-4-(6-chloronaphthalene-2-sulfonyl)piperazine hydrochloride (145 mg) with N,N'-di-tert-butoxycarbonyl-S-methylisothiourea (95 mg).

$^1$H-NMR (CDCl$_3$) δ: 1.20–1.70 (4H, m), 1.48 (9H, s), 1.49 (9H, s), 2.56 (2H, m), 3.06 (4H, m), 3.37 (2H, m), 3.56 (2H, m), 3.71 (2H, m), 7.58 (1H, dd, J=1.8, 8.8 Hz), 7.75 (1H, dd, J=2.0, 8.8 Hz), 7.88–7.96 (3H, m), 8.27 (1H, brs), 8.30 (1H, s), 11.46 (1H, brs). IR (KBr): 3324, 1721, 1644, 1368, 1331, 1165, 1134 cm$^{-1}$.

Working Example 95

1-(6-Chloronaphthalene-2-sulfonyl)-4-(5-guanidinopentanoyl)piperazine hydrochloride The title compound (81 mg) was obtained as colorless solid, according to a similar method described in Working Example 76, by treating 1-(6-chloronaphthalene-2-sulfonyl)-4-[5-(N,N'-di-tert-butoxycarbonylguanidino)pentanoyl]piperazine (145 mg) with hydrochloric acid.

$^1$H-NMR (DMSO-d$_6$) δ: 1.40 (4H, m), 2.25 (2H, m), 2.90–3.10 (6H, m), 3.54 (4H, m), 7.09 (4H, br), 7.60 (1H, m), 7.73 (1H, dd, J=2.2, 8.8 Hz), 7.81 (1H, dd, J=1.8, 8.8 Hz), 8.17 (1H, d, J=8.8 Hz), 8.22–8.33 (2H, m), 8.50 (1H, s). IR (KBr): 3160, 1647, 1628, 1454, 1345, 1331, 1163 cm$^{-1}$.

Working Example 96

1-(6-Chloronaphthalene-2-sulfonyl)-4-(1-tert-butoxy-carbonylpiperidin-4-ylcarbonyl)piperazine The title compound (296 mg) was obtained as colorless crystals, using 1-(6-chloronaphthalene-2-sulfonyl)

piperazine hydrochloride (200 mg) and N-tert-butoxycarbonylisonipecotic acid (132 mg), according to a similar method described in Working Example 46.

$^1$H-NMR (CDCl$_3$) δ: 1.42 (9H, s), 1.45–1.70 (4H, m), 2.50 (1H, m), 2.69 (2H, m), 3.08 (4H, m), 3.61 (2H, brs), 3.69 (2H, brs), 4.08 (2H, m), 7.59 (1H, dd, J=1.8, 8.8 Hz), 7.75 (1H, dd, J=1.8, 8.8 Hz), 7.88–7.95 (3H, m), 8.30 (1H, s). IR (KBr): 1684, 1645, 1429, 1165 cm$^{-1}$.

Working Example 97

1-(6-Chloronaphthalene-2-sulfonyl)-4-(4-piperidinecarbonyl)piperazine hydrochloride The title compound (217 mg) was obtained as colorless solid, according to a similar method described in Working Example 76, by treating 1-(6-chloronaphthalene-2-sulfonyl)-4-(1-tert-butoxycarbonylpiperidin-4-ylcarbonyl)piperazine(276 mg) with hydrochloric acid.

$^1$H-NMR (DMSO-d$_6$) δ: 1.63 (4H, m), 2.84 (4H, m), 2.97 (4H, brs), 3.16 (1H, m), 3.58 (4H, m), 7.72 (1H, dd, J=2.2, 8.8 Hz), 7.81 (1H, dd, J=1.8, 8.8 Hz), 8.16 (1H, d, J=8.8 Hz), 8.22–8.30 (2H, m), 8.51 (1H, s), 8.53 (2H, br). IR (KBr): 3576, 1636, 1458, 1342, 1333, 1234, 1163 cm$^{-1}$.

Working Example 98

4-[4-(4-(6-Chloronaphthalene-2-sulfonyl)piperazine-1-carbonyl)phenyl]pyridine 1-oxide To a solution of 1-(6-chloronaphthalene-2-sulfonyl)-4-[4-(4-pyridyl)benzoyl]piperazine (200 mg) in dichloromethane (25 ml) was added m-chloroperbenzoic acid (140 mg) and the solution was stirred at room temperature for 2 hours. The reaction solution was diluted with dichloromethane, washed with 1 N sodium hydroxide solution and sodium chloride solution, dried and concentrated. The residue was crystallized with dichloromethane/hexane to give a colorless solid of the title compound (188 mg).

$^1$H-NMR (CDCl$_3$) δ: 3.14 (4H, brs), 3.76 (4H, br), 7.43 (2H, d, J=8.4 Hz), 7.48 (2H, d, J=7.2 Hz), 7.55–7.64 (3H, m), 7.76 (1H, dd, J=1.8, 8.8 Hz), 7.90–7.98 (3H, m), 8.26 (2H, d, J=7.2 Hz), 8.32 (1H, s). IR (KBr): 1630, 1460, 1346, 1262, 1165, 729 cm$^{-1}$.

Working Example 99

1-[4-(1-Acetimidoylpiperidin-4-yl)benzoyl]-4-(6-chloronaphthalene-2-sulfonyl)piperazine hydrochloride To a solution of 1-[4-(piperidin-4-yl)benzoyl]-4-(6-chloronaphthalene-2-sulfonyl)piperazine hydrochloride (40 mg) and triethylamine (156 mg) in methanol (15 ml) was added ethyl acetimidate hydrochloride (46 mg), and the solution was stirred at room temperature for 15 hours. The reaction solution was concentrated. To the residue was added 1 N sodium hydroxide solution, and the solution was extracted with dichloromethane. The extract was dried and concentrated. The residue was dissolved in ethyl acetate, to which was added 4 N hydrochloric acid in ethyl acetate. The precipitate was filtered, washed with ether and dried to give a colorless solid of the title compound (42 mg).

$^1$H-NMR (DMSO-d$_6$) δ: 1.60–1.95 (4H, m), 2.30 (3H, s), 2.80–3.33 (7H, m), 3.57 (4H, brs), 4.01 (1H, m), 4.21 (1H, m), 7.28 (4H, s), 7.72 (1H, dd, J=2.2, 8.8 Hz), 7.81 (1H, dd, J=2.0, 8.8 Hz), 8.17 (1H, d, J=8.8 Hz), 8.22–8.34 (2H, m), 8.49 (1H, s), 8.63 (1H, brs), 9.20 (1H, brs). IR (KBr): 3067, 1684, 1632, 1433, 1342, 1281, 1165 cm$^{-1}$.

Working Example 100

1-(1-Acetimidoylpiperidin-4-ylcarbonyl)-4-(6-chloronaphthalene-2-sulfonyl)piperazine hydrochloride The title compound (133 mg) was obtained as colorless crystals, using 1-(piperidin-4-ylcarbonyl)-4-(6-chloronaphthalene-2-sulfonyl)piperazine hydrochloride (180 mg) and ethyl acetimidate hydrochloride (485 mg), according to a similar method described in Working Example 99.

$^1$H-NMR (DMSO-d$_6$) δ: 1.40–1.70 (4H, m), 2.22 (3H, s), 2.80–3.20 (7H, m), 3.55 (2H, m), 3.63 (2H, m), 3.81 (1H, m), 3.99 (1H, m), 7.72 (1H, d, J=8.8 Hz), 7.81 (1H, d, J=8.8 Hz), 8.17 (1H, d, J=8.8 Hz), 8.22–8.31 (2H, m), 8.51 (1H, s), 8.56 (1H, m), 9.03 (1H, m). IR (KBr): 3069, 1674, 1624, 1454, 1345, 1163 cm$^{-1}$.

Working Example 101

1-(6-Chloronaphthalene-2-sulfonyl)-4-(2-guanidino-4-methyl-5-thiazolecarbonyl)piperazine hydrochloride The title compound (240 mg) was obtained as colorless crystals, using 1-(6-chloronaphthalene-2-sulfonyl)piperazine hydrochloride (200 mg) and 2-guanidino-4-methyl-5-thiazolecarboxylic acid (115 mg), followed by treating with 4 N hydrochloric acid in ethyl acetate, according to a similar method described in Working Example 46.

$^1$H-NMR (DMSO-d$_6$) δ: 2.18 (3H, s), 3.06 (4H, brs), 3.61 (4H, brs), 7.72 (1H, dd, J=2.2, 8.8 Hz), 7.82 (1H, dd, J=2.0, 8.8 Hz), 8.18 (1H, d, J=8.8 Hz), 8.22–8.32 (6H, m), 8.50 (1H, s), 12.51 (1H, br). IR (KBr): 3314, 3061, 1694, 1613, 1491, 1462, 1431, 1346, 1333, 1314, 1169 cm$^{-1}$.

Working Example 102

1-(6-Chloronaphthalene-2-sulfonyl)-4-(trans-4-cyanocyclohexane-1-ylcarbonyl)piperazine The title compound (468 mg) was obtained as colorless crystals, using 1-(6-chloronaphthalene-2-sulfonyl)piperazine hydrochloride (400 mg) and trans-4-cyanocyclohexane-1-ylcarboxylic acid (177 mg), according to a similar method described in Working Example 46.

$^1$H-NMR (CDCl$_3$) δ: 1.40–1.80 (6H, m), 2.10–2.22 (2H, m), 2.30–2.50 (2H, m), 3.08 (4H, m), 3.58 (2H, m), 3.70 (2H, m), 7.60 (1H, dd, J=1.8, 8.8 Hz), 7.75 (1H, dd, J=1.8, 8.8 Hz), 7.88–7.96 (3H, m), 8.30 (1H, s). IR (KBr): 2240, 1645, 1454, 1346, 1165, 729 cm$^{-1}$.

Working Example 103

1-(trans-4-Amidinocyclohexane-1-ylcarbonyl)-4-(6-chloronaphthalene-2-sulfonyl)piperazine hydrochloride To 1-(6-chloronaphthalene-2-sulfonyl)-4-(trans-4-cyanocyclohexane-1-ylcarbonyl)piperazine (446 mg) was added 28% hydrochloric acid in dioxane/ethanol (9/1) solution (15 ml) and the solution was allowed to stand at room temperature for 5 hours and concentrated. To the residue was added 15% ammonia in ethanol solution (20 ml) and the solution was stirred for 15 hours. The reaction solution was concentrated and to the residue was added 1 N sodium hydroxide solution. The solution was extracted with dichloromethane, dried and concentrated. The residue was dissolved in ethyl acetate, to which was added 4 N hydrochloric acid in ethyl acetate. The precipitate was filtered to give a colorless solid of the title compound (514 mg).

$^1$H-NMR (DMSO-$d_6$) δ: 1.20–1.83 (8H, m), 2.26–2.55 (2H, m), 2.98 (4H, m), 3.55 (4H, m), 7.72 (1H, dd, J=2.2, 8.8 Hz), 7.82 (1H, dd, J=1.8, 8.8 Hz), 8.17 (1H, d, J=8.8 Hz), 8.22–8.31 (2H, m), 8.50 (1H, s), 8.56 (2H, brs), 8.75 (2H, brs). IR (KBr): 3077, 1686, 1624, 1454, 1345, 1163, 729 cm$^{-1}$.

Working Example 104

1-(trans-4-tert-Butoxycarbonylaminocyclohexane-1-ylcarbonyl)-4-(6-chloronaphthalene-2-sulfonyl)piperazine The title compound (547 mg) was obtained as colorless crystals, using 1-(6-chloronaphthalene-2-sulfonyl)piperazine hydrochloride (400 mg) and trans-4-tert-butoxycarbonylaminocyclohexane-1-ylcarboxylic acid (281 mg), according to a similar method described in Working Example 46.

$^1$H-NMR (CDCl$_3$) δ: 0.96–1.18 (2H, m), 1.42 (9H, s), 1.50–1.70 (2H, m), 1.95–2.10 (2H, m), 2.28 (1H, m), 3.07 (4H, m), 3.39 (1H, m), 3.58 (2H, brs), 3.69 (2H, brs), 4.33 (1H, brs), 7.58 (1H, dd, J=1.8, 8.8 Hz), 7.75 (1H, dd, J=1.8, 8.8 Hz), 7.87–7.96 (3H, m), 8.30 (1H, s). IR (KBr): 3333, 1699, 1634, 1454, 1346, 1165, 731 cm$^{-1}$.

Working Example 105

1-(trans-4-Aminocyclohexane-1-ylcarbonyl)-4-(6-chloronaphthalene-2-sulfonyl)piperazine hydrochloride The title compound (444 mg) was obtained as colorless solid, according to a similar method described in Working Example 76, by treating 1-(trans-4-tert-butoxycarbonylaminocyclohexane-1-ylcarbonyl)-4-(6-chloronaphthalene-2-sulfonyl)piperazine (527 mg) with hydrochloric acid.

$^1$H-NMR (DMSO-$d_6$) δ: 1.20–1.43 (4H, m), 1.59 (2H, m), 1.89 (2H, m), 2.45 (1H, m), 2.90 (1H, m), 2.96 (4H, brs), 3.56 (4H, brs), 7.72 (1H, d, J=8.8 Hz), 7.81 (1H, d, J=8.8 Hz), 7.98 (3H, brs), 8.10–8.30 (3H, m), 8.50 (1H, s). IR (KBr): 2911, 1651, 1638, 1341, 1325, 1148, 731 cm$^{-1}$.

Working Example 106

1-(trans-4-Acetimidoylaminocyclohexane-1-ylcarbonyl)-4-(6-chloronaphthalene-2-sulfonyl)piperazine hydrochloride The title compound (136 mg) was obtained as colorless crystals, using 1-(trans-4-aminocyclohexane-1-ylcarbonyl)-4-(6-chloronaphthalene-2-sulfonyl)piperazine hydrochloride (160 mg) and ethyl acetimidate hydrochloride (418 mg), according to a similar method described in Working Example 99.

$^1$H-NMR (DMSO-$d_6$) δ: 1.15–1.40 (4H, m), 1.57 (2H, m), 1.80 (2H, m), 2.11 (3H, s), 2.45 (1H, m), 2.90–3.05 (5H, m), 3.56 (4H, m), 7.72 (1H, dd, J=2.2, 8.8 Hz), 7.80 (1H, dd, J=1.8, 8.8 Hz), 8.10–8.32 (3H, m), 8.50 (1H, s), 9.01 (1H, m), 9.31 (1H, m), 9.73 (1H, brs). IR (KBr): 3055, 1682, 1635, 1474, 1445, 1345, 1163, 729 cm$^{-1}$.

Working Example 107

1-[trans-4-(2,3-Di-tert-butoxycarbonylguanidino)cyclohexane-1-ylcarbonyl]-4-(6-chloronaphthalene-2-sulfonyl)piperazine The title compound (112 mg) was obtained as colorless solid, according to a similar method described in Working Example 88, by reacting 1-(trans-4-aminocyclohexane-1-ylcarbonyl)-4-(6-chloronaphthalene-2-sulfonyl)piperazine hydrochloride (220 mg) with N,N'-di-tert-butoxycarbonyl-S-methylisothiourea (162 mg).

$^1$H-NMR (CDCl$_3$) δ: 1.00–1.30 (2H, m), 1.48 (18H, s), 1.50–1.70 (4H, m), 2.00–2.20 (2H, m), 2.29 (1H, m), 3.07 (4H, m), 3.58 (2H, m), 3.69 (2H, m), 3.97 (1H, m), 7.59 (1H, dd, J=2.2, 8.8 Hz), 7.75 (1H, dd, J=1.8, 8.8 Hz), 7.88–7.96 (3H, m), 8.18 (1H, d, J=8.8 Hz), 8.30 (1H, s), 11.50 (1H, brs). IR (KBr): 3324, 1720, 1644, 1615, 1345, 1165, 1128 cm$^{-1}$.

Working Example 108

1-(6-Chloronaphthalene-2-sulfonyl)-4-(trans-4-guanidinocyclohexane-1-ylcarbonyl)piperazine hydrochloride The title compound (112 mg) was obtained as colorless solid, according to a similar method described in Working Example 76, by treating 1-[trans-4-(2,3-di-tert-butoxycarbonyl)guanidinocyclohexane-1-ylcarbonyl]-4-(6-chloronaphthalene-2-sulfonyl)piperazine (135 mg) with hydrochloric acid.

$^1$H-NMR (DMSO-$d_6$) δ: 1.20–1.70 (6H, m), 1.73–1.90 (2H, m), 2.95 (4H, brs), 3.56 (4H, brs), 7.71 (1H, d, J=8.6 Hz), 7.80 (1H, d, J=8.4 Hz), 8.10–8.30 (3H, m), 8.49 (1H, s). IR (KBr): 1678, 1636, 1454, 1346, 1254, 1159 cm$^{-1}$.

Working Example 109

1-(trans-4-Formimidoylaminocyclohexane-1-ylcarbonyl)-4-(6-chloronaphthalene-2-sulfonyl)piperazine hydrochloride The title compound (164 mg) was obtained as colorless crystals, using 1-(trans-4-aminocyclohexane-1-ylcarbonyl)-4-(6-chloronaphthalene-2-sulfonyl)piperazine hydrochloride (180 mg) and ethyl formimidate hydrochloride (418 mg), according to a similar method described in Working Example 99.

$^1$H-NMR (DMSO-$d_6$) δ: 1.20–1.45 (4H, m), 1.60 (2H, m), 1.80 (2H, m), 2.42 (1H, m), 2.96 (4H, brs), 3.35 (1H, m), 3.55 (4H, m), 7.72 (1H, dd, J=2.2, 8.8 Hz), 7.81 (1H, dd, J=1.4, 8.8 Hz), 7.95 (1H, m), 8.16 (1H, d, J=8.8 Hz), 8.20–8.30 (2H, m), 8.50 (1H, s), 8.70–9.20 (2H, m), 9.70 (1H, m). IR (KBr): 3017, 1705, 1624, 1454, 1345, 1163 cm$^{-1}$.

Working Example 110

1-[2-(1-tert-Butoxycarbonylpiperidin-4-yl)-4-methyl-5-thiazolecarbonyl]-4-(6-chloronaphthalene-2-sulfonyl)piperazine The title compound (700 mg) was obtained as colorless crystals, using 1-(6-chloronaphthalene-2-sulfonyl)piperazine hydrochloride (400 mg) and 2-(1-tert-butoxycarbonylpiperidine-4-yl)-4-methyl-5-thiazolecarboxylic acid (375 mg), according to a similar method described in Working Example 46.

$^1$H-NMR (CDCl$_3$) δ: 1.46 (9H, s), 1.50–1.78 (2H, m), 1.95–2.10 (2H, m), 2.32 (3H, s), 2.82 (2H, m), 3.02 (1H, m), 3.12 (4H, m), 3.72 (4H, m), 4.18 (2H, m), 7.60 (1H, dd, J=2.0, 8.8 Hz), 7.75 (1H, dd, J=1.8, 8.8 Hz), 7.89–7.96 (3H, m), 8.31 (1H, d, J=1.0 Hz). IR (KBr): 1686, 1634, 1427, 1165, 731 cm$^{-1}$.

Working Example 111

1-(6-Chloronaphthalene-2-sulfonyl)-4-[2-(piperidin-4-yl)-4-methyl-5-thiazolecarbonyl]piperazine hydrochloride The title compound (589 mg) was obtained as colorless solid, according to a similar method described in Working Example 76, by treating 1-[2-(1-tert-butoxycarbonylpiperidine-4-yl)-4-methyl-5-thiazolecarbonyl]-4-(6-chloronaphthalene-2-sulfonyl)piperazine (673 mg) with hydrochloric acid.

$^1$H-NMR (DMSO-d$_6$) δ: 1.70–2.00 (2H, m), 2.03–2.20 (2H, m), 2.21 (3H, s), 2.96 (1H, m), 3.04 (4H, m), 3.20–3.65 (8H, m), 7.72 (1H, d, J=8.8 Hz), 7.80 (1H, d, J=8.4 Hz), 8.10–8.31 (3H, m), 8.49 (1H, s), 8.90 (2H, br). IR (KBr): 2957, 2802, 2718, 1618, 1431, 1345, 1333, 1165 cm$^{-1}$.

Working Example 112

1-[2-(1-Acetimidoylpiperidin-4-yl)-4-methyl-5-thiazolecarbonyl]-4-(6-chloronaphthalene-2-sulfonyl)piperazine hydrochloride The title compound (178 mg) was obtained as colorless crystals, using 1-(6-chloronaphthalene-2-sulfonyl)-4-[4-methyl-2-(piperidin-4-yl)-5-thiazolecarbonyl]piperazine hydrochloride (190 mg) and ethyl acetimidate hydrochloride (418 mg), according to a similar method described in Working Example 99.

$^1$H-NMR (DMSO-d$_6$) δ: 1.60–1.90 (2H, m), 2.00–2.20 (2H, m), 2.21 (3H, s), 2.28 (3H, s), 3.04 (4H, brs), 3.05–3.40 (3H, m), 3.59 (4H, brs), 3.90–4.00 (2H, m), 7.72 (1H, dd, J=1.8, 8.8 Hz), 7.81 (1H, dd, J=1.8, 8.8 Hz), 8.17 (1H, d, J=8.8 Hz), 8.24–8.32 (2H, m), 8.49 (1H, s), 8.68 (1H, m), 9.20 (1H, m). IR (KBr): 3074, 1671, 1624, 1439, 1345, 1163, 727 cm$^{-1}$.

Working Example 113

Ethyl 1-(trans-4-tert-butoxycarbonylaminocyclohexane-1-ylcarbonyl)-4-(6-chloronaphthalene-2-sulfonyl)-2-piperazinecarboxylate The title compound (940 mg) was obtained as colorless crystals, using ethyl 4-(6-chloronaphthalene-2-sulfonyl)-2-piperazinecarboxylate hydrochloride (1258 mg) and trans-4-cyanocyclohexane-1-ylcarboxylic acid (735 mg), according to a similar method described in Working Example 46.

$^1$H-NMR (CDCl$_3$) δ: 0.98–1.25 (2H, m), 1.27 (3H, t, J=7.2 Hz), 1.43 (9H, s), 1.50–2.55 (11H, m), 3.25–3.90 (4H, m), 4.19 (2H, q, J=7.2 Hz), 4.38 (1H, m), 4.43 (1H, brs), 7.58 (1H, dd, J=1.8, 8.8 Hz), 7.75 (1H, dd, J=1.8, 8.8 Hz), 7.87–7.96 (3H, m), 8.32 (1H, s). IR (KBr): 3316, 1738, 1699, 1651, 1366, 1167 cm$^{-1}$.

Working Example 114

1-(trans-4-tert-Butoxycarbonylaminocyclohexane-1-ylcarbonyl)-4-(6-chloronaphthalene-2-sulfonyl)-2-piperazinecarboxylic acid To a solution of ethyl 1-(trans-4-tert-butoxycarbonylaminocyclohexane-1-ylcarbonyl)-4-(6-chloronaphthalene-2-sulfonyl)-2-piperazinecarboxylate (740 mg) in ethanol (15 ml) was added 1 N sodium hydroxide solution (10 ml), and the solution was stirred at room temperature for 15 hours. The reaction solution was concentrated, and the residue was dissolved in water, adjusted to pH 2 with 1 N hydrochloric acid, extracted with dichloromethane. The extract was dried and concentrated to give a colorless solid of the title compound (614 mg).

$^1$H-NMR (DMSO-d$_6$) δ: 1.00–1.30 (2H, m), 1.35 (9H, s), 1.37–2.85 (9H, m), 3.00–3.20 (2H, m), 3.63 (1H, m), 3.93 (1H, m), 4.17 (1H, m), 5.07 (1H, m), 6.73 (1H, m), 7.67–7.83 (2H, m), 8.10–8.30 (3H, m), 8.51 (1H, s). IR (KBr): 3326, 1742, 1686, 1628, 1541, 1520, 1354, 1292, 1165 cm$^{-1}$.

Working Example 115

Ethyl 1-(trans-4-aminocyclohexane-1-ylcarbonyl)-4-(6-chloronaphthalene-2-sulfonyl)-2-piperazinecarboxylate hydrochloride The title compound (132 mg) was obtained as colorless solid, according to a similar method described in Working Example 76, by treating ethyl 1-(trans-4-tert-butoxycarbonylaminocyclohexane-1-ylcarbonyl)-4-(6-chloronaphthalene-2-sulfonyl)-2-piperazinecarboxylate (190 mg) with hydrochloric acid.

$^1$H-NMR (CDCl$_3$) δ: 1.20–1.35 (3H, m), 1.40–2.65 (11H, m), 3.14 (1H, m), 3.45–3.90 (3H, m), 4.10–4.30 (2H, m), 4.40 (1H, m), 5.27 (1H, m), 7.59 (1H, d, J=8.8 Hz), 7.77 (1H, m), 7.80–8.00 (3H, m), 8.32 (3H, brs), 8.33 (1H, s). IR (KBr): 3353, 1732, 1622, 1456, 1348, 1213, 1165 cm$^{-1}$.

Working Example 116

Ethyl 1-(trans-4-acetimidoylaminocyclohexane-1-ylcarbonyl)-4-(6-chloronaphthalene-2-sulfonyl)-2-piperazinecarboxylate hydrochloride The title compound (110 mg) was obtained as colorless crystals, using ethyl 1-(trans-4-aminocyclohexane-1-ylcarbonyl)-4-(6-chloronaphthalene-2-sulfonyl)-2-piperazinecarboxylate hydrochloride (125 mg) and ethyl acetimidate hydrochloride (386 mg), according to a similar method described in Working Example 99.

$^1$H-NMR (DMSO-d$_6$) δ: 1.19 (3H, t, J=7.0 Hz), 1.20–2.70 (11H, m), 2.11 (3H, s), 3.37 (1H, m), 3.67 (1H, m), 3.95–4.40 (5H, m), 5.16 (1H, m), 5.27 (1H, m), 7.74 (1H, d, J=8.8 Hz), 7.81 (1H, d, J=8.4 Hz), 8.15–8.32 (3H, m), 8.54 (1H, s), 8.55 (1H, brs), 8.99 (1H, brs), 9.29 (1H, brs). IR (KBr): 3056, 1738, 1640, 1435, 1344, 1161 cm$^{-1}$.

Working Example 117

1-(trans-4-tert-Butoxycarbonylaminocyclohexane-1-ylcarbonyl)-4-(6-chloronaphthalene-2-sulfonyl)-2-thiomorpholinocarbonylpiperazine To a solution of 1-(trans-4-tert-butoxycarbonylaminocyclohexane-1-ylcarbonyl)-4-(6-chloronaphthalene-2-sulfonyl)-2-piperazinecarboxylic acid (300 mg), HOBt (95 mg) and thiomolpholine (60 mg) in DMF (20 ml) was added WSC (119 mg) and the solution was stirred at room temperature for 3 hours. The reaction solution was concentrated, and the residue was purified with silica gel column chromatography (ethyl acetate) to give colorless crystals of the title compound (216 mg).

$^1$H-NMR (CDCl$_3$) δ: 0.95–1.20 (2H, m), 1.43 (9H, s), 1.50–1.92 (3H, m), 1.98–2.12 (2H, m), 2.28–2.70 (6H, m), 2.79 (1H, dd, J=4.6, 12.0 Hz), 3.40 (1H, m), 3.60–3.95 (7H, m), 4.13 (1H, m), 4.34 (1H, m), 5.36 (1H, brs), 7.59 (1H, dd, J=2.0, 8.8 Hz), 7.75 (1H, dd, J=2.0, 8.8 Hz), 7.86–7.98 (3H, m), 8.33 (1H, s). IR (KBr): 3318, 1699, 1645, 1422, 1366, 1341, 1165 cm$^{-1}$.

Working Example 118

1-(trans-4-Aminocyclohexane-1-ylcarbonyl)-4-(6-chloronaphthalene-2-sulfonyl)-2-thiomorpholinocarbonylpiperazine hydrochloride The title compound (145 mg) was obtained as colorless solid, according to a similar method described in Working Example 76, by treating 1-(trans-4-tert-butoxycarbonylaminocyclohexane-1-ylcarbonyl)-4-(6-chloronaphthalene-2-sulfonyl)-2-thiomorpholinocarbonylpiperazine (188 mg) with hydrochloric acid.

$^1$H-NMR (CDCl$_3$) δ: 1.40–2.60 (11H, m), 2.98 (4H, m), 3.14 (1H, m), 3.40–3.90 (7H, m), 4.35 (1H, m), 5.28 (1H, m), 7.59 (1H, d, J=8.2 Hz), 7.75 (1H, d, J=8.4 Hz), 7.88–8.00 (3H, m), 8.32 (1H, s), 8.33 (3H, brs). IR (KBr): 3385, 1740, 1626, 1454, 1346, 1163 cm$^{-1}$.

Working Example 119

1-(trans-4-Acetimidoylaminocyclohexane-1-ylcarbonyl)-4-(6-chloronaphthalene-2-sulfonyl)-2-thiomorpholinocarbonylpiperazine hydrochloride The title compound (149 mg) was obtained as colorless crystals, using 1-(trans-4-aminocyclohexane-1-ylcarbonyl)-4-(6-chloronaphthalene-2-sulfonyl)-2-thiomorpholinocarbonylpiperazine hydrochloride (135 mg) and ethyl acetimidate hydrochloride (386 mg), according to a similar method described in Working Example 99.

$^1$H-NMR (DMSO-d$_6$) δ: 1.20–2.60 (11H, m), 2.11 (3H, s), 2.76 (4H, m), 3.60–4.40 (9H, m), 5.19 (1H, m), 7.73 (1H, d, J=8.8 Hz), 7.80 (1H, d, J=8.8 Hz), 8.14–8.33 (3H, m), 8.54 (1H, s), 8.74 (1H, brs), 9.02 (1H, brs), 9.33 (1H, brs). IR (KBr): 3021, 1740, 1682, 1626, 1453, 1346, 1161 cm$^{-1}$.

Working Example 120

1-(trans-4-Aminocyclohexane-1-ylcarbonyl)-4-(6-chloronaphthalene-2-sulfonyl)-2-piperazinecarboxylic acid hydrochloride The title compound (130 mg) was obtained as colorless solid, according to a similar method described in Working Example 76, by treating 1-(trans-4-tert-butoxycarbonylaminocyclohexane-1-ylcarbonyl)-4-(6-chloronaphthalene-2-sulfonyl)-2-piperazinecarboxylic acid (200 mg) with hydrochloric acid.

$^1$H-NMR (DMSO-d$_6$) δ: 1.20–2.60 (1OH, m), 2.92 (2H, m), 3.65 (2H, m), 3.90–4.40 (2H, m), 5.08 (1H, m), 7.73 (1H, d, J=8.8 Hz), 7.80 (1H, d, J=8.8 Hz), 7.99 (3H, brs), 8.17 (1H, d, J=8.8 Hz), 8.20–8.33 (2H, m), 8.52 (1H, s). IR (KBr): 1734, 1624, 1453, 1342, 1213, 1163 cm$^{-1}$.

Working Example 121

1-(6-Chloronaphthalene-2-sulfonyl)-4-[4-(4-imidazolyl)benzoyl]piperazine

The title compound (210 mg) was obtained as colorless crystals, using 1-(6-chloronaphthalene-2-sulfonyl)piperazine hydrochloride (200 mg) and 4-(4-imidazolyl)benzoic acid (109 mg), according to a similar method described in Working Example 46.

$^1$H-NMR (CDCl$_3$) δ: 3.11 (4H, brs), 3.73 (4H, brs), 7.26 (1H, s), 7.29 (2H, d, J=8.0 Hz), 7.58 (1H, dd, J=1.8, 8.8 Hz), 7.61 (1H, s), 7.71 (2H, d, J=8.0 Hz), 7.75 (1H, dd, J=1.4, 8.8 Hz), 7.88–7.96 (3H, m), 8.29 (1H, s). IR (KBr): 3065, 1613, 1458, 1435, 1346, 1331, 1285, 1165 cm$^{-1}$.

Working Example 122

1-(6-Cchloronaphthalene-2-sulfonyl)-4-[4-(1-tetrazolyl)benzoyl]piperazine

The title compound (244 mg) was obtained as colorless crystals, using 1-(6-chloronaphthalene-2-sulfonyl)piperazine hydrochloride (200 mg) and 4-(1-tetrazolyl)benzoic acid (110 mg), according to a similar method described in Working Example 46.

$^1$H-NMR (CDCl$_3$) δ: 3.14 (4H, brs), 3.75 (4H, brs), 7.54 (2H, d, J=8.8 Hz), 7.60 (1H, dd, J=1.8, 8.8 Hz), 7.72–7.80 (3H, m), 7.90–7.98 (3H, m), 8.31 (1H, s), 9.01 (1H, s). IR (KBr): 1634, 1470, 1437, 1346, 1165 cm$^{-1}$.

Working Example 123

1-(6-Chloronaphthalene-2-sulfonyl)-4-[4-(2-tetrazolyl)benzoyl]piperazine

The title compound (256 mg) was obtained as colorless crystals, using 1-(6-chloronaphthalene-2-sulfonyl)piperazine hydrochloride (200 mg) and 4-(2-tetrazolyl)benzoic acid (110mg), according to a similar method described in Working Example 46.

$^1$H-NMR (CDCl$_3$) δ: 3.13 (4H, brs), 3.72 (4H, brs), 7.52 (2H, d, J=8.6 Hz), 7.60 (1H, dd, J=1.8, 8.8 Hz), 7.76 (1H, dd, J=1.8, 8.8 Hz), 7.90–7.97 (3H, m), 8.18 (2H, d, J=8.6 Hz), 8.31 (1H, s), 8.67 (1H, s). IR (KBr): 1636, 1456, 1435, 1346, 1285, 1165 cm$^{-1}$.

Working Example 124

1-(6-Bromonaphthalene-2-sulfonyl)-4-[5-(4-pyridyl)-1,3,4-thidiazol-2-carbonyl]piperazine The title compound (89 mg) was obtained as colorless crystals, using 1-(6-bromonaphthalene-2-sulfonyl)piperazine hydrochloride (112 mg) and 5-(4-pyridyl)-1,3,4-thidiazol-2-carboxylic acid (60 mg), according to a similar method described in Working Example 46.

$^1$H-NMR (CDCl$_3$) δ: 3.25 (4H, m), 3.94 (2H, t, J=5.0 Hz), 4.53 (2H, t, J=5.0 Hz), 7.67–7.95 (6H, m), 8.10 (1H, d, J=1.6 Hz), 8.31 (1H, s), 8.79 (2H, brs). IR (KBr): 1620, 1346, 1331, 1279, 1163 cm$^{-1}$.

Working Example 125

1-(6-Bromonaphthalene-2-sulfonyl)-4-[6-(1H-imidazol-1-yl)nicotinoyl]piperazine

The title compound (130 mg) was obtained as colorless crystals, using 1-(6-bromonaphthalene-2-sulfonyl)piperazine hydrochloride (112 mg) and 6-(1H-imidazol-1-yl)nicotinic acid (55 mg), according to a similar method described in Working Example 46.

$^1$H-NMR (CDCl$_3$) δ: 3.15 (4H, brs), 3.76 (4H, brs), 7.22 (1H, s), 7.38 (1H, dd, J=0.8, 8.4 Hz), 7.63 (1H, s), 7.70–7.97 (5H, m), 8.13 (1H, s), 8.30 (1H, s), 8.36 (1H, s), 8.43 (1H, d, J=1.4 Hz). IR (KBr): 1634, 1595, 1495, 1480, 1456, 1435, 1346, 1163 cm$^{-1}$.

Working Example 126

1-(6-Bromonaphthalene-2-sulfonyl)-4-[4-(1H-imidazol-1-ylmethyl)benzoyl]piperazine The title compound (142 mg) was obtained as colorless crystals, using 1-(6-bromonaphthalene-2-sulfonyl)piperazine hydrochloride (112 mg) and 4-(1H-imidazol-1-ylmethyl)benzoic acid (58 mg), according to a similar method described in Working Example 46.

$^1$H-NMR (CDCl$_3$) δ: 3.09 (4H, brs), 3.70 (4H, brs), 5.13 (2H, s), 6.88 (1H, s), 7.10 (1H, s), 7.14 (2H, d, J=8.2 Hz), 7.29 (2H, d, J=8.2 Hz), 7.54 (1H, s), 7.73 (1H, dd, J=1.8, 8.8 Hz), 7.75 (1H, dd, J=1.8, 8.8 Hz), 7.85 (1H, d, J=8.8 Hz), 7.92 (1H, d, J=8.8 Hz), 8.12 (1H, d, J=1.8 Hz), 8.29 (1H, s). IR (KBr): 1634, 1456, 1345, 1329, 1283, 1163 cm$^{-1}$.

Working Example 127

1-(6-Bromonaphthalene-2-sulfonyl)-4-[6-(4-pyridyl)nicotinoyl]piperazine

The title compound (152 mg) was obtained as colorless crystals, using 1-(6-bromonaphthalene-2-sulfonyl)piperazine hydrochloride (112 mg) and 6-(4-pyridyl)nicotinic acid (58 mg), according to a similar method described in Working Example 46.

$^1$H-NMR (CDCl$_3$) δ: 3.15 (4H, brs), 3.75 (4H, brs), 7.69–7.96 (8H, m), 8.13 (1H, s), *8.30 (1H, s), 8.66 (1H, s), 8.75 (2H, d, J=6.0 Hz). IR (KBr): 1636, 1539, 1456, 1435, 1346, 1285, 1165 cm$^{-1}$.

Working Example 128

1-(6-Chloronaphthalene-2-sulfonyl)-4-[4-(1,2,3-triazol-1-yl)benzoyl]piperazine

The title compound (78 mg) was obtained as colorless crystals, using 1-(6-chloronaphthalene-2-sulfonyl)piperazine hydrochloride (100 mg) and 4-(1,2,3-triazol-1-yl)benzoic acid (55 mg), according to a similar method described in Working Example 46.

$^1$H-NMR (CDCl$_3$) δ: 3.14 (4H, brs), 3.73 (4H, brs), 7.49 (2H, d, J=8.6 Hz), 7.61 (1H, dd, J=1.8, 8.8 Hz), 7.72–7.84 (3H, m), 7.87 (1H, s), 7.90–7.98 (3H, m), 8.00 (1H, s), 8.32 (1H, s). IR (KBr): 1636, 1495, 1435, 1346, 1331, 1265, 1165 cm$^{-1}$.

Working Example 129

1-(6-Chloronaphthalene-2-sulfonyl)-4-[4-(1,2,3-triazol-2-yl)benzoyl]piperazine

The title compound (98 mg) was obtained as colorless crystals, using 1-(6-chloronaphthalene-2-sulfonyl)piperazine hydrochloride (100 mg) and 4-(1,2,3-triazol-2-yl)benzoic acid (55 mg), according to a similar method described in Working Example 46.

$^1$H-NMR (CDCl$_3$) δ: 3.13 (4H, brs), 3.74 (4H, brs), 7.44 (2H, d, J=8.6 Hz), 7.60 (1H, dd, J=1.8, 8.8 Hz), 7.76 (1H, dd, J=1.4, 8.8 Hz), 7.83 (2H, s), 7.90–7.97 (3H, m), 8.10 (2H, d, J=8.6 Hz), 8.31 (1H, s). IR (KBr): 1636, 1433, 1410, 1346, 1285, 1261, 1165 cm$^{-1}$.

Working Example 130

Ethyl 4-(6-chloronaphthalene-2-sulfonyl)-1-[4-methyl-2-(4-pyridyl)-5-thiazolecarbonyl]piperazine-2-carboxylate The title compound (200 mg) was obtained as colorless crystals, using ethyl 4-(6-chloronaphthalene-2-sulfonyl)piperazine-2-carboxylate hydrochloride (150 mg) and 4-methyl-2-(4-pyridyl)-5-thiazolecarboxylic acid (101 mg), according to a similar method described in Working Example 46.

$^1$H-NMR (CDCl$_3$) δ: 1.34 (3H, t, J=7.2 Hz), 2.60–3.00 (6H, m), 3.50–3.90 (3H, m), 4.25 (2H, q, J=7.2 Hz), 4.49 (1H, d, J=12.0 Hz), 7.61 (1H, dd, J=1.8, 8.8 Hz), 7.70–7.82 (3H,), 7.88–7.98 (3H, m), 8.34 (1H, s), 8.72 (2H, d, J=6.2 Hz). IR (KBr): 1740, 1645, 1348, 1217, 1165 cm$^{-1}$.

Working Example 131

1-(6-Chloronaphthalene-2-sulfonyl)-4-[2-chloro-4-(4-pyridyl)benzoyl]piperazine

The title compound (304 mg) was obtained as colorless crystals, using 1-(6-chloronaphthalene-2-sulfonyl)piperazine hydrochloride (220 mg) and 2-chloro-4-(4-pyridyl)benzoic acid (148 mg), according to a similar method described in Working Example 46.

$^1$H-NMR (CDCl$_3$) δ: 3.10 (2H, m), 3.24 (2H, m), 3.40 (2H, m), 3.94 (2H, m), 7.31 (1H, d, J=7.8 Hz), 7.44 (2H, d, J=6.0 Hz), 7.50–7.65 (3H, m), 7.76 (1H, d, J=8.4 Hz), 7.90–7.98 (3H, m), 8.32 (1H, s), 8.70 (2H, d, J=6.0 Hz). IR (KBr): 1645, 1595, 1456, 1437, 1346, 1285, 1165 cm$^{-1}$.

Working Example 132

1-[2-Chloro-4-(4-pyridyl)benzoyl]-4-(4-vinylbenzenesulfonyl)piperazine

The title compound (266 mg) was obtained as colorless crystals, using 1-(4-vinylbenzenesulfonyl)piperazine hydrochloride (200 mg) and 2-chloro-4-(4-pyridyl)benzoic acid (162 mg), according to a similar method described in

Working Example 46.

$^1$H-NMR (CDCl$_3$) δ: 3.03 (2H, m), 3.16 (2H, m), 3.39 (2H, m), 3.92 (2H, m), 5.48 (1H, d, J=11.0 Hz), 5.91 (1H, d, J=17.6 Hz), 6.78 (1H, dd, J=11.0, 17.6 Hz), 7.34 (1H, d, J=8.0 Hz), 7.45 (2H, d, J=6.0 Hz) 7.52–7.60 (3H, m), 7.64 (1H, d, J=2.0 Hz), 7.71 (2H, d, J=8.4 Hz), 8.70 (2H, d, J=6.0 Hz). IR (KBr): 1645, 1595, 1435, 1350, 1285, 1167 cm$^{-1}$.

Working Example 133

1-(6-Chloronaphthalene-2-sulfonyl)-4-[6-(pyrrol-1-yl)nicotinoyl]piperazine

The title compound (178 mg) was obtained as colorless crystals, using 1-(6-chloronaphthalene-2-sulfonyl)piperazine hydrochloride (200 mg) and 6-(pyrrol-1-yl)nicotinic acid (109 mg), according to a similar method described in Working Example 46.

$^1$H-NMR (CDCl$_3$) δ: 3.14 (4H, m), 3.76 (4H, m), 6.37 (2H, t, J=2.2 Hz), 7.30 (1H, d, J=8.4 Hz), 7.48 (2H, t, J=2.2 Hz), 7.60 (1H, dd, J=1.8, 8.8 Hz), 7.70–7.80 (2H, m), 7.90–7.98 (3H, m), 8.31 (1H, s), 8.36 (1H, d, J=2.2 Hz). IR (KBr): 1636, 1597, 1495, 1345, 1165 cm$^{-1}$.

Working Example 134

1-(6-Chloronaphthalene-2-sulfonyl)-4-[5-(1-methyl-3-trifluoromethyl-5-pyrazolyl)-2-thenoyl]piperazine The title compound (314 mg) was obtained as colorless crystals, using 1-(6-chloronaphthalene-2-sulfonyl)piperazine hydrochloride (200 mg) and 5-(1-methyl-3-trifluoromethyl-5-pyrazolyl)-2-thiophenecarboxylic acid (160 mg), according to a similar method described in Working Example 46.

$^1$H-NMR (CDCl$_3$) δ: 3.15 (4H, m), 3.87 (4H, m), 3.99 (3H, s), 6.78 (1H, s), 7.19 (2H, s), 7.59 (1H, dd, J=2.2, 8.8 Hz), 7.76 (1H, dd, J=2.0, 8.8 Hz), 7.90–7.95 (3H, m), 8.31 (1H, s). IR (KBr): 1622, 1424, 1346, 1271, 1165, 1136 cm$^{-1}$.

Working Example 135

1-(3-Cyanostyrene-β(E)-sulfonyl)-4-[4-methyl-2-(4-pyridyl)-5-thiazolecarbonyl]piperazine The title compound (318 mg) was obtained as colorless crystals, using 4-methyl-2-(4-pyridyl)-5-thiazolecarboxylic acid (220 mg) and 1-(3-cyanostyrene-β(E)-sulfonyl)piperazine hydrochloride (314 mg), according to a similar method described in Working Example 46.

¹H-NMR (CDCl₃) δ: 2.52 (3H, s), 3.30 (4H, m), 3.80 (4H, m), 6.75 (1H, d, J=15.4 Hz), 7.49 (1H, d, J=15.4 Hz), 7.58 (1H, t, J=8.0 Hz), 7.69–7.82 (5H, m), 8.72 (2H, d, J=6.0 Hz). IR (KBr): 2232, 1634, 1597, 1435, 1346, 1327, 1279, 1256, 1155 cm⁻¹.

Working Example 136

1-(4-Methoxystyrene-β(E)-sulfonyl)-4-[4-methyl-2-(4-pyridyl)-5-thiazolecarbonyl]piperazine The title compound (403 mg) was obtained as colorless crystals, using 4-methyl-2-(4-pyridyl)-5-thiazolecarboxylic acid (220 mg) and 1-(4-methoxystyrene-β(E)-sulfonyl)-piperazine (282 mg), according to a similar method described in Working Example 46.

¹H-NMR (CDCl₃) δ: 2.51 (3H, s), 3.25 (4H, m), 3.78 (4H, m), 3.86 (3H, s), 6.50 (1H, d, J=15.8 Hz), 6.94 (2H, d, J=8.4 Hz), 7.45 (1H, d, J=15.8 Hz), 7.46 (2H, d, J=8.4 Hz), 7.75 (2H, d, J=6.0 Hz), 8.72 (2H, d, J=6.0 Hz). IR (KBr): 1634, 1603, 1512, 1424, 1344, 1325, 1258, 1152 cm⁻¹.

Working Example 137

1-(6-Chloronaphthalene-2-sulfonyl)-4-[4-(5-pyrimidyl)-benzoyl]piperazine

The title compound (120 mg) was obtained as colorless crystals, using 1-(6-chloronaphthalene-2-sulfonyl)piperazine hydrochloride (100 mg) and 4-(5-pyrimidyl)benzoic acid (58 mg), according to a similar method described in Working Example 46.

¹H-NMR (CDCl₃) δ: 3.14 (4H, brs), 3.74 (4H, br), 7.47 (2H, d, J=8.4 Hz), 7.55–7.65 (3H, m), 7.76 (1H, dd, J=1.4, 8.8 Hz), 7.90–7.98 (3H, m), 8.31 (1H, s), 8.93 (2H, s), 9.24 (1H, s). IR (KBr): 1638, 1414, 1346, 1165 cm⁻¹.

Working Example 138

1-(6-Chloronaphthalene-2-sulfonyl)-4-[4-methyl-2-(2-pyrazinyl)-5-thiazolecarbonyl]piperazine The title compound (134 mg) was obtained as colorless crystals, using 1-(6-chloronaphthalene-2-sulfonyl)piperazine hydrochloride (100 mg) and 4-methyl-2-(2-pyrazinyl)-5-thiazolecarboxylic acid (64 mg), according to a similar method described in Working Example 46.

¹H-NMR (CDCl₃) δ: 2.45 (3H, s), 3.15 (4H, m), 3.76 (4H, m), 7.60 (1H, dd, J=1.8, 8.8 Hz), 7.75 (1H, dd, J=1.8, 8.8 Hz), 7.90–7.98 (3H, m), 8.31 (1h, s), 8.53 (1H, dd, J=1.4, 2.6 Hz), 8.63 (1H, d, J=2.6 Hz), 9.37 (1H, d, J=1.4 Hz). IR (KBr): 1634, 1456, 1427, 1346, 1329, 1279, 1252, 1165 cm⁻¹.

Working Example 139

1-(6-Chloronaphthalene-2-sulfonyl)-4-[4-methyl-2-(4-pyridyl)pyrimidine-5-carbonyl]piperazine The title compound (140 mg) was obtained as colorless crystals, using 1-(6-chloronaphthalene-2-sulfonyl)piperazine hydrochloride (100 mg) and 4-methyl-2-(4-pyridyl)pyrimidine-5-carboxylic acid (62 mg), according to a similar method described in Working Example 46.

¹H-NMR (CDCl₃) δ: 2.51 (3H, s), 3.07 (2H, m), 3.23 (2H, m), 3.43 (2H, m), 3.95 (2H, m), 7.62 (1H, dd, J=1.8, 8.8 Hz), 7.76 (1H, dd, J=1.8, 8.8 Hz), 7.90–7.98 (3H, m), 8.27 (2H, d, J=6.2 Hz), 8.32 (1H, d, J=1.2 Hz), 8.50 (1H, s), 8.78 (2H, d, J=6.2 Hz). IR (KBr): 1644, 1422, 1331, 1165 cm⁻¹.

Working Example 140

1-(6-Chloronaphthalene-2-sulfonyl)-4-[4-methyl-5-(4-pyridyl)-2-thiazolecarbonyl]piperazine The title compound (229 mg) was obtained, as colorless crystals, using 1-(6-chloronaphthalene-2-sulfonyl)piperazine hydrochloride (200 mg) and 4-methyl-5-(4-pyridyl)-2-thiazolecarboxylic acid (127 mg), according to a similar method described in Working Example 46.

¹H-NMR (CDCl₃) δ: 2.53 (3H, s), 3.22 (4H, t, J=4.9 Hz), 3.90 (2H, brs), 4.60 (2H, brs), 7.33 (2H, d, J=6.0 Hz), 7.58 (1H, dd, J=1.8, 8.8 Hz), 7.78 (1H, dd, J=1.8, 8.8 Hz), 7.88–7.96 (3H, m), 8.32 (1H, s), 8.68 (2H, d, J=6.0 Hz). IR (KBr): 1622, 1470, 1454, 1346, 1165 cm⁻¹.

Working Example 141

1-[4-(2-Aminothiazol-4-yl)benzoyl]-4-(6-chloronaphthalene-2-sulfonyl)piperazine

The title compound (235 mg) was obtained, as colorless crystals, using 1-(6-chloronaphthalene-2-sulfonyl)piperazine hydrochloride (200 mg) and 4-(2-aminothiazol-4-yl)benzoic acid (127 mg), according to a similar method described in Working Example 46

¹H-NMR (CDCl₃) δ: 3.10 (4H, brs), 3.72 (4H, brs), 5.04 (2H, brs), 6.76 (1H, s), 7.31 (2H, d, J=8.2 Hz), 7.59 (1H, dd, J=1.8, 8.8 Hz), 7.73–7.80 (3H, m), 7.88–7.96 (3H, m), 8.30 (1H, s). IR (KBr): 3314, 1609, 1537, 1522, 1435, 1344, 1331, 1285, 1165 cm⁻¹.

Working Example 142

1-(6-Chloronaphthalene-2-sulfonyl)-4-[3-(4-aminophenyl)propionyl]piperazine

The title compound (205 mg) was obtained, as colorless crystals, using 1-(6-chloronaphthalene-2-sulfonyl)piperazine hydrochloride (200 mg) and 3-(4-aminophenyl)propionic acid (96 mg), according to a similar method described in Working Example 46.

¹H-NMR (CDCl₃) δ: 2.46 (2H, t, J=7.5 Hz), 2.77 (2H, t, J=7.5 Hz), 2.93 (2H, m), 3.04 (2H, m), 3.44 (2H, m), 3.71 (2H, m), 6.52 (2H, d, J=8.2 Hz), 6.90 (2H, d, J=8.2 Hz), 7.59 (1H, dd, J=2.2, 8.8 Hz), 7.73 (1H, dd, J=1.8, 8.8 Hz), 7.88–7.96 (3H, m), 8.29 (1H, s). IR (KBr): 1636, 1518, 1447, 1344, 1329, 1165 cm⁻¹.

Working Example 143

1-(6-Bromonaphthalene-2-sulfonyl)-4-[4-methyl-2-(3-pyridyl)-5-thiazolecarbonyl]piperazine The title compound (156 mg) was obtained, as colorless crystals, using 1-(6-bromonaphthalene-2-sulfonyl)piperazine hydrochloride (112 mg) and 4-methyl-2-(3-pyridyl)-5-thiazolecarboxylic acid (64 mg), according to a similar method described in Working Example 46.

¹H-NMR (CDCl₃) δ: 2.43 (3H, s), 3.15 (4H, m), 3.77 (4H, m), 7.38 (1H, m), 7.73 (1H, dd, J=1.8, 8.8 Hz), 7.76 (1H, dd, J=1.8, 8.8 Hz), 7.86 (1H, d, J=8.8 Hz), 7.93 (1H, d, J=8.8 Hz), 8.10–8.20 (2H, m), 8.30 (1H, s), 8.67 (1H, m), 9.07 (1H, m). IR (KBr): 1628, 1460, 1435, 1346, 1335, 1159 cm⁻¹.

Working Example 144

1-(4-Diisopropylaminomethylbenzoyl)-4-(1-octanesulfonyl)piperazine

The title compound (200 mg) was obtained, as syrups, using 1-(4-diisopropylaminomethylbenzoyl)piperazine (200 mg) and 1-octanesulfonylchloride (154 mg), according to a similar method described in Working Example 23.

$^1$H-NMR (CDCl$_3$) δ: 0.88 (3H, m), 1.02 (12H, d, J=6.6 Hz), 1.20–1.50 (10H, m), 2.80–3.10 (6H, m), 3.30 (2H, m), 3.65 (2H, s), 3.20–3.90 (4H, br), 7.29 (2H, d, J=8.2 Hz), 7.41 (2H, d, J=8.2 Hz). IR (Neat): 1634, 1460, 1431, 1364, 1285, 1155 cm$^{-1}$.

Working Example 145

1-(4-Chlorostyrene-β-sulfonyl)-4-[4-methyl-2-(4-pyridyl)-5-thiazolecarbonyl]piperazine To a solution of 1-[4-methyl-2-(4-pyridyl)-5-thiazolecarbonyl]piperazine dihydrochloride (200 mg) in ethyl acetate (10 ml)/sodium bicarbonate (10 ml) was added 4-chlorostyrene-β-sulfonylchloride (275 mg), and the mixture was stirred at room temperature for 1 hour. The ethyl acetate layer was separated, washed with brine, dried and concentrated. The residue was purified with silica gel column chromatography (ethyl acetate) to give colorless crystals of the title compound (169 mg).

$^1$H-NMR (CDCl$_3$) δ: 2.51 (3H, s), 3.28 (4H, m), 3.79 (4H, m), 6.64 (1H, d, J=15.4 Hz), 7.43 (4H, s), 7.46 (1H, d, J=15.4 Hz), 7.76 (2H, d, J=6.2 Hz), 8.72 (2H, d, J=6.2 Hz). IR (KBr): 1628, 1597, 1441, 1344, 1325, 1283, 1155 cm$^{-1}$.

Working Example 146

1-(4'-Chlorobiphenyl-4-sulfonyl)-4-[4-methyl-2-(4-pyridyl)-5-thiazolecarbonyl]piperazine The title compound (237 mg) was obtained, as colorless p crystals, using 1-[4-methyl-2-(4-pyridyl)-5-thiazolecarbonyl]piperazine dihydrochloride (200 mg) and 4'-chlorobiphenyl-4-sulfonylchloride (177 mg), according to a similar method described in Working Example 145.

$^1$H-NMR (CDCl$_3$) δ: 2.46 (3H, s), 3.13 (4H, m), 3.78 (4H, m), 7.47 (2H, d, J=8.4 Hz), 7.56 (2H, d, J=8.4 Hz), 7.70–7.77 (4H, m), 7.82 (2H, d, J=8.4 Hz), 8.71 (2H, d, J=6.2 Hz). IR (KBr): 1632, 1597, 1435, 1350, 1167 cm$^{-1}$.

Working Example 147

1-(2-Naphthalenesulfonyl)-4-[4-methyl-2-(4-pyridyl)-5-thiazolecarbonyl]piperazine The title compound (143 mg) was obtained, as colorless crystals, using 1-[4-methyl-2-(4-pyridyl)-5-thiazolecarbonyl]piperazine dihydrochloride (200 mg) and 2-naphthalenesulfonylchloride (140 mg), according to a similar method described in Working Example 145.

$^1$H-NMR (CDCl$_3$) δ: 2.43 (3H, s), 3.15 (4H, m), 3.76 (4H, m), 7.60–7.78 (5H, m), 7.90–8.05 (3H, m), 8.35 (1H, s), 8.70 (2H, d, J=6.2 Hz). IR (KBr): 1626, 1437, 1348, 1165 cm$^{-1}$.

Working Example 148

1-(4-Bromobenzenesulfonyl)-4-[4-methyl-2-(4-pyridyl)-5-thiazolecarbonyl]piperazine The title compound (177 mg) was obtained, as colorless crystals, using 1-[4-methyl-2-(4-pyridyl)-5-thiazolecarbonyl]piperazine dihydrochloride (200 mg) and 4-bromobenzenesulfonylchloride (158 mg), according to a similar method described in Working Example 145.

$^1$H-NMR (CDCl$_3$) δ: 2.47 (3H, s), 3.09 (4H, m), 3.76 (4H, m), 7.61 (2H, d, J=8.4 Hz), 7.68–7.80 (4H, m), 8.72 (2H, d, J=6.2 Hz). IR (KBr): 1632, 1431, 1352, 1169 cm$^{-1}$.

Working Example 149

1-(6-Chloronaphthalene-2-sulfonyl)-4-[5-(4-pyridyl)-1,3,4-dithiadiazole-2-carbonyl]piperazine The title compound (157 mg) was obtained, as colorless crystals, using 1-(6-chloronaphthalene-2-sulfonyl)piperazine hydrochloride (200 mg) and 5-(4-pyridyl)-1,3,4-dithiadiazole-2-carboxylic acid (120 mg), according to a similar method described in Working Example 46.

$^1$H-NMR (CDCl$_3$) δ: 3.26 (4H, m), 3.94 (2H, m), 4.53 (2H, m), 7.59 (1H, dd, J=2.0, 8.8 Hz), 7.74–7.85 (3H, m), 7.88–7.98 (3H, m), 8.33 (1H, s), 8.80 (2H, d, J=6.2 Hz). IR (KBr): 1622, 1346, 1281, 1165 cm$^{-1}$.

Working Example 150

1-(6-Chloronaphthalene-2-sulfonyl)-4-[4-methyl-2-(3-pyridyl)-5-thiazolecarbonyl]piperazine The title compound (255 mg) was obtained, as colorless crystals, using 1-(6-chloronaphthalene-2-sulfonyl)piperazine hydrochloride (200 mg) and 4-methyl-2-(3-pyridyl)-5-thiazolecarboxylic acid (128 mg), according to a similar method described in Working Example 46.

$^1$H-NMR (CDCl$_3$) δ: 2.43 (3H, s), 3.15 (4H, m), 3.77 (4H, m), 7.38 (1H, dd, J=4.8, 7.6 Hz), 7.60 (1H, d, J=8.8 Hz), 7.76 (1H, d, J=8.8 Hz), 7.89–7.98 (3H, m), 8.16 (1H, d, J=7.6 Hz), 8.32 (1H, s), 8.67 (1H, d, J=4.8 Hz), 9.07 (1H, s). IR (KBr): 1634, 1433, 1346, 1331, 1165 cm$^{-1}$.

Working Example 151

1-(6-Chloronaphthalene-2-sulfonyl)-4-[4-ethyl-2-(4-pyridyl)-5-thiazolecarbonyl]piperazine The title compound (209 mg) was obtained, as colorless crystals, using 1-(6-chloronaphthalene-2-sulfonyl)piperazine hydrochloride (150 mg) and 4-ethyl-2-(4-pyridyl)-5-thiazolecarboxylic acid (101 mg), according to a similar method described in Working Example 46.

$^1$H-NMR (CDCl$_3$) δ: 1.27 (3H, t, J=7.0 Hz), 2.71 (2H, q, J=7.0 Hz), 3.14 (4H, m), 3.76 (4H, m), 7.60 (1H, dd, J=2.2, 8.8 Hz), 7.70–7.80 (3H, m), 7.90–7.98 (3H, m), 8.32 (1H, s), 8.70 (2H, d, J=6.2 Hz). IR (KBr): 1628, 1439, 1346, 1287, 1163 cm$^{-1}$.

Working Example 152

1-(6-Chloronaphthalene-2-sulfonyl)-4-[4-ethyl-2-(3-pyridyl)-5-thiazolecarbonyl]piperazine The title compound (200 mg) was obtained, as colorless crystals, using 1-(6-chloronaphthalene-2-sulfonyl)piperazine hydrochloride (150 mg) and 4-ethyl-2-(3-pyridyl)-5-thiazolecarboxylic acid (101 mg), according to a similar method described in Working Example 46.

$^1$H-NMR (CDCl$_3$) δ: 1.27 (3H, t, J=7.0 Hz), 2.70 (2H, q, J=7.0 Hz), 3.15 (4H, m), 3.76 (4H, m), 7.37 (1H, m), 7.60 (1H, dd, J=1.8, 8.8 Hz), 7.76 (1H, dd, J=1.8, 8.8 Hz), 7.90–7.98 (3H, m), 8.17 (1H, m), 8.31 (1H, s), 8.66 (1H, dd, J=1.6, 5.0 Hz), 9.08 (1H, d, J=1.6 Hz). IR (KBr): 1628, 1458, 1431, 1346, 1333, 1157 cm$^{-1}$.

Working Example 153

1-(6-Chloronaphthalene-2-sulfonyl)-4-[6-(1H-imidazol-1-yl)nicotinoyl]piperazine

The title compound (101 mg) was obtained, as colorless, crystals, using 1-(6-chloronaphthalene-2-sulfonyl)

piperazine hydrochloride (100 mg) and 6-(1H-imidazol-1-yl)nicotinic acid (55 mg), according to a similar method described in Working Example 46.

$^1$H-NMR (CDCl$_3$) δ: 3.15 (4H, m), 3.76 (4H, m), 7.21 (1H, s), 7.37 (1H, d, J=8.4 Hz), 7.60 (1H, dd, J=1.8, 8.8 Hz), 7.63 (1H, s), 7.76 (1H, dd, J=1.8, 8.8 Hz), 7.84 (1H, dd, J=2.2, 8.4 Hz), 7.90–7.98 (3H, m), 8.31 (1H, s), 8.35 (1H, s), 8.42 (1H, d, J=2.2 Hz). IR (KBr): 1645, 1595, 1497, 1346, 1333, 1291, 1167 cm$^{-1}$.

Working Example 154

1-(6-Chloronaphthalene-2-sulfonyl)-4-[4-(1H-imidazol-1-ylmethyl)benzoyl]piperazine The title compound (108 mg) was obtained, as colorless crystals, using 1-(6-chloronaphthalene-2-sulfonyl)-piperazine hydrochloride (100 mg) and 4-(1H-imidazol-1-ylmethyl)benzoic acid (58 mg), according to a similar method described in Working Example 46.

$^1$H-NMR (CDCl$_3$) δ: 3.10 (4H, brs), 3.67 (4H, br), 5.13 (2H, s), 6.88 (1H, s), 7.10 (1H, s), 7.13 (2H, d, J=8.4 Hz), 7.29 (2H, d, J=8.4 Hz), 7.54 (1H, s), 7.60 (1H, dd, J=1.8, 8.8 Hz), 7.75 (1H, dd, J=1.8, 8.8 Hz), 7.88–7.96 (3H, m), 8.29 (1H, s). IR (KBr): 1634, 1456, 1433, 1345, 1283, 1165 cm$^{-1}$.

Working Example 155

4-(6-Chloronaphthalene-2-sulfonyl)-1-[4-methyl-2-(4-pyridyl)-5-thiazolecarbonyl]piperazine-2-carboxylic acid To a solution of ethyl 4-(6-chloronaphthalene-2-sulfonyl)-1-[4-methyl-2-(4-pyridyl)-5-thiazolecarbonyl]-piperazine-2-carboxylate (100 mg) in methanol (20 ml) was added 1 N sodium hydroxide aqueous solution (5 ml), and the mixture was stirred at room temperature for 1 hour. The reaction solution was concentrated, and 1 N hydrochloric acid aqueous solution (5 ml) was added to the residue. The precipitate was filtered and dried to give a colorless solid of the title compound (17 mg).

$^1$H-NMR (DMSO-d$_6$) δ: 2.20–5.30 (10H, m), 7.72 (1H, d, J=8.4 Hz), 7.77–7.86 (3H, m), 8.17 (1H, d, J=8.8 Hz), 8.22–8.32 (2H, m), 8.51 (1H, s), 8.69 (2H, d, J=4.8 Hz). IR (KBr): 1732, 1634, 1346, 1163 cm$^{-1}$.

Working Example 156

1-(3-Chlorostyrene-β(E)-sulfonyl)-4-[4-methyl-2-(4-pyridyl)-5-thiazolecarbonyl]piperazine The title compound (73 mg) was obtained, as colorless crystals, using 1-[4-methyl-2-(4-pyridyl)-5-thiazolecarbonyl]piperazine dihydrochloride (150 mg) and 3-chlorostyrene-β(E)-sulfonylchloride (108 mg), according to a similar method described in Working Example 145.

$^1$H-NMR (CDCl$_3$) δ: 2.52 (3H, s), 3.28 (4H, m), 3.37 (4H, m), 6.68 (1H, d, J=15.4 Hz), 7.35–7.53 (5H, m), 7.76 (2H, d, J=6.0 Hz), 8.72 (2H, d, J=6.0 Hz). IR (KBr): 1634, 1595, 1429, 1346, 1327, 1279, 1256, 1155 cm$^{-1}$.

Working Example 157

1-[4-Methyl-2-(4-pyridyl)-5-thiazolecarbonyl]-4-(4-nitrobenzenesulfonyl)piperazine The title compound (186 mg) was obtained, as colorless crystals, using 1-[4-methyl-2-(4-pyridyl)-5-thiazolecarbonyl]piperazine dihydrochloride (200 mg) and 4-nitrobenzenesulfonylchloride (125 mg), according to a similar method described in Working Example 145.

$^1$H-NMR (CDCl$_3$) δ: 2.47 (3H, s), 3.15 (4H, m), 3.78 (4H, m), 7.74 (2H, d, J=6.0 Hz), 7.96 (2H, d, J=8.8 Hz), 8.42 (2H, d, J=8.8 Hz), 8.72 (2H, d, J=6.0 Hz). IR (KBr): 1634, 1530, 1429, 1352, 1171 cm$^{-1}$.

Working Example 158

1-(4-Fluorobenzenesulfonyl)-4-[4-methyl-2-(4-pyridyl)-5-thiazolecarbonyl]piperazine The title compound (122 mg) was obtained, as colorless crystals, using 1-[4-methyl-2-(4-pyridyl)-5-thiazolecarbonyl]piperazine dihydrochloride (150 mg) and 4-fluorobenzenesulfonylchloride (85 mg), according to a similar method described in Working Example 145.

$^1$H-NMR (CDCl$_3$) δ: 2.47 (3H, s), 3.08 (4H, m), 3.76 (4H, m), 7.26 (2H, t, J=8.6 Hz), 7.74 (2H, d, J=6.0 Hz), 7.79 (2H, dd, J=4.8, 8.6 Hz), 8.72 (2H, d, J=6.0 Hz). IR (KBr): 1634, 1593, 1493, 1435, 1350, 1171 cm$^{-1}$.

Working Example 159

1-(4-Chlorobenzenesulfonyl)-4-[4-methyl-2-(4-pyridyl)-5-thiazolecarbonyl]piperazine The title compound (68 mg) was obtained, as colorless crystals, using 1-[4-methyl-2-(4-pyridyl)-5-thiazolecarbonyl]piperazine dihydrochloride (150 mg) and 4-chlorobenzenesulfonylchloride (96 mg), according to a similar method described in Working Example 145.

$^1$H-NMR (CDCl$_3$) δ: 2.47 (3H, s), 3.09 (4H, m), 3.76 (4H, m), 7.55 (2H, d, J=8.4 Hz), 7.70 (2H, d, J=8.4 Hz), 7.74 (2H, d, J=6.2 Hz), 8.72 (2H, d, J=6.2 Hz). IR (KBr): 1634, 1427, 1352, 1279, 1256, 1169 cm$^{-1}$.

Working Example 160

1-[4-Methyl-2-(4-pyridyl)-5-thiazolecarbonyl]-4-(p-styrenesulfonyl)piperazine

The title compound (122 mg) was obtained, as colorless crystals, using 1-[4-methyl-2-(4-pyridyl)-5-thiazolecarbonyl]piperazine dihydrochloride (200 mg) and p-styrenesulfonylchloride (123 mg), according to a similar method described in Working Example 145.

$^1$H-NMR (CDCl$_3$) δ: 2.47 (3H, s), 3.09 (4H, m), 3.75 (4H, m), 5.48 (1H, d, J=10.8 Hz), 5.92 (1H, d, J=17.6 Hz), 6.78 (1H, dd, J=10.8, 17.6 Hz), 7.57 (2H, d, J=8.4 Hz), 7.71 (2H, d, J=8.4 Hz), 7.74 (2H, d, J=6.0 Hz), 8.71 (2H, d, J=6.0 Hz). IR (KBr): 1634, 1595, 1427, 1350, 1167 cm$^{-1}$.

Working Example 161

1-[4-Methyl-2-(4-pyridyl)-5-thiazolecarbonyl]-4-(4-toluenesulfonyl)piperazine

The title compound (129 mg) was obtained, as colorless crystals, using 1-[4-methyl-2-(4-pyridyl)-5-thiazolecarbonyl]piperazine dihydrochloride (150 mg) and 4-toluenesulfonylchloride (79 mg), according to a similar method described in Working Example 145.

$^1$H-NMR (CDCl$_3$) δ: 2.45 (3H, s), 2.47 (3H, s), 3.06 (4H, m), 3.75 (4H, m), 7.36 (2H, d, J=8.4 Hz), 7.64 (2H, d, J=8.4 Hz), 7.74 (2H, d, J=6.0 Hz), 8.71 (2H, d, J=6.0 Hz). IR (KBr): 1628, 1435, 1346, 1281, 1256, 1165 cm$^{-1}$.

Working Example 162

1-[4-Methyl-2-(4-pyridyl)-5-thiazolecarbonyl]-4-[5-(2-pyridyl)thiophene-2-sulfonyl]piperazine The title compound (46 mg) was obtained, as colorless crystals, using 1-[4-methyl-2-(4-pyridyl)-5- thiazolecarbonyl]piperazine dihydrochloride (150 mg) and 5-(2-pyridyl) thiophene-2-sulfonylchloride (119 mg), according to a similar method described in Working Example 145.

$^1$H-NMR (CDCl$_3$) δ: 2.48 (3H, s), 3.20 (4H, m), 3.79 (4H, m), 7.29 (1H, m), 7.54 (1H, d, J=4.0 Hz), 7.57 (1H, d, J=4.0 Hz), 7.67–7.84 (4H, m), 8.61 (1H, d, J=4.8 Hz), 8.71 (2H, d, J=6.2 Hz). IR (KBr): 1634, 1426, 1354, 1163 cm$^{-1}$.

Working Example 163

1-[5-(3-Isoxazolyl)thiophene-2-sulfonyl]-4-[4-methyl-2-(4-pyridyl)-5-thiazolecarbonyl]piperazine The title compound (84 mg) was obtained, as colorless crystals, using 1-[4-methyl-2-(4-pyridyl)-5-thiazolecarbonyl]piperazine dihydrochloride (150 mg) and 5-(3-isoxazolyl)thiophene-2-sulfonylchloride (114 mg), according to a similar method described in Working Example 145.

$^1$H-NMR (CDCl$_3$) δ: 2.49 (3H, s), 3.19 (4H, m), 3.81 (4H, m), 6.56 (1H, d, J=1.8 Hz), 7.54 (2H, s), 7.75 (2H, d, J=6.0 Hz), 8.33 (1H, d, J=1.8 Hz), 8.72 (2H, d, J=6.0 Hz). IR (KBr): 1634, 1597, 1418, 1358, 1163 cm$^{-1}$.

Working Example 164

1-[5-(Benzenesulfonyl)thiophene-2-sulfonyl]-4-[4-methyl-2-(4-pyridyl)-5-thiazolecarbonyl]piperazine The title compound (167 mg) was obtained, as colorless crystals, using 1-[4-methyl-2-(4-pyridyl)-5-thiazolecarbonyl]piperazine dihydrochloride (150 mg) and 5-(benzenesulfonyl)thiophene-2-sulfonylchloride (134 mg), according to a similar method described in Working Example 145.

$^1$H-NMR (CDCl$_3$) δ: 2.50 (3H, s), 3.17 (4H, m), 3.80 (4H, m), 7.54–7.70 (3H, m), 7.72 (1H, d, J=1.8 Hz), 7.78 (2H, d, J=6.0 Hz), 7.94–8.02 (2H, m), 8.34 (1H, d, J=1.8 Hz), 8.74 (2H, d, J=6.0 Hz). IR (KBr): 1634, 1447, 1362, 1323, 1155 cm$^{-1}$.

Working Example 165

1-[4-Methyl-2-(4-pyridyl)-5-thiazolecarbonyl]-4-[5-(5-trifluoromethyl-2-pyridinesulfonyl)thiophene-2-sulfonyl]piperazine The title compound (234 mg) was obtained, as colorless crystals, using 1-[4-methyl-2-(4-pyridyl)-5-thiazolecarbonyl]piperazine dihydrochloride (150 mg) and 5-(5-trifluoromethyl-2-pyridinesulfonyl)thiophene-2-sulfonylchloride (163 mg), according to a similar method described in Working Example 145.

$^1$H-NMR (CDCl$_3$) δ: 2.50 (3H, s), 3.17 (4H, m), 3.53 (4H, m), 7.78 (2H, d, J=6.2 Hz), 7.97 (1H, d, J=1.6 Hz), 8.20–8.40 (3H, m), 8.73 (2H, d, J=6.2 Hz), 8.98 (1H, s). IR (KBr): 1634, 1595, 1327, 1165, 1142 cm$^{-1}$.

Working Example 166

1-(4-Carboxybenzenesulfonyl)-4-[4-methyl-2-(4-pyridyl)-5-thiazolecarbonyl]piperazine To a solution of 1-[4-methyl-2-(4-pyridyl)-5-thiazolecarbonyl]piperazine dihydrochloride (180 mg) and triethylamine (253 mg) in dichloromethane (20 ml) was added 4-chlorosulfonylbenzoic acid (108 mg), and the mixture was stirred at room temperature for 1 hour. The reaction solution was concentrated, and the residue was dissolved in water and neutralized with 1 N hydrochloric acid. The precipitate was filtered, washed with water and dried to give a colorless solid of the title compound (174 mg).

$^1$H-NMR (DMSO-d$_6$) δ: 2.36 (3H, s), 3.04 (4H, m), 3.63 (4H, m), 7.80–7.90 (4H, m), 8.17 (2H, d, J=8.8 Hz), 8.71 (2H, d, J=5.8 Hz). IR (KBr): 1715, 1638, 1431, 1358, 1283, 1254, 1169 cm$^{-1}$.

Working Example 167

1-(4-Methoxycarbonylbenzenesulfonyl)-4-[4-methyl-2-(4-pyridyl)-5-thiazolecarbonyl]piperazine To a solution of 1-[4-methyl-2-(4-pyridyl)-5-thiazolecarbonyl]piperazine dihydrochloride (180 mg) and triethylamine (253 mg) in dichloromethane (20 ml) was added 4-chlorosulfonylbenzoic acid (108 mg), and the mixture was stirred at room temperature for 1 hour. To the reaction solution was added a solution of diazomethane in ether until the solution remained yellow. The mixture was concentrated and the residue was purified with silica gel column chromatography (ethyl acetate) to give colorless crystals of the title compound (158 mg).

$^1$H-NMR (CDCl$_3$) δ: 2.46 (3H, s), 3.11 (4H, m), 3.77 (4H, m), 3.99 (3H, s), 7.74 (2H, d, J=6.2 Hz), 7.84 (2H, d, J=8.6 Hz), 8.24 (2H, d, J=8.6 Hz), 8.72 (2H, d, J=6.2 Hz). IR (KBr): 1728, 1634, 1435, 1354, 1281, 1171, 1107 cm$^{-1}$.

Working Example 168

1-(4-Cyanostyrene-β(E)-sulfonyl)-4-[4-methyl-2-(4-pyridyl)-5-thiazolecarbonyl]piperazine The title compound (225 mg) was obtained, as colorless crystals, using 4-methyl-2-(4-pyridyl)-5-thiazolecarboxylic acid (152 mg) and 1-(4-cyanostyrene-β(E)-sulfonyl)piperazine (190 mg), according to a similar method described in Working Example 46.

$^1$H-NMR (CDCl$_3$) δ: 2.52 (3H, s), 3.31 (4H, m), 3.80 (4H, m), 6.78 (1H, d, J=15.2 Hz), 7.51 (1H, d, J=15.2 Hz), 7.61 (2H, d, J=8.4 Hz), 7.70–7.80 (4H, m), 8.73 (2H, d, J=6.2 Hz). IR (KBr): 2228, 1634, 1597, 1429, 1348, 1325, 1279, 1256, 1155 cm$^{-1}$.

Working Example 169

1-[4-Methyl-2-(4-pyridyl)-5-thiazolecarbonyl]-4-(4-trifluoromethylstyrene-β(E)-sulfonyl)piperazine The title compound (170 mg) was obtained, as colorless crystals, using 4-methyl-2-(4-pyridyl)-5-thiazolecarboxylic acid (82 mg) and 1-(4-trifluoromethylstyrene-β(E)-sulfonyl)piperazine hydrochloride (130 mg), according to a similar method described in Working Example 46.

$^1$H-NMR (CDCl$_3$) δ: 2.51 (3H, s), 3.30 (4H, m), 3.80 (4H, m), 6.76 (1H, d, J=15.6 Hz), 7.53 (1H, d, J=15.6 Hz), 7.62 (2H, d, J=8.4 Hz), 7.71 (2H, d, J=8.4 Hz), 7.75 (2H, d, J=6.0 Hz), 8.72 (2H, d, J=6.0 Hz). IR (KBr): 1634, 1429, 1348, 1325, 1155, 1127, 1067 cm$^{-1}$.

Working Example 170

1-(2H-Benzopyran-3-ylsulfonyl)-4-[4-methyl-2-(4-pyridyl)-5-thiazolecarbonyl]piperazine The title compound (120 mg) was obtained, as colorless solid, using 4-methyl-2-(4-pyridyl)-5-thiazolecarboxylic acid (70 mg) and 1-(2H-benzopyran-3-ylsulfonyl)piperazine hydrochloride (100 mg), according to a similar method described in Working Example 46.

$^1$H-NMR (CDCl$_3$) δ: 2.52 (3H, s), 3.33 (4H, m), 3.78 (4H, m), 4.88 (2H, s), 6.92 (1H, d, J=8.0 Hz), 7.01 (1H, m), 7.20 (1H, dd, J=1.4, 8.0 Hz), 7.29 (1H, s), 7.32 (1H, m), 7.76 (2H, d, J=6.2 Hz), 8.72 (2H, d, J=6.2 Hz). IR (KBr): 1634, 1607, 1429, 1346, 1329, 1279, 1159 cm$^{-1}$.

Working Example 171

1-(2H-3,4-Dihydrobenzopyran-3-ylsulfonyl)-4-[4-methyl-2-(4-pyridyl)-5-thiazolecarbonyl]piperazine A solution of 1-(2H-benzopyran-3-ylsulfonyl)-4-[4-methyl-2-(4-pyridyl)-5-thiazolecarbonyl]piperazine (50 mg) in methanol was hydrogenated in the presence of palladium carbon to give a colorless solid of the title compound (50 mg).

$^1$H-NMR (CDCl$_3$) δ: 2.45 (3H, s), 3.10–3.40 (6H, m), 3.45–3.82 (5H, m), 4.34–4.52 (2H, m), 6.82–7.20 (4H, m), 7.76 (2H, d, J=6.2 Hz), 8.73 (2H, d, J=6.2 Hz). IR (KBr): 1628, 1491, 1439, 1424, 1327, 1315, 1150 cm$^{-1}$.

Working Example 172

1-[4-(4-Pyridyl)benzoyl]-4-(p-styrenesulfonyl)piperazine

The title compound (315 mg) was obtained, as colorless crystals, using 1-(p-styrenesulfonyl)piperazine hydrochloride (288 mg) and 4-(4-pyridyl)benzoic acid (240 mg), according to a similar method described in Working Example 46.

$^1$H-NMR (CDCl$_3$) δ: 3.07 (4H, brs), 3.78 (4H, brs), 5.48 (1H, d, J=10.6 Hz), 5.92 (1H, d, J=17.6 Hz), 6.78 (1H, dd, J=10.6, 17.6 Hz), 7.42–7.50 (4H, m), 7.57 (2H, d, J=8.4 Hz), 7.65 (2H, d, J=8.0 Hz), 7.71 (2H, d, J=8.4 Hz), 8.69 (2H, d, J=6.0 Hz). IR (KBr): 1628, 1593, 1431, 1346, 1283, 1171 cm$^{-1}$.

Working Example 173

1-[4-(3-Pyridyl)benzoyl]-4-(p-styrenesulfonyl)piperazine

The title compound (355 mg) was obtained, as colorless crystals, using 1-(p-styrenesulfonyl)piperazine hydrochloride (288 mg) and 4-(3-pyridyl)benzoic acid (200 mg), according to a similar method described in Working Example 46.

$^1$H-NMR (CDCl$_3$) δ: 3.07 (4H, brs), 3.71 (4H, brs), 5.48 (1H, d, J=11.0 Hz), 5.92 (1H, d, J=17.6 Hz), 6.78 (1H, dd, J=11.0, 17.6 Hz), 7.36–7.76 (9H, m), 7.89 (1H, m), 8.62 (1H, dd, J=1.6, 4.8 Hz), 8.82 (1H, d, J=1.6 Hz). IR (KBr): 1624, 1458, 1431, 1346, 1285, 1171 cm$^{-1}$.

Working Example 174

1-(6-Chloronaphthalene-2-sulfonyl)-4-[4-(2-pyradinyl)-benzoyl]piperazine

The title compound (136 mg) was obtained, as colorless crystals, using 1-(6-chloronaphthalene-2-sulfonyl)-piperazine hydrochloride (100 mg) and 4-(2-pyradinyl)-benzoic acid (58 mg), according to a similar method described in Working Example 46.

$^1$H-NMR (CDCl$_3$) δ: 3.13 (4H, brs), 3.78 (4H, br), 7.45 (2H, d, J=8.0 Hz), 7.60 (1H, dd, J=2.2, 8.8 Hz), 7.76 (1H, dd, J=1.6, 8.8 Hz), 7.90–7.97 (3H, m), 8.03 (2H, d, J=8.0 Hz), 8.31 (1H, s), 8.55 (1H, d, J=2.6 Hz), 8.65 (1H, dd, J=1.4, 2.6 Hz), 9.02 (1H, d, J=1.4 Hz). IR (KBr): 1628, 1464, 1433, 1350, 1289, 1167 cm$^{-1}$.

Working Example 175

1-(4-Cyanobenzenesulfonyl)-4-[4-methyl-2-(4-pyridyl)-5-thiazolecarbonyl]piperazine The title compound (314 mg) was obtained, as colorless crystals, using 1-[4-methyl-2-(4-pyridyl)-5-thiazolecarbonyl]piperazine dihydrochloride (300 mg) and 4-cyanobenzenesulfonylchloride (167 mg), according to a similar method described in Working Example 145.

$^1$H-NMR (CDCl$_3$) δ: 2.55 (3H, s), 3.30 (4H, m), 3.80 (4H, m), 6.77 (1H, d, J=15.4 Hz), 7.50 (1H, d, J=15.4 Hz), 7.60 (2H, d, J=8.4 Hz), 7.70–7.80 (4H, m), 8.72 (2H, d, J=6.2 Hz). IR (KBr): 2234, 1630, 1595, 1456, 1441, 1348, 1285, 1260, 1165 cm$^{-1}$.

Working Example 176

1-[4-Methyl-2-(4-pyridyl)-5-thiazolecarbonyl]-4-(4-trifluoromethoxybenzenesulfonyl)piperazine The title compound (152 mg) was obtained, as colorless crystals, using 1-[4-methyl-2-(4-pyridyl)-5-thiazole-carbonyl]piperazine dihydrochloride (150 mg) and 4-trifluoromethoxybenzenesulfonylchloride (108 mg), according to a similar method described in Working Example 145.

$^1$H-NMR (CDCl$_3$) δ: 2.47 (3H, s), 3.11 (4H, m), 3.77 (4H, m), 7.40 (2H, d, J=8.8 Hz), 7.74 (2H, d, J=6.0 Hz), 7.82 (2H, d, J=8.8 Hz), 8.71 (2H, d, J=6.0 Hz). IR (KBr): 1630, 1595, 1439, 1356, 1273, 1256, 1221, 1163 cm$^{-1}$.

Working Example 177

1-(5-Chloro-3-methylbenzo[b]thiophene-2-sulfonyl)-4-[4-methyl-2-(4-pyridyl)-5-thiazolecarbonyl]piperazine The title compound (158 mg) was obtained, as colorless crystals, using 1-[4-methyl-2-(4-pyridyl)-5-thiazolecarbonyl]piperazine dihydrochloride (150 mg) and 5-chloro-3-methylbenzo[b]thiophene-2-sulfonylchloride (117 mg), according to a similar method described in Working Example 145.

$^1$H-NMR (CDCl$_3$) δ: 2.47 (3H, s), 2.69 (3H, s), 3.28 (4H, m), 3.79 (4H, m), 7.50 (1H, dd, J=1.8, 8.4 Hz), 7.74 (2H, d, J=6.0 hz), 7.78 (1H, d, J=8.4 Hz), 7.83 (1H, d, J=1.8 Hz), 8.72 (2H, d, J=6.0 Hz). IR (KBr): 1634, 1431, 1352, 1281, 1165 cm$^{-1}$.

Working Example 178

1-(6-Chloronaphthalene-2-sulfonyl)-4-[4-(3-pyrazolyl)-benzoyl]piperazine

The title compound (253 mg) was obtained, as colorless crystals, using 1-(6-chloronaphthalene-2-sulfonyl)piperazine hydrochloride (200 mg) and 4-(3-pyrazolyl)benzoic acid (109 mg), according to a similar method described in Working Example 46.

$^1$H-NMR (CDCl$_3$) δ: 3.12 (4H, brs), 3.75 (4H, brs), 6.63 (1H, d, J=2.2 Hz), 7.35 (2H, d, J=8.4 Hz), 7.55–7.65 (2H, m), 7.72–7.82 (3H, m), 7.88–7.98 (3H, m), 8.31 (1H, s). IR (KBr): 3196, 1628, 1615, 1435, 1346, 1283, 1264, 1165 cm$^{-1}$.

Working Example 179

1-[4-(2-Amino-4-pyrimidyl)benzoyl]-4-(6-chloronaphthalene-2-sulfonyl)piperazine

The title compound (273 mg) was obtained, as colorless crystals, using 1-(6-chloronaphthalene-2-sulfonyl)piperazine hydrochloride (200 mg) and 4-(2-amino-4-pyrimidyl)benzoic acid (124 mg), according to a similar method described in Working Example 46.

$^1$H-NMR (CDCl$_3$) δ: 3.11 (4H, brs), 3.74 (4H, brs), 5.11 (2H, s), 7.01 (1H, d, J=5.0 Hz), 7.39 (2H, d, J=8.4 Hz), 7.60 (1H, dd, J=1.8, 8.8 Hz), 7.75 (1H, dd, J=1.8, 8.8 Hz), 7.88–8.02 (5H, m), 8.30 (1H, s), 8.37 (1H, d, J=5.0 Hz). IR (KBr): 3468, 3289, 3160, 1622, 1574, 1462, 1346, 1335, 1289, 1157 cm$^{-1}$.

Working Example 180

1-(6-Chloronaphthalene-2-sulfonyl)-4-(4-(tert-butoxycarbonylcarbazoyl)benzoyl]piperazine The title compound (339 mg) was obtained, as colorless crystals, using 1-(6-chloronaphthalene-2-sulfonyl)piperazine hydrochloride (200 mg) and 4-(tert-butoxycarbonylcarbazoyl)benzoic acid (162 mg), according to a similar method described in Working Example 46.

$^1$H-NMR (CDCl$_3$) δ: 1.49 (9H, s), 3.10 (4H, brs), 3.49 (2H, br), 3.84 (2H, br), 6.70 (1H, brs), 7.32 (2H, d, J=8.2 Hz), 7.60 (1H, dd, J=1.8, 8.8 Hz), 7.70–7.82 (3H, m), 7.88–7.96 (3H, m), 8.20 (1H, brs), 8.30 (1H, s). IR (KBr): 3266, 1682, 1628, 1456, 1437, 1346, 1285, 1265, 1252, 1165 cm$^{-1}$.

Working Example 181

1-(6-Chloronaphthalene-2-sulfonyl)-4-(4-carbazoylbenzoyl)piperazine hydrochloride The title compound (241 mg) was obtained, as colorless solid, by treating 1-(6-chloronaphthalene-2-sulfonyl)-4-[4-(tert-butoxycarbonylcarbazoyl)benzoyl]piperazine (319 mg) with hydrochloric acid, according to a similar method described in Working Example 76.

$^1$H-NMR (DMSO-d$_6$) δ: 3.07 (4H, brs), 3.65 (4H, brs), 7.47 (2H, d, J=8.4 Hz), 7.72 (1H, d, J=8.8 Hz), 7.81 (1H, d, J=8.8 Hz), 7.89 (2H, d, J=8.4 Hz), 8.18 (1H, d, J=8.0 Hz), 8.22–8.32 (2H, m), 8.49 (1H, s), 11.47 (1H, br). IR (KBr): 3075, 2853, 2610, 1620, 1346, 1335, 1289, 1155 cm$^{-1}$.

Working Example 182

1-[4-(5-Aminoisoxazol-3-yl)benzoyl]-4-(6-chloronaphthalene-2-sulfonyl)piperazine The title compound (243 mg) was obtained, as colorless crystals, using 1-(6-chloronaphthalene-2-sulfonyl)piperazine hydrochloride (200 mg) and 4-(5-aminoisoxazol-3-yl)benzoic acid (118 mg), according to a similar method described in Working Example 46.

$^1$H-NMR (DMSO-d$_6$) δ: 3.06 (4H, brs), 3.61 (4H, brs), 5.40 (1H, s), 6.81 (2H, brs), 7.38 (2H, d, J=8.2 Hz), 7.68–7.86 (4H, m), 8.18 (1H, d, J=8.6 Hz), 8.26 (1H, s), 8.28 (1H, d, J=8.6 Hz), 8.50 (1H, s). IR (KBr): 3420, 1636, 1609, 1474, 1441, 1344, 1331, 1289, 1159 cm$^{-1}$.

Working Example 183

1-[4-(3-Aminopyrazol-5-yl)benzoyl]-4-(6-chloronaphthalene- 2-sulfonyl)piperazine The title compound (264 mg) was obtained, as colorless amorphous solid using 1-(6-chloronaphthalene-2-sulfonyl)piperazine hydrochloride (200 mg) and 4-(3-aminopyrazol-5-yl)benzoic acid (117 mg), according to a similar method described in Working Example 46.

$^1$H-NMR (CDCl$_3$) δ: 3.10 (4H, brs), 3.72 (4H, brs), 5.89 (1H, s), 7.29 (2H, d, J=8.4 Hz), 7.52 (2H, d, J=8.4 Hz), 7.59 (1H, dd, J=1.8, 8.8 Hz), 7.75 (1H, dd, J=1.8, 8.8 Hz), 7.88–7.96 (3H, m), 8.30 (1H, s). IR (KBr): 3214, 1626, 1433, 1346, 1331, 1285, 1165 cm$^{-1}$.

Working Example 184

1-[4-(5-Amino-1,3,4-oxadiazol-2-yl)benzoyl]-4-(6-chloronaphthalene-2-sulfonyl)piperazine The title compound (226 mg) was obtained, as colorless crystals, using 1-(6-chloronaphthalene-2-sulfonyl)piperazine hydrochloride (200 mg) and 4-(5-amino-1,3,4-oxadiazol-2-yl)benzoic acid (118 mg), according to a similar method described in Working Example 46.

$^1$H-NMR (DMSO-d$_6$) δ: 3.08 (4H, brs), 3.60 (4H, br), 7.32 (2H, brs), 7.47 (2H, d, J=8.2 Hz), 7.68–7.86 (4H, m), 8.18 (1H, d, J=8.8 Hz), 8.24–8.32 (2H, m), 8.50 (1H, s). IR (KBr): 3303, 3108, 1665, 1630, 1595, 1426, 1333, 1155 cm$^{-1}$.

Working Example 185

1-(4-tert-Butoxycarbonylamidinobenzenesulfonyl)-4-[4-methyl-2-(4-pyridyl)-5-thiazolecarbonyl]piperazine A solution of 1-(4-cyanobenzenesulfonyl)-4-[4-methyl-2-(4-pyridyl)-5-thiazolecarbonyl]piperazine (233 mg) and ethanol (0.3 ml) in dichloromethane (20 ml) was saturated with hydrogen chloride under ice-cooling and the mixture was allowed to stand for 1 day, and the reaction solution was concentrated. To the residue was added a saturated solution of ammonia in ethanol (20 ml), and the mixture was stirred at room temperature for 15 hours. The reaction solution was concentrated, and the residue was dissolved in DMF (20 ml). To the solution were added triethylamine (1 ml) and di-t-butyl dicarbonate (1 ml), and the mixture was stirred at 40° C. for 30 minutes. The reaction solution was concentrated, and the residue was purified with silica gel column chromatography (ethyl acetate) to give a colorless solid of the title compound (139 mg).

$^1$H-NMR (CDCl$_3$) δ: 1.56 (9H, s), 2.47 (3H, s), 3.06 (4H, m), 3.75 (4H, m), 7.76 (2H, d, J=6.2 Hz), 7.82 (2H, d, J=8.6 Hz), 8.03 (2H, d, J=8.6 Hz), 8.72 (2H, d, J=6.2 Hz). IR (KBr): 1622, 1522, 1435, 1354, 1281, 1256, 1169, 1140 cm$^{-1}$.

Working Example 186

1-(4-Amidinobenzenesulfonyl)-4-[4-methyl-2-(4-pyridyl)-5-thiazolecarbonyl]piperazine dihydrochloride The title compound (120 mg) was obtained, as colorless solid, by treating 1-(4-tert-butoxycarbonylamidinobenzenesulfonyl)-4-[4-methyl-2-(4-pyridyl)-5-thiazolecarbonyl]piperazine (139 mg) with hydrochloric acid according to a similar method described in Working Example 76.

$^1$H-NMR (DMSO-d$_6$) δ: 2.41 (3H, s), 3.09 (4H, brs), 3.66 (4H, brs), 7.98 (2H, d, J=8.4 Hz), 8.11 (2H, d, J=8.4 Hz), 8.22 (2H, m), 8.89 (2H, d, J=5.2 Hz), 9.47 (2H, s), 9.67 (2H, s). IR (KBr): 2980(br), 1682, 1634, 1522, 1464, 1441, 1424, 1350, 1279, 1169 cm$^{-1}$.

Working Example 187

1-(3-tert-Butoxycarbonylamidinostyrene-β-sulfonyl)
-4-[4-methyl-2-(4-pyridyl)-5-thiazolecarbonyl]
piperazine The title compound (211 mg) was obtained, as colorless solid, from 1-(3-cyanostyrene-β-sulfonyl)-4-[4-methyl-2-(4-pyridyl)-5-thiazolecarbonyl]piperazine (272 mg), according to a similar method described in Working Example 185.

$^1$H-NMR (CDCl$_3$) δ: 1.56 (9H, s), 2.53 (3H, s), 3.29 (4H, m), 3.79 (4H, m), 6.80 (1H, d, J=15.4 Hz), 7.46–7.67 (3H, m), 7.74–7.85 (3H, m), 8.14 (1H, s), 8.71 (2H, d, J=6.0 Hz). IR (KBr): 1622, 1520, 1435, 1348, 1318, 1281, 1256, 1155 cm$^{-1}$.

Working Example 188

1-(3-Amidinostyrene-β-sulfonyl)-4-[4-methyl-2-(4-pyridyl)-5-thiazolecarbonyl]piperazine
dihydrochloride The title compound (186 mg) was obtained, as colorless solid, by treating 1-(3-tert-butoxycarbonylamidinostyrene-β-sulfonyl)-4-[4-methyl-2-(4-pyridyl)-5-thiazolecarbonyl]piperazine (190 mg) with hydrochloric acid according to a similar method described in Working Example 76.

$^1$H-NMR (DMSO-d$_6$) δ: 2.46 (3H, s), 3.24 (4H, brs), 3.70 (4H, brs), 7.54 (2H, s), 7.70 (1H, t, J=8.0 Hz), 7.91 (1H, d, J=8.0 Hz), 8.09 (1H, d, J=8.0 Hz), 8.19 (2H, m), 8.36 (1H, s), 8.88 (2H, m), 9.29 (2H, s), 9.53 (2H, s). IR (KBr): 3005(br), 1678, 1632, 1522, 1464, 1441, 1426, 1345, 1279, 1154 cm$^{-1}$.

Working Example 189

1-(4-Amidinostyrene-β-sulfonyl)-4-[4-methyl-2-(4-pyridyl)-5-thiazolecarbonyl]piperazine A solution of 1-(4-cyanostyrene-β-sulfonyl)-4-[4-methyl-2-(4-pyridyl)-5-thiazolecarbonyl]piperazine (122 mg) and methanol (15 ml) in dichloromethane (15 ml) was saturated with hydrogen chloride under ice-cooling and allowed to stand for 1 day. The reaction solution was concentrated, and to the residue was added a saturated solution of ammonia in ethanol (20 ml). The mixture was stirred at room temperature for 15 hours. The reaction solution was concentrated, and the residue was purified with silica gel column chromatography (ethyl acetate/methanol=20/1) to give a colorless solid of the title compound (19 mg).

$^1$H-NMR (CDCl$_3$) δ: 2.52 (3H, s), 3.30 (4H, m), 3.80 (4H, m), 6.75 (1H, d, J=15.4 Hz), 7.53 (1H, d, J=15.4 Hz), 7.59 (2H, d, J=8.6 Hz), 7.75 (2H, d, J=6.0 Hz), 7.88 (2H4 d, J=8.6 Hz), 8.72 (2H, d, J=6.0 Hz). IR (KBr): 3196, 1680, 1615, 1431, 1346, 1325, 1279, 1258, 35 1155 cm$^{-1}$.

Working Example 190

1-[4-(6-tert-Butoxycarbonylamino-3-pyridyl)
benzoyl]-4-(6-chloronaphthalene-2-sulfonyl)
piperazine The title compound (265 mg) was obtained, as colorless crystals, using 1-(6-chloronaphthalene-2-sulfonyl)piperazine hydrochloride (200 mg) and 4-(6-tert-butoxycarbonylamino-3-pyridyl)benzoic acid (181 mg), according to a similar method described in Working Example 46.

$^1$H-NMR (CDCl$_3$) δ: 1.54 (9H, s), 3.13 (4H, brs), 3.75 (4H, brs), 7.39 (2H, d, J=8.4 Hz), 7.41 (1H, brs), 7.54 (2H, d, J=8.4 Hz), 7.60 (1H, dd, J=1.8, 8.8 Hz), 7.76 (1H, dd, J=1.8, 8.8 Hz), 7.84 (1H, dd, J=2.4, 8.8 Hz), 7.90–7.97 (3H, m), 8.02 (1H, d, J=8.8 Hz), 8.31 (1H, s), 8.43 (1H, d, J=2.4 Hz). IR (KBr): 3407, 1725, 1634, 1530, 1348, 1285, 1252, 1165 cm$^{-1}$.

Working Example 191

1-[4-(6-Amino-3-pyridyl)benzoyl]-4-(6-chloronaphthalene-2-sulfonyl)piperazine
hydrochloride The title compound (204 mg) was obtained, as colorless solid, by treating 1-[4-(6-tert-butoxycarbonylamino-3-pyridyl)benzoyl]-4-(6-chloronaphthalene-2-sulfonyl)piperazine (245 mg) with hydrochloric acid, according to a similar method described in Working Example 76.

$^1$H-NMR (DMSO-d$_6$) δ: 3.07 (4H, brs), 3.50 (4H, br), 7.07 (1H, m), 7.43 (2H, d, J=8.4 Hz), 7.68 (2H, d, J=8.4 Hz), 7.72 (1H, dd, J=1.8, 8.8 Hz), 7.82 (1H, dd, J=1.8, 8.8 Hz), 8.08 (2H, br), 8.18 (1H, d, J=8.4 Hz), 8.23–8.33 (4H, m), 8.50 (1H, s). IR (KBr): 3079, 1672, 1626, 1345, 1283, 1163 cm$^{-1}$.

Working Example 192

1-[4-(2-tert-Butoxycarbonylamino-3,4,5,6-tetrahydro-4-pyrimidyl)-benzoyl]-4-(6-chloronaphthalene-2-sulfonyl)piperazine The title compound (287 mg) was obtained, as colorless crystals, using 1-(6-chloronaphthalene-2-sulfonyl)piperazine hydrochloride (200 mg) and 4-(2-tert-butoxycarbonylamino-3,4,5,6-tetrahydro-4-pyrimidyl)benzoic acid (155 mg), according to a similar method described in Working Example 46.

$^1$H-NMR (CDCl$_3$) δ: 1.46 (9H, s), 1.90 (1H, m), 2.17 (1H, m), 2.90–3.90 (11H, m), 4.64 (1H, m), 7.30 (4H, s), 7.60 (1H, dd, J=1.8, 8.8 Hz), 7.76 (1H, dd, J=1.4, 8.8 Hz), 7.90–7.97 (3H, m), 8.31 (1H, s). IR (KBr): 3280, 1640, 1346, 1157 cm$^{-1}$.

Working Example 193

1-[4-(2-Amino-3,4,5,6-tetrahydro-4-pyrimidyl)
benzoyl]-4-(6-chloro-naphthalene-2-sulfonyl)
piperazine hydrochloride The title compound (189 mg) was obtained, as colorless solid, by treating 1-[4-(2-tert-butoxycarbonylamino-3,4,5,6-tetrahydro-4-pyrimidyl)benzoyl]-4-(6-chloronaphthalene-2-sulfonyl)piperazine (257 mg) with hydrochloric acid, according to a similar method described in Working Example 76.

$^1$H-NMR (DMSO-d$_6$) δ: 1.85 (1H, m), 2.10 (1H, m), 2.90–3.80 (10H, m), 4.68 (1H, m), 6.88–7.04 (2H, m), 7.31 (2H, d, J=8.0 Hz), 7.37 (2H,d, J=8.0 Hz), 7.73 (1H, d, J=8.8 Hz), 7.81 (1H, d, J=8.8 Hz), 8.12–8.32 (4H, m), 8.49 (1H, s). IR (KBr): 3216, 3073, 1674, 1632, 1437, 1346, 1333, 1159 cm$^{-1}$.

Working Example 194

1-[4-(2-tert-Butoxycarbonylamino-5-pyrimidyl)
benzoyl]-4-(6-chloro-naphthalene-2-sulfonyl)
piperazine The title compound (315 mg) was obtained, as colorless crystals, using 1-(6-chloronaphthalene-2-sulfonyl)

piperazine hydrochloride (200 mg) and 4-(2-tert-butoxycarbonylamino-5-pyrimidyl)benzoic acid (182 mg), according to a similar method described in Working Example 46.

$^1$H-NMR (CDCl$_3$) δ: 1.56 (9H, s), 3.13 (4H, brs), 3.74 (4H, brs), 7.42 (2H, d, J=8.4 Hz), 7.52 (2H, d, J=8.4 Hz), 7.60 (1H, dd, J=2.0, 8.8 Hz), 7.69 (1H, brs), 7.76 (1H, dd, J=1.8, 8.8 Hz), 7.89–7.97 (3H, m), 8.31 (1H, s), 8.76 (2H, s). IR (KBr): 3403, 1717, 1624, 1481, 1350, 1327, 1165 cm$^{-1}$.

Working Example 195

1-[4-(2-Amino-5-pyrimidyl)benzoyl]-4-(6-chloronaphthalene-2-sulfonyl)piperazine

The title compound (112 mg) was obtained, as colorless solid, by treating 1-[4-(2-tert-butoxycarbonylamino-5-pyrimidyl)benzoyl]-4-(6-chloronaphthalene-2-sulfonyl) piperazine (280 mg) with hydrochloric acid according to a similar method described in Working Example 76, and followed by transformation into a free form with sodium bicarbonate aqueous solution and recrystallization from ethyl acetate.

$^1$H-NMR (CDCl$_3$) δ: 3.12 (4H, brs), 3.75 (4H, brs), 5.16 (2H, brs), 7.39 (2H, d, J=8.4 Hz), 7.49 (2H, d, J=8.4 Hz), 7.60 (1H, dd, J=1.8, 8.8 Hz), 7.76 (1H, dd, J=1.8, 8.8 Hz), 7.89–7.97 (3H, m), 8.31 (1H, s), 8.51 (2H, s). IR (KBr): 3333, 3200, 1649, 1626, 1607, 1429, 1331, 1155 cm$^{-1}$.

Working Example 196

1-(6-Chloronaphthalene-2-sulfonyl)-4-[3-(4-pyridyl) propionyl]-piperazine

The title compound (162 mg) was obtained, as colorless crystals, using 1-(6-chloronaphthalene-2-sulfonyl) piperazine hydrochloride (150 mg) and 3-(4-pyridyl) propionic acid (66 mg), according to a similar method described in Working Example 46.

$^1$H-NMR (CDCl$_3$) δ: 2.54 (2H, t, J=7.6 Hz), 2.89 (2H, t, J=7.6 Hz), 3.04 (4H, m), 3.52 (2H, m), 3.72 (2H, m), 7.07 (2H, d, J=6.2 Hz), 7.60 (1H, dd, J=2.0, 8.8 Hz), 7.74 (1H, dd, J=1.8, 8.8 Hz), 7.88–7.98 (3H, m), 8.30 (1H, s), 8.43 (2H, d, J=6.2 Hz). IR (KBr): 1640, 1346, 1331, 1244, 1167 cm$^{-1}$.

Working Example 197

1-[4-(2-tert-Butoxycarbonylamino-3,4,5,6-tetrahydro-5-pyrimidyl)-benzoyl]-4-(6-chloronaphthalene-2-sulfonyl)piperazine The title compound (262 mg) was obtained, as colorless crystals, using 1-(6-chloronaphthalene-2-sulfonyl) piperazine hydrochloride (200 mg) and 4-(2-tertbutoxycarbonylamino-3,4,5,6-tetrahydro-5-pyrimidyl) benzoic acid (184 mg), according to a similar method described in Working Example 46.

$^1$H-NMR(DMSO-d$_6$) δ: 1.34 (9H, s), 2.90–3.20 (5H, m), 3.20–3.80 (8H, m), 7.28 (2H, d, J=8.0 Hz), 7.34 (2H, d, J=8.0 Hz), 7.72 (1H, dd, J=2.0, 8.8 Hz), 7.80 (1H, dd, J=1.8, 8.8 Hz), 8.17 (1H, d, J=8.8 Hz), 8.23–8.35 (4H, m), 8.48 (1H, s). IR (KBr): 3281, 2847, 1644, 1450, 1431, 1362, 1281, 1157 cm$^{-1}$.

Working Example 198

1-[4-(2-Amino-3,4,5,6-tetrahydro-5-pyrimidyl) benzoyl]-4-(6-chloro-naphthalene-2-sulfonyl) piperazine hydrochloride The title compound (188 mg) was obtained, as colorless solid, by treating 1-[4-(2-tert-butoxycarbonylamino-3,4,5,6-tetrahydro-5-pyrimidyl)benzoyl]-4-(6-chloronaphthalene-2-sulfonyl)piperazine (235 mg) with hydrochloric acid, according to a similar method described in Working Example 76.

$^1$H-NMR (DMSO-d$_6$) δ: 3.05 (4H, brs), 3.15 (1H, m),, 3.20–3.75 (8H, m), 7.15 (2H, brs), 7.30 (2H, d, J=8.4 Hz), 7.36 (2H, d, J=8.4 Hz), 7.73 (1H, dd, J=2.0, 8.8 Hz), 7.82 (1H, dd, J=1.8, 8.8 Hz), 8.15–8.32 (5H, m), 8.50 (1H, d, J=1.4 Hz). IR (KBr): 3200, 3061, 1671, 1638, 1427, 1348, 1289, 1159 cm$^{-1}$.

Working Example 199

1-(6-Chloronaphthalene-2-sulfonyl)-4-(4-pyridylmethoxyacetyl)piperazine

The title compound (165 mg) was obtained, as colorless crystals, using 1-(6-chloronaphthalene-2-sulfonyl) piperazine hydrochloride (200 mg) and 4-pyridylmethoxyacetic acid (117 mg), according to a similar method described in Working Example 46.

$^1$H-NMR (CDCl$_3$) δ: 3.08 (4H, brs), 3.61 (2H, m), 3.72 (2H, m), 4.14 (2H, s), 4.51 (2H, s), 7.15 (2H, d, J=5.8 Hz), 7.60 (1H, dd, J=2.0, 8.8 Hz), 7.72 (1H, dd, J=1.8, 8.8 Hz), 7.86–7.96 (3H, m), 8.28 (1H, s), 8.52 (2H, d, J=5.8 Hz). IR (KBr): 1665, 1445, 1345, 1333, 1283, 1242, 1169, 1134 cm$^{-1}$.

Working Example 200

1-[4-Methyl-2-(4-pyridyl)-5-thiazolecarbonyl]-4-(2-trifluoroacetyl-1,2,3,4-tetrahydroisoquinoline-7-sulfonyl)piperazine The title compound (435 mg) was obtained, as colorless crystals, using 1-[4-methyl-2-(4-pyridyl)-5-thiazolecarbonyl]piperazine dihydrochloride (353 mg) and 2-trifluoroacetyl-1,2,3,4-tetra-hydroisoquinoline-7-sulfonylchloride (327 mg), according to a similar method described in Working Example 145.

$^1$H-NMR (CDCl$_3$) δ: 2.47 (3H, s), 3.00–3.15 (6H, m), 3.77 (4H, m), 3.85–4.00 (2H, m), 4.82 (1/3×2H, s), 4.88 (2/3×2H, s), 7.33–7.44 (1H, m), 7.52–7.66 (2H, m), 7.74 (2H, d, J=6.2 Hz), 8.72 (2H,d, J=6.2 Hz). IR (KBr): 1696, 1634, 1433, 1348, 1167 cm$^{-1}$.

Working Example 201

1-[4-Methyl-2-(4-pyridyl)-5-thiazolecarbonyl]-4-(1, 2,3,4-tetrahydroisoquinoline-7-sulfonyl)piperazine To a solution of 1-[4-methyl-2-(4-pyridyl)-5-thiazolecarbonyll-4-(2-trifluoroacetyl-1,2,3,4-tetrahydroisoquinoline-7-sulfonyl)piperazine (400 mg) in methanol (10 ml) was added 15% ammonia in methanol (15 ml), and the mixture was stirred at room temperature for 10 minutes. The reaction solution was concentrated, and to the residue was added ethyl acetate-i N hydrochloric acid. The aqueous layer was separated, adjusted to pH 10 with 1 N sodium hydroxide aqueous solution and extracted with dichloromethane. The extract was dried and concentrated to give an amorphous powder of the title compound (337 mg).

$^1$H-NMR (CDCl$_3$) δ: 2.47 (3H, s), 2.90 (2H, t, J=5.8 Hz), 3.06 (4H, m), 3.19 (2H, t, J=5.8 Hz), 3.75 (4H, m), 4.08 (2H, s), 7.27 (1H, d, J=8.0 Hz), 7.41 (1H, d, J=1.8 Hz), 7.49 (1H, dd, J=1.8, 8.0 Hz), 7.75 (2H, d, J=6.2 Hz), 8.72 (2H, d, J=6.2 Hz). IR (KBr): 1638, 1429, 1348, 1161, 727 cm$^{-1}$.

Working Example 202

1-(2-Acetimidoyl-1,2,3,4-tetrahydroisoquinoline-7-sulfonyl)-4-[4-methyl-2-(4-pyridyl)-5-thiazolecarbonyl]piperazine dihydrochloride The title compound (186 mg) was obtained, as colorless solid, using 1-[4-methyl-2-(4-pyridyl)-5-thiazolecarbonyl]-

4-(1,2,3,4-tetrahydroisoquinoline-7-sulfonyl)piperazine (150 mg) and ethyl acetimidate hydrochloride (383 mg), according to a similar method described in Working Example 99.

$^1$H-NMR (DMSO-d$_6$) δ: 2.38 (6H, s), 3.01 (4H, brs), 3.11 (2H, m), 3.68 (4H, m), 3.80 (2H, m), 4.81 (1/2×2H, s), 4.87 (1/2×2H, s), 7.50–7.75 (3H, m), 7.92 (2H, d, J=6.2 Hz), 8.69 (1H, brs), 8.76 (2H, d, J=6.2 Hz), 9.25–9.38 (1H, m). IR (KBr): 3065, 1672, 1632, 1426, 1345, 1279, 1161 cm$^1$.

Working Example 203

1-[4-(1-Imidazolyl)benzoyl]-4-[6-(2,2,2-trichloroethoxycarbonylamino)naphthalene-2-sulfonyl]piperazine The title compound (435 mg) was obtained, as colorless crystals, using 1-[4-(1-imidazolyl)benzoyl]piperazine dihydrochloride (329 mg) and 6-(2,2,2-trichloroethoxycarbonylamino)naphthalene-2-sulfonylchloride (417 mg), according to a similar method described in Working Example 145.

$^1$H-NMR (CDCl$_3$) δ: 3.12 (4H, brs), 3.74 (4H, brs), 4.89 (2H, s), 7.23 (1H, s), 7.28 (1H, t, J=1.2 Hz), 7.40 (2H, d, J=9.0 Hz), 7.46 (2H, d, J=9.0 Hz), 7.57 (1H, dd, J=2.2, 8.8 Hz), 7.72 (1H, dd, J=1.8, 8.8 Hz), 7.87 (1H, s), 7.92–7.99 (2H, m), 8.21 (1H, s), 8.27 (1H, s). IR (KBr): 1744, 1634, 1609, 1211, 1163 cm$^{-1}$.

Working Example 204

1-(6-Aminonaphthalene-2-sulfonyl)-4-[4-(1-imidazolyl)benzoyl]-piperazine

To a solution of 1-[4-(1-imidazolyl)benzoyl]-4-[6-(2,2,2-trichloroethoxycarbonylamino)naphthalene-2-sulfonyl] piperazine (400 mg) in acetic acid (5 ml) was added zinc powder (1 g), and the mixture was stirred at room temperature for 1 day. The reaction solution was filtered, and the filtrate was concentrated. The residue was dissolved in 0.5 N hydrochloric acid, washed with ethyl acetate and made alkaline with 1 N sodium hydroxide aqueous solution. The precipitate was collected by filtration, washed with water and dried to give a colorless solid of the title compound (187 mg).

$^1$H-NMR (DMSO-d$_6$) δ: 2.98 (4H, m), 3.57 (4H, br), 5.95 (2H, s), 6.89 (1H, s), 7.06 (1H, d, J=8.8 Hz), 7.13 (1H, s), 7.47 (2H, d, J=8.2 Hz), 7.48 (1H, d, J=8.8 Hz), 7.66 (1H, d, J=8.8 Hz), 7.69 (2H, d, J=8.2 Hz), 7.81 (1H, s), 7.83 (1H, d, J=8.8 Hz), 8.08 (1H, s), 8.34 (1H, s). IR (KBr): 3353, 1628, 1524, 1507, 1437, 1345, 1310, 1285, 1159 cm$^{-1}$.

Working Example 205

1-[4-(1-Imidazolyl)benzoyl]-4-[7-(2,2,2-trichloroethoxycarbonylamino)naphthalene-2-sulfonyl]piperazine The title compound (520 mg) was obtained, as colorless crystals, using 1-[4-(1-imidazolyl)benzoyl]piperazine dihydrochloride (329 mg) and 7-(2,2,2-trichloroethoxycarbonylamino)naphthalene-2-sulfonylchloride (417 mg), according to a similar method described in Working Example 145.

$^1$H-NMR (CDCl$_3$) δ: 3.12 (4H, brs), 3.70 (4H, brs), 4.89 (2H, s), 7.24 (1H, s), 7.25–7.32 (2H, m), 7.40 (2H, d, J=9.0 Hz), 7.46 (2H, d, J=9.0 Hz), 7.61 (1H, dd, J=2.2, 8.8 Hz), 7.67 (1H, dd, J=1.8, 8.8 Hz), 7.89 (1H, s), 7.93 (1H, d, J=8.8 Hz), 7.96 (1H, d, J=8.8 Hz), 8.24 (1H, s), 8.27 (1H, s). IR (KBr): 3223, 1748, 1611, 1507, 1283, 1206, 1167, 1103 cm$^{-1}$.

Working Example 206

1-(7-Aminonaphthalene-2-sulfonyl)-4-[4-(1-imidazolyl)benzoyl]piperazine

To a solution of 1-[4-(1-imidazolyl)benzoyl]-4-[7-(2,2,2-trichloroethoxycarbonylamino)naphthalene-2-sulfonyl] piperazine (475 mg) in acetic acid (5 ml) was added zinc powder (1 g), and the mixture was stirred at room temperature for 1 day. The reaction solution was filtered, and the filtrate was concentrated. The residue was dissolved in 0.5 N hydrochloric acid, washed with ethyl acetate and made alkaline with 1 N sodium hydroxide aqueous solution. The precipitate was collected by filtration, and the filtrate was washed with water and dried to give a colorless solid of the title compound (325 mg).

$^1$H-NMR (DMSO-d$_6$) δ: 3.02 (4H, m), 3.59 (4H, br), 5.73 (2H, s), 6.99 (1H, s), 7.12 (1H, s), 7.14 (1H, d, J=8.2 Hz), 7.29 (1H, d, J=8.2 Hz), 7.47 (2H, d, J=8.0 Hz), 7.64–7.80 (4H, m), 7.85 (1H, d, J=8.6 Hz), 7.93 (1H, s), 8.30 (1H, s). IR (KBr): 3351, 1632, 1510, 1460, 1437, 1342, 1163 cm$^{-1}$.

Working Example 207

1-[4-(1-Imidazolyl)benzoyl]-4-(p-styrenesulfonyl) piperazine

The title compound (234 mg) was obtained, as colorless solid, using 1-[4-(1-imidazolyl)benzoyl]piperazine dihydrochloride (200 mg) and p-styrenesulfonylchloride (123 mg), according to a similar method described in Working Example 145.

$^1$H-NMR (CDCl$_3$) δ: 3.06 (4H, brs), 3.74 (4H, brs), 5.48 (1H, d, J=10.6 Hz), 5.92 (1H, d, J=17.6 Hz), 6.78 (1H, dd, J=10.6, 17.6 Hz), 7.23 (1H, s), 7.29 (1H, t, J=1.2 Hz), 7.42 (2H, d, J=8.8 Hz), 7.48 (2H, d, J=8.8 Hz), 7.57 (2H, d, J=8.6 Hz), 7.71 (2H, d, J=8.6 Hz), 7.87 (1H, s). IR (KBr): 1632, 1611, 1433, 1348, 1285, 1262, 1165 cm$^{-1}$.

Working Example 208

1-(6-Chloronaphthalene-2-sulfonyl)-4-[4-(guanidinomethyl)benzoyl]piperazine hydrochloride The title compound (250 mg) was obtained, as colorless solid, by treating 1-[4-(tert-butoxycarbonylguanidinomethyl)benzoyl]-4-(6-chloronaphthalene-2-sulfonyl)piperazine (300 mg) with hydrochloric acid according to a similar method described in Working Example 76.

$^1$H-NMR (DMSO-d$_6$) δ: 3.06 (4H, brs), 3.57 (4H, brs), 4.40 (2H, d, J=6.2 Hz), 7.33 (4H, s), 7.72 (1H, dd, J=1.8, 8.8 Hz), 7.82 (1H, dd, J=1.4, 8.8 Hz), 8.18 (1H, d, J=8.8 Hz), 8.23–8.31 (2H, m), 8.49 (1H, s). IR (KBr): 3150, 1689, 1613, 1441, 1344, 1283, 1265, 1163 cm$^{-1}$.

Working Example 209

1-(6-Fluoronaphthalene-2-sulfonyl)-4-[4-(1-imidazolyl)benzoyl]piperazine

The title compound (176 mg) was obtained, as colorless crystals, using 1-[4-(1-imidazolyl)benzoyl]piperazine dihydrochloride (200 mg) and 6-fluoronaphthalene-2-sulfonylchloride (150 mg), according to a similar method described in Working Example 145.

¹H-NMR (CDCl₃) δ: 3.13 (4H, brs), 3.74 (4H,brs), 7.23 (1H, t, J=1.2 Hz), 7.28 (1H, t, J=1.2 Hz), 7.40 (2H, d, J=8.8 Hz), 7.45 (2H, d, J=8.8 Hz), 7.57 (1H, dd, J=2.2, 8.8 Hz), 7.76 (1H, dd, J=1.4, 8.8 Hz), 7.86 (1H, s), 7.92–8.05 (3H, m), 8.33 (1H, s). IR (KBr): 1634, 1611, 1468, 1435, 1346, 1252, 1163 cm⁻¹.

Working Example 210

1-(trans-4-Propioimidoylaminocyclohexane-1-ylcarbonyl)-4-(6-chloronaphthalene-2-sulfonyl)piperazine hydrochloride The title compound (114 mg) was obtained, as colorless solid, using 1-(trans-4-aminocyclohexane-1-ylcarbonyl)-4-(6-chloronaphthalene-2-sulfonyl)piperazine hydrochloride (130 mg) and ethyl propioimidate hydrochloride (379 mg), according to a similar method described in Working Example 99.

¹H-NMR (DMSO-d₆) δ: 1.15 (3H, t, J=7.6 Hz), 1.20–1.50 (4H, m), 1.55–1.70 (2H, m), 1.73–1.87 (2H, m), 2.37 (2H, q, J=7.6 Hz), 2.50 (1H, m), 2.96 (4H, brs), 3.41 (1H, m), 3.57 (4H, m), 7.72 (1H, dd, J=1.8, 8.8 Hz), 7.82 (1H, dd, J=1.8, 8.8 Hz), 8.17 (1H, d, J=8.8 Hz), 8.22–8.32 (2H, m), 8.50 (1H, s), 8.62 (1H, brs), 9.02 (1H, brs), 9.38 (1H, brd, J=7.8 Hz). IR (KBr): 3067, 1676, 1640, 1456, 1346, 1331, 1165 cm⁻¹.

Working Example 211

Methyl 4-(trans-4-acetimidoylaminocyclohexane-1-ylcarbonyl)-1-(6-chloronaphthalene-2-sulfonyl)piperazine-2-acetate hydrochloride The title compound (175 mg) was obtained, as colorless solid, by treating methyl 4-(trans- 4-tert-butoxycarbonylaminocyclohexane-1-ylcarbonyl)-1-(6-chloronaphthalene-2-sulfonyl)piperazine-2-acetate hydrochloride (240 mg) with hydrochloric acid according to a similar method described in Working Example 76 to give methyl 4-(trans-4-aminocyclohexane-1-ylcarbonyl)-1-(6-chloronaphthalene-2-sulfonyl)piperazine-2-acetate hydrochloride, which was reacted with ethyl acetimidate hydrochloride (488 mg) according to a similar method described in Working Example 99.

¹H-NMR (CDCl₃) δ: 1.00–4.60 (25H, m), 7.56 (1H, m), 7.70–8.00 (4H, m), 8.40 (1H, s), 8.73 (1H, br), 9.06 (1H, br), 9.65 (1H, br). IR (KBr): 3063, 1732, 1682, 1634, 1454, 1435, 1329, 1159 cm⁻¹.

Working Example 212

1-(trans-4-Acetimidoylaminocyclohexane-1-ylcarbonyl)-4-(6-chloronaphthalene-2-sulfonyl)piperazine-2-carboxylic acid hydrochloride The title compound (71 mg) was obtained, as colorless solid, using 1-(trans-4-aminocyclohexane-1-ylcarbonyl)-4-(6-chloronaphthalene-2-sulfonyl)piperazine-2-carboxylic acid hydrochloride (140 mg) and ethyl acetimidate hydrochloride (335 mg) according to a similar method described in Working Example 99.

¹H-NMR (DMSO-d₆) δ: 1.10–4.40 (16H, m), 2.11 (3H, s), 4.98–5.10 (1H, m), 7.65–7.82 (2H, m), 7.95 (1H, brs), 8.10–8.33 (3H, m), 8.52 (1H, s), 9.03 (1H, brs), 9.34 (1H, brs). IR (KBr): 3065(br), 1732, 1680, 1630, 1439, 1346, 1163 cm⁻¹.

Working Example 213

1-(trans-4-Acetylaminocyclohexane-1-ylcarbonyl)-4-(6-chloronaphthalene-2-sulfonyl)piperazine To a solution of 1-(trans-4-aminocyclohexane-1-ylcarbonyl)-4-(6-chloronaphthalene-2-sulfonyl)piperazine hydrochloride (50 mg) and triethylamine (30 mg) in dichloromethane (10 ml) was added acetic anhydride (50 mg), and the mixture was stirred at room temperature for 3 hours. The reaction solution was concentrated, and the residue was purified with silica gel column chromatography (ethyl acetate) to give colorless crystals of the title compound (41 mg).

¹H-NMR (CDCl₃) δ: 1.00–1.20 (2H, m), 1.45–1.75 (4H, m), 1.94 (3H, s), 1.95–2.10 (2H, m), 2.29 (1H, m), 3.08 (4H, m), 3.50–3.80 (5H, m), 5.20 (1H, d ,J=7.2 Hz), 7.59 (1H, dd, J=1.8, 8.8 Hz), 7.75 (1H, dd, J=1.8, 8.8 Hz), 7.86–7.97 (3H, m), 8.31 (1H, s). IR (KBr): 3264, 1634, 1454, 1346, 1163, 729 cm⁻¹.

Working Example 214

1-(trans-4-Methoxycarbonylacetimidoylaminocyclohexane-1-ylcarbonyl)-4-(6-chloronaphthalene-2-sulfonyl)piperazine To a solution of 1-(trans-4-acetimidoylaminocyclohexane-1-ylcarbonyl)-4-(6-chloronaphthalene-2-sulfonyl)piperazine (300 mg) and triethylamine (199 mg) in dichloromethane (30 ml) was added methyl chlorocarbonate (192 mg), and the mixture was stirred at room temperature for 30 minutes. The reaction solution was concentrated, and the residue was purified with silica gel column chromatography (ethyl acetate) to give colorless crystals of the title compound (171 mg).

¹H-NMR (CDCl₃) δ: 1.15 (2H, m), 1.45–1.75 (4H, m), 1.95–2.10 (2H, m), 2.11 (3H, s), 2.36 (1H, m), 3.09 (4H, m), 3.38 (1H, m), 3.65 (4H, m), 3.67 (3H, s), 7.59 (1H, dd, J=1.8, 8.8 Hz), 7.76 (1H, dd, J=1.8, 8.8 Hz), 7.86–7.97 (3H, m), 8.31 (1H, s), 9.90 (1H, br). IR (KBr): 1652, 1630, 1599, 1447, 1346, 1260, 1165, 1080, 731 cm⁻¹.

Working Example 215

1-(cis-4-tert-butoxycarbonylaminocyclohexane-1-ylcarbonyl)-4-(6-chloronaphthalene-2-sulfonyl)piperazine The title compound (313 mg) was obtained, as colorless crystals, using 1-(6-chloronaphthalene-2-sulfonyl)piperazine hydrochloride (200 mg) and cis-4-tert-butoxycarbonylaminocyclohexane- 1-ylcarboxylic acid (141 mg), according to a similar method described in Working Example 46.

¹H-NMR (CDCl₃) δ: 1.20–1.38 (2H, m), 1.41 (9H, s), 1.42–1.87 (6H, m), 2.43 (1H, m), 3.07 (4H, t, J=5.4 Hz), 3.50–3.80 (5H, m), 4.70 (1H, m), 7.59 (1H, dd, J=2.0, 8.8 Hz), 7.75 (1H, dd, J=1.8, 8.8 Hz), 7.87–7.97 (3H, m), 8.30 (1H, s). IR (KBr): 3324, 1703, 1644, 1456, 1364, 1346, 1331, 1165 cm¹.

Working Example 216

1-(cis-4-Aminocyclohexane-1-ylcarbonyl)-4-(6-chloronaphthalene-2-sulfonyl)piperazine hydrochloride The title compound (270 mg) was obtained, as colorless solid, by treating 1-(cis-4-tert-butoxycarbonylaminocyclohexane-1-ylcarbonyl)-4-(6-chloronaphthalene-2-sulfonyl)piperazine (293 mg) with hydrochloric acid according to a similar method described in Working Example 76.

¹H-NMR (DMSO-d₆) δ: 1.30–1.75 (8H, m), 2.66 (1H, m), 2.96 (4H, m), 3.17 (1H, m), 3.55 (4H, m), 7.72 (1H, dd,

J=2.0, 8.8 Hz), 7.81 (1H, d, J=8.8 Hz), 7.83 (3H, brs), 8.12–8.30 (3H, m), 8.50 (1H, s). IR (KBr): 2944, 1622, 1454, 1345, 1331, 1163 cm$^{-1}$.

Working Example 217

1-(cis-4-Acetimidoylaminocyclohexane-1-ylcarbonyl)-4-(6-chloronaphthalene-2-sulfonyl) piperazine hydrochloride The title compound (95 mg) was obtained, as colorless solid, using 1-(cis-4-aminocyclohexane-1-ylcarbonyl)-4-(6-chloronaphthalene-2-sulfonyl)piperazine hydrochloride (120 mg) and ethyl acetimidate hydrochloride (314 mg) according to a similar method described in Working Example 99.

$^1$H-NMR (DMSO-d$_6$) δ: 1.30–1.75 (8H, m), 2.13 (3H, s), 2.64 (1H, m), 2.96 (4H, m), 3.56 (4H, m), 3.66 (1H, m), 7.72 (1H, d, J=8.8 Hz), 7.81 (1H, d, J=8.8 Hz), 8.12–8.30 (3H, m), 8.50 (1H, s), 8.57 (1H, brs), 9.05–9.20 (2H, m). IR (KBr): 3056, 1684, 1624, 1453, 1346, 1331, 1163 cm$^{-1}$.

Working Example 218

1-[trans-4-(1-Acetoxyethoxycarbonylacetimidoylamino) cyclohexane-1-ylcarbonyl]-4-(6-chloronaphthalene-2-sulfonyl)piperazine A solution of 1-(trans-4-acetimidoylaminocyclohexane-1-ylcarbonyl)-4-(6-chloronaphthalene-2-sulfonyl)piperazine hydrochloride (100 mg), 0-(1-acetoxyethoxycarbonyl)-4-nitrophenol (63 mg) and diisopropylethylamine (72 mg) in DMF (4 ml) was stirred at 50t for 15 hours. The reaction solution was concentrated, and the residue was dissolved in ethyl acetate, washed with water, sodium hydrogen carbonate aqueous solution and brine, dried and concentrated. The residue was purified with silica gel column chromatography (ethyl acetate) to give a colorless solid of the title compound (89 mg).

$^1$H-NMR (CDCl$_3$) δ: 1.30 (2H, m), 1.49 (3H, d, J=5.6 Hz), 1.45–1.80 (4H, m), 1.99 (2H, m), 2.05 (3H, s), 2.12 (3H, s), 2.35 (1H, m), 3.09 (4H, m), 3.39 (1H, m), 3.59 (2H, m), 3.72 (2H, m), 6.84 (1H, q, J=5.6 Hz), 7.60 (1H, dd, J=2.0, 8.8 Hz), 7.76 (1H, dd, J=1.8, 8.8 Hz), 7.87–7.97 (3H, m), 8.31 (1H, s), 9.88 (1H, br). IR (KBr): 3300, 1748, 1686, 1647, 1597, 1559, 1452, 1346, 1258, 1165, 1115, 1080 cm$^{-1}$.

Working Example 219

1-[trans-4-(2-Acetoxy-1,1-dimethylethoxycarbonylacetimidoylamino) cyclohexane-1-ylcarbonyl]-4-(6-chloro-naphthalene-2-sulfonyl)piperazine The title compound (60 mg) was obtained, as colorless solid, reacting 1-(trans-4-acetimidoylaminocyclohexane-1-ylcarbonyl)-4-(6-chloronaphthalene-2-sulfonyl)piperazine hydrochloride (100 mg) with 0-(2-acetoxy-1,1-dimethylethoxycarbonyl)-4-nitrophenol (70 mg) according to a similar method described in Working Example 218.

$^1$H-NMR (CDCl$_3$) δ: 1.20–1.80 (6H, m), 1.48 (6H, s), 2.00 (2H, m), 2.07 (3H, s), 2.10 (3H, s), 2.36 (1H, m), 3.09 (4H, m), 3.37 (1H, m), 3.59 (2H, m), 3.71 (2H, m), 4.29 (2H, s), 7.60 (1H, dd, J=1.8, 8.8 Hz), 7.76 (1H, dd, J=1.8, 8.8 Hz), 7.87–7.96 (3H, m), 8.31 (1H, s), 9.78 (1H, br). IR (KBr): 3300, 1736, 1638, 1599, 1555, 1453, 1346, 1258, 1163 cm$^{-1}$.

Working Example 220

Methyl 1-(trans-4-aminocyclohexane-1-ylcarbonyl)-4-(6-chloronaphthalene-2-sulfonyl)piperazine-2-acetate hydrochloride The title compound (87 mg) was obtained, as colorless solid, by treating methyl 1-(trans-4-tert-butoxycarbonylaminocyclohexane-1-ylcarbonyl)-4-(6-chloronaphthalene-2-sulfonyl)piperazine-2-acetate (140 mg) with hydrochloric acid according to a similar method described in Working Example 76.

$^1$H-NMR (DMSO-d$_6$) δ: 1.14–1.40 (4H, m), 1.59 (2H, m), 1.89 (2H, m), 2.15–5.00 (14H, m), 7.65–7.93 (5H, m), 8.16 (1H, d, J=8.8 Hz), 8.20–8.30 (2H, m), 8.49 (1H, s). IR (KBr): 2946, 1730, 1624, 1439, 1339, 1165 cm$^{-1}$.

Working Example 221

Methyl 1-(trans-4-acetimidoylaminocyclohexane-1-ylcarbonyl)-4-(6-chloronaphthalene-2-sulfonyl) piperazine-2-acetate hydrochloride The title compound (57 mg) was obtained, as colorless solid, using methyl 1-(trans-4-aminocyclohexane-1-ylcarbonyl)-4-(6-chloronaphthalene-2-sulfonyl)piperazine-2-acetate hydrochloride (75 mg) and ethyl acetoimidate hydrochloride (335 mg) according to a similar method described in Working Example 99.

$^1$H-NMR (DMSO-d$_6$) δ: 1.10–1.90 (8H, m), 2.11 (3H, s), 2.20–2.50 (3H, m), 2.70–2.90 (2H, m), 3.20–5.00 (6H, m), 3.55 (2/3×3H, s), 3.61 (1/3×3H, s), 7.72 (1H, dd, J=1.8, 8.8 Hz), 7.80 (1H,d, J=8.8 Hz), 8.16 (1H, d, J=8.8 Hz), 8.20–8.33 (2H, m), 8.50 (1H, s), 8.57 (1H, s), 9.05 (1H, s), 9.38 (1H, brd, J=7.8 Hz). IR (KBr): 3059, 1732, 1686, 1640, 1439, 1389, 1267, 1165 cm$^{-1}$.

Working Example 222

1-(6-Chloronaphthalene-2-sulfonyl)-4-(cis- 4-guanidino-cyclohexane-1-ylcarbonyl)piperazine hydrochloride A solution of 1-(cis-4-aminocyclohexane-1-ylcarbonyl)-4-(6-chloronaphthalene-2-sulfonyl)piperazine hydrochloride (100 mg), 1-amidinopyrazole hydrochloride (47 mg) and triethylamine (100 mg) in methanol (10 ml)was stirred at room temperature for 1 day. The reaction solution was concentrated, and to the residue was added dichloromethane. The mixture was washed with 1 N sodium hydroxide aqueous solution, dried and concentrated. The residue was dissolved in ethyl acetate and transformed into hydrochloride with hydrochloric acid to give a colorless solid of the title compound (88 mg).

$^1$H-NMR (DMSO-d$_6$) δ: 1.20–1.70 (8H, m), 2.60 (1H, m), 2.96 (4H, m), 3.40–3.70 (5H, m), 7.00 (4H, br), 7.49 (1H, m), 7.72 (1H, dd, J=1.4, 8.8 Hz), 7.80 (1H, d, J=8.6 Hz), 8.16 (1H, d, J=8.8 Hz), 8.20–8.32 (2H, m), 8.50 (1H, s). IR (KBr): 3160, 1644, 1624, 1454, 1345, 1331, 1163 cm$^{-1}$.

Working Example 223

1-(trans-4-tert-Butoxycarbonylmethylaminocyclohexane-1-ylcarbonyl)-4-(6-chloronaphthalene-2-sulfonyl) piperazine To a solution of 1-(trans-4-tert-butoxycarbonylaminocyclohexane-1-ylcarbonyl)-4-(6-chloronaphthalene-2-sulfonyl)piperazine (500 mg) in N,N-dimethylformamide (20 ml) was added 60% sodium hydride in oil (55 mg), and the mixture was stirred for 10 minutes. To the mixture was added methyl iodide (1 ml), and the mixture was stirred at room temperature for 15 hours. The reaction solution was concentrated, and the residue was purified with silica gel column chromatography (ethyl acetate) to give a colorless solid of the title compound (560 mg).

¹H-NMR (CDCl₃) δ: 1.20–1.80 (8H, m), 1.43 (9H, s), 2.27 (1H, m), 2.70 (3H, s), 3.07 (4H, m), 3.59 (2H, m), 3.70 (2H, m), 3.78 (1H, m), 7.59 (1H, dd, J=1.8, 8.8 Hz), 7.75 (1H, dd, J=1.8, 8.8 Hz), 7.87–7.97 (3H, m), 8.30 (1H, s). IR (KBr): 1682, 1651, 1454, 1366, 1346, 1325, 1165 cm⁻¹.

Working Example 224

1-(6-Chloronaphthalene-2-sulfonyl)-4-(trans-4-methylaminocyclohexane-1-ylcarbonyl)-piperazine hydrochloride The title compound (411 mg) was obtained, as colorless solid, by treating 1-(trans-4-tert-butoxycarbonylmethylaminocyclohexane-1-ylcarbonyl)-4-(6-chloronaphthalene-2-sulfonyl)piperazine (535 mg) with hydrochloric acid according to a similar method described in Working Example 76.

¹H-NMR (DMSO-d₆) δ: 1.29 (4H, m), 1.65 (2H, m), 1.99 (2H, m), 2.40–2.50 (4H, m), 2.85 (1H, m), 2.96 (4H, m), 3.56 (4H, m), 7.73 (1H, dd, J=2.0, 8.8 Hz), 7.78 (1H, dd, J=1.8, 8.8 Hz), 8.17 (1H, d, J=8.8 Hz), 8.22–8.30 (2H, m), 8.51 (1H, s), 8.79 (2H, brs). IR (KBr): 2948, 2728, 1624, 1458, 1346, 1155 cm⁻¹.

Working Example 225

1-(trans-4-Acetimidoylmethylaminocyclohexane-1-ylcarbonyl)-4-(6-chloronaphthalene-2-sulfonyl) piperazine hydrochloride The title compound (89 mg) was obtained, as colorless solid, using 1-(6-chloronaphthalene-2-sulfonyl)-4-(trans-4-methylaminocyclohexane-1-ylcarbonyl)piperazine hydrochloride (100 mg) and ethyl acetimidate hydrochloride (254 mg) according to a similar method described in Working Example 99.

¹H-NMR (DMSO-d₆) δ: 1.20–1.75 (8H, m), 2.23 (2/3×3H, s), 2.30 (1/3×3H, s), 2.50 (1H, m), 2.84 (2/3×3H, s), 2.92 (1/3×3H, s), 2.96 (4H, m), 3.56 (4H, m), 3.70 (1H, m), 7.72 (1H, dd, J=1.8, 8.8 Hz), 7.81 (1H, d, J=8.8 Hz), 8.12–8.30 (3H, m), 8.50 (1H, s). IR (KBr): 3079, 1620, 1454, 1344, 1331, 1163 cm⁻¹.

Working Example 226

1-(4-Aminobenzoyl)-4-(6-chloronaphthalene-2-sulfonyl)piperazine

The title compound (285 mg) was obtained, as colorless crystals, using 1-(6-chloronaphthalene-2-sulfonyl) piperazine hydrochloride (250 mg) and 4-aminobenzoic acid (105 mg), according to a similar method described in Working Example 46.

¹H-NMR (CDCl₃) δ: 3.08 (4H, m), 3.73 (4H, m), 3.88 (2H, s), 6.59 (2H, d, J=8.6 Hz), 7.15 (2H, d, J=8.6 Hz), 7.59 (1H, dd, J=1.8, 8.8 Hz), 7.75 (1H, dd, J=1.8, 8.8 Hz), 7.88–7.96 (3H, m), 8.30 (1H, s). IR (KBr): 3351, 3223, 1624, 1605, 1345, 1329, 1285, 1262, 1165 cm⁻¹.

Working Example 227

1-(6-Chloronaphthalene-2-sulfonyl)-4-(trans-4-thioureidocyclohexane-1-ylcarbonyl)piperazine To a suspension of 1-(trans-4-aminocyclohexane-1-ylcarbonyl)-4-(6-chloronaphthalene-2-sulfonyl)piperazine (200 mg) in dichloromethane (10 ml) was added triethylamine (107 mg), and further added benzoylisothiocyanate (83 mg), and the mixture was stirred at room temperature for 15 minutes. The reaction solution was concentrated, and the residue was purified with silica gel column chromatography (ethyl acetate) to give a colorless solid of 1-(trans-4-benzoylthioureidocyclohexane-1-ylcarbonyl)-4-(6-chloro-3 naphthalene-2-sulfonyl)piperazine (268 mg). The obtained compound was dissolved in tetrahydrofurane (10 ml) and methanol (4 ml). To the solution was added 1 N sodium hydroxide aqueous solution (2 ml), and the mixture was stirred at room temperature for 2 hours . The reaction solution was concentrated, and the residue was made acidic with dilute hydrochloric acid and extracted with ethyl acetate. The extract was concentrated, and the residue was purified with silica gel column chromatography (ethyl acetate) to give a colorless solid of the title compound (155 mg).

1H-NMR (DMSO-d₆) δ: 1.00–1.95 (8H, m), 2.40 (1H, m), 2.96 (4H, m), 3.55 (4H, m), 3.75 (1H, m), 6.77 (1H, brs), 7.48 (2H, brs), 7.72 (1H, dd, J=2.2, 8.8 Hz), 7.80 (1H, dd, J=1.8, 8.8 Hz), 8.16 (1H, d, J=8.8 Hz), 8.20–8.33 (2H, m), 8.49 (1H, s). IR (KBr): 3291, 3169, 1636, 1605, 1439, 1346, 1165 cm⁻¹.

Working Example 228

1-(6-Chloronaphthalene-2-sulfonyl)-4-[trans-4-(2-imidazolylamino)cyclohexane-1-ylcarbonyl] piperazine hydrochloride To a solution of 1-(6-chloronaphthalene-2-sulfonyl)-4-(trans-4-thioureidocyclohexane-1-ylcarbonyl)piperazine (145 mg) in methanol (20 ml) was added methyl iodide (1.5 ml), and the mixture was stirred at room temperature overnight. The reaction solution was concentrated, and to the residue was added ethanol (20 ml). To the solution was added 2,2-dimethoxyethylamine (89 mg), and the mixture was heated for 15 hours under reflux. The reaction solution was concentrated, and to the residue was added concentrated hydrochloric acid (20 ml), which was stirred at 45° C. for 30 minutes. The reaction solution was concentrated, and the residue was dissolved in dichloromethane (20 ml). To the solution were added triethylamine (2 ml) and di-tert-butyl dicarbonate(2 ml), and the mixture was stirred at room temperature for 30 minutes. The reaction solution was concentrated, and the residue was purified with silica gel column chromatography (ethyl acetate) to give a colorless solid of 1-(6-chloro-naphthalene-2-sulfonyl)-4-[trans-4-(1-tert-butoxy-carbonyl-2-imidazolylamino)cyclohexane-1-ylcarbonyl]-piperazine (78 mg).

¹H-NMR (CDCl₃) δ: 1.10–1.30 (2H, m), 1.57 (9H, s), 1.60–1.75 (4H, m), 2.17–2.40 (3H, m), 3.08 (4H, m), 3.50–3.80 (5H, m), 6.38 (1H, brd, J=7.6 Hz), 6.52 (1H, d, J=2.0 Hz), 6.76 (1H, d, J=2.0 Hz), 7.59 (1H, dd, J=1.8, 8.8 Hz), 7.75 (1H, dd, J=1.8, 8.8 Hz), 7.87–7.96 (3H, m), 8.30 (1H, s).

The title compound (42 mg) was obtained, as colorless solid, by treating 1-(6-chloronaphthalene-2-sulfonyl)-4-[trans-4-(1-tert-butoxycarbonyl-2-imidazolylamino) cyclohexane-1-ylcarbonyl]piperazine (78 mg) with hydrochloric acid according to a similar method described in Working Example 7.

¹H-NMR (DMSO-d₆) δ: 1.10–1.50 (4H, m), 1.57 (2H, m), 1.85 (2H, m), 2.49 (1H, m), 2.96 (4H, m), 3.34 (1H, m), 3.56 (4H, m), 6.91 (2H, s), 7.71 (1H, dd, J=1.8, 8.8 Hz), 7.80 (1H, d, J=8.8 Hz), 7.95 (1H, d, J=8.0 Hz), 8.16 (1H, d, J=8.8 Hz), 8.20–8.32 (2H, m), 8.49 (1H, s), 11.88 (2H, brs). IR (KBr): 3121, 2938, 1671, 1628, 1346, 1169 cm⁻¹.

Working Example 229

1-(6-Chloronaphthalene-2-sulfonyl)-4-[trans-4-(2-imidazolinylamino)cyclohexane-1-ylcarbonyl]piperazine hydrochloride To a solution of 1-(trans-4-aminocyclohexane-1-ylcarbonyl)-4-(6-chloronaphthalene-2-sulfonyl)piperazine hydrochloride (100 mg) and triethylamine (120 mg) in ethanol (10 ml) was added 2-methylthioimidazoline (116 mg), and the mixture was heated for 48 hours under reflux. The reaction solution was concentrated, and the residue was purified with silica gel column chromatography (dichloromethane/methanol containing 10% ammonia=10/1) and transformed into hydrochloride with 4 N hydrochloric acid in ethyl acetate to give a colorless solid of the title compound (30 mg).

$^1$H-NMR (DMSO-d$_6$) δ: 1.10–1.40 (4H, m), 1.55 (2H, m), 1.82 (2H, m), 2.48 (1H, m), 2.95 (4H, m), 3.23 (1H, m), 3.55 (8H, m), 7.72 (1H, d, J=8.8 Hz), 7.80 (1H, d, J=8.8 Hz), 8.16 (1H, d, J=8.8 Hz), 8.20–8.32 (2H, m), 8.50 (1H, s). IR (KBr): 3121, 3032, 2944, 1672, 1628, 1346, 1167 cm$^{-1}$.

Working Example 230

1-(6-Chloronaphthalene-2-sulfonyl)-4-[trans-4-(1,2,4-triazol-4-yl)cyclohexane-1-ylcarbonyl]piperazine A solution of 1-(trans-4-aminocyclohexane-1-ylcarbonyl)-4-(6-chloronaphthalene-2-sulfonyl)piperazine hydrochloride (200 mg) and N,N-dimethylformamide azine dihydrochloride (120 mg) in pyridine (10 ml) was heated for 48 hours under reflux. The reaction solution was concentrated, and the residue was purified with silica gel column chromatography (dichloromethane/methanol containing 10% ammonia=10/1) to give a colorless solid of the title compound (120 mg).

$^1$H-NMR (CDCl$_3$) δ: 1.60–1.95 (6H, m), 2.24 (2H, m), 2.49 (1H, m), 3.10 (4H, m), 3.63 (2H, m), 3.73 (2H, m), 4.07 (1H, m), 7.60 (1H, dd, J=1.8, 8.8 Hz), 7.75 (1H, dd, J=1.8, 8.8 Hz), 7.88–7.97 (3H, m), 8.18 (2H, s), 8.31 (1H, s). IR (KBr): 1634, 1454, 1345, 1331, 1163 cm$^1$.

Working Example 231

1-(7-Chloro-2H-benzopyran-3-sulfonyl)-4-[4-methyl-2-(4-pyridyl)-5-thiazolecarbonyl]piperazine The title compound (110 mg) was obtained, as colorless crystals, using 1-(7-chloro-2H-benzopyran-3-sulfonyl)piperazine hydrochloride (100 mg) and 4-methyl-2-(4-pyridyl)-5-thiazolecarboxylic acid (63 mg), according to a similar method described in Working Example 46.

$^1$H-NMR (CDCl$_3$) δ: 2.52 (3H, s), 3.32 (4H, m), 3.78 (4H, m), 4.88 (2H, d, J=0.6 Hz), 6.94 (1H, d, J=1.8 Hz), 7.00 (1H, dd, J=1.8, 8.0 Hz), 7.13 (1H, d, J=8.0 Hz), 7.25 (1H, s), 7.76 (2H, d, J=6.0 Hz), 8.73 (2H, d, J=6.0 Hz). IR (KBr): 1634, 1599, 1424, 1348, 1327, 1256, 1157 cm$^{-1}$.

Working Example 232

1-(6-Chloro-2H-benzopyran-3-sulfonyl)-4-[4-methyl-2-(4-pyridyl)-5-thiazolecarbonyl]piperazine The title compound (121 mg) was obtained, as colorless crystals, using 1-(6-chloro-2H-benzopyran-3-sulfonyl)piperazine hydrochloride (100 mg) and 4-methyl-2-(4-pyridyl)-5-thiazolecarboxylic acid (63 mg), according to a similar method described in Working Example 46.

$^1$H-NMR (CDCl$_3$) δ: 2.52 (3H, s), 3.33 (4H, m), 3.78 (4H, m), 4.88 (2H, d, J=1.0 Hz), 6.86 (1H, d, J=8.8 Hz), 7.16–7.30 (3H, m), 7.76 (2H, d, J=6.2 Hz), 8.73 (2H, d, J=6.2 Hz). IR (KBr): 1626, 1480, 1429, 1346, 1157 cm$^{-1}$.

Working Example 233

1-(5-Chloro-2H-benzopyran-3-sulfonyl)-4-[4-methyl-2-(4-pyridyl)-5-thiazolecarbonyl]piperazine The title compound (118 mg) was obtained, as colorless crystals, using 1-(5-chloro-2H-benzopyran-3-sulfonyl)piperazine hydrochloride (100 mg) and 4-methyl-2-(4-pyridyl)-5-thiazolecarboxylic acid (63 mg), according to a similar method described in Working Example 46.

$^1$H-NMR (CDCl$_3$) δ: 2.52 (3H, s), 3.34 (4H, m), 3.79 (4H, m), 4.86 (2H, d, J=1.0 Hz), 6.84 (1H, dt, J=1.0, 8.2 Hz), 7.06 (1H, dd, J=1.0, 8.2 Hz), 7.24 (1H, t, J=8.2 Hz), 7.60 (1H, d, J=1.0 Hz), 7.76 (2H,d, J=6.0 Hz), 8.73 (2H, d, J=6.0 Hz). IR (KBr): 1636, 1597, 1449, 1429, 1348, 1325, 1159 cm$^{-1}$.

Working Example 234

1-(4-Chlorobenzoylmethanesulfonyl)-4-[4-methyl-2-(4-pyridyl)-5-thiazolecarbonyl]piperazine The title compound (126 mg) was obtained, as colorless crystals, using 1-(4-chlorobenzoylmethanesulfonyl)piperazine hydrochloride (100 mg) and 4-methyl-2-(4-pyridyl)-5-thiazolecarboxylic acid (65 mg), according to a similar method described in Working Example 46.

$^1$H-NMR (CDCl$_3$) δ: 2.54 (3H, s), 3.43 (4H, m), 3.73 (4H, m), 4.58 (2H, s), 7.51 (2H, d, J=8.6 Hz), 7.78 (2H, d, J=6.0 Hz), 7.97 (2H, d, J=8.6 Hz), 8.73 (2H, d, J=6.0 Hz). IR (KBr): 1684, 1632, 1591, 1429, 1348, 1279, 1163 cm$^{-1}$.

Working Example 235

1-[4-(2-Aminoimidazol-1-yl)benzoyl]-4-(6-chloronaphthalene-2-sulfonyl)piperazine hydrochloride The title compound (138 mg) was obtained, as colorless crystals, by subjecting 1-(6-chloronaphthalene-2-sulfonyl)piperazine hydrochloride (347 mg) to condensation with a 1:3 mixture (228 mg) of 4-(2-aminoimidazol-1-yl)benzoic acid and 4-(1-tert-butoxycarbonyl-2-imidazolylamino)benzoic acid according to a similar method described in Working Example 46, followed by column separation and transformation into hydrochloride with hydrochloric acid in ethyl acetate.

$^1$H-NMR (DMSO-d$_6$) δ: 3.08 (4H, brs), 3.81 (4H, m), 7.12 (1H, d, J=2.0 Hz), 7.20 (1H, d, J=2.0 Hz), 7.54 (4H, s), 7.70–7.87 (4H, m), 8.18 (1H, d, J=8.6 Hz), 8.24–8.34 (2H, m), 8.51 (1H, s), 12.42 (1H, s). IR (KBr): 3077, 1655, 1630, 1611, 1439, 1346, 1331, 1283, 1165 cm$^{-1}$.

Working Example 236

1-(6-Chloronaphthalene-2-sulfonyl)-4-[4-(2-imidazolylamino)benzoyl]piperazine hydrochloride The title compound (49 mg) was obtained, as colorless crystals, by subjecting 1-(6-chloronaphthalene-2-sulfonyl)piperazine hydrochloride (347 mg) to condensation with a 1:3 mixture (228 mg) of 4-(2-aminoimidazol-1-yl)benzoic acid and 4-(1-tert-butoxycarbonyl-2-imidazolylamino)benzoic acid according to a similar method described in Working Example 46, followed by column separation and transformation into hydrochloride with hydrochloric acid in ethyl acetate.

$^1$H-NMR (DMSO-d$_6$) δ: 3.06 (4H, brs), 3.59 (4H, brs), 7.18 (2H, s), 7.20 (2H, d, J=8.8 Hz), 7.35 (2H, d, J=8.8 Hz), 7.73 (1H, dd, J=2.0, 8.8 Hz), 7.82 (1H, dd, J=1.8, 8.8 Hz), 8.18 (1H, d, J=8.8 Hz), 8.23–8.33 (2H, m), 8.50 (1H, s), 10.60 (1H, s). IR (KBr): 2909, 1642, 1609, 1346, 1159 cm$^{-1}$.

Working Example 237

1-[2-(4-Chlorophenyl)ethynesulfonyl)-4-[4-methyl-2-(4-pyridyl)-5-thiazolecarbonyl]piperazine A solution of 4-methyl-2-(4-pyridyl)-5-thiazolecarboxylic acid (72 mg) in thionyl chloride (3 ml) was heated for 1 hour under reflux. The reaction solution was concentrated, and the residue was dissolved in dichloromethane (10 ml). To the solution was added 1-[2-(4-chlorophenyl)ethynesulfonyl)piperazine hydrochloride (100 mg) and added dropwise triethylamine (90 mg), and the mixture was stirred at room temperature for 15 minutes. The reaction solution was concentrated, and the residue was purified with silica gel column chromatography (ethyl acetate) to give colorless crystals of the title compound (130 mg).

$^1$H-NMR (CDCl$_3$) δ: 2.53 (3H, s), 3.33 (4H, m), 3.86 (4H, m), 7.43 (2H, d, J=8.8 Hz), 7.54 (2H, d, J=8.8 Hz), 7.77 (2H, d, J=6.0 Hz), 8.73 (2H, d, J=6.0 Hz). IR (KBr): 2182, 1632, 1435, 1360, 1169 cm$^{-1}$.

Working Example 238

1-(trans-4-tert-Butoxycarbonylaminocyclohexane-1-ylcarbonyl)-4-(5-chloro-2H-benzopyran-3-sulfonyl) piperazine hydrochloride The title compound (285 mg) was obtained, as colorless crystals, using 1-(5-chloro-2H-benzopyran-3-sulfonyl) piperazine hydrochloride (200 mg) and trans-4-tert-butoxycarbonylaminocyclohexane-1-ylcarboxylic acid (140 mg), according to a similar method described in Working Example 46.

$^1$H-NMR (CDCl$_3$) δ: 1.10 (2H, m), 1.44 (9H, s), 1.55–1.80 (4H, aim), 2.09 (2H, m), 2.37 (1H, m), 3.24 (4H, m), 3.42 (1H, m), 3.60 (2H, m), 3.71 (2H, m), 4.38 (1H, brs), 4.87 (2H, s), 6.92 (1H, d, J=1.8 Hz), 6.98 (1H, dd, J=1.8, 8.0 Hz), 7.12 (1H, d, J=8.0 Hz), 7.22 (1H, s). IR (KBr): 1694, 1634, 1454, 1157 cm$^{-1}$.

Working Example 239

1-(trans-4-Aminocyclohexane-1-ylcarbonyl)-4-(7-chloro-2H-benzopyran-3-sulfonyl)piperazine hydrochloride The title compound (231 mg) was obtained, as colorless solid, by treating 1-(trans-4-tert-butoxycarbonylaminocyclohexane-1-ylcarbonyl)-4-(7-chloro-2H-benzopyran-3-sulfonyl)piperazine (260 mg) with hydrochloric acid according to a similar method described in Working Example 76.

$^1$H-NMR (DMSO-d,) δ: 1.20–1.50 (4H, m), 1.69 (2H, m), 1.94 (2H, m), 2.52 (1H, m), 2.95 (1H, m), 3.12 (4H, m), 3.56 (4H, m), 4.95 (2H, s), 7.05 (1H, s), 7.09 (1H, d, J=8.4 Hz), 7.40 (1H, s), 7.46 (1H, d, J=8.4 Hz), 7.87 (3H, brs). IR (KBr): 3412, 2920, 1647, 1599, 1337, 1146 cm$^{-1}$.

Working Example 240

1-(trans-4-Acetimidoylaminocyclohexane-1-ylcarbonyl)-4-(7-chloro-2H-benzopyran-3-sulfonyl) piperazine hydrochloride The title compound (158 mg) was obtained, as colorless solid, using 1-(trans-4-aminocyclohexane-1-ylcarbonyl)-4-(7-chloro-2H-benzopyran-3-sulfonyl)piperazine hydrochloride (150 mg) and ethyl acetimidate hydrochloride (389 mg) according to a similar method described in Working Example 99.

$^1$H-NMR (DMSO-d$_6$) δ: 1.20–1.95 (8H, m), 2.13 (3H, s), 2.60 (1H, m), 3.13 (4H, brs), 3.57 (4H, brs), 4.10 (1H, m), 4.96 (2H, s), 7.05 (1H, d, J=1.8 Hz), 7.11 (1H, dd, J=1.8, 8.2 Hz), 7.41 (1H, s), 7.47 (1H, d, J=8.2 Hz), 8.59 (1H, brs), 9.07 (1H, brs), 9.41 (1H, m). IR (KBr): 3231, 3077, 1636, 1601, 1439, 1344, 1327, 1150 cm$^{-1}$.

Working Example 241

1-[trans-4-(N$^2$-Methoxycarbonylacetimidoylamino) cyclohexane-1-ylcarbonyl]-4-(7-chloro-2H-benzopyrane-3-sulfonyl)piperazine The title compound (64 mg) was obtained, as colorless solid, using 1-(trans-4-acetimidoylaminocyclohexane-1-ylcarbonyl)-4-(7-chloro-2H-benzopyrane-3-sulfonyl) piperazine hydrochloride (100 mg) and methyl chlorocarbonate (60 mg) according to a similar method described in Working Example 214.

$^1$H-NMR (CDCl$_3$) δ: 1.20–1.50 (2H, m), 1.55–1.90 (4H, m), 2.09 (2H, m), 2.18 (3H, s), 2.43 (1H, m), 3.26 (4H, m), 3.46 (1H, m), 3.61 (2H, m), 3.69 (3H, s), 3.72 (2H, m), 4.87 (2H, s), 6.92 (1H, d, J=1.8 Hz), 6.98 (1H, dd, J=1.8, 8.2 Hz), 7.12 (1H, d, J=8.2 Hz), 7.23 (1H, s). IR (KBr): 3312, 1640, 1601, 1561, 1445, 1260, 1150 cm$^{-1}$.

Working Example 242

1-[trans-4-(N$^2$-Ethoxycarbonylacetimidoylamino) cyclohexane-1-ylcarbonyl]-4-(6-chloronaphthalene-2-sulfonyl)piperazine The title compound (128 mg) was obtained, as colorless solid, using 1-(trans-4-acetimidoylaminocyclohexane-1-ylcarbonyl)-4-(6-chloronaphthalene-2-sulfonyl)piperazine (200 mg) and ethyl chlorocarbonate (68 mg) according to a similar method described in Working Example 214.

$^1$H-NMR (CDCl$_3$) δ: 1.00–1.40 (5H, m), 1.45–1.80 (4H, m), 2.02 (2H, m), 2.13 (3H, s), 2.36 (1H, m), 3.08 (4H, m), 3.38 (1H, m), 3.59 (2H, m), 3.71 (2H, m), 4.09 (2H, q, J=7.0 Hz), 7.5.9 (1H, d, J=8.4 Hz), 7.75 (1H, d, J=8.4 Hz), 7.90–8.00 (3H, m), 8.31 (1H, s), 9.85 (1H, br). IR (KBr): 3300(br), 1638, 1601, 1560, 1453, 1346, 1258, 1202, 1165, 1080 cm$^{-1}$.

Working Example 243

1-[trans-4-(N$^2$-Isopropoxycarbonylacetimidoylamino)cyclohexane-1-ylcarbonyl]-4-(6-chloronaphthalene-2-sulfonyl) piperazine The title compound (126 mg) was obtained, as colorless solid, using 1-(trans-4-acetimidoylaminocyclohexane-1-ylcarbonyl)-4-(6-chloronaphthalene-2-sulfonyl)piperazine (200 mg) and isopropyl chlorocarbonate (77 mg) according to a similar method described in Working Example 214.

$^1$H-NMR (CDCl$_3$) δ: 1.16–1.40 (8H, m), 1.45–1.85 (4H, m), 2.02 (2H, m), 2.11 (3H, s), 2.35 (1H, m), 3.09 (4H, m), 3.37 (1H, m), 3.59 (2H, m), 3.71 (2H, m), 4.84 (1H, m), 7.59 (1H, d, J=8.8 Hz), 7.75 (1H, d, J=8.8 Hz), 7.86–8.00 (3H, m), 8.31 (1H, s), 9.89 (1H, br). IR (KBr): 3274(br), 1649, 1601, 1557, 1441, 1346, 1258, 1165, 1113 cm$^{-1}$.

Working Example 244

1-(trans-4-tert-Butoxycarbonylaminocyclohexane-1-ylcarbonyl)-4-(4-styrenesulfonyl)piperazine The title compound (462 mg) was obtained, as colorless crystals, using 1-(4-styrenesulfonyl)piperazine hydrochloride (300 mg) and trans-4-tert-butoxycarbonylaminocyclohexane-1-ylcarboxylic acid (251 mg), according to a similar method described in Working Example 46.

$^1$H-NMR (CDCl$_3$) δ: 1.09 (2H, m), 1.43 (9H, s), 1.50–1.75 (4H, m), 2.07 (2H, m), 2.30 (1H, m), 3.01 (4H, m), 3.40 (1H, m), 3.57 (2H, m), 3.68 (2H, m), 4.33 (1H, brs), 5.46 (1H, d, J=11.0 Hz), 5.90 (1H, d, J=17.6 Hz), 6.76 (1H, dd, J=11.0, 17.6 Hz), 7.55 (2H, d, J=8.4 Hz), 7.70 (2H, d, J=8.4 Hz). IR (KBr): 1701, 1640, 1350, 1167 cm$^{-1}$.

Working Example 245

1-(trans-4-Aminocyclohexane-1-ylcarbonyl)-4-(4-styrene-sulfonyl)piperazine hydrochloride The title compound (357 mg) was obtained, as colorless solid, by treating 1-(trans-4-tert-butoxycarbonylaminocyclohexane-1-ylcarbonyl)-4-(4-styrenesulfonyl)piperazine (435 mg) with hydrochloric acid according to a similar method described in Working Example 76.

$^1$H-NMR (DMSO-d$_6$) δ: 1.20–1.50 (4H, m), 1.62 (2H, m), 1.91 (2H, :4 m), 2.48 (1H, m), 2.88 (5H, m), 3.55 (4H, m), 5.49 (2H, d, J=11.0 Hz), 6.04 (1H, d, J=18.0 Hz), 6.85 (1H, dd, J=11.0, 18.0 Hz), 7.69 (2H, d, J=8.6 Hz), 7.75 (2H, d, J=8.6 Hz), 7.90 (3H, brs). IR (KBr): 3117, 3036, 1617, 1518, 1431, 1346, 1277, 1165 cm$^{-1}$.

Working Example 246

1-(trans-4-Acetimidoylaminocyclohexane-1-ylcarbonyl)-4-(4-styrenesulfonyl)piperazine The title compound (166 mg) was obtained, as colorless crystals, using 1-(trans-4-aminocyclohexane-1-ylcarbonyl)-4-(4-styrenesulfonyl)piperazine hydrochloride (300 mg) and ethyl acetoimidate hydrochloride (896 mg) according to a similar method described in Working Example 99.

$^1$H-NMR (CDCl$_3$) δ: 1.18 (2H, m), 1.50–1.80 (4H, m), 1.95 (3H, s), 2.07 (2H, m), 2.35 (1H, m), 3.01 (4H, m), 3.46 (1H, m), 3.57 (2H, m), 3.69 (2H, m), 5.47 (1H, d, J=11.0 Hz)l, 5.90 (1H, d, J=17.6 Hz), 6.76 (1H, dd, J=11.0, 17.6 Hz), 7.55 (2H, d, J=8.4 Hz), 7.70 (2H, d, J=8.4 Hz). IR (KBr): 3300, 2940, 1632, 1449, 1433, 1348, 1165 cm$^{-1}$.

Working Example 247

1-(trans-4-Bisethoxycarbonylguanidinocyclohexane-1-ylcarbonyl)-4-(6-chloronaphthalene-2-sulfonyl)piperazine To a solution of 1-(trans-4-aminocyclohexane-1-ylcarbonyl)-4-(6-chloronaphthalene-2-sulfonyl)piperazine hydrochloride (1.0 g) and triethylamine (1.07 g) in ethanol (30 ml) was added N,N'-bis(tert-butoxycarbonyl)-S-methylisothiourea (922 mg), and the mixture was heated for 48 hours under reflux. The reaction solution was concentrated, and the residue was purified with silica gel column chromatography (hexane/ethyl acetate=1/1) to give colorless crystals of the title compound (612 mg).

$^1$H-NMR (CDCl$_3$) δ: 1.22 (2H, m), 1.29 (3H, t, J=6.8 Hz), 1.30 (3H, t, J=6.8 Hz), 1.50–1.75 (4H, m), 2.10 (2H, m), 2.32 (1H, m), 3.07 (4H, m), 3.58 (2H, m), 3.70 (2H, m), 3.98 (1H, m), 4.12 (2H, q, J=6.8 Hz), 4.20 (2H, q, J=6.8 Hz), 7.59 (1H, dd, J=2.2, 8.8 Hz), 7.75 (1H, dd, J=1.8, 8.8 Hz), 7.86–8.00 (3H, m), 8.18 (1H, d, J=7.6 Hz), 8.30 (1H, s), 11.74 (1H, s). IR (KBr): 3328, 1726, 1640, 1431, 1264, 1165 cm$^{-1}$.

Working Example 248

1-(trans-4-Ethoxycarbonylguanidinocyclohexane-1-ylcarbonyl)-4-(6-chloronaphthalene-2-sulfonyl)piperazine To a solution of 1-(trans-4-bisethoxycarbonylguanidinocyclohexane-1-ylcarbonyl)-4-(6-chloronaphthalene-2-sulfonyl)piperazine (180 mg) in ethanol (4 ml) and tetrahydrofurane (4 ml) was added 1 N sodium hydroxide aqueous solution (4 ml), and the mixture was stirred at room temperature for 15 hours. The reaction solution was concentrated, and the residue was extracted with dichloromethane. The extract was washed with water, dried and concentrated to give colorless crystals of the title compound (161 mg).

$^1$H-NMR (CDCl$_3$) δ: 1.18 (2H, m), 1.26 (3H, t, J=7.0 Hz), 1.50–1.80 (4H, m), 2.08 (2H, m), 2.35 (1H, m), 3.08 (4H, m), 3.24 (1H, m), 3.58 (2H, m), 3.69 (2H, m), 4.06 (2H, q, J=7.0 Hz), 6.10 (2H, br), 7.59 (1H, dd, J=1.8, 8.8 Hz), 7.75 (1H, dd, J=1.8, 8.8 Hz), 7.88–7.98 (3H, m), 8.30 (1H, s). IR (KBr): 3380, 1626, 1588, 1346, 1306, 1277, 1165 cm$^{-1}$.

Working Example 249

1-(5-Chlorobenzofuran-2-sulfonyl)-4-[4-methyl-2-(4-pyridyl)-5-thiazolecarbonyl]piperazine The title compound (108 mg) was obtained, as colorless crystals, using 1-(5-chlorobenzofuran-2-sulfonyl)piperazine hydrochloride (100 mg) and 4-methyl-2-(4-pyridyl)-5-thiazolecarboxylic acid (65 mg), according to a similar method described in Working Example 46.

$^1$H-NMR (CDCl$_3$) δ: 2.48 (3H, s), 3.38 (4H, m), 3.78 (4H, m), 7.35 (1H, d, J=0.8 Hz), 7.47 (1H, dd, J=1.8, 8.8 Hz), 7.53 (1H, d, J=8.8 Hz), 7.70 (1H, m), 7.77 (2H, m), 8.75 (2H, brs). IR (KBr): 1636, 1597, 1441, 1368, 1279, 1256, 1165 cm$^{-1}$.

Working Example 250

1-(6-Chlorobenzofuran-2-sulfonyl)-4-[4-methyl-2-(4-pyridyl)-5-thiazolecarbonyl]piperazine The title compound (110 mg) was obtained, as colorless crystals, using 1-(6-chlorobenzofuran-2-sulfonyl)piperazine hydrochloride (200 mg) and 4-methyl-2-(4-pyridyl)-5-thiazolecarboxylic acid (130 mg), according to a similar method described in Working Example 46.

$^1$H-NMR (CDCl$_3$) δ: 2.49 (3H, s), 3.37 (4H, m), 3.78 (4H, m), 7.35–7.42 (2H, m), 7.61 (1H, d, J=2.0 Hz), 7.64 (1H, d, J=8.8 Hz), 7.75 (2H, d, J=6.2 Hz), 8.72 (2H, d, J=6.2 Hz). IR (KBr): 1634, 1462, 1445, 1368, 1167 cm$^{-1}$.

Working Example 251

1-(trans-4-tert-Butoxycarbonylaminocyclohexane-1-ylcarbonyl)-4-(5-chlorobenzofuran-2-sulfonyl)piperazine The title compound (214 mg) was obtained, as colorless crystals, using 1-(5-chlorobenzofuran-2-sulfonyl)piperazine hydrochloride (200 mg) and trans-4-tert-butoxycarbonylaminocyclohexane-1-ylcarboxylic acid (148 mg), according to a similar method described in Working Example 46.

$^1$H-NMR (CDCl$_3$) δ: 1.08 (2H, m), 1.43 (9H, s), 1.50–1.80 (4H, m), 2.07 (2H, m), 2.30 (1H, m), 3.30 (4H, m), 3.42 (1H, m), 3.60 (2H, m), 3.71 (2H, m), 4.35 (1H, brs), 7.33 (1H, s), 7.44 (1H, dd, J=1.8, 8.8 Hz), 7.50 (1H, d, J=8.8 Hz), 7.68 (1H, d, J=1.8 Hz). IR (KBr): 3330, 1699, 1645, 1441, 1366, 1165 cm$^{-1}$.

Working Example 252

1-(trans-4-Aminocyclohexane-1-ylcarbonyl)-4-(5-chlorobenzofuran-2-sulfonyl)piperazine hydrochloride The title compound (176 mg) was obtained, as colorless solid, by treating 1-(trans-4-tert-butoxycarbonylaminocyclohexane-1-ylcarbonyl)-4-(5-chlorobenzofuran-2-sulfonyl)piperazine (200 mg) with hydrochloric acid according to a similar method described in Working Example 76.

$^1$H-NMR (DMSO-d$_6$) δ: 1.20–1.50 (4H, m), 1.64 (2H, m), 1.91 (2H, m), 2.92 (1H, m), 3.19 (5H, m), 3.57 (4H, m), 7.58 (1H, dd, J=2.2, 9.0 Hz), 7.66 (1H, s), 7.80 (1H, d, J=9.0 Hz), 7.91 (1H, d, J=2.2 Hz), 7.98 (3H, brs). IR (KBr): 2920, 1647, 1443, 1364, 1155, 1127 cm$^{-1}$.

Working Example 253

1-(trans-4-Acetimidoylaminocyclohexane-1-ylcarbonyl)-4-(5-chlorobenzofuran-2-sulfonyl)piperazine hydrochloride The title compound (104 mg) was obtained, as colorless solid, using 1-(trans-4-aminocyclohexane-1-ylcarbonyl)-4-(5-chlorobenzofuran-2-sulfonyl)piperazine hydrochloride (160 mg) and ethyl acetimidate hydrochloride (428 mg) according to a similar method described in Working Example 99.

$^1$H-NMR (DMSO-d$_6$) δ: 1.20–1.50 (4H, m), 1.63 (2H, m), 1.84 (2H, m), 2.12 (3H, s), 2.50 (1H, m), 3.19 (4H, m), 3.35 (1H, m), 3.57 (4H, m), 7.59 (1H, dd, J=2.2, 9.0 Hz), 7.67 (1H, d, J=0.8 Hz), 7.80 (1H, d, J=9.0 Hz), 7.92 (1H, d, J=2.2 Hz), 8.56 (1H, brs), 9.04 (1H, brs), 9.36 (1H, m). IR (KBr): cm$^{-1}$.

Working Example 254

1-(5-Chloro-1-methylindole-2-sulfonyl)-4-[4-methyl-2-(4-pyridyl)-5-thiazolecarbonyl]piperazine The title compound (50 mg) was obtained, as colorless solid, using 1-(5-chloro-1-methylindole-2-sulfonyl) piperazine hydrochloride (228 mg) and 4-methyl-2-(4-pyridyl)-5-thiazolecarboxylic acid (220 mg), according to a similar method described in Working Example 46.

$^1$H-NMR (CDCl$_3$) δ: 2.48 (3H, s), 3.29 (4H, m), 3.78 (4H, m), 3.96 (3H, s), 7.09 (1H, s), 7.32 (1H, d, J=8.8 Hz), 7.39 (1H, dd, J=1.8, 8.8 Hz), 7.67 (1H, d, J=1.8 Hz), 7.74 (2H, d, J=6.0 Hz), 8.71 (2H, d, J=6.0 Hz). IR (KBr): 1632, 1597, 1462, 1354, 1154 cm$^{-1}$.

Working Example 255

1-(6-Chloronaphthalene-2-sulfonyl)-4-(4-diisopropyl-aminomethylbenzoyl)piperidine A mixture of 4-(4-diisopropylaminomethylbenzoyl)-1-tritylpiperidine (1.3 g) and 80% acetic acid aqueous solution (20 ml) was stirred at 80° C. for 1 hour and concentrated. To the residue was added water, and the solution was extracted with ethyl acetate. The extract was washed with water, dried (MgSO$_4$) and concentrated to give an oil of 4-(4-diisopropylaminomethylbenzoyl)piperidine (1.0 g). To a solution of the oil (302 mg) in THF (10 ml) was added 6-chloronaphthalene-2-sulfonylchloride (261 mg), and the mixture was stirred at room temperature for 1 hour. To the mixture was added sodium hydrogen carbonate aqueous solution, and the mixture was extracted with ethyl acetate. The extract was washed with water, dried (MgSO$_4$) and concentrated. The residue was subjected to silica gel chromatography and eluted with hexane-ethyl acetate (4:1) to give the title compound (0.15g).

NMR (CDCl$_3$): 0.98(12H, d, J=6.6 Hz), 1.92(4H, m), 2.62(2H, m), 2.97(2H, m), 3.20(1H, m), 3.65(2H, s), 3.83 (2H, m), 7.43(2H, d, J=8.2 Hz), 7.58(1H, m), 7.76(2H, d, J=8.2 Hz), 30 7.82(1H, m), 7.91(3H, m), 8,34(1H, s).

Working Example 256

1-(3,4-Methylenedioxybenzenesulfonyl)-4-[4-methyl-2-(4-pyridyl)thiazole-5-carbonyl]piperazine To a solution of 1-tert-butoxycarbonyl-4-(3,4-methylenedioxybenzenesulfonyl)piperazine (0.5g) in ethyl acetate (2 ml) was added 4 N HCl in ethyl acetate (10 ml), and the mixture was stirred at room temperature for 30 minutes. The precipitated crystals were filtered to give 3,4-methylenedioxybenzenesulfonylpiperazine hydrochloride (0.39g). To a solution of the crystals (100 mg) in dichloromethane (3 ml) were added triethylamine (0.05 ml), 4-methyl-2-(4-pyridyl)thiazole-5-carboxylic acid (74 mg) and WSC (70 mg), and the mixture was stirred at room temperature for 2 hours and concentrated. To the residue was added water, and the solution was extracted with ethyl acetate. The extract was washed with water, dried (MgSO$_4$) and concentrated to give the title compound as crystals (90 mg). The crystals were filtered and washed with ether. NMR (CDCl$_3$): 2.48(3H, s), 3.07(4H, m), 3.75(4H, m), 6.12(2H, s), 6.93(1H, d, J=8.2 Hz), 7.17(2H, s), 7.31(1H, d, J=8.2 Hz), 7.74(2H, d, J=6.2 Hz), 8.71(2H, d, J=6.2 Hz). IR(KBr):1626, 1479, 1427, 1342, 1250 cm$^1$.

Working Example 257

Ethyl 1-(6-Chloronaphthalene-2-sulfonyl)-4-[4-(4-pyridyl)benzoyl)-2-piperazinecarboxylate hydrochloride To a mixture of ethyl 2-piperazinecarboxylate dihydrochloride (231 mg), 4-(4-pyridyl)benzoic acid (199 mg), HOBT (191 mg), triethylamine (0.34 ml) and dichloromethane (8 ml) was added WSC (230 mg), and the mixture was stirred at room temperature for 20 hours and concentrated. To the residue was added water, and the solution was extracted with ethyl acetate. The extract was washed with water, dried (MgSO$_4$) and concentrated. The residue was dissolved in THF (5 ml). To the solution were added triethylamine (0.17 ml) and 6-chloronaphthalene-2-sulfonylchloride, and the mixture was stirred at room temperature for 2 hours and concentrated. To the residue was added water, and the solution was extracted with ethyl acetate. The extract was washed with water, dried (MgSO$_4$) and concentrated. The residue was subjected to silica gel chromatography, eluted with hexane-acetone (1:1) and concentrated. The residue was dissolved in ethyl acetate (5 ml), and to the solution was added 4 N HCl-ethyl acetate (1 ml). The precipitated crystals (180 mg) were filtered.

NMR (DMSO-d$_6$): 0.91 (3H, br), 3.38 (2H, m), 3.79 (4H, m), 3.84 (2H, q, J=7.0 Hz), 4.78 (1H, br), 7.49 (2H, d, J=7.8 Hz), 7.70 (1H, dd, 1.8, 8.8), 7.86 (1H, d, J=8.8 Hz), 8.06 (2H, d, J=7.8 Hz), 8.14 (1H, d, J=6.6 Hz), 8.22 (3H, m), 8.33 (2H, d, J=6.4 Hz), 8.53 (1H, s), 8.96 (2H, d, J=6.4 Hz).

Working Example 258

1-(6-Chloronaphthalene-2-sulfonyl)-4-[4-(4-pyridyl)benzoyl]-2-piperazinecarboxylic acid A mixture of ethyl 1-(6-chloronaphthalene-2-sulfonyl)-4-(4-pyridyl)benzoyl-2-piperazinecarboxylate hydrochloride (100 mg), THF-EtOH (1:1, 2 ml) and 1 N NaOH (1.3 ml) was stirred at room temperature for 20 minutes, and to the mixture was added 1 N HCl (1.3 ml) and further added water to give the title compound (38 mg).

NMR (DMSO-$d_6$): 3.35 (5H, m), 3.80 (1H, m), 4.66 (1H, brs), 7.41 (2H, d, J=8.2 Hz), 7.65–7.80 (6H, m), 8.11–8.25 (3H, m), 8.51 (1H, s), 8.66 (2H, d, J=6 Hz).

Working Example 259

1-(6-Chloronaphthalene-2-sulfonyl)-4-[2-(2-tert-butoxycarbonylamino-5-pyridyl)-4-methylthiazole-5-carbonyl]-piperazine The title compound was obtained, using 1-(6-chloronaphthalene-2-sulfonyl)piperazine hydrochloride and 2-(2-tert-butoxycarbonylamino-5-pyridyl)-4-methyl-5-thiazolecarboxylic acid according to a similar method described in Working Example 46.

NMR (DMSO-$d_6$): 1.49 (9H, s), 2.30 (3H, s), 3.08 (4H, brs), 3.65 (4H, brs), 7.71 (1H, d, J=9.2 Hz), 7.81 (1H, d, J=8.6 Hz), 7.91 (1H, d, J=8.8 Hz), 8.15–8.29 (4H, m), 8.50 (1H, s), 8.72 (1H, d, J=2.2 Hz), 10.13 (1H, s).

Working Example 260

1-(6-Chloronaphthalene-2-sulfonyl)-4-[2-(2-amino-5-pyridyl)-4-methylthiazole-5-carbonyl)piperazine A mixture of 1-(6-chloronaphthalene-2-sulfonyl)-4-(2-(2-tert-butoxycarbonylamino-5-pyridyl)- 4-methyl-thiazole-5-carbonyl)piperazine (180 mg) and trifluoroacetic acid (1.0 ml) was stirred at room temperature for 1 hour and concentrated. To the residue was added sodium hydrogen carbonate aqueous solution, and the mixture was extracted with ethyl acetate. The extract was washed with water, dried (MgSO$_4$) and concentrated. The residue was crystallized from ethyl acetate to give solvate of the title compound (134 mg).

NMR (DMSO-$d_6$): 1.18 (3H, t, J=7.0 Hz), 1.99 (3H, s), 2.25 (3H, s), 3.06 (4H, br), 3.64 (4H, br), 4.02 (2H, q, J=7.0 Hz), 10 6.48 (1H, d, J=8.6 Hz), 6.56 (2H, s), 7.71 (1H, d, J=8.8 Hz), 7.80 (2H, m), 8.17 (1H, s), 8.50 (1H, s).

Working Example 261

1-(trans-4-tert-Butoxycarbonylaminomethylcyclohexane-1-carbonyl)-4-(6-chloronaphthalene-2-sulfonyl)piperazine The title compound was obtained, using 1-(6-chloronaphthalene-2-sulfonyl)piperazine hydrochloride and trans-4-tert-butoxycarbonylaminomethylcyclohexane-1-carboxylic acid according to a similar method described in Working Example 46.

NMR (CDCl$_3$): 0.94 (2H, m), 1.42 (9H, s), 1.30–1.81 (6H, m), 2.29 (1H, m), 2.91–3.09 (6H, m), 3.59 (2H, brs), 3.69 (2H, brs), 4.52 (1H, s), 7.58 (1H, dd, J=1.8, 8.8 Hz), 7.90 (3H, m), 8.30 (1H, s).

Working Example 262

1-(trans-4-Aminomethylcyclohexane-1-carbonyl)-4-(6-chloronaphthalene-2-sulfonyl)piperazine hydrochloride A mixture of 1-(trans-4-tert-butoxycarbonylaminomethylcyclohexane-1-carbonyl)-4-(6-chloronaphthalene-2-sulfonyl)piperazine (0. 7g) and 4 N HCl-ethyl acetate (10 ml) was stirred at room temperature for 1 hour, and the precipitated crystals of the title compound (0.48g) were filtered.

NMR (DMSO-$d_6$): 0.89–1.76 (8H, m), 2.45 (1H, m), 2.59 (2H, m), 2.96 (4H, br), 3.55 (4H, br), 3.76 (1H, brs), 7.71 (1H, dd, J=1.8, 8.8 Hz), 7.79 (1H, dd, J=1.8, 8.8 Hz), 7.89 (2H, br), 8.16 (1H, d, J=8.8 Hz), 8.26 (1H, d, J=8.8 Hz), 8.50(1H, s).

Working Example 263

1-(trans-4-Guanidinomethylcyclohexane-1-carbonyl)-4-(6-chloronaphthalene-2-sulfonyl)piperazine hydrochloride A mixture of 1-(trans-4-aminomethylcyclohexane-1-carbonyl)-4-(6-chloronaphthalene-2-sulfonyl)piperazine hydrochloride (200 mg) and $N^1$, $N^2$-bis-tert-butoxycarbonyl-S-methylisothiourea (131 mg) in ethanol (2 ml) was heated for 1 hour under ref lux. The mixture was concentrated, and the precipitated crystals were filtered. The crystals were dissolved in 4 N HCl-ethyl acetate (4 ml), and the mixture was stirred for 15 hours at room temperature and concentrated. The precipitated crystals were filtered to give the title compound (120 mg).

NMR (DMSO-d6): 0.93–1.75 (8H, m), 2.41 (3H, m), 2.95 (4H, br), 3.55 (4H, br), 4.43 (1H, br), 7.70 (1H, d, J=8.8 Hz), 7.79 (1H, d, J=8.8 Hz), 8.16 (1H, d, J=8.8 Hz), 8.42 (1H, d, J=9.6 Hz), 8.49 (1H, s).

Working Example 264

1-[4-(2-Amidino-1-ethenyl)benzoyl]-4-(6-chloronaphthalene-2-sulfonyl)piperazine hydrochloride The title compound was obtained, as colorless crystals, using 4-(6-chloronaphthalene-2-sulfonyl)-1-[4-(2-cyano-1-ethenyl)benzoyl]piperazine according to a similar method described in Working Example 103.

$^1$H-NMR (DMSO-$d_6$) δ: 3.07 (4H, brs), 3.30–3.90 (4H, m), 6.80 (1H, d, J=16.4 Hz), 7.44 (2H, d, J=8.0 Hz), 7.60 (2H, d, J=8.0 Hz), 7.73 (1H, dd, J=8.8, 2.2 Hz), 7.79–7.92 (2H, m), 8.19 (1H, d, J=8.8 Hz), 8.24–8.32 (2H, m), 8.50 (1H, s), 8.76 (2H, brs), 9.19 (2H, brs). IR (KBr): 3056, 1684, 1609, 1343, 1287, 1161, 725, 579 cm$^{-1}$.

Working Example 265

1-[4-(2-Amidinoethyl)benzoyl]-4-(6-chloronaphthalene-2-sulfonyl)piperazine hydrochloride The title compound was obtained, as colorless crystals, using 4-(6-chloronaphthalene-2-sulfonyl)-1-[4-(2-cyano-ethyl)benzoyl]piperazine according to a similar method described in Working Example 103.

$^1$H-NMR (DMSO-$d_6$) δ: 2.61–2.73 (2H,m), 2.89–3.01 (2H, m), 3.05 (4H, brs), 3.55 (4H, br), 7.27 (4H, s), 7.72 (1H, dd, J=8.6, 2.2 Hz), 7.82 (1H, dd, J=8.6, 1.8 Hz), 8.18 (1H, d, J=8.8 Hz), 8.24–8.30 (2H, m), 8.49 (1H, s), 8.59 (2H, brs), 9.04 (2H, brs). IR (KBr): 3059, 1686, 1620, 1348, 1167, 727, 581 cm$^{-1}$.

Working Example 266

1-(7-chloro-2H-benzothiopyran-3-sulfonyl)-4-[4-methyl-2-(4-pyridyl)-5-thiazolecarbonyl]piperazine The title compound (108 mg) was obtained, as colorless crystals, using 1-(7-chloro-2H-benzothiopyrane-3-sulfonyl)

piperazine hydrochloride (100 mg) and 4-methyl-2-(4-pyridyl)-5-thiazolecarboxylic acid (60 mg) according to a similar method described in Working Example 46.

$^1$H-NMR (CDCl$_3$) δ: 2.52 (3H, s), 3.31 (4H, m), 3.62 (2H, d, J=0.6 Hz), 3.78 (4H, m), 7.13–7.36 (4H, m), 7.79 (2H, m), 8.72 (2H, m). IR (KBr): 1630, 1435, 1345, 1327, 1285, 1258, 1155 cm$^{-1}$.

Working Example 267

1-(7-chlorochromone-3-sulfonyl)-4-[4-methyl-2-(4-pyridyl)-5-thiazolecarbonyl]piperazine The title compound (123 mg) was obtained, as colorless crystals, using 1-(7-chlorochromon-3-sulfonyl)piperazine hydrochloride (100 mg) and 4-methyl-2-(4-pyridyl)-5-thiazolecarboxylic acid (60 mg) according to a similar method described in Working Example 46.

$^1$H-NMR (CDCl$_3$) δ: 2.51 (3H, s), 3.52 (4H, m), 3.76 (4H, m), 7.50 (1H, dd, J=1.8, 8.4 Hz), 7.59 (1H, d, J=1.8 Hz), 7.76 (2H, d, J=6.2 Hz), 8.18 (1H, d, J=8.4 Hz), 8.66 (1H, s), 8.72 (2H, d, J=6.2 Hz). IR (KBr): 1655, 1628, 1615, 1425, 1360, 1348, 1337, 1283, 1171, 1159 cm$^{-1}$.

Working Example 268

1-[trans-4-(N$^2$-pivaloyloxymethoxycarbonylacetimidoyl-amino)cyclohexan-1-ylcarbonyl]-4-(6-chloronaphthalene-2-sulfonyl)piperazine The title compound (271 mg) was obtained, as colorless crystals, by reacting 1-(trans-4-acetimidoylaminocyclohexan-1-ylcarbonyl)-4-(6-chloronaphthalene-2-sulfonyl)piperazine (500 mg) and O-(pivaloyloxymethoxycarbonyl)-4-nitrophenol (343 mg) according to a similar method described in Working Example 218.

$^1$H-NMR (CDCl$_3$) δ: 1.20 (9H, s), 1.32 (2H, m), 1.50–1.80 (4H, m), 2.04 (2H, m), 2.14 (3H, s), 2.34 (1H, m), 3.09 (4H, m), 3.40 (1H, m), 3.60 (2H, m), 3.71 (2H, m), 5.76 (2H, s), 7.60 (1H, dd, J=1.6, 8.8 Hz), 7.76 (1H, dd, J=1.8, 8.8 Hz), 7.88–7.97 (3H, m), 8.31 (1H, s). IR (KBr): 1746, 1694, 1645, 1632, 1557, 1454, 1348, 1258, 1165 cm$^{-1}$.

Working Example 269

1-[trans-4-(N$^2$-(5-methyl-2-oxo-1,3-dioxolen-4-ylmethoxycarbonyl)acetimidoylamino]cyclohexan-1-ylcarbonyl]-4-(6-chloronaphthalene-2-sulfonyl)piperazine The title compound (363 mg) was obtained, as colorless crystals, by reacting 1-(trans-4-acetimidoylaminocyclohexan-1-ylcarbonyl)-4-(6-chloronaphthalene-2-sulfonyl)piperazine (500 mg) and 0-(5-methyl-2-oxo-1,3-dioxolen-4-ylmethoxycarbonyl)-4-nitrophenol (341 mg) according to a similar method described in Working Example 218.

$^1$H-NMR (CDCl$_3$) δ: 1.33 (2H, m), 1.50–1.80 (4H, m), 2.08 (2H, m), 2.13 (3H, s), 2.14 (2H, s), 2.38 (1H, m), 3.09 (4H, m), 3.40 (1H, m), 3.60 (2H, m), 3.70 (2H, m), 4.81 (2H, s), 7.60 (1H, dd, J=2.0, 8.8 Hz), 7.76 (1H, dd, J=2.0, 8.8 Hz), 7.87–7.96 (3H, m), 8.31 (1H, s), 9.80 (1H, br). IR (KBr): 1819, 1645, 1634, 1597, 1559, 1435, 1346, 1258, 1198, 1163 cm$^{-1}$.

Working Example 270

1-(7-chloro-4-hydroxyquinoline-3-sulfonyl)-4-[4-methyl-2-(4-pyridyl)-5-thiazolecarbonyl]piperazine The title compound (589 mg) was obtained, as colorless crystals, using 1-(7-chloro-4-hydroxyquinoline-3-sulfonyl)piperazine hydrochloride (500 mg) and 4-methyl-2-(4-pyridyl)-5-thiazolecarboxylic acid (302 mg) according to a similar method described in Working Example 46.

$^1$H-NMR (DMSO-d6) δ: 2.39 (3H, s), 3.35 (4H, m), 3.60 (4H, m), 7.48 (1H, dd, J=1.8, 8.8 Hz), 7.73 (1H, d, J=1.8 Hz), 7.84 (2H, d, J=6.0 Hz), 8.15 (1H, d, J=8.8 Hz), 8.55 (1H, s), 8.70 (2H, d, J=6.0 Hz). IR (KBr): 1620, 1601, 1460, 1321, 1281, 1159 cm$^{-1}$.

Working Example 271

1-(4,7-dichloroquinoline-3-sulfonyl)-4-[4-methyl-2-(4-pyridyl)-5-thiazolecarbonyl]piperazine A suspension of 1-(7-chloro-4-hydroxyquinoline-3-sulfonyl)-4-[4-methyl-2-(4-pyridyl)-5-thiazolecarbonyl]-piperazine (200 mg) in phosphoryl chloride (6 ml) was refluxed for 2 hours. The reaction mixture was concentrated, and ice water was added to the residue. To the mixture was added an aqueous solution of sodium hydrogen carbonate, and the mixture was extracted with dichloromethane. The extract was dried and concentrated to give brown crystals of the title compound (223 mg).

$^1$H-NMR (CDCl$_3$) δ: 2.50 (3H, s), 3.47 (4H, m), 3.78 (4H, m), 7.74 (1H, dd, J=2.0, 9.0 Hz), 7.77 (2H, d, J=6.0 Hz), 8.21 (1H, d, J=2.0 Hz), 8.38 (1H, d, J=9.0 Hz), 8.72 (2H, d, J=6.0 Hz). IR (KBr): 1634, 1601, 1470, 1435, 1362, 1339, 1167, 1152 cm$^{-1}$.

Working Example 272

1-(7-chloroquinoline-3-sulfonyl)-4-[4-methyl-2-(4-pyridyl)-5-thiazolecarbonyl]piperazine A suspension of 1-(4,7-dichloroquinoline-3-sulfonyl)-4-[4-methyl-2-(4-pyridyl)-5-thiazolecarbonyl]piperazine (200 mg) and zinc powder (250 mg) in acetic acid (6 ml) was stirred at 80° C. for 2 hours, the mixture was concentrated. The residue was dissolved in dichloromethane-methanol, and insoluble materials were filtered off. The filtrate was concentrated to give brown solid which was successively washed with 1 N hydrochloric acid, sodium hydrogen carbonate solution and water, and dried to afford the title compound (43 mg).

$^1$H-NMR (DMSO-d$_6$) δ: 2.39 (3H, s), 3.10–3.70 (4H, m), 7.45 (1H, d, J=8.4 Hz), 7.71 (1H, s), 7.85 (2H, d, J=6.0 Hz), 8.14 (1H, d, J=8.4 Hz), 8.53 (2H, s), 8.70 (2H, d, J=6.0 Hz). IR (KBr): 1620, 1593, 1524, 1460, 1348, 1157, 1136 cm$^{-1}$.

Working Example 273

1-(5-chlorobenzo[b]thiophene-2-sulfonyl)-4-[4-methyl-2-(4-pyridyl)-5-thiazolecarbonyl]piperazine To a solution of 5-chlorobenzo[b]thiophene (245 mg) in THF (5 ml) was added a solution of 1.6 M n-butyl lithium in hexane (1.0 ml) under ice-cooling, and the mixture was stirred for 10 minutes. The reaction solution was added to a solution of sulfuryl chloride (0.241 ml) in hexane (5 ml) under ice-cooling, and the reaction mixture was stirred for 1 hour, to which was added water. The reaction mixture was extracted with ether, and the extract was added to a mixture of 1-Boc-piperazine (298 mg), sodium hydrogen carbonate solution (5 ml) and ethyl acetate (5 ml), and the whole was stirred at room temperature for 1 hour. The organic layer was separated, washed with brine, dried and concentrated. The residue was purified with silica gel column chromatography (hexane:ethyl acetate=3:1) to give 1-(tert-butoxycarbonyl)-4-(5-chlorobenzo[b]thiophene-2-sulfonyl)piperazine (68 mg), to which was added 4 N hydrochloric acid in ethyl acetate (5 ml), and the mixture was stirred at room temperature for 1 hour and concentrated. The residue was dissolved in DMF (5 ml). To the solution were added 4-methyl-2-(4-pyridyl)-5-thiazolecarboxylic acid (44 mg), triethylamine (0.028 ml), HOBt (31 mg) and WSC hydrochloride (38 mg), and the mixture was stirred at room temperature for 4 hours. The reaction mixture was partitioned between ethyl acetate and water, and the organic layer was separated, washed with water and brine, dried and concentrated to give the crystals which was washed with ethyl acetate and ether to give colorless crystals of the title compound (33 mg).

$^1$H-NMR (CDCl$_3$) δ: 2.47 (3H, s), 3.24 (4H, t, J=4.9 Hz), 3.75–3.85 (4H, m), 7.51 (1H, dd, J=8.8, 2.2 Hz), 7.72–7.77 (3H, m), 7.83 (1H, d, J=8.8 Hz), 7.91 (1H, d, J=1.8 Hz), 8.72 (2H, d, J=6.2 Hz). IR (KBr): 1632, 1435, 1283, 1159, 945, 725 cm$^{-1}$.

Experimental Example 1

Inhibitory effect on human activated coagulation factor X (FXa)

Method:

In 0.05M Tris buffer solution (pH 8.3) 225 μl containing 0.145 M sodium chloride and 2 mM calcium chloride, test compound dissolved in dimethyl-sulfoxide 5 μl and human FXa (0.3 unit/ml) 10 μl were reacted at 37° C. for 10 minutes. To the reaction solution was added substrate (3 mM, S-2765) 10 μl and the mixture was further reacted at 37° C. for 10 minutes. To the reaction solution was added 50% acetic acid aqueous solution 25 μl to stop the reaction.

IC$_{50}$ values (concentration of the test compound which inhibits 50% of FXa activity) were calculated by measuring change of absorbance at 405 nm with microplate reader (MTP-32, Corona Electric).

Result: IC$_{50}$ values of the test compound are shown in Table 1. As is clear from the results shown in Table 1, the test compounds of the present invention exhibit inhibitory action on FXa.

TABLE 1

| Working Example No. | IC50 (μM) |
| --- | --- |
| 64 | 0.019 |

Experimental Example 2

(1) Measurement of in vitro blood coagulation time (a) Measurement of prothrombin time (PT)

Using a clinical assay kit, PT-Test Wako (Wako Pure Chemical), coagulation time was measured with automatic measuring apparatus of coagulation time (STA compact, DIAGNOSTICA STAGO). To human normal plasma (fresh human plasma: FFP; Sekisui Kagaku Kogyou) 97 μl was added test compound dissolved in dimethylsulfoxide (DMSO) 3 μl, and the mixture was heated at 37° C. for 4 minutes. To the above plasma 50 μl was added thromboplastin derived from rabbit brain 100 μl, and coagulation time was measured.

Concentration prolonging coagulation time twice was calculated based on coagulation time when DMSO was added instead of test compound.

(b) Measurement of activated partial thromboplastin time (APTT)

Using a clinical assay kit, STA-APTT-LT (DIAGNOSTICA STAGO), coagulation time was measured with automatic measuring apparatus of coagulation time (STA compact, DIAGNOSTICA STAGO). To human normal plasma (fresh human plasma: FFP; Sekisui Kagaku Kogyou) 97 μl was added test compound dissolved in dimethylsulfoxide (DMSO) 39 μl and further added activated partial thromboplastin 50 μl per plasma 50 μl, and the mixture was heated at 37° C. for 4 minutes. To the mixture was added 20 mmol/l CaCl$_2$ solution 50 μl, and coagulation time was measured.

Concentration prolonging coagulation time twice were calculated based on coagulation time when DMSO was added instead of test compound.

(c) Measurement of thrombin time (TT)

Coagulation time was measured with automatic measuring apparatus of coagulation time (Biomatic BIO, Sarstedt). Thrombin derived from human plasma (Sigma) was dissolved in distilled water to give a 2.3 NIH units/ml solution. To human normal plasma (fresh human plasma: FFP; Sekisui Kagaku Kogyou) 97 μl was added test compound dissolved in dimethylsulfoxide (DMSO) 3 μl, and the mixture was heated at 37° C. for 3minutes. To the above plasma 100 μl was added thrombin solution 200 μl, and coagulation time was measured.

Concentration prolonging coagulation time twice was calculated based on coagulation time when DMSO was added instead of test compound.

(2) Measurement ex vivo blood coagulation time (mouse)

(a) Intravenous Administration

Male ICR mice (25–35 g, Slc) were employed. Test compounds 5 ml/kg were administered once to these animals through tail vein, under anesthesia with sodium pentobarbital (50 mg/kg, i.p.). Five minutes after administration, blood 0.8 ml was collected from abdominal aorta using3.8% trisodium citrate (whole blood:trisodium citrate solution= 9:1 by volume). The trisodium citrate supplemented blood was centrifuged at 3000 rpm for 15 minutes to obtain plasma. To the plasma 50 μl was added thromboplastin derived from rabbit brain 100 μl, and coagulation time was measured with automatic measuring apparatus of coagulation time (STA compact, DIAGNOSTICA STAGO), using a clinical assay kit, PT-Test Wako (Wako Pure Chemical).

Test compounds were dissolved in physiological saline, and as control, physiological saline was administered instead of test compounds. Activity of each test compound was shown in ratio (%) determined by comparing coagulation time of test compound group with that of control group.

(b) Oral Administration

Male ICR mice (25–35 g, Slc) fasting for more than 12 hours were employed.

Test compounds 5ml/kg were orally administered to these animals. One hour after administration, blood 0.8 ml was collected from abdominal aorta under anesthesia with sodium pentobarbital (50 mg/kg, i.p.).

Test compounds were suspended in 0.5% methylcellulose, and as control, 0.5% methylcellulose was administered instead of test compounds. The other conditions are the same as the above described experiment (Intravenous Administration).

(3) Measurement of ex vivo blood coagulation time (rat)

(a) Oral Administration

Male Sprague-Dawley rats (250–350 g, Nippon Clea) fasting for more than 12 hours were employed. Test compounds were orally administered to these animals. Two hours after administration, blood 2 ml was collected from abdominal aorta using 3.8% trisodium citrate (whole blood- :trisodium citrate solution=9:1 by volume), under anesthesia with sodium pentobarbital (50 mg/kg, i.p.). The trisodium citrate supplemented blood was centrifuged at 3000 rpm for 15 minutes to obtain plasma. To the plasma 50 μl was added thromboplastin derived from rabbit brain 100 μl, and coagulation time was measured with automatic measuring apparatus of coagulation time (STA compact, DIAGNOSTICA STAGO), using a clinical assay kit, PT-Test Wako (Wako Pure Chemical).

Test compounds were suspended in 0.5% methylcellulose, and as control, 0.5% methylcellulose was administered instead of test compounds. Activity of each test compound was shown in ratio (%) determined by comparing coagulation time of test compound group with that of control group.

(b) Intravenous Administration

Male Sprague-Dawley rats (250–350 g, Nippon Clea) were employed. Test compounds 5 ml/kg were administered once to these animals through tail vein, under anesthesia with sodium pentobarbital (50 mg/kg, i.p.). Five minutes after administration, blood 2 ml was collected from abdominal aorta.

Test compounds were dissolved in physiological saline, and as control, physiological saline was administered instead of test compounds. The other conditions are the same as described above (Oral administration).

(4) Arteriovenous Shunt Method (rat)

(a) Oral Administration

Method of Umetsu et al. (Thromb. Haemostas., 39: 74–83, 1978) was carried out. Male Sprague-Dawley rats (250–350 g, Nippon Clea) fasting for more than 12 hours were employed. Test compounds 5 ml/kg were orally administered to these animals. Two hours after administration, extra-corporeal circulation system made of polyethylene tube to which silk thread was inserted was prepared between the right carotid artery and the left jugular vein, under anesthesia with sodium pentobarbital (50 mg/kg, i.p.). In order to prevent the blood from coagulating, a physiological saline containing heparin (50 U/ml) was filled in the tube.

The blood was circulated for 15 minutes, and wet weight of thrombus attached to the silk thread was measured.

Test compounds were suspended in 0.5% methylcellulose, and as control, 0.5% methylcellulose was administered instead of test compounds. Antithrombotic activity (% inhibition of thrombus formation) of each test compound was determined by comparing wet weight of thrombus of test compound group with that of control group.

(b) Intravenous Administration

Male Sprague-Dawley rats (250–350 g, Nippon Clea) were employed. Extracorporeal circulation system was prepared between the right carotid artery and the left jugular vein, under anesthesia with sodium pentobarbital (50 mg/kg, i.p.). Test compounds 5 ml/kg were intravenously administered to these animals. Five minutes after administration, circulation was started.

Test compounds were dissolved in physiological saline, and as control, physiological saline was administered instead of test compounds. The other experimental conditions are the same as the above described experiment (Oral Administration).

INDUSTRIAL APPLICABILITY

The compounds (I) or a salt thereof of the present invention have potent inhibitory action on FXa, low side effect such as bleeding, and are useful as anti-coagulant and absorbable by oral administration. Therefore, they are used advantageously for the prevention or treatment of various thrombotic diseases including arterial and venous thrombus, etc.

What is claimed is:

1. A compound of the formula:

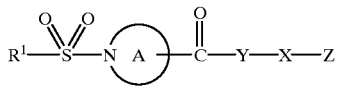

wherein $R^1$ is an optionally substituted hydrocarbon group or an optionally substituted heterocyclic group;

the ring A is an optionally substituted divalent nitrogen-containing heterocyclic group, in addition to being substituted by the group of the formula:

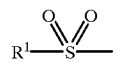

and the group of the formula:

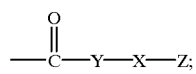

wherein said divalent nitrogen containing heterocycle is of the formula:

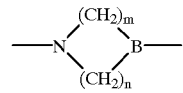

wherein B is a nitrogen atom, and m and n are each 2;

Y is an optionally substituted divalent cyclic hydrocarbon group or an optionally substituted divalent heterocyclic group;

X is a direct bond or an optionally substituted alkylene chain;

Z is (1) an amino group substituted with an optionally substituted hydrocarbon group, (2) an optionally substituted imidoyl group or (3) an optionally substituted nitrogen-containing heterocyclic group;

provided that when X is a direct bond and Z is an optionally substituted 6-membered nitrogen-containing aromatic heterocyclic group, Y is an optionally substituted divalent cyclic hydrocarbon group or an optionally substituted divalent unsaturated heterocyclic group;

or a salt thereof.

2. A compound according to claim 1, wherein $R^1$ is (1) a $C_{1-10}$ alkyl group, (2) a $C_{2-6}$ alkenyl group, (3) a $C_{2-6}$ alkynyl group, (4) a $C_{3-9}$ cycloalkyl group, (5) a $C_{3-6}$ cycloalkenyl group, (6) a $C_{4-6}$ cycloalkanedienyl group, (7) a $C_{6-14}$ aryl group or (8) a heterocyclic group selected from the group consisting of (i) a 5- to 6-membered aromatic monocyclic heterocyclic group, (ii) an 8- to 12-membered aromatic fused heterocyclic group and (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said groups (1)–(8) being unsubstituted or substituted by 1 to 5 substituents selected from the group consisting of (a) a $C_{1-6}$ alkyl group optionally substituted with $C_{1-6}$ alkoxy, halogen, $C_{1-6}$ alkyl, amino, hydroxy, cyano group or amidino,
(b) a $C_{2-6}$ alkenyl group optionally substituted with $C_{1-6}$ alkoxy, halogen, $C_{1-6}$ alkyl, amino, hydroxy, cyano group or amidino,
(c) a $C_{2-6}$ alkynyl group optionally substituted with $C_{1-6}$ alkoxy, halogen, $C_{1-6}$ alkyl, amino, hydroxy, cyano group or amidino,
(d) a $C_{6-14}$ aryl group optionally substituted with $C_{1-6}$ alkoxy, halogen, $C_{1-6}$ alkyl, amino, hydroxy, cyano group or amidino,
(e) a $C_{3-7}$ cycloalkyl or $C_{3-6}$ cycloalkenyl group optionally substituted with $C_{1-6}$ alkoxy, halogen, $C_{1-6}$ alkyl, amino, hydroxy, cyano group or amidino,
(f) a heterocyclic group selected from the group consisting of (i) a 5- to 6-membered aromatic monocyclic heterocyclic group, (ii) an 8- to 12-membered aromatic fused heterocyclic group and (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms, which may be substituted by $C_{1-6}$ alkyl, $C_{1-6}$ alkanoyl or benzoyl,
(g) an amino group optionally substituted with $C_{1-6}$ alkyl group, $C_{1-6}$ alkanoyl, benzoyl, optionally halogenated $C_{1-6}$ alkoxy-carbonyl, $C_{1-6}$ alkylimidoyl, formimidoyl or amidino,
(g') a 3- to 8-membered cyclic amino group.

3. A compound according to claim 1, wherein $R^1$ is an optionally substituted hydrocarbon group.

4. A compound according to claim 1, wherein $R^1$ is an aryl group optionally substituted with a halogen atom.

5. A compound according to claim 1, wherein Y is an optionally substituted divalent aromatic heterocyclic group.

6. A compound according to claim 1, wherein Y is an optionally substituted phenylene group.

7. A compound according to claim 1, wherein Y is an optionally substituted cyclohexylene group.

8. A compound according to claim 1, wherein Z is an optionally substituted nitrogen-containing heterocyclic group.

9. A compound according to claim 1, wherein Z is an optionally substituted amidino group.

10. A compound according to claim 1, wherein Z is an optionally substituted guanidino group.

11. A compound according to claim 1, wherein Z is (1) a mono- or di-$C_{1-6}$ alkylamino group which maybe further substituted with phenyl at the alkyl moiety, (2) guanidino, (3) formimidoyl-amino, (4) acetimidoylamino or (5) piperidino.

12. A compound according to claim 1, wherein
Z is a group of the formula: —N(R")—C(R')=N—R or a group of the formula: —C(R')=N—R wherein
R" is a hydrogen atom or a $C_{1-6}$ alkyl group,
R is a hydrogen atom, a $C_{1-6}$ alkyl group, a $C_{1-6}$ alkanoyl group or a benzoyl group,
R' is a hydrogen atom, a $C_{1-6}$ alkyl group, a $C_{1-6}$ alkanoyl group, a benzoyl group, an amino group optionally substituted with 1–2 substituents selected from $C_{1-6}$ alkyl, $C_{1-6}$ alkanoyl and benzoyl, or a $C_{1-6}$ alkoxy group.

13. A compound according to claim 1, wherein
Z is a group of the formula: —NH—C(R')=NH or a group of the formula: —C(R')=NH wherein
R' is a $C_{1-6}$ alkyl group or an amino group optionally substituted with 1–2 substituents selected from $C_{1-6}$ alkyl, $C_{1-6}$ alkanoyl and benzoyl.

14. A compound according to claim 1, wherein $R^1$ is
(1) a $C_{1-10}$ alkyl group,
(2) a $C_{2-6}$ alkenyl group,
(3) a $C_{2-6}$ alkynyl group,
(4) a $C_{6-14}$ aryl group or
(5) a heterocyclic group selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said groups (1)–(5) being unsubstituted or substituted by
(a) a $C_{1-6}$ alkyl group optionally substituted with $C_{1-6}$ alkoxy, halogen, $C_{1-6}$ alkyl, amino, hydroxy, cyano or amidino,
(b) a $C_{6-14}$ aryl group optionally substituted with $C_{1-6}$ alkoxy, halogen, $C_{1-6}$ alkyl, amino, hydroxy, cyano or amidino,
(c) a heterocyclic group selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms, which may be substituted by $C_{1-6}$ alkyl, $C_{1-6}$ alkanoyl or benzoyl,
(d) an amino group optionally substituted with $C_{1-6}$ alkyl, $C_{1-6}$ alkanoyl, benzoyl, optionally halogenated $C_{1-6}$ alkoxy-carbonyl, $C_{1-6}$ alkylimidoyl, formimidoyl or amidino,
(e) an imidoyl group optionally substituted with $C_{1-6}$ alkyl, $C_{1-6}$ alkanoyl, benzoyl or optionally halogenated $C_{1-6}$ alkoxy-carbonyl,
(f) an amidino group optionally substituted with $C_{1-6}$ alkyl, $C_{1-6}$ alkanoyl, benzoyl or optionally halogenated $C_{1-6}$ alkoxy-carbonyl,
(g) a hydroxy group optionally substituted with $C_{1-6}$ alkyl, $C_{1-6}$ alkanoyl, benzoyl or optionally halogenated $C_{1-6}$ alkoxy-carbonyl,
(h) a carboxyl group,
(i) a $C_{1-6}$ alkoxy-carbonyl group,
(j) a $C_{7-12}$ aryloxycarbonyl group being unsubstituted or substituted by
  hydroxy,
  amino optionally having 1 to 2 substituents selected from the group consisting of $C_{1-6}$ alkyl, $C_{1-6}$ alkanoyl and benzoyl,
  halogen,
  nitro,
  cyano,
  $C_{1-6}$ alkyl optionally substituted with 1 to 5 halogen atoms or
  $C_{1-6}$ alkoxy optionally substituted with 1 to 5 halogen atoms,
(k) a $C_{6-10}$ aryl-$C_{1-4}$ alkoxy-carbonyl group being unsubstituted or substituted by hydroxy,
amino optionally having 1 to 2 substituents selected from the group consisting of $C_{3-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(l) a halogen atom,
(m) a cyano group,
(n) a nitro group or
(o) a carbonyl group having one substituent selected from the group consisting of $C_{1-6}$ alkyl, $C_{3-6}$ cycloalkyl, $C_{6-10}$ aryl, $C_{7-11}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
the ring A is a group of the formula:

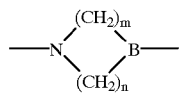

wherein B is a nitrogen atom, and m and n are each 2, said group being unsubstituted or substituted, in addition to the group of the formula:

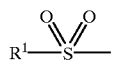

and the group of the formula:

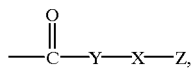

by
(a) a carboxyl group,
(b) a $C_{1-6}$ alkoxy-carbonyl group,
(c) a $C_{7-12}$ aryloxycarbonyl group being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms or
(d) a $C_{6-10}$ aryl-$C_{1-4}$ alkoxy-carbonyl group being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms;
Y is
(1) a $C_{3-9}$ cycloalkylene group,
(2) a $C_{6-10}$ arylene group,
(3) a $C_{7-10}$ aralkylene group,
(4) a 5- to 6-membered divalent aromatic heterocyclic group containing, besides carbon atoms, 1 to 3 hetero-atoms selected from the group consisting of oxygen atom, sulfur atom and nitrogen atom or
(5) a 5- to 6-membered divalent saturated or unsaturated non-aromatic heterocyclic group containing, besides carbon atoms, 1 to 3 hetero-atoms selected from the group consisting of oxygen atom, sulfur atom and nitrogen atom,
each of said groups (1)–(5) being unsubstituted or substituted by
(a) a halogen atom,
(b) a cyano group,
(c) a $C_{1-6}$ alkyl group optionally substituted with halogen, amino, carboxyl or hydroxy or
(d) a $C_{1-6}$ alkoxy group optionally substituted with 1 to 5 halogen atoms;
X is a direct bond or a straight-chain $C_{1-6}$ alkylene; and
Z is
(1) an amino group substituted with 1 or 2 substituents selected from the group consisting of (1-1) a $C_{1-10}$ alkyl group and (1-2) a $C_{6-14}$ aryl group;
(2) a group of the formula: —N(R")—C(R')=N—R or a group of the formula: —C(R')=N—R wherein
  R" is a hydrogen atom or a $C_{1-6}$ alkyl group,
  R is a hydrogen atom, a $C_{1-6}$ alkyl group, a $C_{1-6}$ alkanoyl group or a benzoyl group, and
  R' is a hydrogen atom, a $C_{1-6}$ alkyl group, a $C_{1-6}$ alkanoyl group, a benzoyl group or an amino group optionally substituted with 1 or 2 substituents selected from the group consisting of $C_{1-6}$ alkyl, $C_{1-6}$ alkanoyl or benzoyl, or a $C_{1-6}$ alkoxy group; or
(3) a 5- to 6-membered aromatic or non-aromatic monocyclic nitrogen-containing heterocyclic group which contains, besides carbon atoms, 1 to 3 nitrogen atoms and optionally contains 1 to 3 hetero-atoms selected from the group consisting of an oxygen atom and a sulfur atom and which may be substituted by
(a) a halogen atom,
(b) an amino group,
(c) a $C_{1-6}$ alkyl group optionally substituted with halogen, amino, carboxyl or hydroxy,
(d) a carboxyl group,
(e) a $C_{1-6}$ alkoxy-carbonyl group,
(f) a $C_{7-12}$ aryloxycarbonyl group being unsubstituted or substituted by
hydroxy,
amino optionally having 1 to 2 substituents selected from the group consisting of $C_{1-6}$ alkyl, $C_{1-6}$ alkanoyl and benzoyl,
halogen, nitro,
cyano,
$C_{1-6}$ alkyl optionally substituted with 1 to 5 halogen atoms or
$C_{1-6}$ alkoxy optionally substituted with 1 to 5 halogen atoms or
(g) a $C_{6-10}$ aryl-$C_{1-4}$ alkoxy-carbonyl group being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms.

15. A compound according to claim 1, which is 1-(6-chloronaphthalene-2-sulfonyl)-4-[4-(4-pyridyl)-benzoyl] piperazine, 1-(6-chloronaphthalene-2-sulfonyl)-4-[4-(1H-imidazol-1-yl)benzoyl]piperazine, 1-(6-chloronaphthalene-2-sulfonyl)-4-[2-(4-pyridyl)-4-methyl-5-thiazolylcarbonyl] piperazine, 1-(6-chloronaphthalene-2-sulfonyl)-4-(trans-4-guanidinocyclohexan-1-ylcarbonyl)piperazine, or a salt thereof.

16. 1-(trans-4-Acetimidoylaminocyclohexane-1-ylcarbonyl)-4-(6-chloronaphthalene-2-sulfonyl)piperazine or salt thereof.

17. 1-(trans-4-Methoxycarbonylacetimidoylaminocyclohexane-1-ylcarbonyl)-4-(6-chloronaphthalene-2-sulfonyl)piperazine or salt thereof. optionally having $C_{1-6}$ alkyl, $C_{7-10}$ aralkyl or $C_{6-10}$ aryl,
(h) an imidoyl group optionally substituted with $C_{1-6}$ alkyl group, $C_{1-6}$ alkanoyl, benzoyl or optionally halogenated $C_{1-6}$ alkoxy-carbonyl,
(i) an amidino group optionally substituted with $C_{1-6}$ alkyl group, $C_{1-6}$ alkanoyl, benzoyl or optionally halogenated $C_{1-6}$ alkoxy-carbonyl,
(j) a hydroxy group optionally substituted with $C_{1-6}$ alkyl group, $C_{1-6}$ alkanoyl, benzoyl or optionally halogenated $C_{1-6}$ alkoxy-carbonyl,
(k) a thiol group optionally substituted with $C_{1-6}$ alkyl group, $C_{1-6}$ alkanoyl, benzoyl or optionally halogenated $C_{1-6}$ alkoxy-carbonyl,
(l) a carboxyl group,
(l') a $C_{1-6}$ alkoxy-carbonyl group,
(l") a $C_{7-12}$ aryloxycarbonyl group being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(l''') a $C_{6-10}$ aryl-$C_{1-4}$ alkoxy-carbonyl group being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(m) a carbamoyl group,
(m') a carbamoyl group having one substituent selected from the group consisting of
$C_{1-6}$ alkyl,
$C_{3-6}$ cycloalkyl,
$C_{6-10}$ aryl,
$C_{7-10}$ aralkyl and
heterocyclic groups selected from the group consisting of
(i) a 5- to 6-membered aromatic monocyclic heterocyclic group,
(ii) an 8- to 12-membered aromatic fused heterocyclic group and
(iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(m") a carbamoyl group having one substituent selected from the group consisting of
$C_{1-6}$ alkyl,
$C_{3-6}$ cycloalkyl,
$C_{6-10}$ aryl,
$C_{7-10}$ aralkyl and
heterocyclic groups selected from the group consisting of
(i) a 5- to 6-membered aromatic monocyclic heterocyclic group,
(ii) an 8- to 12-membered aromatic fused heterocyclic group and
(iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or $C_{1-6}$ alkoxy optionally substituted with 1 to 5 halogen atoms; and having another substituent selected from the group consisting of $C_{1-6}$ alkyl, $C_{3-6}$ cycloalkyl and $C_{7-10}$ aralkyl, (m''') a 3- to 8-membered cyclic amino-carbonyl group optionally having $C_{1-6}$ alkyl, $C_{7-10}$ aralkyl or $C_{6-10}$ aryl, (n) a thiocarbamoyl group, (n') a thiocarbamoyl group having one substituent selected from the group consisting of
$C_{1-6}$ alkyl,
$C_{3-6}$ cycloalkyl,
$C_{6-10}$ aryl,
$C_{7-10}$ aralkyl and
heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
  each of said alkyl, cycloalkyl, aryl, aralkyl and heterocyclic groups being unsubstituted or substituted by
  hydroxy,
  amino optionally having 1 to 2 substituents selected from the group consisting of $C_{1-6}$ alkyl, $C_{1-6}$ alkanoyl and benzoyl,
  halogen,
  nitro,
  cyano,
  $C_{1-6}$ alkyl optionally substituted with 1 to 5 halogen atoms or $C_{1-6}$ alkoxy optionally substituted with 1 to 5 halogen atoms, (n'') a thiocarbamoyl group having one substituent selected from the group consisting of
$C_{1-6}$ alkyl,
$C_{3-6}$ cycloalkyl,
$C_{6-10}$ aryl,
$C_{7-10}$ aralkyl and
heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic groups and containing 1 to 4 hetero-atoms selected from the group consisting of oxygen atom, sulfur atom and nitrogen atom besides carbon atoms;
  each of said alkyl, cycloalkyl, aryl, aralkyl and heterocyclic groups being unsubstituted or substituted by
  hydroxy,
  amino optionally having 1 to 2 substituents selected from the group consisting of $C_{1-6}$ alkyl,
  $C_{1-6}$ alkanoyl and benzoyl,
  halogen,
  nitro,
  cyano,
  $C_{1-6}$ alkyl optionally substituted with 1 to 5 halogen atoms or
  $C_{1-6}$ alkoxy optionally substituted with 1 to 5 halogen atoms; and having another substituent selected from the group consisting of $C_{1-6}$ alkyl, $C_{3-6}$ cycloalkyl and $C_{7-10}$ aralkyl, (n''') a 3- to 8-membered cyclic aminothiocarbonyl group optionally having $C_{1-6}$ alkyl, $C_{7-10}$ aralkyl or $C_{6-10}$ aryl, (o) a halogen atom, (p) a cyano group, (q) a nitro group, (r) a sulfonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
  each of said alkyl, cycloalkyl, aryl, aralkyl and heterocyclic groups being unsubstituted or substituted by
  hydroxy,
  amino optionally having 1 to 2 substituents selected from the group consisting of $C_{1-6}$ alkyl, $C_{1-6}$ alkanoyl and benzoyl,
  halogen,
  nitro,
  cyano,
  $C_{1-6}$ alkyl optionally substituted with 1 to 5 halogen atoms or
  $C_{1-6}$ alkoxy optionally substituted with 1 to 5 halogen atoms, (s) a formyl group and (s') a carbonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
  each of said alkyl, cycloalkyl, aryl, aralkyl and heterocyclic groups being unsubstituted or substituted by
  hydroxy,
  amino optionally having 1 to 2 substituents selected from the group consisting of $C_{1-6}$ alkyl, $C_{1-6}$ alkanoyl and benzoyl,
  halogen,
  nitro,
  cyano,
  $C_{1-6}$ alkyl optionally substituted with 1 to 5 halogen atoms or
  $C_{1-6}$ alkoxy optionally substituted with 1 to 5 halogen atoms;

wherein said ring A is optionally further substituted by
  (a) a hydroxy group,
  (b) a halogen atom,
  (c) a nitro group,
  (d) a cyano group, (e) an amino group optionally substituted with 1 or 2 substituents selected from the group consisting of
  (e-1) a $C_{1-6}$ alkyl group optionally substituted with $C_{1-6}$ alkoxy, halogen, $C_{1-6}$ alkyl, amino, hydroxy, cyano group or amidino,
  (e-2) a carbamoyl group,
  (e-2') a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
    (i) a 5- to 6-membered aromatic monocyclic heterocyclic group,
    (ii) an 8- to 12-membered aromatic fused heterocyclic group and
    (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
    each of said alkyl, cycloalkyl, aryl, aralkyl and heterocyclic groups being unsubstituted or substituted by
    hydroxy,
    amino optionally having 1 to 2 substituents selected from $C_{1-6}$ alkyl, $C_{1-6}$ alkanoyl and benzoyl,
    halogen,
    nitro,
    cyano,
    $C_{1-6}$ alkyl optionally substituted with 1 to 5 halogen atoms or
    $C_{1-6}$ alkoxy optionally substituted with 1 to 5 halogen atoms,
  (e-2") a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
    (i) a 5- to 6-membered aromatic monocyclic heterocyclic group,
    (ii) an 8- to 12-membered aromatic fused heterocyclic group and
    (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
    each of said alkyl, cycloalkyl, aryl, aralkyl and heterocyclic groups being unsubstituted or substituted by
    hydroxy,
    amino optionally having 1 to 2 substituents selected from the group consisting of $C_{1-6}$ alkyl, $C_{1-6}$ alkanoyl and benzoyl,
    halogen,
    nitro,
    cyano,
    $C_{1-6}$ alkyl optionally substituted with 1 to 5 halogen atoms or
    $C_{1-6}$ alkoxy optionally substituted with 1 to 5 halogen atoms;
    and having another substituent selected from the group consisting of $C_{1-6}$ alkyl, $C_{3-6}$ cycloalkyl and $C_{7-10}$ aralkyl,
  (e-2''') a 3- to 8-membered cyclic amino-carbonyl group optionally having $C_{1-6}$ alkyl, $C_{7-10}$ aralkyl or $C_{6-10}$ aryl,
  (e-3) a sulfonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
    (i) a 5- to 6-membered aromatic monocyclic heterocyclic group,
    (ii) an 8- to 12-membered aromatic fused heterocyclic group and
    (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
    each of said alkyl, cycloalkyl, aryl, aralkyl and heterocyclic groups being unsubstituted or substituted by
    hydroxy,
    amino optionally having 1 to 2 substituents selected from the group consisting of $C_{1-6}$ alkyl, $C_{1-6}$ alkanoyl and benzoyl,
    halogen,
    nitro,
    cyano,
    $C_{1-6}$ alkyl optionally substituted with 1 to 5 halogen atoms or
    $C_{1-6}$ alkoxy optionally substituted with 1 to 5 halogen atoms,
  (e-4) a formyl group and
  (e-4') a carbonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
    (i) a 5- to 6-membered aromatic monocyclic heterocyclic group,
    (ii) an 8- to 12-membered aromatic fused heterocyclic group and
    (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
    each of said alkyl, cycloalkyl, aryl, aralkyl and heterocyclic groups being unsubstituted or substituted by
    hydroxy,
    amino optionally having 1 to 2 substituents selected from the group consisting of $C_{1-6}$ alkyl, $C_{1-6}$ alkanoyl and benzoyl,
    halogen,
    nitro,
    cyano,
    $C_{1-6}$ alkyl optionally substituted with 1 to 5 halogen atoms or
    $C_{1-6}$ alkoxy optionally substituted with 1 to 5 halogen atoms,
(f) a $C_{1-6}$ alkyl group optionally substituted with halogen, amino, carboxyl or hydroxy,
(g) a $C_{1-6}$ alkoxy group optionally substituted with 1 to 5 halogen atoms,
(h) a carboxyl group,
(h') a $C_{1-6}$ alkoxy-carbonyl group,
(h") a $C_{7-12}$ aryloxycarbonyl group being unsubstituted or substituted by
  hydroxy,
  amino optionally having 1 to 2 substituents selected from the group consisting of $C_{1-6}$ alkyl, $C_{1-6}$ alkanoyl and benzoyl, halogen,
nitro,
cyano,
$C_{1-6}$ alkyl optionally substituted with 1 to 5 halogen atoms or
$C_{1-6}$ alkoxy optionally substituted with 1 to 5 halogen atoms,
(h''') a $C_{6-10}$ aryl-$C_{1-4}$ alkoxy-carbonyl group being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(i) a carbamoyl group,
(i') a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or $C_{1-6}$ alkoxy optionally substituted with 1 to 5 halogen atoms,
(i'') a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms;
and having another substituent selected from the group consisting of $C_{1-6}$ alkyl, $C_{3-6}$ cycloalkyl and $C_{7-10}$ aralkyl or
(i''') a 3- to 8-membered cyclic amino-carbonyl group optionally having $C_{1-6}$ alkyl, $C_{7-10}$ aralkyl or $C_{6-10}$ aryl;
Y is
(1) a $C_{3-9}$ cycloalkylene group,
(2) a $C_{3-6}$ cycloalkenylene group,
(3) a $C_{4-6}$ cycloalkanedienylene group,
(4) a $C_{6-10}$ arylene group,
(5) a $C_{7-10}$ aralkylene group,
(6) a 5- to 6-membered divalent aromatic heterocyclic group containing, besides carbon atoms, 1 to 3 hetero-atoms selected from the group consisting of oxygen atom, sulfur atom and nitrogen atom or
(7) a 5- to 6-membered divalent saturated or unsaturated non-aromatic heterocyclic group containing, besides carbon atoms, 1 to 3 hetero-atoms selected from the group consisting of oxygen atom, sulfur atom and nitrogen atom,
each of said groups (1)–(7) being unsubstituted or substituted by
  (a) a hydroxy group,
  (b) a halogen atom,
  (c) a nitro group,
  (d) a cyano group,
  (e) an amino group optionally substituted with 1 or 2 substituents selected from the group consisting of
    (e-1) a $C_{1-6}$ alkyl group optionally substituted with $C_{1-6}$ alkoxy, halogen, $C_{1-6}$ alkyl, amino, hydroxy, cyano group or amidino,
    (e-2) a carbamoyl group,
    (e-2') a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
      (i) a 5- to 6-membered aromatic monocyclic heterocyclic group,
      (ii) an 8- to 12-membered aromatic fused heterocyclic group and
      (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
    each of said alkyl, cycloalkyl, aryl, aralkyl and heterocyclic groups being unsubstituted or substituted by
    hydroxy,
    amino optionally having 1 to 2 substituents selected from the group consisting of $C_{1-6}$ alkyl, $C_{1-6}$ alkanoyl and benzoyl,
    halogen,
    nitro,
    cyano,
    $C_{1-6}$ alkyl optionally substituted with 1 to 5 halogen atoms or $C_{1-6}$ alkoxy optionally substituted with 1 to 5 halogen atoms, (e-2") a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
- (i) a 5- to 6-membered aromatic monocyclic heterocyclic group,
- (ii) an 8- to 12-membered aromatic fused heterocyclic group and
- (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by
- hydroxy,
- amino optionally having 1 to 2 substituents selected from the group consisting of $C_{1-6}$ alkyl, $C_{1-6}$ alkanoyl and benzoyl,
- halogen,
- nitro,
- cyano,
- $C_{1-6}$ alkyl optionally substituted with 1 to 5 halogen atoms or
- $C_{1-6}$ alkoxy optionally substituted with 1 to 5 halogen atoms;

and having another substituent selected from the group consisting of $C_{1-6}$ alkyl, $C_{3-6}$ cycloalkyl and $C_{7-10}$ aralkyl, (e-21'") a 3- to 8-membered cyclic amino-carbonyl group optionally having $C_{1-6}$ alkyl, $C_{7-10}$ aralkyl or $C_{6-10}$ aryl, (e-3) a sulfonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
- (i) a 5- to 6-membered aromatic monocyclic heterocyclic group,
- (ii) an 8- to 12-membered aromatic fused heterocyclic group and
- (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by
- hydroxy,
- amino optionally having 1 to 2 substituents selected from the group consisting of $C_{1-6}$ alkyl, $C_{1-6}$ alkanoyl and benzoyl,
- halogen,
- nitro,
- cyano,
- $C_{1-6}$ alkyl optionally substituted with 1 to 5 halogen atoms or $C_{1-6}$ alkoxy optionally substituted with 1 to 5 halogen atoms, (e-4) a formyl group and (e-4') a carbonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
- (i) a 5- to 6-membered aromatic monocyclic heterocyclic group,
- (ii) an 8- to 12-membered aromatic fused heterocyclic group and
- (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by
- hydroxy,
- amino optionally having 1 to 2 substituents selected from the group consisting of $C_{1-6}$ alkyl, $C_{1-6}$ alkanoyl and benzoyl,
- halogen,
- nitro,
- cyano,
- $C_{1-6}$ alkyl optionally substituted with 1 to 5 halogen atoms or
- $C_{1-6}$ alkoxy optionally substituted with 1 to 5 halogen atoms, (f) a $C_{1-6}$ alkyl group optionally substituted with halogen, amino, carboxyl or hydroxy, (g) a $C_{1-6}$ alkoxy group optionally substituted with 1 to 5 halogen atoms, (h) a carboxyl group, (h') a $C_{1-6}$ alkoxy-carbonyl group, (h") a $C_{7-12}$ aryloxycarbonyl group being unsubstituted or substituted by
- hydroxy,
- amino optionally having 1 to 2 substituents selected from the group consisting of $C_{1-6}$ alkyl, $C_{1-6}$ alkanoyl and benzoyl,
- halogen,
- nitro,
- cyano,
- $C_{1-6}$ alkyl optionally substituted with 1 to 5 halogen atoms or
- $C_{1-6}$ alkoxy optionally substituted with 1 to 5 halogen atoms, (h'") a $C_{6-10}$ aryl-$C_{1-4}$ alkoxy-carbonyl group being unsubstituted or substituted by
- hydroxy,
- amino optionally having 1 to 2 substituents selected from the group consisting of $C_{1-6}$ alkyl, $C_{1-6}$ alkanoyl and benzoyl,
- halogen,
- nitro,
- cyano,
- $C_{1-6}$ alkyl optionally substituted with 1 to 5 halogen atoms or
- $C_{1-6}$ alkoxy optionally substituted with 1 to 5 halogen atoms, (i) a carbamoyl group, (i') a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
- (i) a 5- to 6-membered aromatic monocyclic heterocyclic group,
- (ii) an 8- to 12-membered aromatic fused heterocyclic group and
- (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms, (i") a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
(i) a 5- to 6-membered aromatic monocyclic heterocyclic group,
(ii) an 8- to 12-membered aromatic fused heterocyclic group and
(iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms;

and having another substituent selected from the group consisting of $C_{1-6}$ alkyl, $C_{3-6}$ cycloalkyl and $C_{7-10}$ aralkyl or (i''') a 3- to 8-membered cyclic amino-carbonyl group optionally having $C_{1-6}$ alkyl, $C_{7-10}$ aralkyl or $C_{6-10}$ aryl;

X is
(1) a direct bond or (2) a straight-chain lower ($C_{1-6}$) alkylene optionally substituted with
(a) a $C_{1-6}$ alkyl group,
(b) a halogen atom,
(c) a hydroxy group,
(d) a carboxyl group,
(d') a $C_{1-6}$ alkoxy-carbonyl group,
(d") a $C_{7-12}$ aryloxycarbonyl group being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms or (d''') a $C_{6-10}$ aryl-$C_{1-4}$ alkoxy-carbonyl group being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms; and Z is
(1) an amino group substituted with 1 or 2 substituents selected from the group consisting of (1-1) a $C_{1-10}$ alkyl group, (1-2) a $C_{2-6}$ alkenyl group, (1-3) a $C_{2-6}$ alkynyl group, (1-4) a $C_{3-9}$ cycloalkyl group, (1-5) a $C_{3-6}$ cycloalkenyl group, (1-6) a $C_{1-6}$ cycloalkanedienyl group and (1-7) a $C_{6-14}$ aryl group;

each of said groups (1-1)–(1-7) being unsubstituted or substituted by 1 to 5 substituents selected from the group consisting of
(a) a $C_{1-6}$ alkyl group optionally substituted with $C_{1-6}$ alkoxy, halogen, $C_{1-6}$ alkyl, amino, hydroxy, cyano group or amidino,
(b) a $C_{2-6}$ alkenyl group optionally substituted with $C_{1-6}$ alkoxy, halogen, $C_{1-6}$ alkyl, amino, hydroxy, cyano group or amidino,
(c) a $C_{2-6}$ alkynyl group optionally substituted with $C_{1-6}$ alkoxy, halogen, $C_{1-6}$ alkyl, amino, hydroxy, cyano group or amidino,
(d) a $C_{6-14}$ aryl group optionally substituted with $C_{1-6}$ alkoxy, halogen, $C_{1-6}$ alkyl, amino, hydroxy, cyano group or amidino,
(e) a $C_{3-7}$ cycloalkyl or $C_{3-6}$ cycloalkenyl group optionally substituted with $C_{1-6}$ alkoxy, halogen, $C_{1-6}$ alkyl, amino, hydroxy, cyano group or amidino,
(f) a heterocyclic group selected from the group consisting of
(i) a 5- to 6-membered aromatic monocyclic heterocyclic group,
(ii) an 8- to 12-membered aromatic fused heterocyclic group and
(iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms, which may be substituted by $C_{1-6}$ alkyl, $C_{1-6}$ alkanoyl or benzoyl,
(g) an amino group optionally substituted with $C_{1-6}$ alkyl group, $C_{1-6}$ alkanoyl, benzoyl, optionally halogenated $C_{1-6}$ alkoxy-carbonyl, $C_{1-6}$ alkylimidoyl, formimidoyl or amidino,
(g') a 3- to 8-membered cyclic amino group optionally having $C_{1-6}$ alkyl, $C_{7-10}$ aralkyl or $C_{6-10}$ aryl,
(h) an imidoyl group optionally substituted with $C_{1-6}$ alkyl group, $C_{1-6}$ alkanoyl, benzoyl or optionally halogenated $C_{1-6}$ alkoxy-carbonyl,
(i) an amidino group optionally substituted with $C_{1-6}$ alkyl group, $C_{1-6}$ alkanoyl, benzoyl or optionally halogenated $C_{1-6}$ alkoxy-carbonyl,
(j) a hydroxy group optionally substituted with $C_{1-6}$ alkyl group, $C_{1-6}$ alkanoyl, benzoyl or optionally halogenated $C_{1-6}$ alkoxy-carbonyl, (k) a thiol group optionally substituted with $C_{1-6}$ alkyl group, $C_{1-6}$ alkanoyl, benzoyl or optionally halogenated $C_{1-6}$ alkoxy-carbonyl,
(l) a carboxyl group,
(l') a $C_{1-6}$ alkoxy-carbonyl group,
(l") a $C_{7-12}$ aryloxycarbonyl group being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(l''') a $C_{6-10}$ aryl-$C_{1-4}$ alkoxy-carbonyl group being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(m) a carbamoyl group,
(m') a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
 (i) a 5- to 6-membered aromatic monocyclic heterocyclic group,
 (ii) an 8- to 12-membered aromatic fused heterocyclic group and
 (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(m") a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
 (i) a 5- to 6-membered aromatic monocyclic heterocyclic group,
 (ii) an 8- to 12-membered aromatic fused heterocyclic group and
 (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms;
and having another substituent selected from the group consisting of $C_{1-6}$ alkyl, $C_{3-6}$ cycloalkyl and $C_{7-10}$ aralkyl,
(m''') a 3- to 8-membered cyclic amino-carbonyl group optionally having $C_{1-6}$ alkyl, $C_{7-10}$ aralkyl or $C_{6-10}$ aryl,
(n) a thiocarbamoyl group,
(n') a thiocarbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
 (i) a 5- to 6-membered aromatic monocyclic heterocyclic group,
 (ii) an 8- to 12-membered aromatic fused heterocyclic group and
 (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(n") a thiocarbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
 (i) a 5- to 6-membered aromatic monocyclic heterocyclic group,
 (ii) an 8- to 12-membered aromatic fused heterocyclic group and
 (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms;
and having another substituent selected from the group consisting of $C_{1-6}$ alkyl, $C_{3-6}$ cycloalkyl and $C_{7-10}$ aralkyl,
(n''') a 3- to 8-membered cyclic aminothiocarbonyl group optionally having $C_{1-6}$ alkyl, $C_{7-10}$ aralkyl or $C_{6-10}$ aryl,
(o) a halogen atom,
(p) a cyano group,
(q) a nitro group,
(r) a sulfonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(s) a formyl group and
(s') a carbonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms;
(1A) a 3- to 8-membered cyclic amino group optionally having $C_{1-6}$ alkyl, $C_{7-10}$ aralkyl or $C_{6-10}$ aryl, and said cyclic amino group being unsubstituted or substituted by 1 to 5 substituents selected from the group consisting of
(a) a $C_{1-6}$ alkyl group optionally substituted with $C_{1-6}$ alkoxy, halogen, $C_{1-6}$ alkyl, amino, hydroxy, cyano group or amidino,
(b) a $C_{2-6}$ alkenyl group optionally substituted with $C_{1-6}$ alkoxy, halogen, $C_{3-6}$ alkyl, amino, hydroxy, cyano group or amidino,
(c) a $C_{2-6}$ alkynyl group optionally substituted with $C_{1-6}$ alkoxy, halogen, $C_{1-6}$ alkyl, amino, hydroxy, cyano group or amidino,
(d) a $C_{6-14}$ aryl group optionally substituted with $C_{1-6}$ alkoxy, halogen, $C_{1-6}$ alkyl, amino, hydroxy, cyano group or amidino,
(e) a $C_{3-7}$ cycloalkyl or $C_{3-6}$ cycloalkenyl group optionally substituted with $C_{1-6}$ alkoxy, halogen, $C_{1-6}$ alkyl, amino, hydroxy, cyano group or amidino,
(f) a heterocyclic group selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms, which may be substituted by $C_{1-6}$ alkyl, $C_{1-6}$ alkanoyl or benzoyl,
(g) an amino group optionally substituted with $C_{1-6}$ alkyl group, $C_{1-6}$ alkanoyl, benzoyl, optionally halogenated $C_{1-6}$ alkoxy-carbonyl, $C_{1-6}$ alkylimidoyl, formimidoyl or amidino,
(g') a 3- to 8-membered cyclic amino group optionally having $C_{1-6}$ alkyl, $C_{7-10}$ aralkyl or $C_{6-10}$ aryl,
(h) an imidoyl group optionally substituted with $C_{1-6}$ alkyl group, $C_{1-6}$ alkanoyl, benzoyl or optionally halogenated $C_{1-6}$ alkoxy-carbonyl,
(i) an amidino group optionally substituted with $C_{1-6}$ alkyl group, $C_{1-6}$ alkanoyl, benzoyl or optionally halogenated $C_{1-6}$ alkoxy-carbonyl,
(j) a hydroxy group optionally substituted with $C_{1-6}$ alkyl group, $C_{1-6}$ alkanoyl, benzoyl or optionally halogenated $C_{1-6}$ alkoxy-carbonyl,
(k) a thiol group optionally substituted with $C_{1-6}$ alkyl group, $C_{1-6}$ alkanoyl, benzoyl or optionally halogenated $C_{1-6}$ alkoxy-carbonyl,
(l) a carboxyl group,
(l') a $C_{1-6}$ alkoxy-carbonyl group,
(l'') a $C_{7-12}$ aryloxycarbonyl group being unsubstituted or substituted by
hydroxy,
amino optionally having 1 to 2 substituents selected from the group consisting of $C_{1-6}$ alkyl, $C_{1-6}$ alkanoyl and benzoyl, halogen,
nitro,
cyano,
$C_{1-6}$ alkyl optionally substituted with 1 to 5 halogen atoms or
$C_{1-6}$ alkoxy optionally substituted with 1 to 5 halogen atoms,
(1''') a $C_{6-10}$ aryl-$C_{1-4}$ alkoxy-carbonyl group being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(m) a carbamoyl group,
(m') a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(m'') a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms; and having another substituent selected from the group consisting of $C_{1-6}$ alkyl, $C_{3-6}$ cycloalkyl and $C_{7-10}$ aralkyl,
(m''') a 3- to 8-membered cyclic amino-carbonyl group optionally having $C_{1-6}$ alkyl, $C_{7-10}$ aralkyl or $C_{6-10}$ aryl,
(n) a thiocarbamoyl group,
(n') a thiocarbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(n'') a thiocarbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms;
and having another substituent selected from the group consisting of $C_{1-6}$ alkyl, $C_{3-6}$ cycloalkyl and $C_{7-10}$ aralkyl, (n''') a 3- to 8-membered cyclic aminothiocarbonyl group optionally having $C_{1-6}$ alkyl, $C_{7-10}$ aralkyl or $C_{6-10}$ aryl, (o) a halogen atom, (p) a cyano group, (q) a nitro group, (r) a sulfonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms, (s) a formyl group and (s') a carbonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms;

(1B) a group of the formula: —N(R'')—C(R')=N—R wherein R'' is
(i) a hydrogen atom or
(ii) a hydrocarbon group selected from the group consisting of a $C_{1-10}$ alkyl group, a $C_{2-6}$ alkenyl group, a $C_{2-6}$ alkynyl group, a $C_{3-9}$ cycloalkyl group, a $C_{3-6}$ cycloalkenyl group, a $C_{1-6}$ cycloalkanedienyl group and a $C_{6-14}$ aryl group;

each of said hydrocarbon groups being unsubstituted or substituted by 1 to 5 substituents selected from the group consisting of (a) a $C_{1-6}$ alkyl group optionally substituted with $C_{1-6}$ alkoxy, halogen, $C_{1-6}$ alkyl, amino, hydroxy, cyano group or amidino, (b) a $C_{2-6}$ alkenyl group optionally substituted with $C_{1-6}$ alkoxy, halogen, $C_{1-6}$ alkyl, amino, hydroxy, cyano group or amidino, (c) a $C_{2-6}$ alkynyl group optionally substituted with $C_{1-6}$ alkoxy, halogen, $C_{1-6}$ alkyl, amino, hydroxy, cyano group or amidino, (d) a $C_{6-14}$ aryl group optionally substituted with $C_{1-6}$ alkoxy, halogen, $C_{1-6}$ alkyl, amino, hydroxy, cyano group or amidino, (e) a $C_{3-7}$ cycloalkyl or $C_{3-6}$ cycloalkenyl group optionally substituted with $C_{1-6}$ alkoxy, halogen, $C_{1-6}$ alkyl, amino, hydroxy, cyano group or amidino, (f) a heterocyclic group selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms,
which may be substituted by $C_{1-6}$ alkyl, $C_{1-6}$ alkanoyl or benzoyl, (g) an amino group optionally substituted with $C_{1-6}$ alkyl group, $C_{1-6}$ alkanoyl, benzoyl, optionally halogenated $C_{1-6}$ alkoxy-carbonyl, $C_{1-6}$ alkylimidoyl, formimidoyl or amidino, (g') a 3- to 8-membered cyclic amino group optionally having $C_{1-6}$ alkyl, $C_{7-10}$ aralkyl or $C_{6-10}$ aryl, (h) an imidoyl group optionally substituted with $C_{1-6}$ alkyl group, $C_{1-6}$ alkanoyl, benzoyl or optionally halogenated $C_{1-6}$ alkoxy-carbonyl, (i) an amidino group optionally substituted with $C_{1-6}$ alkyl group, $C_{1-6}$ alkanoyl, benzoyl or optionally halogenated $C_{1-6}$ alkoxy-carbonyl, (j) a hydroxy group optionally substituted with $C_{1-6}$ alkyl group, $C_{1-6}$ alkanoyl, benzoyl or optionally halogenated $C_{1-6}$ alkoxy-carbonyl, (k) a thiol group optionally substituted with $C_{1-6}$ alkyl group, $C_{1-6}$ alkanoyl, benzoyl or optionally halogenated $C_{1-6}$ alkoxy-carbonyl, (l) a carboxyl group, (l') a $C_{1-6}$ alkoxy-carbonyl group, (l'') a $C_{7-12}$ aryloxycarbonyl group being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms, (l''') a $C_{6-10}$ aryl-$C_{1-4}$ alkoxy-carbonyl group being unsubstituted or substituted by
hydroxy, amino optionally having 1 to 2 substituents selected from the group consisting of $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (m) a carbamoyl group, (m') a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by hydroxy, amino optionally having 1 to 2 substituents selected from the group consisting of $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (m") a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by hydroxy, amino optionally having 1 to 2 substituents selected from the group consisting of $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms;

and having another substituent selected from the group consisting of $C_{1-6}$ alkyl, $C_{3-6}$ cycloalkyl and $C_{7-10}$ aralkyl, (m''') a 3- to 8-membered cyclic amino-carbonyl group optionally having $C_{1-6}$ alkyl, $C_{7-10}$ aralkyl or $C_{6-10}$ aryl, (n) a thiocarbamoyl group, (n') a thiocarbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by hydroxy, amino optionally having 1 to 2 substituents selected from the group consisting of $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (n") a thiocarbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by hydroxy, amino optionally having 1 to 2 substituents selected from the group consisting of $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms;

and having another substituent selected from the group consisting of $C_{1-6}$ alkyl, $C_{3-6}$ cycloalkyl and $C_{7-10}$ aralkyl, (n''') a 3- to 8-membered cyclic aminothiocarbonyl group optionally having $C_{1-6}$ alkyl, $C_{7-10}$ aralkyl or $C_{6-10}$ aryl, (o) a halogen atom, (p) a cyano group, (q) a nitro group, (r) a sulfonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
  each of said alkyl, cycloalkyl, aryl, aralkyl and heterocyclic groups being unsubstituted or substituted by
  hydroxy,
  amino optionally having 1 to 2 substituents selected from the group consisting of $C_{1-6}$ alkyl, $C_{1-6}$ alkanoyl and benzoyl,
  halogen,
  nitro,
  cyano,
  $C_{1-6}$ alkyl optionally substituted with 1 to 5 halogen atoms or
  $C_{1-6}$ alkoxy optionally substituted with 1 to 5 halogen atoms,
(s) a formyl group and
(s') a carbonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
  each of said alkyl, cycloalkyl, aryl, aralkyl and heterocyclic groups being unsubstituted or substituted by
  hydroxy,
  amino optionally having 1 to 2 substituents selected from the group consisting of $C_{1-6}$ alkyl, $C_{1-6}$ alkanoyl and benzoyl,
  halogen,
  nitro,
  cyano,
  $C_{1-6}$ alkyl optionally substituted with 1 to 5 halogen atoms or
  $C_{1-6}$ alkoxy optionally substituted with 1 to 5 halogen atoms, R is
(i) a hydrogen atom,
(ii) a hydrocarbon group selected from the group consisting of a $C_{1-10}$ alkyl group, a $C_{2-6}$ alkenyl group, a $C_{2-6}$ alkynyl group, a $C_{3-9}$ cycloalkyl group, a $C_{3-6}$ cycloalkenyl group, a $C_{4-6}$ cycloalkanedienyl group and a $C_{6-14}$ aryl group;
each of said hydrocarbon groups being unsubstituted or substituted by 1 to 5 substituents selected from the group consisting of
  (a) a $C_{1-6}$ alkyl group optionally substituted with $C_{1-6}$ alkoxy, halogen, $C_{1-6}$ alkyl, amino, hydroxy, cyano group or amidino,
  (b) a $C_{2-6}$ alkenyl group optionally substituted with $C_{1-6}$ alkoxy, halogen, $C_{1-6}$ alkyl, amino, hydroxy, cyano group or amidino,
  (c) a $C_{2-6}$ alkynyl group optionally substituted with $C_{1-6}$ alkoxy, halogen, $C_{1-6}$ alkyl, amino, hydroxy, cyano group or amidino,
  (d) a $C_{6-14}$ aryl group optionally substituted with $C_{1-6}$ alkoxy, halogen, $C_{1-6}$ alkyl, amino, hydroxy, cyano group or amidino,
  (e) a $C_{3-7}$ cycloalkyl or $C_{3-6}$ cycloalkenyl group optionally substituted with $C_{1-6}$ alkoxy, halogen, $C_{1-6}$ alkyl, amino, hydroxy, cyano group or amidino,
  (f) a heterocyclic group selected from the group consisting of
    (i) a 5- to 6-membered aromatic monocyclic heterocyclic group,
    (ii) an 8- to 12-membered aromatic fused heterocyclic group and
    (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms, which may be substituted by $C_{1-6}$ alkyl, $C_{1-6}$ alkanoyl or benzoyl,
  (g) an amino group optionally substituted with $C_{1-6}$ alkyl group, $C_{1-6}$ alkanoyl, benzoyl, optionally halogenated $C_{1-6}$ alkoxy-carbonyl, $C_{1-6}$ alkylimidoyl, formimidoyl or amidino,
  (g') a 3- to 8-membered cyclic amino group optionally having $C_{1-6}$ alkyl, $C_{7-10}$ aralkyl or $C_{6-10}$ aryl,
  (h) an imidoyl group optionally substituted with $C_{1-6}$ alkyl group, $C_{1-6}$ alkanoyl, benzoyl or optionally halogenated $C_{1-6}$ alkoxy-carbonyl,
  (i) an amidino group optionally substituted with $C_{1-6}$ alkyl group, $C_{1-6}$ alkanoyl, benzoyl or optionally halogenated $C_{1-6}$ alkoxy-carbonyl,
  (j) a hydroxy group optionally substituted with $C_{1-6}$ alkyl group, $C_{1-6}$ alkanoyl, benzoyl or optionally halogenated $C_{1-6}$ alkoxy-carbonyl,
  (k) a thiol group optionally substituted with $C_{1-6}$ alkyl group, $C_{1-6}$ alkanoyl, benzoyl or optionally halogenated $C_{1-6}$ alkoxy-carbonyl,
  (l) a carboxyl group,
  (l') a $C_{1-6}$ alkoxy-carbonyl group,
  (l") a $C_{7-12}$ aryloxycarbonyl group being unsubstituted or substituted by
    hydroxy,
    amino optionally having 1 to 2 substituents selected from the group consisting of $C_{1-6}$ alkyl, $C_{1-6}$ alkanoyl and benzoyl,
    halogen,
    nitro,
    cyano,
    $C_{1-6}$ alkyl optionally substituted with 1 to 5 halogen atoms or
    $C_{1-6}$ alkoxy optionally substituted with 1 to 5 halogen atoms,
  (l''') a $C_{6-10}$ aryl-$C_{1-4}$ alkoxy-carbonyl group being unsubstituted or substituted by
    hydroxy,
    amino optionally having 1 to 2 substituents selected from the group consisting of $C_{1-6}$ alkyl, $C_{1-6}$ alkanoyl and benzoyl,
    halogen,
    nitro,
    cyano,
    $C_{1-6}$ alkyl optionally substituted with 1 to 5 halogen atoms or $C_{1-6}$ alkoxy optionally substituted with 1 to 5 halogen atoms,
(m) a carbamoyl group,
(m') a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(m") a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms;
and having another substituent selected from the group consisting of $C_{1-6}$ alkyl, $C_{3-6}$ cycloalkyl and $C_{7-10}$ aralkyl,
(m''') a 3- to 8-membered cyclic amino-carbonyl group optionally having $C_{1-6}$ alkyl, $C_{7-10}$ aralkyl or $C_{6-10}$ aryl,
(n) a thiocarbamoyl group,
(n') a thiocarbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(n") a thiocarbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms;
and having another substituent selected from the group consisting of $C_{1-6}$ alkyl, $C_{3-6}$ cycloalkyl and $C_{7-10}$ aralkyl,
(n''') a 3- to 8-membered cyclic aminothiocarbonyl group optionally having $C_{1-6}$ alkyl, $C_{7-10}$ aralkyl or $C_{6-10}$ aryl,
(o) a halogen atom,
(p) a cyano group,
(q) a nitro group,
(r) a sulfonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(s) a formyl group and
(s') a carbonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
(i) a 5- to 6-membered aromatic monocyclic heterocyclic group,
(ii) an 8- to 12-membered aromatic fused heterocyclic group and
(iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms, or
(iii) a carbonyl group having a hydrogen atom or one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
(i) a 5- to 6-membered aromatic monocyclic heterocyclic group,
(ii) an 8- to 12-membered aromatic fused heterocyclic group and
(iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms, and R' is
(i) a hydrogen atom,
(ii) a hydrocarbon group selected from the group consisting of a $C_{1-10}$ alkyl group, a $C_{2-6}$ alkenyl group, a $C_{2-6}$ alkynyl group, a $C_{3-9}$ cycloalkyl group, a $C_{3-6}$ cycloalkenyl group, a $C_{4-6}$ cycloalkanedienyl group and a $C_{6-14}$ aryl group;
each of said hydrocarbon groups being unsubstituted or substituted by 1 to 5 substituents selected from the group consisting of
(a) a $C_{1-6}$ alkyl group optionally substituted with $C_{1-6}$ alkoxy, halogen, $C_{1-6}$ alkyl, amino, hydroxy, cyano group or amidino,
(b) a $C_{2-6}$ alkenyl group optionally substituted with $C_{1-6}$ alkoxy, halogen, $C_{1-6}$ alkyl, amino, hydroxy, cyano group or amidino,
(c) a $C_{2-6}$ alkynyl group optionally substituted with $C_{1-6}$ alkoxy, halogen, $C_{1-6}$ alkyl, amino, hydroxy, cyano group or amidino,
(d) a $C_{6-14}$ aryl group optionally substituted with $C_{1-6}$ alkoxy, halogen, $C_{1-6}$ alkyl, amino, hydroxy, cyano group or amidino,
(e) a $C_{3-7}$ cycloalkyl or $C_{3-6}$ cycloalkenyl group optionally substituted with $C_{1-6}$ alkoxy, halogen, $C_{1-6}$ alkyl, amino, hydroxy, cyano group or amidino,
(f) a heterocyclic group selected from the group consisting of
(i) a 5- to 6-membered aromatic monocyclic heterocyclic group,
(ii) an 8- to 12-membered aromatic fused heterocyclic group and
(iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms,
which may be substituted by $C_{1-6}$ alkyl, $C_{1-6}$ alkanoyl or benzoyl,
(g) an amino group optionally substituted with $C_{1-6}$ alkyl group, $C_{1-6}$ alkanoyl, benzoyl, optionally halogenated $C_{1-6}$ alkoxy-carbonyl, $C_{1-6}$ alkylimidoyl, formimidoyl or amidino,
(g') a 3- to 8-membered cyclic amino group optionally having $C_{1-6}$ alkyl, $C_{7-10}$ aralkyl or $C_{6-10}$ aryl,
(h) an imidoyl group optionally substituted with $C_{1-6}$ alkyl group, $C_{1-6}$ alkanoyl, benzoyl or optionally halogenated $C_{3-6}$ alkoxy-carbonyl,
(i) an amidino group optionally substituted with $C_{1-6}$ alkyl group, $C_{1-6}$ alkanoyl, benzoyl or optionally halogenated $C_{1-6}$ alkoxy-carbonyl,
(j) a hydroxy group optionally substituted with $C_{1-6}$ alkyl group, $C_{1-6}$ alkanoyl, benzoyl or optionally halogenated $C_{1-6}$ alkoxy-carbonyl,
(k) a thiol group optionally substituted with $C_{1-6}$ alkyl group, $C_{1-6}$ alkanoyl, benzoyl or optionally halogenated $C_{1-6}$ alkoxy-carbonyl,
(l) a carboxyl group,
(l') a $C_{1-6}$ alkoxy-carbonyl group,
(l") a $C_{7-12}$ aryloxycarbonyl group being unsubstituted or substituted by hydroxy,
amino optionally having 1 to 2 substituents selected from the group consisting of $C_{16}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(l''') a $C_{6-10}$ aryl-C, alkoxy-carbonyl group being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(m) a carbamoyl group,
(m') a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(m'') a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms;
and having another substituent selected from the group consisting of $C_{1-6}$ alkyl, $C_{3-6}$ cycloalkyl and $C_{7-10}$ aralkyl,
(m''') a 3- to 8-membered cyclic amino-carbonyl group optionally having $C_{1-6}$ alkyl, $C_{7-10}$ aralkyl or $C_{6-10}$ aryl,
(n) a thiocarbamoyl group,
(n') a thiocarbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms,
(n'') a thiocarbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro, cyano, $C_{1-6}$ alkyl optionally substituted with 1 to 5 halogen atoms or $C_{1-6}$ alkoxy optionally substituted with 1 to 5 halogen atoms;

and having another substituent selected from the group consisting of $C_{1-6}$ alkyl, $C_{3-6}$ cycloalkyl and $C_{7-10}$ aralkyl, (n''') a 3- to 8-membered cyclic aminothiocarbonyl group optionally having $C_{1-6}$ alkyl, $C_{7-10}$ aralkyl or $C_{6-10}$ aryl, (o) a halogen atom, (p) a cyano group, (q) a nitro group, (r) a sulfonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic groups and containing 1 to 4 hetero-atoms selected from the group consisting of oxygen atom, sulfur atom and nitrogen atom besides carbon atoms;
  each of said alkyl, cycloalkyl, aryl, aralkyl and heterocyclic groups being unsubstituted or substituted by
    hydroxy,
    amino optionally having 1 to 2 substituents selected from the group consisting of $C_{1-6}$ alkyl, $C_{1-6}$ alkanoyl and benzoyl,
    halogen,
    nitro,
    cyano,
    $C_{1-6}$ alkyl optionally substituted with 1 to 5 halogen atoms or
    $C_{1-6}$ alkoxy optionally substituted with 1 to 5 halogen atoms, (s) a formyl group and (s') a carbonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
  each of said alkyl, cycloalkyl, aryl, aralkyl and heterocyclic groups being unsubstituted or substituted by
    hydroxy,
    amino optionally having 1 to 2 substituents selected from the group consisting of $C_{1-6}$ alkyl, $C_{1-6}$ alkanoyl and benzoyl,
    halogen,
    nitro,
    cyano,
    $C_{1-6}$ alkyl optionally substituted with 1 to 5 halogen atoms or
    $C_{1-6}$ alkoxy optionally substituted with 1 to 5 halogen atoms, (iii) a carbonyl group having a hydrogen atom or one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
  (i) a 5- to 6-membered aromatic monocyclic heterocyclic group,
  (ii) an 8- to 12-membered aromatic fused heterocyclic group and
  (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
  each of said alkyl, cycloalkyl, aryl, aralkyl and heterocyclic groups being unsubstituted or substituted by
    hydroxy,
    amino optionally having 1 to 2 substituents selected from the group consisting of $C_{1-6}$ alkyl, $C_{1-6}$ alkanoyl and benzoyl,
    halogen,
    nitro,
    cyano,
    $C_{1-6}$ alkyl optionally substituted with 1 to 5 halogen atoms or
    $C_{1-6}$ alkoxy optionally substituted with 1 to 5 halogen atoms, (iv) an amino group optionally substituted with $C_{1-6}$ alkyl group, $C_{1-6}$ alkanoyl, benzoyl, optionally halogenated $C_{1-6}$ alkoxy-carbonyl, $C_{1-6}$ alkylimidoyl, formimidoyl or amidino, (iv') a 3- to 8-membered cyclic amino group optionally having $C_{1-6}$ alkyl, $C_{7-10}$ aralkyl or $C_{6-10}$ aryl, (iv") an amino group substituted with 1 or 2 substituents selected from the group consisting of
  (1-1) a $C_{1-10}$ alkyl group,
  (1-2) a $C_{2-6}$ alkenyl group,
  (1-3) a $C_{2-6}$ alkynyl group,
  (1-4) a $C_{3-9}$ cycloalkyl group,
  (1-5) a $C_{3-6}$ cycloalkenyl group,
  (1-6) a $C_{4-6}$ cycloalkanedienyl group and
  (1-7) a $C_{6-14}$ aryl group;
  each of said groups (1-1)–(1-7) being unsubstituted or substituted by 1 to 5 substituents selected from the group consisting of
    (a) a $C_{1-6}$ alkyl group optionally substituted with $C_{1-6}$ alkoxy, halogen, $C_{1-6}$ alkyl, amino, hydroxy, cyano group or amidino,
    (b) a $C_{2-6}$ alkenyl group optionally substituted with $C_{1-6}$ alkoxy, halogen, $C_{1-6}$ alkyl, amino, hydroxy, cyano group or amidino,
    (c) a $C_{2-6}$ alkynyl group optionally substituted with $C_{1-6}$ alkoxy, halogen, $C_{1-6}$ alkyl, amino, hydroxy, cyano group or amidino,
    (d) a $C_{6-14}$ aryl group optionally substituted with $C_{1-6}$ alkoxy, halogen, $C_{1-6}$ alkyl, amino, hydroxy, cyano group or amidino,
    (e) a $C_{3-7}$ cycloalkyl or $C_{3-6}$ cycloalkenyl group optionally substituted with $C_{1-6}$ alkoxy, halogen, $C_{1-6}$ alkyl, amino, hydroxy, cyano group or amidino,
    (f) a heterocyclic group selected from the group consisting of
      (i) a 5- to 6-membered aromatic monocyclic heterocyclic group, (ii) an 8- to 12-membered aromatic fused heterocyclic group and (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms, which may be substituted by $C_{1-6}$ alkyl, $C_{1-6}$ alkanoyl or benzoyl, (g) an amino group optionally substituted with $C_{1-6}$ alkyl group, $C_{1-6}$ alkanoyl, benzoyl, optionally halogenated $C_{1-6}$ alkoxy-carbonyl, $C_{1-6}$ alkylimidoyl, formimidoyl or amidino, (g') a 3- to 8-membered cyclic amino group optionally having $C_{1-6}$ alkyl, $C_{7-10}$ aralkyl or $C_{6-10}$ aryl, (h) an imidoyl group optionally substituted with $C_{1-6}$ alkyl group, $C_{1-6}$ alkanoyl, benzoyl or optionally halogenated $C_{1-6}$ alkoxy-carbonyl, (i) an amidino group optionally substituted with $C_{1-6}$ alkyl group, $C_{1-6}$ alkanoyl, benzoyl or optionally halogenated $C_{1-6}$ alkoxy-carbonyl, (j) a hydroxy group optionally substituted with $C_{1-6}$ alkyl group, $C_{1-6}$ alkanoyl, benzoyl or optionally halogenated $C_{1-6}$ alkoxy-carbonyl, (k) a thiol group optionally substituted with $C_{1-6}$ alkyl group, $C_{1-6}$ alkanoyl, benzoyl or optionally halogenated $C_{1-6}$ alkoxy-carbonyl, (l) a carboxyl group, (l') a $C_{1-6}$ alkoxy-carbonyl group, (l") a $C_{7-12}$ aryloxycarbonyl group being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms, (l'") a $C_{6-10}$ aryl-$C_{1-4}$ alkoxy-carbonyl group being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms, (m) a carbamoyl group, (m') a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
(i) a 5- to 6-membered aromatic monocyclic heterocyclic group,
(ii) an 8- to 12-membered aromatic fused heterocyclic group and
(iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms, (m") a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
(i) a 5- to 6-membered aromatic monocyclic heterocyclic group,
(ii) an 8- to 12-membered aromatic fused heterocyclic group and
(iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
hydroxy,
amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms;
and having another substituent selected from the group consisting of $C_{1-6}$ alkyl, $C_{3-6}$ cycloalkyl and $C_{7-10}$ aralkyl, (m'") a 3- to 8-membered cyclic amino-carbonyl group optionally having $C_{1-6}$ alkyl, $C_{7-10}$ aralkyl or $C_{6-10}$ aryl, (n) a thiocarbamoyl group, (n') a thiocarbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
(i) a 5- to 6-membered aromatic monocyclic heterocyclic group,
(ii) an 8- to 12-membered aromatic fused heterocyclic group and
(iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by hydroxy,
   amino optionally having 1 to 2 substituents selected from the group consisting of $C_{1-6}$ alkyl, $C_{1-6}$ alkanoyl and benzoyl,
halogen,
nitro,
cyano,
$C_{1-6}$ alkyl optionally substituted with 1 to 5 halogen atoms or
$C_{1-6}$ alkoxy optionally substituted with 1 to 5 halogen atoms, (n") a thiocarbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
   (i) a 5- to 6-membered aromatic monocyclic heterocyclic group,
   (ii) an 8- to 12-membered aromatic fused heterocyclic group and
   (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
   hydroxy,
   amino optionally having 1 to 2 substituents selected from the group consisting of $C_{1-6}$ alkyl, $C_{1-6}$ alkanoyl and benzoyl,
   halogen,
   nitro,
   cyano,
   $C_{1-6}$ alkyl optionally substituted with 1 to 5 halogen atoms or
   $C_{1-6}$ alkoxy optionally substituted with 1 to 5 halogen atoms;
and having another substituent selected from the group consisting of $C_{1-6}$ alkyl, $C_{3-6}$ cycloalkyl and $C_{7-10}$ aralkyl, (n''') a 3- to 8-membered cyclic aminothiocarbonyl group optionally having $C_{1-6}$ alkyl, $C_{7-10}$ aralkyl or $C_{6-10}$ aryl,
(o) a halogen atom,
(p) a cyano group,
(q) a nitro group,
(r) a sulfonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
   (i) a 5- to 6-membered aromatic monocyclic heterocyclic group,
   (ii) an 8- to 12-membered aromatic fused heterocyclic group and
   (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
   hydroxy,
   amino optionally having 1 to 2 substituents selected from the group consisting of $C_{1-6}$ alkyl, $C_{1-6}$ alkanoyl and benzoyl,
   halogen,
   nitro,
   cyano,
   $C_{1-6}$ alkyl optionally substituted with 1 to 5 halogen atoms or
   $C_{1-6}$ alkoxy optionally substituted with 1 to 5 halogen atoms, (s) a formyl group and
(s') a carbonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
   (i) a 5- to 6-membered aromatic monocyclic heterocyclic group,
   (ii) an 8- to 12-membered aromatic fused heterocyclic group and
   (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;
each of said alkyl, cycloalkyl, aryl, aralkyl and heterocyclic groups being unsubstituted or substituted by
   hydroxy,
   amino optionally having 1 to 2 substituents selected from the group consisting of $C_{1-6}$ alkyl, $C_{1-6}$ alkanoyl and benzoyl,
   halogen,
   nitro,
   cyano,
   $C_{1-6}$ alkyl optionally substituted with 1 to 5 halogen atoms or
   $C_{1-6}$ alkoxy optionally substituted with 1 to 5 halogen atoms, or (v) a hydroxy group optionally substituted with $C_{1-6}$ alkyl group, $C_{1-6}$ alkanoyl, benzoyl or optionally halogenated $C_{1-6}$ alkoxy-carbonyl;

(2) a group of the formula: —C(R')=N—R wherein each symbol is as defined above; or
(3) a 5- to 6-membered aromatic or non-aromatic monocyclic nitrogen-containing heterocyclic group which contains, besides carbon atoms, 1 to 3 nitrogen atoms and optionally contains 1 to 3 hetero-atoms selected from the group consisting of an oxygen atom and a sulfur atom and which may be substituted by
   (a) a hydroxy group,
   (b) a halogen atom,
   (c) a nitro group,
   (d) a cyano group,
   (e) an amino group optionally substituted with 1 or 2 substituents selected from the group consisting of
      (e-1) a $C_{1-6}$ alkyl group optionally substituted with $C_{1-6}$ alkoxy, halogen, $C_{1-6}$ alkyl, amino, hydroxy, cyano group or amidino,
      (e-2) a carbamoyl group,
      (e-2') a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
         (i) a 5- to 6-membered aromatic monocyclic heterocyclic group,
         (ii) an 8- to 12-membered aromatic fused heterocyclic group and
         (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by hydroxy, amino optionally having 1 to 2 substituents selected from the group consisting of $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (e-2") a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of (i) a 5- to 6-membered aromatic monocyclic heterocyclic group, (ii) an 8- to 12-membered aromatic fused heterocyclic group and (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by hydroxy, amino optionally having 1 to 2 substituents selected from the group consisting of $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms;

and having another substituent selected from the group consisting of $C_{1-6}$ alkyl, $C_{3-6}$ cycloalkyl and $C_{7-10}$ aralkyl, (e-2''') a 3- to 8-membered cyclic amino-carbonyl group optionally having $C_{1-6}$ alkyl, $C_{7-10}$ aralkyl or $C_{6-10}$ aryl, (e-3) a sulfonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of (i) a 5- to 6-membered aromatic monocyclic heterocyclic group, (ii) an 8- to 12-membered aromatic fused heterocyclic group and (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by hydroxy, amino optionally having 1 to 2 substituents selected from the group consisting of $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (e-4) a formyl group and (e-4') a carbonyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of (i) a 5- to 6-membered aromatic monocyclic heterocyclic group, (ii) an 8- to 12-membered aromatic fused heterocyclic group and (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by hydroxy, amino optionally having 1 to 2 substituents selected from the group consisting of $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (f) a $C_{1-6}$ alkyl group optionally substituted with halogen, amino, carboxyl or hydroxy, (g) a $C_{1-6}$ alkoxy group optionally substituted with 1 to 5 halogen atoms, (h) a carboxyl group, (h') a $C_{1-6}$ alkoxy-carbonyl group, (h") a $C_{7-12}$ aryloxycarbonyl group being unsubstituted or substituted by hydroxy, amino optionally having 1 to 2 substituents selected from the group consisting of $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (h''') a $C_{6-10}$ aryl-$C_{1-4}$ alkoxy-carbonyl group being unsubstituted or substituted by hydroxy, amino optionally having 1 to 2 substituents selected from the group consisting of $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (i) a carbamoyl group, (i') a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
 (i) a 5- to 6-membered aromatic monocyclic heterocyclic group,
 (ii) an 8- to 12-membered aromatic fused heterocyclic group and
 (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by hydroxy, amino optionally having 1 to 2 substituents selected from the group consisting of $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms, (i") a carbamoyl group having one substituent selected from the group consisting of $C_{1-6}$ alkyl, $C_{3-6}$ cycloalkyl, $C_{6-10}$ aryl, $C_{7-10}$ aralkyl and heterocyclic groups selected from the group consisting of
 (i) a 5- to 6-membered aromatic monocyclic heterocyclic group,
 (ii) an 8- to 12-membered aromatic fused heterocyclic group and
 (iii) a 3- to 8-membered saturated or unsaturated non-aromatic heterocyclic group and containing 1 to 4 hetero-atoms selected from the group consisting of oxygen atom, sulfur atom and nitrogen atom besides carbon atoms;

each of said alkyl, cycloalkyl, aryl, aralkyl and heterocyclic groups being unsubstituted or substituted by hydroxy, amino optionally having 1 to 2 substituents selected from the group consisting of $C_{1-6}$ alkyl, $C_{1-6}$ alkanoyl and benzoyl, halogen, nitro, cyano, $C_{1-6}$ alkyl optionally substituted with 1 to 5 halogen atoms or $C_{1-6}$ alkoxy optionally substituted with 1 to 5 halogen atoms;

and having another substituent selected from the group consisting of $C_{1-6}$ alkyl, $C_{3-6}$ cycloalkyl and $C_{7-10}$ aralkyl or (i''') a 3- to 8-membered cyclic amino-carbonyl group optionally having $C_{1-6}$ alkyl, $C_{7-10}$ aralkyl or $C_{6-10}$ aryl.

* * * * *